(12) United States Patent
Pinkerton et al.

(10) Patent No.: US 9,776,979 B2
(45) Date of Patent: Oct. 3, 2017

(54) EBI2 MODULATORS

(71) Applicant: Sanford-Burnham Medical Research Institute, La Jolla, CA (US)

(72) Inventors: Anthony B. Pinkerton, San Diego, CA (US); Robert Ardecky, La Jolla, CA (US); Eduard A. Sergienko, San Diego, CA (US); Marcos Gonzalez-Lopez, La Jolla, CA (US); Santhi Reddy Ganji, La Jolla, CA (US); Jiwen Zou, San Diego, CA (US)

(73) Assignee: SANFORD-BURNHAM MEDICAL RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 14/910,653

(22) PCT Filed: Sep. 26, 2014

(86) PCT No.: PCT/US2014/057897
§ 371 (c)(1),
(2) Date: Feb. 5, 2016

(87) PCT Pub. No.: WO2015/048570
PCT Pub. Date: Apr. 2, 2015

(65) Prior Publication Data
US 2016/0214951 A1 Jul. 28, 2016

Related U.S. Application Data

(60) Provisional application No. 61/883,100, filed on Sep. 26, 2013, provisional application No. 61/883,092, filed on Sep. 26, 2013.

(51) Int. Cl.
| | |
|---|---|
| *C07D 295/16* | (2006.01) |
| *C07D 471/04* | (2006.01) |
| *C07D 471/10* | (2006.01) |
| *C07F 5/02* | (2006.01) |
| *C07D 209/12* | (2006.01) |
| *C07D 211/26* | (2006.01) |
| *C07D 215/14* | (2006.01) |
| *C07D 235/10* | (2006.01) |
| *C07D 257/04* | (2006.01) |
| *C07D 295/26* | (2006.01) |
| *C07D 317/46* | (2006.01) |
| *C07D 333/56* | (2006.01) |
| *C07D 401/06* | (2006.01) |
| *C07D 403/12* | (2006.01) |
| *C07D 495/04* | (2006.01) |
| *C07F 9/6509* | (2006.01) |

(52) U.S. Cl.
CPC ......... *C07D 295/16* (2013.01); *C07D 209/12* (2013.01); *C07D 211/26* (2013.01); *C07D 215/14* (2013.01); *C07D 235/10* (2013.01); *C07D 257/04* (2013.01); *C07D 295/26* (2013.01); *C07D 317/46* (2013.01); *C07D 333/56* (2013.01); *C07D 401/06* (2013.01); *C07D 403/12* (2013.01); *C07D 471/04* (2013.01); *C07D 471/10* (2013.01); *C07D 495/04* (2013.01); *C07F 5/025* (2013.01); *C07F 9/650958* (2013.01)

(58) Field of Classification Search
CPC .. C07D 209/12; C07D 211/26; C07D 215/14; C07D 235/10; C07D 257/04; C07D 295/26; C07D 317/46; C07D 333/56; C07D 401/06; C07D 403/12; C07D 471/04; C07D 471/10; C07D 495/04; C07F 5/025; C07F 9/650958
See application file for complete search history.

(56) References Cited

U.S. PATENT DOCUMENTS

2005/0245499 A1   11/2005   Straub et al.

FOREIGN PATENT DOCUMENTS

| WO | WO 2004/037796 | * | 5/2004 | .......... C07D 241/00 |
|---|---|---|---|---|
| WO | WO 2005/080362 | * | 9/2005 | .......... C07D 295/18 |
| WO | WO-2015048570 A2 | | 4/2015 | |

OTHER PUBLICATIONS

Basse, et al., Novel Organic Proteasome Inhibitors Identified by Virtual and in Vitro Screening, J. Med. Chem., 53, 509-513 (2010).*
Zou, et al., Synthesis, biological evaluation, and structure-activity relationship study of novel cytotoxic aza-caffeic acid derivatives, Bioorganic & Medicinal Chemistry, 18(17), 6351-6359, ISSN: 0968-0896 (2010).*
Zeng, et al., A Newly Synthesized Sinapic Acid Derivative Inhibits Endothelial Activation In Vitro and In Vivo, Molecular Pharmacology, 83(5), 1099-1108, ISSN: 1521-0111 (2013).*
Wolff, Manfred E., Burger's Medicinal Chemistry and Drug Discovery, Fifth Ed., vol. 1: Principles and Practice, John Wiley & Sons, 1995, 975.*
West, Anthony R., Solid State Chemistry and Its Applications, Wiley, New York, 1988, 358.*
Banker, Gilbert S. et al., Modem Pharmaceutics, Marcel Dekker, New York, 1996.*
Azzi et al. Beta-arrestin-mediated activation of MAPK by inverse agonists reveals distinct active conformations for G protein-coupled receptors. PNAS USA 100(20):11406-11411 (2003).
Beisser et al. The Epstein-Barr virus BILF1 gene encodes a G protein-coupled receptor that inhibits phosphorylation of RNA-dependent protein kinase. J Virol 79:441-449 (2005).

(Continued)

*Primary Examiner* — Erich A Leeser
(74) *Attorney, Agent, or Firm* — Wilson Sonsini Goodrich & Rosati

(57) ABSTRACT

Provided herein are small molecule Epstein-Barr virus-induced G-protein coupled receptor 2 (EBI2) modulator compounds, compositions comprising the compounds, and methods of using the compounds and compositions comprising the compounds. EBI2 is a therapeutic target for the treatment of a variety of diseases or conditions. In some embodiments, EBI2 is a therapeutic target for the treatment of diseases or conditions such as, but not limited to, autoimmune diseases or conditions, cancer, and cardiovascular disease.

5 Claims, No Drawings

(56) References Cited

OTHER PUBLICATIONS

Benned-Jensen et al. Distinct expression and ligand-binding profiles of two constitutively active GPR17 splice variants. J Pharmacol 159:1092-1105 (2010).

Benned-Jensen et al. Ligand modulation of the Epstein-Barr virus-induced seven-transmembrane receptor EBI2: identification of a potent and efficacious inverse agonist. J Biol Chem 286(33):29292-29302 (2011).

Benned-Jensen et al. Structural motifs of importance for the constitutive activity of the orphan 7TM receptor EBI2: analysis of receptor activation in the absence of an agonist. Mol Pharmacol 74:1008-1021 (2008).

Berridge et al. Changes in the levels of inositol phosphates after agonist-dependent hydrolysis of membrane phosphoinositides. Biochem J 212:473-482 (1983).

Birkenbach et al. Epstein-Barr virus latent infection membrane protein increases vimentin expression in human B-cell lines. J Virol 63:4079-4084 (1989).

Birkenbach et al. Epstein-Barr virus-induced genes: first lymphocyte-specific G protein-coupled peptide receptors. J Virol 67:2209-2220 (1993).

Buck et al. Disulfide trapping to localize small-molecule agonists and antagonists for a G protein-coupled receptor. PNAS USA 102:2719-2724 (2005).

Cahir-McFarland et al. Role of NF-kappa B in cell survival and transcription of latent membrane protein 1-expressing or Epstein-Barr virus latency III-infected cells J Virol 78:4108-4119 (2004).

Cannon et al. The Kaposi's sarcoma-associated herpesvirus G protein-coupled receptor has broad signaling effects in primary effusion lymphoma cells.J Virol 77:57-67 (2003).

Casarosa et al. Constitutive signaling of the human cytomegalovirus-encoded chemokine receptor US28. J Biol Chem 276:1133-1137 (2001).

Claeysen et al. A single mutation in the 5-HT4 receptor (5-HT4-R D100(3.32)A) generates a Gs-coupled receptor activated exclusively by synthetic ligands (RASSL). J Biol Chem 278:699-702 (2003).

Costa et al. Antagonists with negative intrinsic activity at delta opioid receptors coupled to GTP-binding proteins. PNAS US 86:7321-7325 (1989).

Couty et al. Kaposi's sarcoma-associated herpesvirus G protein-coupled receptor signals through multiple pathways in endothelial cells. J Biol Chem 276:33805-33811 (2001).

Cussac et al. Mutant 5-hydroxytryptamine 1A receptor D116A is a receptor activated solely by synthetic ligands with a rich pharmacology. Pharmacol Exp Ther 331:222-233 (2009).

Daugvilaite et al. Oxysterol-EBI2 signaling in immune regulation and viral infection. Eur J Immunol 44(7):1904-1912 (2014).

De Lean et al. A ternary complex model explains the agonist-specific binding properties of the adenylate cyclase-coupled beta-adrenergic receptor. J Biol Chem 255:7108-7117 (1980).

Elling et al. Metal ion site engineering indicates a global toggle switch model for seven-transmembrane receptor activation. J Biol Chem 281:17337-17346 (2006).

Farzarn et al. Two orphan seven-transmembrane segment receptors which are expressed in CD4-positive cells support simian immunodeficiency virus infection. J Exp Med 186:405-411 (1997).

Fraile-Ramos et al. The human cytomegalovirus US28 protein is located in endocytic vesicles and undergoes constitutive endocytosis and recycling. Mol Biol Cell 12:1737-1749 (2001).

Gatto et al. Guidance of B cells by the orphan G protein-coupled receptor EBI2 shapes humoral immune responses.Immunity 31:259-269 (2009).

Gerhard et al. The status quality, and expansion of the NTH full-length cDNA project: the Mammalian Gene Collection (MGC). Genome Res. 14(1013):2121-2127 (2004).

Gessier et al. Identification and Characterization of Small Molecule Modulators of the Epstein-Barr Virus-Induced Gene 2 (EBI2) Receptor. J Med Chem 57(8):3358-3368 (2014).

Goltz et al. Sequence analysis of the genome of porcine lymphotropic herpesvirus 1 and gene expression during post-transplant lymphoproliferative disease of pigs. Virology 294:383-393 (2002).

Gruijthuijsen et al. The rat cytomegalovirus R33-encoded G protein-coupled receptor signals in a constitutive fashion. J Virol 76:1328-1338 (2002).

Han et al. Identification of an agonist-induced conformational change occurring adjacent to the ligand-binding pocket of the M(3) muscarinic acetylcholine receptor. J Biol Chem 280:34849-34858 (2005).

Holst et al. Common structural basis for constitutive activity of the ghrelin receptor family. J Biol Chem 279:53806-53817 (2004).

Holst et al. High constitutive signaling of the ghrelin receptor—identification of a potent inverse agonist. Mol Endocrinol 17:2201-2210.

Holst et al. Tumorigenesis induced by the HHV8-encoded chemokine receptor requires ligand modulation of high constitutive activity. J Clin Invest 108:1789-1796 (2001).

Jensen et al Molecular interaction of a potent nonpeptide agonist with the chemokine receptor CCR8. Mol Pharmacol 72:327-340 (2007).

Johansen et al. Biosynthesis of peptide precursors and protease inhibitors using new constitutive and inducible eukaryotic expression vectors. FEBS Lett 267:289-294 (1990).

Joost et al. Phylogenetic analysis of 277 human G-protein-coupled receptors as a tool for the prediction of orphan receptor ligands. Genome Biol 3(11):RESEARCH0063.1-0063.16 (2002).

Kledal et al. Selective recognition of the membrane-bound CX3C chemokine, fractalkine, by the human cytomegalovirus-encoded broad-spectrum receptor US28. FEBS Lett. 441:209-214 (1998).

Lapinsh et al. Classification of G-protein coupled receptors by alignment-independent extraction of principal chemical properties of primary amino acid sequences. Protein Sci. 11:795-805 (2002).

Liu et al. Galpha protein selectivity determinant specified by a viral chemokine receptor-conserved region in the C tail of the human herpesvirus 8 g protein-coupled receptor. J Virol 78:2460-2471 (2004).

Liu et al. Oxysterols direct immune cell migration via EBI2. Nature 475(7357):519-523 (2011).

Lyngaa et al. Cell transformation mediated by the Epstein-Barr virus G protein-coupled receptor BILF1 is dependent on constitutive signaling. Oncogene 29:4388-4398 (2010).

Mao et al. Specific involvement of G proteins in regulation of serum response factor-mediated gene transcription by different receptors. J Biol Chem 273:27118-27123 (1998).

Matthews et al. Calcium/calmodulin-dependent protein kinase types II and IV differentially regulate CREB-dependent gene expression. Mol Cell Biol. 14:6107-6116 (1994).

Maussang et al Human cytomegalovirus-encoded chemokine receptor US28 promotes tumorigenesis. PNAS USA 103:13068-13073 (2006).

McCune et al. Regulation of the cellular localization and signaling properties of the alpha(1B)- and alpha(1D)-adrenoceptors by agonists and inverse agonists. Mol Pharmacol 57:659-666 (2000).

Melchjorsen et al. Expression and function of chemokines during viral infections: from molecular mechanisms to in vivo function. J Leukoc Biol. 74:331-343 (2003).

Melchjorsen et al. Herpes simplex virus selectively induces expression of the CC chemokine RANTES/CCL5 in macrophages through a mechanism dependent on PKR and ICP0. J Virol 76:2780-2788 (2002).

Montaner et al. The Kaposi's sarcoma-associated herpesvirus G protein-coupled receptor promotes endothelial cell survival through the activation of AKT/protein kinase B. Cancer Res. 61:2641-2648 (2001).

Moorman et al. Disruption of the gene encoding the gammaHV68 v-GPCR leads to decreased efficiency of reactivation from latency. Virology 307:179-190 (2003).

Nakayama et al. Human B cells immortalized with Epstein-Barr virus upregulate CCR6 and CCR10 and downregulate CXCR4 and CXCR5. J Virol 76:3072-3077 (2002).

(56) References Cited

OTHER PUBLICATIONS

Nijenhuis et al. AgRP(83-132) acts as an inverse agonist on the human-melanocortin-4 receptor. Mol Endocrinol 15:164-171 (2001).
Paulsen et al. Epstein-Barr virus-encoded BILF1 is a constitutively active G protein-coupled receptor. J. Virol. 79:536-546 (2005).
PCT/US2014/057897 International Search Report and Written Opinion dated Mar. 16, 2015.
Pereira et al. EBI2 mediates B cell segregation between the outer and centre follicle. Nature 460(7259):1121-1126 (2009).
Pereira et al. Finding the right niche: B-cell migration in the early phases of T-dependent antibody responses. Int. Immunol. 22:413-419 (2010).
Perez et al. Discovery of novel protease activated receptors 1 antagonists with potent antithrombotic activity in vivo. J Med Chem 52(19):5826-5836 (2009).
Ponimaskin et al. 5-Hydroxytryptamine 4(a) receptor is coupled to the Galpha subunit of heterotrimeric G13 protein. J Biol Chem 277:20812-20819 (2002).
Rajagopal et al. Teaching old receptors new tricks: biasing seven-transmembrane receptors. Nat Rev Drug Discov 9:373-386 (2010).
Rooseboom et al. Enzyme-catalyzed activation of anticancer prodrugs. Pharmacological Reviews 56:53-102 (2004).
Rosenkilde et al. Agonists and inverse agonists for the herpesvirus 8-encoded constitutively active seven-transmembrane oncogene product, ORF-74. J Biol Chem 274:956-961 (1999).
Rosenkilde et al. High constitutive activity of a virus-encoded seven transmembrane receptor in the absence of the conserved DRY motif (Asp-Arg-Tyr) in transmembrane helix 3. Mol Pharmacol. 68:11-19 (2005).
Rosenkilde et al. Molecular pharmacological phenotyping of EBI2. An orphan seven-transmembrane receptor with constitutive activity. J Biol Chem 381:13199-13208 (2006).
Rosenkilde et al. The CXC chemokine receptor encoded by herpesvirus saimiri, ECRF3, shows ligand-regulated signaling through Gi, Gq, and G12/13 proteins but constitutive signaling only through Gi and G12/13 proteins. J Biol Chem 279:32524-32533 (2004).
Sabroe et al. Cloning and characterization of the guinea pig eosinophil eotaxin receptor, C-C chemokine receptor-3: blockade using a monoclonal antibody in vivo. J Immunol 161:6139-6147 (1998).
Shepard et al. Constitutive activation of NF-kappa B and secretion of interleukin-8 induced by the G protein-coupled receptor of Kaposi's sarcoma-associated herpesvirus involve G alpha(13) and RhoA. J Biol Chem 276:45979-45987 (2001).
Shin et al. Molecular modeling and site-specific mutagenesis of the histamine-binding site of the histamine H4 receptor. Mol Pharmacol. 62:38-47 (2002).
Strader et al. Identification of residues required for ligand binding to the beta-adrenergic receptor. PNAS USA 84:4384-4388 (1987).
Yang et al. Transgenic expression of the chemokine receptor encoded by human herpesvirus 8 induces an angioproliferative disease resembling Kaposi's sarcoma. J Exp Med 191:445-454 (2000).
Yoshida et al. Molecular cloning of a novel human CC chemokine EBI1-ligand chemokine that is a specific functional ligand for EBI1, CCR7. J Biol Chem 272:13803-13809 (1997).

\* cited by examiner

EBI2 MODULATORS

CROSS-REFERENCE

This application is filed pursuant to 35 U.S.C. §371 as a United States National Phase Application of International Application No. PCT/US2014/057897 entitled "EBI2 MODULATORS," filed Sep. 26, 2014, which claims the benefit of U.S, Application Ser. No. 61/883,092, filed Sep. 26, 2013, and U.S. Application Ser. No. 61/883,100, filed Sep. 26, 2013, each of which are incorporated herein by reference in their entirety.

SUMMARY OF THE INVENTION

Described herein are compounds that modulate the activity of Epstein-Barr virus-induced G-protein coupled receptor 2 (EBI2), also known as G-protein coupled receptor 183. EBI2 is a therapeutic target for the treatment of a variety of diseases or conditions. In some embodiments, EBI2 is a therapeutic target for the treatment of diseases or conditions such as, but not limited to, autoimmune diseases or conditions, cancer, and cardiovascular disease.

In one aspect, provided herein is a compound having the structure of Formula (I):

Formula (I)

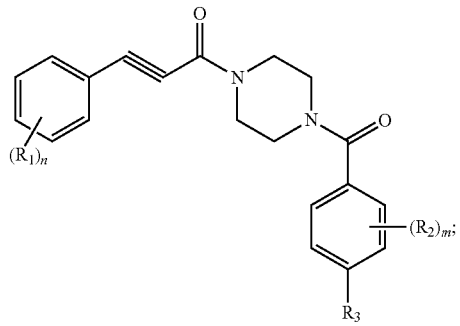

wherein:
- each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl; or two $R_1$ on adjacent carbon atoms are combined with the adjacent carbon atoms to form a —$OCH_2O$— ring;
- each $R_2$ is independently F, Cl, Br, —CN, —$CF_3$, —$OCF_3$, —OH, —$C_1$-$C_6$alkyl, or —$OC_1$-$C_6$alkyl;
- $R_3$ is F, Cl, Br, —CN, —$CF_3$, —$OCF_3$, —OH, —$C_1$-$C_6$alkyl, —$OC_1$-$C_6$alkyl, —C(=O)$C_1$-$C_6$alkyl, $CO_2H$, $B(OH)_2$, or $PO_3H$;
- each $R_4$ is independently H or $C_1$-$C_6$alkyl;
- each $R_5$ is independently H or $C_1$-$C_6$alkyl;
- m is an integer selected from 0-3; and
- n is an integer selected from 1-3;

or a pharmaceutically acceptable salt, pharmaceutically acceptable solvate, or pharmaceutically acceptable prodrug thereof.

In another aspect, provided herein is a compound having the structure of Formula (II):

Formula (II)

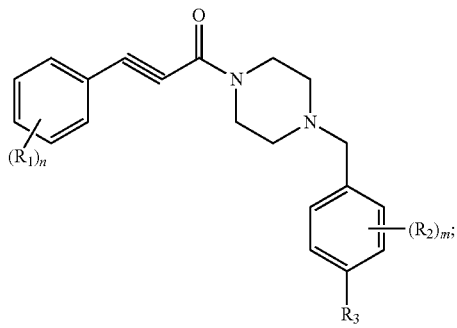

wherein:
- each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl;
- each $R_2$ is independently F, Cl, Br, —CN, —$CF_3$, —$OCF_3$, —OH, —$C_1$-$C_6$alkyl, or —$OC_1$-$C_6$alkyl;
- $R_3$ is F, Cl, Br, —CN, —$CF_3$, —$OCF_3$, —OH, —$C_1$-$C_6$alkyl, —$OC_1$-$C_6$alkyl, —C(=O)$C_1$-$C_6$alkyl, $CO_2H$, $B(OH)_2$, or $PO_3H$;
- each $R_4$ is independently H or $C_1$-$C_6$alkyl;
- each $R_5$ is independently H or $C_1$-$C_6$alkyl;
- m is an integer selected from 0-2; and
- n is an integer selected from 1-3;

or a pharmaceutically acceptable salt, pharmaceutically acceptable solvate, or pharmaceutically acceptable prodrug thereof.

In one embodiment is a compound of Formula (I) or Formula (II) wherein $R_3$ is F, Cl, Br, —$CF_3$, —$CH_3$, —$OCF_3$, or —$OCH_3$. In another embodiment is a compound of Formula (I) or Formula (II) wherein $R_1$ is F, Cl, Br, —$CF_3$, —$CH_3$, —$OCF_3$, or —$OCH_3$. In another embodiment is a compound of Formula (I) or Formula (II) wherein $R_2$ is F, Cl, Br, —$CF_3$, —$CH_3$, or —$OCH_3$. In another embodiment is a compound of Formula (I) or Formula (II) wherein n is 1 and m is 0. In another embodiment is a compound of Formula (I) or Formula (II) wherein n is 2 and m is 0. In another embodiment is a compound of Formula (I) or Formula (II) wherein n is 1 and m is 1. In another embodiment is a compound of Formula (I) or Formula (II) wherein n is 2 and m is 1. In another embodiment is a compound of Formula (I) or Formula (II) wherein n is 1 and m is 2.

In another aspect, provided herein is a compound having the structure of Formula (III):

Formula (III)

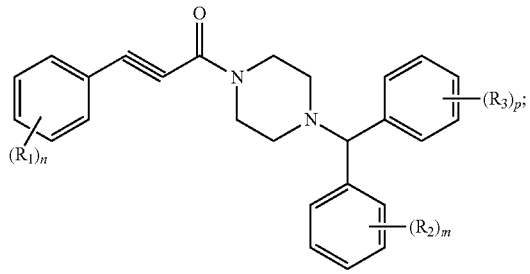

wherein:
each $R_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl; or two $R_1$ on adjacent carbon atoms are combined with the adjacent carbon atoms to form a —OCH$_2$O— ring;
each $R_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl;
each $R_3$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl;
each $R_4$ is independently H or C$_1$-C$_6$alkyl;
each $R_5$ is independently H or C$_1$-C$_6$alkyl;
m is an integer selected from 0-3;
n is an integer selected from 0-3; and
p is an integer selected from 0-3;
or a pharmaceutically acceptable salt, pharmaceutically acceptable solvate, or pharmaceutically acceptable prodrug thereof.

In one embodiment is a compound of Formula (III) wherein p is 0. In another embodiment is a compound of Formula (III) wherein p is 1 and $R_3$ is F, Cl, Br, I, —CN, —NR$_4$R$_5$, —NO$_2$, —OH, —CF$_3$, —OCF$_3$, —OC$_1$-C$_6$alkyl, or C$_1$-C$_6$alkyl. In another embodiment is a compound of Formula (III) wherein p is 1 and $R_3$ is F, Cl, Br, —CF$_3$, —OC$_1$-C$_6$alkyl, or C$_1$-C$_6$alkyl.

In another aspect, provided herein is a compound having the structure of Formula (IV):

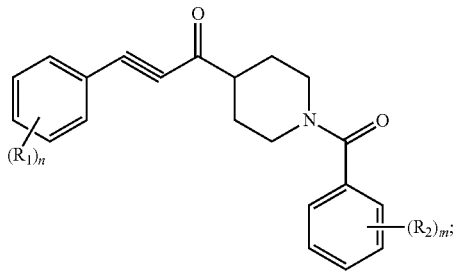

Formula (IV)

wherein:
each $R_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl; or two $R_1$ on adjacent carbon atoms are combined with the adjacent carbon atoms to form a —OCH$_2$O— ring;
each $R_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, —C(=O)C$_1$-C$_6$alkyl, CO$_2$H, B(OH)$_2$, PO$_3$H, C$_3$-C$_8$cycloalkyl, C$_1$-C$_6$heteroalkyl, C$_1$-C$_6$haloalkyl, C$_2$-C$_8$heterocycloalkyl, aryl, or heteroaryl;
each $R_4$ is independently H or C$_1$-C$_6$alkyl;
each $R_5$ is independently H or C$_1$-C$_6$alkyl;
m is an integer selected from 0-3; and
n is an integer selected from 0-3;
or a pharmaceutically acceptable salt, pharmaceutically acceptable solvate, or pharmaceutically acceptable prodrug thereof.

In another aspect, provided herein is a compound having the structure of Formula (V):

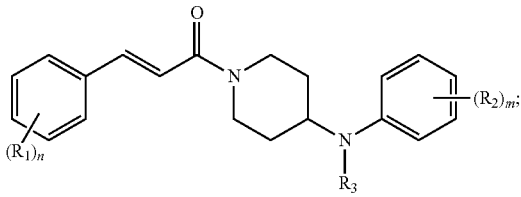

Formula (V)

wherein:
each $R_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl; or two $R_1$ on adjacent carbon atoms are combined with the adjacent carbon atoms to form a —OCH$_2$O— ring;
each $R_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, —C(=O)C$_1$-C$_6$alkyl, CO$_2$H, B(OH)$_2$, PO$_3$H, aryl, or heteroaryl;
$R_3$ is H, C$_1$-C$_6$alkyl, or aryl;
each $R_4$ is independently H or C$_1$-C$_6$alkyl;
each $R_5$ is independently H or C$_1$-C$_6$alkyl;
m is an integer selected from 0-3; and
n is an integer selected from 0-3;
or a pharmaceutically acceptable salt, pharmaceutically acceptable solvate, or pharmaceutically acceptable prodrug thereof.

In another aspect, provided herein is a compound having the structure of Formula (VI):

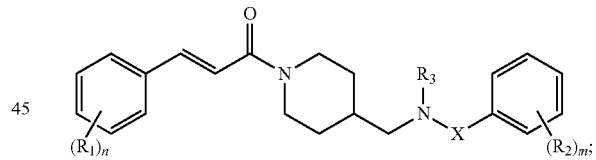

Formula (VI)

wherein:
X is a bond, —CH$_2$—, —C(H)(Ph)-, —C(=O)—, or —S(=O)$_2$—;
each $R_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl; or two $R_1$ on adjacent carbon atoms are combined with the adjacent carbon atoms to form a —OCH$_2$O— ring;
each $R_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_1$-C$_6$heteroalkyl, C$_1$-C$_6$haloalkyl, C$_2$-C$_8$heterocycloalkyl, —C(=O)C$_1$-C$_6$alkyl, CO$_2$H, B(OH)$_2$, PO$_3$H, aryl, or heteroaryl;
$R_3$ is H, C$_1$-C$_6$alkyl, or aryl;
each $R_4$ is independently H or C$_1$-C$_6$alkyl;
each $R_5$ is independently H or C$_1$-C$_6$alkyl;
m is an integer selected from 0-3; and
n is an integer selected from 0-3;

or a pharmaceutically acceptable salt, pharmaceutically acceptable solvate, or pharmaceutically acceptable prodrug thereof.

In one embodiment is a compound of Formula (VI) wherein X is —$CH_2$—. In another embodiment is a compound of Formula (VI) wherein X is —C(=O)—. In another embodiment is a compound of Formula (V) or (VI) wherein $R_3$ is H. In another embodiment is a compound of Formula (V) or (VI) wherein $R_3$ is —$CH_3$. In another embodiment is a compound of Formula (III), (IV), (V), or (VI) wherein each $R_1$ is independently F, Cl, Br, I, —CN, —$NR_4R_5$, —$NO_2$, —OH, —$CF_3$, —$OCF_3$, —$OC_1$-$C_6$alkyl, or $C_1$-$C_6$alkyl. In another embodiment is a compound of Formula (III), (IV), (V), or (VI) wherein each $R_1$ is independently F, Cl, Br, —$CF_3$, —$OC_1$-$C_6$alkyl, or $C_1$-$C_6$alkyl. In another embodiment is a compound of Formula (III), (IV), (V), or (VI) wherein each $R_2$ is independently F, Cl, Br, I, —CN, —$NR_4R_5$, —$NO_2$, —OH, —$CF_3$, —$OCF_3$, —$OC_1$-$C_6$alkyl, or $C_1$-$C_6$alkyl. In another embodiment is a compound of Formula (III), (IV), (V), or (VI) wherein each $R_2$ is independently F, Cl, Br, —$CF_3$, —$OC_1$-$C_6$alkyl, or $C_1$-$C_6$alkyl. In another embodiment is a compound of Formula (I) or Formula (II) wherein $R_2$ is F, Cl, Br, —$CF_3$, —$CH_3$, or —$OCH_3$. In another embodiment is a compound of Formula (III), (IV), (V), or (VI) wherein n is 1 and m is 0. In another embodiment is a compound of Formula (III), (IV), (V), or (VI) wherein n is 1 and m is 1. In another embodiment is a compound of Formula (III), (IV), (V), or (VI) wherein n is 1 and m is 2. In another embodiment is a compound of Formula (III), (IV), (V), or (VI) wherein n is 2 and m is 1. In another embodiment is a compound of Formula (III), (IV), (V), or (VI) wherein n is 0 and m is 0.

Any combination of the groups described above or below for the various variables is contemplated herein. Throughout the specification, groups and substituents thereof are chosen by one skilled in the field to provide stable moieties and compounds.

In another aspect, provided herein is a pharmaceutical composition comprising a compound of Formula (I), (II), (III), (IV), (V), or (VI), or a pharmaceutically acceptable salt, solvate, prodrug and a pharmaceutically acceptable excipient. In one embodiment, the pharmaceutical composition comprising the compound of Formula (I), (II), (III), (IV), (V), or (VI), or a pharmaceutically acceptable salt, pharmaceutically acceptable solvate, pharmaceutically acceptable prodrug, or N-oxide thereof, is formulated for a route of administration selected from oral administration, parenteral administration, buccal administration, nasal administration, topical administration, or rectal administration.

In another aspect is a method of treating an autoimmune disease or condition comprising administering to an individual in need a therapeutically effective amount of a compound of Formula (I), (II), (III), (IV), (V), or (VI), or a pharmaceutically acceptable salt, pharmaceutically acceptable solvate, or pharmaceutically acceptable prodrug thereof. In some embodiments, the autoimmune disease is selected from type-1-diabetes, multiple sclerosis, rheumatoid arthritis and lupus. In another embodiment is a method or treating type-1-diabetes comprising administering to an individual in need a therapeutically effective amount of a compound of Formula (I), (II), (III), (IV), (V), or (VI), or a pharmaceutically acceptable salt, pharmaceutically acceptable solvate, or pharmaceutically acceptable prodrug thereof. In another embodiment is a method of treating multiple sclerosis comprising administering to an individual in need a therapeutically effective amount of a compound of Formula (I), (II), (III), (IV), (V), or (VI), or a pharmaceutically acceptable salt, pharmaceutically acceptable solvate, or pharmaceutically acceptable prodrug thereof. In another embodiment is a method of treating rheumatoid arthritis comprising administering to an individual in need a therapeutically effective amount of a compound of Formula (I), (II), (III), (IV), (V), or (VI), or a pharmaceutically acceptable salt, pharmaceutically acceptable solvate, or pharmaceutically acceptable prodrug thereof. In another embodiment is a method of treating lupus comprising administering to an individual in need a therapeutically effective amount of a compound of Formula (I), (II), (III), (IV), (V), or (VI), or a pharmaceutically acceptable salt, pharmaceutically acceptable solvate, or pharmaceutically acceptable prodrug thereof.

In another aspect is a method of treating a cardiovascular disease or condition comprising administering to an individual in need a therapeutically effective amount of a compound of Formula (I), (II), (III), (IV), (V), or (VI), or a pharmaceutically acceptable salt, pharmaceutically acceptable solvate, or pharmaceutically acceptable prodrug thereof. In one embodiment, the cardiovascular disease is atherosclerosis.

In another aspect is a method of treating a viral infection comprising administering to an individual in need a therapeutically effective amount of a compound of Formula (I), (II), (III), (IV), (V), or (VI), or a pharmaceutically acceptable salt, pharmaceutically acceptable solvate, or pharmaceutically acceptable prodrug thereof. In some embodiments, the viral infection is an Epstein-Barr viral infection.

In another aspect is a method of treating cancer comprising administering to an individual in need a therapeutically effective amount of a compound of Formula (I), (II), (III), (IV), (V), or (VI), or a pharmaceutically acceptable salt, pharmaceutically acceptable solvate, pharmaceutically acceptable prodrug, or N-oxide thereof. In one embodiment, the cancer is blood, brain, breast, colorectal, gastrointestinal, liver, lung, ovarian, pancreatic, prostate, skin or uterine cancer. In some embodiments, the cancer produces molecules involved in Epstein-Barr virus (EBV)-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

In another aspect, described herein is a method of treating a disease, disorder or condition mediated by EBI2 in a subject in need thereof, which method comprises administering to the subject a therapeutically effective amount of a compound of Formula (I), (II), (III), (IV), (V), or (VI), or a pharmaceutically acceptable salt thereof. In another aspect, described herein is a method of treating a disease in a subject mediated by EBI2, which method comprises administering to the subject a pharmaceutical composition comprising a compound of Formula (I), (II), (III), (IV), (V), or (VI), or a pharmaceutically acceptable salt thereof. In some embodiments, the disease, disorder or condition is an autoimmune disease or condition. In some embodiments, the autoimmune disease or condition is selected from type-1-diabetes, multiple sclerosis, rheumatoid arthritis and lupus. In some embodiments, the disease, disorder or condition is a cardiovascular disease or condition. In some embodiments, the cardiovascular disease or condition is atherosclerosis. In some embodiments, the disease, disorder or condition is a viral infection. In some embodiments, the viral infection is an Epstein-Barr viral infection. In some embodiments, the disease, disorder or condition is cancer. In some embodiments, the cancer is blood, brain, breast, colorectal, gastrointestinal, liver, lung, ovarian, pancreatic, prostate, skin or uterine cancer. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

Also provided is the use a compound of Formula (I), (II), (III), (IV), (V), or (VI), or a pharmaceutically acceptable salt, pharmaceutically acceptable solvate, or pharmaceutically acceptable prodrug thereof for the treatment of an autoimmune disease or condition in a human. In some embodiments is the use a compound of Formula (I), (II), (III), (IV), (V), or (VI), or a pharmaceutically acceptable salt, pharmaceutically acceptable solvate, or pharmaceutically acceptable prodrug thereof for the treatment of an autoimmune disease or condition in a human, wherein the autoimmune disease or condition is selected from type-1-diabetes, multiple sclerosis, rheumatoid arthritis and lupus.

Further provided is the use a compound of Formula (I), (II), (III), (IV), (V), or (VI), or a pharmaceutically acceptable salt, pharmaceutically acceptable solvate, or pharmaceutically acceptable prodrug thereof for the treatment of a cardiovascular disease or condition in a human. In some embodiments is the use a compound of Formula (I), (II), (III), (IV), (V), or (VI), or a pharmaceutically acceptable salt, pharmaceutically acceptable solvate, or pharmaceutically acceptable prodrug thereof for the treatment of atherosclerosis in a human.

Further provided is the use a compound of Formula (I), (II), (III), (IV), (V), or (VI), or a pharmaceutically acceptable salt, pharmaceutically acceptable solvate, or pharmaceutically acceptable prodrug thereof for the treatment of a viral infection in a human. In some embodiments is the use a compound of Formula (I), (II), (III), (IV), (V), or (VI), or a pharmaceutically acceptable salt, pharmaceutically acceptable solvate, or pharmaceutically acceptable prodrug thereof for the treatment of an Epstein-Barr viral infection in a human.

Further provided is the use of a compound of Formula (I), (II), (III), (IV), (V), or (VI), or a pharmaceutically acceptable salt, pharmaceutically acceptable solvate, pharmaceutically acceptable prodrug, or N-oxide thereof for the treatment of cancer in a human. In some embodiments is the use of a compound of Formula ((I), (II), (III), (IV), (V), or (VI), or a pharmaceutically acceptable salt, pharmaceutically acceptable solvate, pharmaceutically acceptable prodrug, or N-oxide thereof for the treatment of a blood, brain, breast, colorectal, gastrointestinal, liver, lung, ovarian, pancreatic, prostate, skin or uterine cancer in a human. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

Also provided is the use a compound of Formula (I), (II), (III), (IV), (V), or (VI), or a pharmaceutically acceptable salt, pharmaceutically acceptable solvate, or pharmaceutically acceptable prodrug thereof for the manufacture of a medicament for the treatment of an autoimmune disease or condition in a human. In some embodiments is the use a compound of Formula (I), (II), (III), (IV), (V), or (VI), or a pharmaceutically acceptable salt, pharmaceutically acceptable solvate, or pharmaceutically acceptable prodrug thereof for the manufacture of a medicament for the treatment of an autoimmune disease or condition in a human, wherein the autoimmune disease or condition is selected from type-1-diabetes, multiple sclerosis, rheumatoid arthritis and lupus.

Further provided is the use of a compound of Formula (I), (II), (III), (IV), (V), or (VI), or a pharmaceutically acceptable salt, pharmaceutically acceptable solvate, or pharmaceutically acceptable prodrug thereof for the manufacture of a medicament for the treatment of a cardiovascular disease or condition in a human. In some embodiments is the use a compound of Formula (I), (II), (III), (IV), (V), or (VI), or a pharmaceutically acceptable salt, pharmaceutically acceptable solvate, or pharmaceutically acceptable prodrug thereof for the manufacture of a medicament for the treatment of atherosclerosis in a human.

Further provided is the use a compound of Formula (I), (II), (III), (IV), (V), or (VI), or a pharmaceutically acceptable salt, pharmaceutically acceptable solvate, or pharmaceutically acceptable prodrug thereof for the manufacture of a medicament for the treatment of a viral infection in a human. In some embodiments is the use a compound of Formula (I), (II), (III), (IV), (V), or (VI), or a pharmaceutically acceptable salt, pharmaceutically acceptable solvate, or pharmaceutically acceptable prodrug thereof for the manufacture of a medicament for the treatment of an Epstein-Barr viral infection in a human.

Further provided is the use of a compound of Formula (I), (II), (III), (IV), (V), or (VI), or a pharmaceutically acceptable salt, pharmaceutically acceptable solvate, pharmaceutically acceptable prodrug, or N-oxide thereof for the manufacture of a medicament for the treatment of cancer in a human. In some embodiments is the use of a compound of Formula (I), (II), (III), (IV), (V), or (VI), or a pharmaceutically acceptable salt, pharmaceutically acceptable solvate, pharmaceutically acceptable prodrug, or N-oxide thereof for the manufacture of a medicament for the treatment of a blood, brain, breast, colorectal, gastrointestinal, liver, lung, ovarian, pancreatic, prostate, skin or uterine cancer in a human. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

In any of the aforementioned aspects are further embodiments in which: (a) the effective amount of the compound of Formula (I), (II), (III), (IV), (V), or (VI), is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (I), (II), (III), (IV), (V), or (VI), or a pharmaceutically acceptable salt thereof, to a subject are further embodiments comprising administering at least one additional agent in addition to the administration of a compound having the structure of Formula (I), (II), (III), (IV), (V), or (VI), or a pharmaceutically acceptable salt thereof. In various embodiments, the compound of Formula (I), (II), (III), (IV), (V), or (VI), and the additional agent are administered in any order, including simultaneously. In some embodiments, the compound of Formula (I), (II), (III), (IV), (V), or (VI), and the additional agent are administered to the subject in the same pharmaceutical composition or in separate pharmaceutical compositions.

In another aspect, provided herein is a method of treating an autoimmune disease, comprising administering to an individual in need thereof a therapeutically effective amount of a compound of Formula (VII) having the structure:

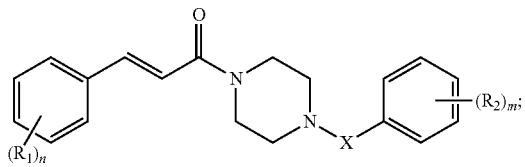

Formula (VII)

wherein:

X is a bond, —$CH_2$—, —C(H)(Ph)-, or —S(=O)$_2$—;

each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl; or two $R_1$ on adjacent carbon atoms are combined with the adjacent carbon atoms to form a —$OCH_2O$— ring;

each $R_2$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, —C(=O)$C_1$-$C_6$alkyl, $CO_2H$, $B(OH)_2$, $PO_3H$, $C_3$-$C_8$cycloalkyl, $C_1$-$C_6$heteroalkyl, $C_1$-$C_6$haloalkyl, $C_2$-$C_8$heterocycloalkyl, aryl, or heteroaryl;

each $R_4$ is independently H or $C_1$-$C_6$alkyl;

each $R_5$ is independently H or $C_1$-$C_6$alkyl;

m is an integer selected from 0-3; and n is an integer selected from 0-3;

or a pharmaceutically acceptable salt, pharmaceutically acceptable solvate, or pharmaceutically acceptable prodrug thereof.

In one embodiment is a method of treating an autoimmune disease, comprising administering to an individual in need thereof a therapeutically effective amount of a compound of Formula (VII) wherein X is a bond. In another embodiment, X is —$CH_2$—. In another embodiment, X is —C(H)(Ph)-. In another embodiment, X is —S(=O)$_2$—. In another embodiment, each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl. In another embodiment, each $R_1$ is independently F, Cl, Br, I, —CN, —$NR_4R_5$, —$NO_2$, —OH, —$CF_3$, —$OCF_3$, —$OC_1$-$C_6$alkyl, or $C_1$-$C_6$alkyl. In another embodiment, each $R_1$ is independently F, Cl, Br, —$CF_3$, —$OC_1$-$C_6$alkyl, or $C_1$-$C_6$alkyl. In another embodiment, each $R_2$ is independently F, Cl, Br, I, —CN, —$NR_4R_5$, —$NO_2$, —OH, —$CF_3$, —$OCF_3$, —$OC_1$-$C_6$alkyl, or $C_1$-$C_6$alkyl. In another embodiment, each $R_2$ is independently F, Cl, Br, —$CF_3$, —$OC_1$-$C_6$alkyl, or $C_1$-$C_6$alkyl. In another embodiment, n is 1 and m is 0. In another embodiment, n is 1 and m is 1. In another embodiment, n is 1 and m is 2. In another embodiment, n is 2 and m is 1. In another embodiment, n is 0 and m is 0. In another embodiment, the autoimmune disease is type-1-diabetes. In another embodiment, the autoimmune disease is multiple sclerosis. In another embodiment, the autoimmune disease is rheumatoid arthritis. In another embodiment, the autoimmune disease is lupus.

In another aspect, provided herein is a method of treating a cardiovascular disease, comprising administering to an individual in need thereof a therapeutically effective amount of a compound of Formula (VII) having the structure:

Formula (VII)

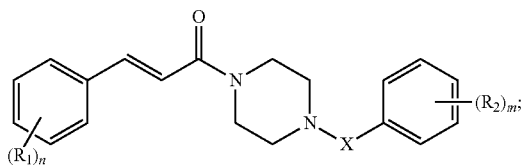

wherein:

X is a bond, —CH$_2$—, —C(H)(Ph)-, or —S(=O)$_2$—;

each R$_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl; or two R$_1$ on adjacent carbon atoms are combined with the adjacent carbon atoms to form a —OCH$_2$O— ring;

each R$_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, —C(=O)C$_1$-C$_6$alkyl, CO$_2$H, B(OH)$_2$, PO$_3$H, C$_3$-C$_8$cycloalkyl, C$_1$-C$_6$heteroalkyl, C$_1$-C$_6$haloalkyl, C$_2$-C$_8$heterocycloalkyl, aryl, or heteroaryl;

each R$_4$ is independently H or C$_1$-C$_6$alkyl;

each R$_5$ is independently H or C$_1$-C$_6$alkyl;

m is an integer selected from 0-3; and n is an integer selected from 0-3;

or a pharmaceutically acceptable salt, pharmaceutically acceptable solvate, or pharmaceutically acceptable prodrug thereof.

In one embodiment is a method of treating a cardiovascular disease, comprising administering to an individual in need thereof a therapeutically effective amount of a compound of Formula (VII) wherein X is a bond. In another embodiment, X is —CH$_2$—. In another embodiment, X is —C(H)(Ph)-. In another embodiment, X is —S(=O)$_2$—. In another embodiment, each R$_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl. In another embodiment, each R$_1$ is independently F, Cl, Br, I, —CN, —NR$_4$R$_5$, —NO$_2$, —OH, —CF$_3$, —OCF$_3$, —OC$_1$-C$_6$alkyl, or C$_1$-C$_6$alkyl. In another embodiment, each R$_1$ is independently F, Cl, Br, —CF$_3$, —OC$_1$-C$_6$alkyl, or C$_1$-C$_6$alkyl. In another embodiment, each R$_2$ is independently F, Cl, Br, I, —CN, —NR$_4$R$_5$, —NO$_2$, —OH, —CF$_3$, —OCF$_3$, —OC$_1$-C$_6$alkyl, or C$_1$-C$_6$alkyl. In another embodiment, each R$_2$ is independently F, Cl, Br, —CF$_3$, —OC$_1$-C$_6$alkyl, or C$_1$-C$_6$alkyl. In another embodiment, n is 1 and m is 0. In another embodiment, n is 1 and m is 1. In another embodiment, n is 1 and m is 2. In another embodiment, n is 2 and m is 1. In another embodiment, n is 0 and m is 0. In another embodiment, the cardiovascular disease is atherosclerosis.

In another aspect, provided herein is a method of treating a viral infection, comprising administering to an individual in need thereof a therapeutically effective amount of a compound of Formula (VII) having the structure:

Formula (VII)

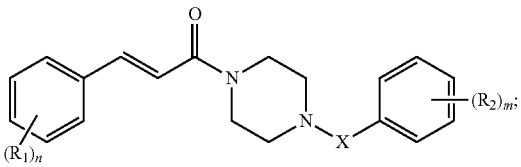

wherein:

X is a bond, —CH$_2$—, —C(H)(Ph)-, or —S(=O)$_2$—;

each R$_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl; or two R$_1$ on adjacent carbon atoms are combined with the adjacent carbon atoms to form a —OCH$_2$O— ring;

each R$_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, —C(=O)C$_1$-C$_6$alkyl, CO$_2$H, B(OH)$_2$, PO$_3$H, C$_3$-C$_8$cycloalkyl, C$_1$-C$_6$heteroalkyl, C$_1$-C$_6$haloalkyl, C$_2$-C$_8$heterocycloalkyl, aryl, or heteroaryl;

each R$_4$ is independently H or C$_1$-C$_6$alkyl;

each R$_5$ is independently H or C$_1$-C$_6$alkyl;

m is an integer selected from 0-3; and n is an integer selected from 0-3;

or a pharmaceutically acceptable salt, pharmaceutically acceptable solvate, or pharmaceutically acceptable prodrug thereof.

In one embodiment is a method of treating a viral infection, comprising administering to an individual in need thereof a therapeutically effective amount of a compound of Formula (VII) wherein X is a bond. In another embodiment, X is —CH$_2$—. In another embodiment, X is —C(H)(Ph)-. In another embodiment, X is —S(=O)$_2$—. In another embodiment, each R$_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl. In another embodiment, each R$_1$ is independently F, Cl, Br, I, —CN, —NR$_4$R$_5$, —NO$_2$, —OH, —CF$_3$, —OCF$_3$, —OC$_1$-C$_6$alkyl, or C$_1$-C$_6$alkyl. In another embodiment, each R$_1$ is independently F, Cl, Br, —CF$_3$, —OC$_1$-C$_6$alkyl, or C$_1$-C$_6$alkyl. In another embodiment, each R$_2$ is independently F, Cl, Br, I, —CN, —NR$_4$R$_5$, —NO$_2$, —OH, —CF$_3$, —OCF$_3$, —OC$_1$-C$_6$alkyl, or C$_1$-C$_6$alkyl. In another embodiment, each R$_2$ is independently F, Cl, Br, —CF$_3$, —OC$_1$-C$_6$alkyl, or C$_1$-C$_6$alkyl. In another embodiment, n is 1 and m is 0. In another embodiment, n is 1 and m is 1. In another embodiment, n is 1 and m is 2. In another embodiment, n is 2 and m is 1. In another embodiment, n is 0 and m is 0. In another embodiment, the viral infection is an Epstein-Barr viral infection.

In another aspect, provided herein is a method of treating an autoimmune disease, comprising administering to an individual in need thereof a therapeutically effective amount of a compound of Formula (VIII) having the structure:

Formula (VIII)

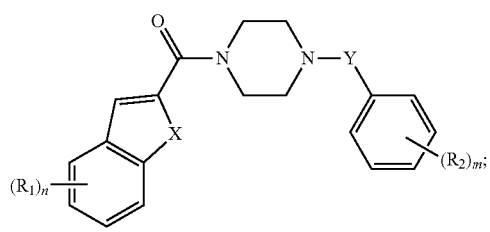

Formula (VIII)

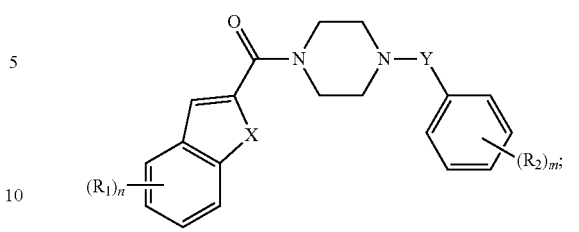

wherein:

X is —N(H)—, —N($R_3$)—, —O—, or —S—;

Y is a bond, —$CH_2$—, —C(H)(Ph)-, —C(=O)—, or —S(=O)$_2$—;

each $R_1$ is independently F, Cl, Br, I, —CN, —N$R_4R_5$, —$NO_2$, —OH, —$CF_3$, —$OCF_3$, —O$C_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl; or two $R_1$ on adjacent carbon atoms are combined with the adjacent carbon atoms to form a —O$CH_2$O— ring;

each $R_2$ is independently F, Cl, Br, I, —CN, —N$R_4R_5$, —$NO_2$, —OH, —$CF_3$, —$OCF_3$, —O$C_1$-$C_6$alkyl, $C_1$-$C_6$alkyl, —C(=O)$C_1$-$C_6$alkyl, $CO_2$H, B(OH)$_2$, $PO_3$H, $C_3$-$C_8$cycloalkyl, $C_1$-$C_6$heteroalkyl, $C_1$-$C_6$haloalkyl, $C_2$-$C_8$heterocycloalkyl, aryl, or heteroaryl;

$R_3$ is $C_1$-$C_6$alkyl;

each $R_4$ is independently H or $C_1$-$C_6$alkyl;

each $R_5$ is independently H or $C_1$-$C_6$alkyl;

m is an integer selected from 0-3; and n is an integer selected from 0-3;

or a pharmaceutically acceptable salt, pharmaceutically acceptable solvate, or pharmaceutically acceptable prodrug thereof.

In one embodiment is a method of treating an autoimmune disease, comprising administering to an individual in need thereof a therapeutically effective amount of a compound of Formula (VIII) wherein Y is a bond. In another embodiment, Y is —$CH_2$—. In another embodiment, Y is —C(H)(Ph)-. In another embodiment, Y is —S(=O)$_2$—. In another embodiment, each $R_1$ is independently F, Cl, Br, I, —CN, —N$R_4R_5$, —$NO_2$, —OH, —$CF_3$, —$OCF_3$, —O$C_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl. In another embodiment, each $R_1$ is independently F, Cl, Br, I, —CN, —N$R_4R_5$, —$NO_2$, —OH, —$CF_3$, —$OCF_3$, —O$C_1$-$C_6$alkyl, or $C_1$-$C_6$alkyl. In another embodiment, each $R_1$ is independently F, Cl, Br, —$CF_3$, —O$C_1$-$C_6$alkyl, or $C_1$-$C_6$alkyl. In another embodiment, each $R_2$ is independently F, Cl, Br, I, —CN, —N$R_4R_5$, —$NO_2$, —OH, —$CF_3$, —$OCF_3$, —O$C_1$-$C_6$alkyl, or $C_1$-$C_6$alkyl. In another embodiment, each $R_2$ is independently F, Cl, Br, —$CF_3$, —O$C_1$-$C_6$alkyl, or $C_1$-$C_6$alkyl. In another embodiment, n is 1 and m is 0. In another embodiment, n is 1 and m is 1. In another embodiment, n is 1 and m is 2. In another embodiment, n is 2 and m is 1. In another embodiment, n is 0 and m is 0. In another embodiment, the autoimmune disease is type-1-diabetes. In another embodiment, the autoimmune disease is multiple sclerosis. In another embodiment, the autoimmune disease is rheumatoid arthritis. In another embodiment, the autoimmune disease is lupus.

In another aspect, provided herein is a method of treating a cardiovascular disease, comprising administering to an individual in need thereof a therapeutically effective amount of a compound of Formula (VIII) having the structure:

wherein:

X is —N(H)—, —N($R_3$)—, —O—, or —S—;

Y is a bond, —$CH_2$—, —C(H)(Ph)-, —C(=O)—, or —S(=O)$_2$—;

each $R_1$ is independently F, Cl, Br, I, —CN, —N$R_4R_5$, —$NO_2$, —OH, —$CF_3$, —$OCF_3$, —O$C_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl; or two $R_1$ on adjacent carbon atoms are combined with the adjacent carbon atoms to form a —O$CH_2$O— ring;

each $R_2$ is independently F, Cl, Br, I, —CN, —N$R_4R_5$, —$NO_2$, —OH, —$CF_3$, —$OCF_3$, —O$C_1$-$C_6$alkyl, $C_1$-$C_6$alkyl, —C(=O)$C_1$-$C_6$alkyl, $CO_2$H, B(OH)$_2$, $PO_3$H, $C_3$-$C_8$cycloalkyl, $C_1$-$C_6$heteroalkyl, $C_1$-$C_6$haloalkyl, $C_2$-$C_8$heterocycloalkyl, aryl, or heteroaryl;

$R_3$ is $C_1$-$C_6$alkyl;

each $R_4$ is independently H or $C_1$-$C_6$alkyl;

each $R_5$ is independently H or $C_1$-$C_6$alkyl;

m is an integer selected from 0-3; and n is an integer selected from 0-3;

or a pharmaceutically acceptable salt, pharmaceutically acceptable solvate, or pharmaceutically acceptable prodrug thereof.

In one embodiment is a method of treating a cardiovascular disease, comprising administering to an individual in need thereof a therapeutically effective amount of a compound of Formula (VII) wherein X is a bond. In another embodiment, X is —$CH_2$—. In another embodiment, X is —C(H)(Ph)-. In another embodiment, X is —S(=O)$_2$—. In another embodiment, each $R_1$ is independently F, Cl, Br, I, —CN, —N$R_4R_5$, —$NO_2$, —OH, —$CF_3$, —$OCF_3$, —O$C_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl. In another embodiment, each $R_1$ is independently F, Cl, Br, I, —CN, —N$R_4R_5$, —$NO_2$, —OH, —$CF_3$, —$OCF_3$, —O$C_1$-$C_6$alkyl, or $C_1$-$C_6$alkyl. In another embodiment, each $R_1$ is independently F, Cl, Br, —$CF_3$, —O$C_1$-$C_6$alkyl, or $C_1$-$C_6$alkyl. In another embodiment, each $R_2$ is independently F, Cl, Br, I, —CN, —N$R_4R_5$, —$NO_2$, —OH, —$CF_3$, —$OCF_3$, —O$C_1$-$C_6$alkyl, or $C_1$-$C_6$alkyl. In another embodiment, each $R_2$ is independently F, Cl, Br, —$CF_3$, —O$C_1$-$C_6$alkyl, or $C_1$-$C_6$alkyl. In another embodiment, n is 1 and m is 0. In another embodiment, n is 1 and m is 1. In another embodiment, n is 1 and m is 2. In another embodiment, n is 2 and m is 1. In another embodiment, n is 0 and m is 0. In another embodiment, the cardiovascular disease is atherosclerosis.

In another aspect, provided herein is a method of treating a viral infection, comprising administering to an individual in need thereof a therapeutically effective amount of a compound of Formula (VIII) having the structure:

Formula (VIII)

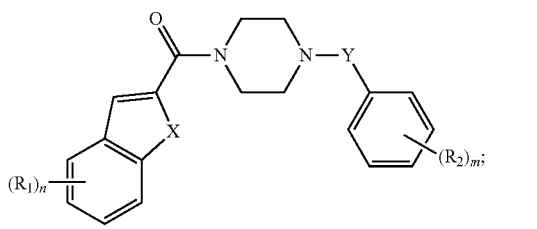

wherein:

X is —N(H)—, —N(R₃)—, —O—, or —S—;

Y is a bond, —CH₂—, —C(H)(Ph)-, —C(=O)—, or —S(=O)₂—;

each $R_1$ is independently F, Cl, Br, I, —CN, —NR₄R₅, —NO₂, —OH, —CF₃, —OCF₃, —OC₁-C₆alkyl, C₁-C₆alkyl, C₃-C₈cycloalkyl, C₁-C₆heteroalkyl, C₁-C₆haloalkyl, C₂-C₈heterocycloalkyl, aryl, or heteroaryl; or two $R_1$ on adjacent carbon atoms are combined with the adjacent carbon atoms to form a —OCH₂O— ring;

each $R_2$ is independently F, Cl, Br, I, —CN, —NR₄R₅, —NO₂, —OH, —CF₃, —OCF₃, —OC₁-C₆alkyl, C₁-C₆alkyl, —C(=O)C₁-C₆alkyl, CO₂H, B(OH)₂, PO₃H, C₃-C₈cycloalkyl, C₁-C₆heteroalkyl, C₁-C₆haloalkyl, C₂-C₈heterocycloalkyl, aryl, or heteroaryl;

$R_3$ is C₁-C₆alkyl;

each $R_4$ is independently H or C₁-C₆alkyl;

each $R_5$ is independently H or C₁-C₆alkyl;

m is an integer selected from 0-3; and n is an integer selected from 0-3;

or a pharmaceutically acceptable salt, pharmaceutically acceptable solvate, or pharmaceutically acceptable prodrug thereof.

In one embodiment is a method of treating a viral infection, comprising administering to an individual in need thereof a therapeutically effective amount of a compound of Formula (VII) wherein X is a bond. In another embodiment, X is —CH₂—. In another embodiment, X is —C(H)(Ph)-. In another embodiment, X is —S(=O)₂—. In another embodiment, each $R_1$ is independently F, Cl, Br, I, —CN, —NR₄R₅, —NO₂, —OH, —CF₃, —OCF₃, —OC₁-C₆alkyl, C₁-C₆alkyl, C₃-C₈cycloalkyl, C₁-C₆heteroalkyl, C₁-C₆haloalkyl, C₂-C₈heterocycloalkyl, aryl, or heteroaryl. In another embodiment, each $R_1$ is independently F, Cl, Br, I, —CN, —NR₄R₅, —NO₂, —OH, —CF₃, —OCF₃, —OC₁-C₆alkyl, or C₁-C₆alkyl. In another embodiment, each $R_1$ is independently F, Cl, Br, —CF₃, —OC₁-C₆alkyl, or C₁-C₆alkyl. In another embodiment, each $R_2$ is independently F, Cl, Br, I, —CN, —NR₄R₅, —NO₂, —OH, —CF₃, —OCF₃, —OC₁-C₆alkyl, or C₁-C₆alkyl. In another embodiment, each $R_2$ is independently F, Cl, Br, —CF₃, —OC₁-C₆alkyl, or C₁-C₆alkyl. In another embodiment, n is 1 and m is 0. In another embodiment, n is 1 and m is 1. In another embodiment, n is 1 and m is 2. In another embodiment, n is 2 and m is 1. In another embodiment, n is 0 and m is 0. In another embodiment, the viral infection is an Epstein-Barr viral infection.

In any of the embodiments disclosed herein, the subject is a human.

In some embodiments, compounds and compositions provided herein are administered to a human.

In some embodiments, compounds and compositions provided herein are orally administered.

In other embodiments, compounds provided herein are used for the formulation of a medicament for the modulation of the activity of EBI2 in a subject.

Articles of manufacture, which include packaging material, a compound of Formula (I), (II), (III), (IV), (V), (VI), (VII), (VIII), (IX), or (X), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from modulation of EBI2, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

A robust antibody response is essential for efficient identification and eradication of pathogenic microbes and toxins, whereas dysregulation of the antibody response can lead to autoimmune disease. Specific antigen encounter by B lymphocytes induces clonal expansion that encompasses several distinct stages of differentiation. During this differentiation process, a critical cell fate decision is made wherein some B cells will undergo terminal differentiation into antibody-producing cells, while a separate cohort will assume a distinct pathway of differentiation to become long-lived memory B cells.

EBI2 is expressed on B cells and is highly induced upon activation. EBI2 was cloned in 1993 as one out of nine up-regulated genes in Epstein-Barr virus (EBV)-infected Burkitt lymphoma cells. These nine genes were up-regulated from 4- to 100-fold upon EBV infection, and two 7TM receptors were identified among the up-regulated genes (Epstein-Barr-induced receptors 1 and 2, EBI1 and -2). EBI2 displayed the highest up-regulation (200-fold) among the nine EBV-induced genes. Initial expression analyses of the nine genes uncovered an expression of EBI2 in peripheral blood mononuclear cells (PBMCs), tonsils, spleen, and lung tissue.

EBI2 has been characterized in terms of signaling activities at the level of G-proteins as well as at the level of the transcriptional activity. Recent gene targeting experiments revealed that EBI2−/− B cells exhibited defective migration, resulting in strongly impaired T cell-dependent antibody responses.

The role of EBI2 in diseases involving an immune system dysregulation or diseases involving EBV infection is compelling. Many of these diseases overlap, as, in addition to EBI2, EBV regulates many different proteins related to the immune system, such as chemokines and their receptors. There are many disorders in which immune dysregulation have been implicated. Autoimmune and autoinflammatory disorders, such as type-1-diabetes, multiple sclerosis, rheumatoid arthritis, and systemic lupus erythematosus, have been connected to an aberrant activation of the immune system.

Inflammation substantially contributes to the pathophysiology of cardiovascular disease, and especially of atherosclerosis. As high levels of oxysterols (physiologic ligands for EBI2) are present in an atherosclerotic plaque and EBI2 is expressed on monocytes, which have a central role in atherosclerosis, the oxysterol-EBI2 pathway may be involved in the recruitment of immune cells to atherosclerotic lesions. Thus, EBI2 blockade might provide a therapeutic benefit in atherosclerosis.

In some embodiments, the compounds described herein are EBI2 antagonists.

In some embodiments, the compounds described herein are EBI2 inverse agonists.

Compounds

In one aspect, provided herein is a compound having the structure of Formula (I):

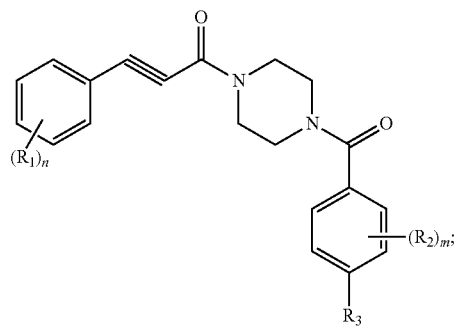

Formula (I)

wherein:
- each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl; or two $R_1$ on adjacent carbon atoms are combined with the adjacent carbon atoms to form a —OCH$_2$O— ring;
- each $R_2$ is independently F, Cl, Br, —CN, —CF$_3$, —OCF$_3$, —OH, —C$_1$-C$_6$alkyl, or —OC$_1$-C$_6$alkyl;
- $R_3$ is F, Cl, Br, —CN, —CF$_3$, —OCF$_3$, —OH, —C$_1$-C$_6$alkyl, —OC$_1$-C$_6$alkyl, —C(=O)C$_1$-C$_6$alkyl, CO$_2$H, B(OH)$_2$, or PO$_3$H;
- each $R_4$ is independently H or C$_1$-C$_6$alkyl;
- each $R_5$ is independently H or C$_1$-C$_6$alkyl;
- m is an integer selected from 0-3; and
- n is an integer selected from 1-3;

or a pharmaceutically acceptable salt, pharmaceutically acceptable solvate, or pharmaceutically acceptable prodrug thereof.

In some embodiments is a compound of Formula (I) wherein $R_3$ is F, Cl, Br, —CF$_3$, —CH$_3$, —OCF$_3$, or —OCH$_3$. In some embodiments is a compound of Formula (I) wherein $R_3$ is F. In some embodiments is a compound of Formula (I) wherein $R_3$ is Cl. In some embodiments is a compound of Formula (I) wherein $R_3$ is Br. In some embodiments is a compound of Formula (I) wherein $R_3$ is —CF$_3$. In some embodiments is a compound of Formula (I) wherein $R_3$ is —CH$_3$. In some embodiments is a compound of Formula (I) wherein $R_3$ is —OCF$_3$. In some embodiments is a compound of Formula (I) wherein $R_3$ is —OCH$_3$.

In some embodiments is a compound of Formula (I) wherein $R_1$ is independently F, Cl, Br, —CF$_3$, —CH$_3$, —OCF$_3$, or —OCH$_3$. In some embodiments is a compound of Formula (I) wherein $R_1$ is F. In some embodiments is a compound of Formula (I) wherein $R_1$ is Cl. In some embodiments is a compound of Formula (I) wherein $R_1$ is Br. In some embodiments is a compound of Formula (I) wherein $R_1$ is —CF$_3$. In some embodiments is a compound of Formula (I) wherein $R_1$ is —CH$_3$. In some embodiments is a compound of Formula (I) wherein $R_1$ is —OCF$_3$. In some embodiments is a compound of Formula (I) wherein $R_1$ is —OCH$_3$.

In some embodiments is a compound of Formula (I) wherein $R_2$ is independently F, Cl, Br, —CF$_3$, —CH$_3$, or —OCH$_3$. In some embodiments is a compound of Formula (I) wherein $R_2$ is F. In some embodiments is a compound of Formula (I) wherein $R_2$ is Cl. In some embodiments is a compound of Formula (I) wherein $R_2$ is Br. In some embodiments is a compound of Formula (I) wherein $R_1$ is —CF$_3$. In some embodiments is a compound of Formula (I) wherein $R_2$ is —CH$_3$. In some embodiments is a compound of Formula (I) wherein $R_2$ is —OCF$_3$. In some embodiments is a compound of Formula (I) wherein $R_1$ is —OCH$_3$.

In another embodiment is a compound of Formula (I) wherein n is 1 and m is 0. In another embodiment is a compound of Formula (I) wherein n is 2 and m is 0. In another embodiment is a compound of Formula (I) wherein n is 1 and m is 1. In another embodiment is a compound of Formula (I) wherein n is 2 and m is 1. In another embodiment is a compound of Formula (I) wherein n is 1 and m is 2. In another embodiment is a compound of Formula (I) wherein n is 2 and m is 2. In another embodiment is a compound of Formula (I) wherein n is 3 and m is 1. In another embodiment is a compound of Formula (I) wherein n is 3 and m is 2.

In another embodiment is a compound of Formula (I) wherein n is 1, m is 0, $R_3$ is F, Cl, Br, —CF$_3$, —CH$_3$, —OCF$_3$, or —OCH$_3$, and $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (I) wherein n is 1, m is 0, $R_3$ is F, Cl, Br, —CF$_3$, —CH$_3$, —OCF$_3$, or —OCH$_3$, and $R_1$ is F, Cl, Br, —CF$_3$, —CH$_3$, —OCF$_3$, or —OCH$_3$. In another embodiment is a compound of Formula (I) wherein n is 1, m is 0, $R_3$ is F, Cl, Br, —CF$_3$, —CH$_3$, or —OCH$_3$, and $R_1$ is F, Cl, Br, or —CF$_3$.

In another embodiment is a compound of Formula (I) wherein n is 2, m is 0, $R_3$ is F, Cl, Br, —CF$_3$, —CH$_3$, —OCF$_3$, or —OCH$_3$, and $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (I) wherein n is 2, m is 0, $R_3$ is F, Cl, Br, —CF$_3$, —CH$_3$, —OCF$_3$, or —OCH$_3$, and $R_1$ independently is F, Cl, Br, —CF$_3$, —CH$_3$, —OCF$_3$, or —OCH$_3$. In another embodiment is a compound of Formula (I) wherein n is 2, m is 0, $R_3$ is F, Cl, Br, —CF$_3$, —CH$_3$, or —OCH$_3$, and $R_1$ is independently F, Cl, Br, or —CF$_3$.

In another embodiment is a compound of Formula (I) wherein m is 1, n is 1, $R_3$ is F, Cl, Br, —CF$_3$, —CH$_3$, —OCF$_3$, or —OCH$_3$, and $R_1$ and $R_2$ are independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (I) wherein m is 1, n is 1, $R_3$ is F, Cl, Br, —CF$_3$, —CH$_3$, —OCF$_3$, or —OCH$_3$, and $R_1$ and $R_2$ are independently F, Cl, Br, —CF$_3$, —CH$_3$, —OCF$_3$, or —OCH$_3$. In another embodiment is a compound of Formula (I) wherein m is 1, n is 1, $R_3$ is F, Cl, Br, —CF$_3$, —CH$_3$, or —OCH$_3$, and $R_1$ and $R_2$ are independently F, Cl, Br, or —CF$_3$.

In another embodiment is a compound of Formula (I) wherein m is 0, n is 2, $R_3$ is F, Cl, Br, —CF$_3$, —CH$_3$, —OCF$_3$, or —OCH$_3$, and each $R_1$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (I) wherein m is 0, n is 2, R₃ is F, Cl, Br, —CF₃, —CH₃, —OCF₃, or —OCH₃, and each R₁ is independently F, Cl, Br, —CF₃, —CH₃, —OCF₃, or —OCH₃. In another embodiment is a compound of Formula (I) wherein m is 0, n is 2, R₃ is F, Cl, Br, —CF₃, —CH₃, or —OCH₃, and each R₁ is independently F, Cl, Br, or —CF₃.

In some embodiments is a compound having the structure of Formula (II):

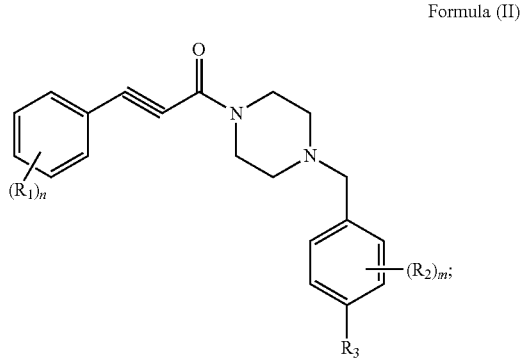

Formula (II)

wherein:
each R₁ is independently F, Cl, Br, —CN, —NR₄R₅, —NO₂, —CF₃, —OCF₃, —OH, —C₁-C₆alkyl, or —OC₁-C₆alkyl;
each R₂ is independently F, Cl, Br, —CN, —CF₃, —OCF₃, —OH, —C₁-C₆alkyl, or —OC₁-C₆alkyl; R₃ is F, Cl, Br, —CN, —CF₃, —OCF₃, —OH, —C₁-C₆alkyl, —OC₁-C₆alkyl, —C(=O)C₁-C₆alkyl, CO₂H, B(OH)₂, or PO₃H;
each R₄ is independently H or C₁-C₆alkyl;
each R₅ is independently H or C₁-C₆alkyl;
m is an integer selected from 0-2; and
n is an integer selected from 1-3;
or a pharmaceutically acceptable salt, pharmaceutically acceptable solvate, or pharmaceutically acceptable prodrug thereof.

In some embodiments is a compound of Formula (II) wherein R₃ is F, Cl, Br, —CF₃, —CH₃, —OCF₃, or —OCH₃. In some embodiments is a compound of Formula (II) wherein R₃ is F. In some embodiments is a compound of Formula (II) wherein R₃ is Cl. In some embodiments is a compound of Formula (II) wherein R₃ is Br. In some embodiments is a compound of Formula (II) wherein R₃ is —CF₃. In some embodiments is a compound of Formula (II) wherein R₃ is —CH₃. In some embodiments is a compound of Formula (II) wherein R₃ is —OCF₃. In some embodiments is a compound of Formula (II) wherein R₃ is —OCH₃.

In some embodiments is a compound of Formula (II) wherein each R₁ is independently F, Cl, Br, —CF₃, —CH₃, —OCF₃, or —OCH₃. In some embodiments is a compound of Formula (II) wherein R₁ is F. In some embodiments is a compound of Formula (II) wherein R₁ is Cl. In some embodiments is a compound of Formula (II) wherein R₁ is Br. In some embodiments is a compound of Formula (II) wherein R₁ is —CF₃. In some embodiments is a compound of Formula (II) wherein R₁ is —CH₃. In some embodiments is a compound of Formula (II) wherein R₁ is —OCF₃. In some embodiments is a compound of Formula (II) wherein R₁ is —OCH₃.

In some embodiments is a compound of Formula (II) wherein each R₂ is independently F, Cl, Br, —CF₃, —CH₃, or —OCH₃. In some embodiments is a compound of Formula (II) wherein R₂ is F. In some embodiments is a compound of Formula (II) wherein R₂ is Cl. In some embodiments is a compound of Formula (II) wherein R₂ is Br. In some embodiments is a compound of Formula (II) wherein R₁ is —CF₃. In some embodiments is a compound of Formula (II) wherein R₂ is —CH₃. In some embodiments is a compound of Formula (II) wherein R₂ is —OCF₃. In some embodiments is a compound of Formula (II) wherein R₁ is —OCH₃.

In another embodiment is a compound of Formula (II) wherein n is 1 and m is 0. In another embodiment is a compound of Formula (II) wherein n is 2 and m is 0. In another embodiment is a compound of Formula (II) wherein n is 1 and m is 1. In another embodiment is a compound of Formula (II) wherein n is 2 and m is 1. In another embodiment is a compound of Formula (II) wherein n is 1 and m is 2. In another embodiment is a compound of Formula (II) wherein n is 2 and m is 2. In another embodiment is a compound of Formula (II) wherein n is 3 and m is 1. In another embodiment is a compound of Formula (II) wherein n is 3 and m is 2.

In another embodiment is a compound of Formula (II) wherein n is 1, m is 0, R₃ is F, Cl, Br, —CF₃, —CH₃, —OCF₃, or —OCH₃, and R₁ is F, Cl, Br, —CN, —NR₄R₅, —NO₂, —CF₃, —OCF₃, —OH, —C₁-C₆alkyl, or —OC₁-C₆alkyl. In another embodiment is a compound of Formula (II) wherein n is 1, m is 0, R₃ is F, Cl, Br, —CF₃, —CH₃, —OCF₃, or —OCH₃, and R₁ is F, Cl, Br, —CF₃, —CH₃, —OCF₃, or —OCH₃. In another embodiment is a compound of Formula (II) wherein n is 1, m is 0, R₃ is F, Cl, Br, —CF₃, —CH₃, or —OCH₃, and R₁ is F, Cl, Br, or —CF₃.

In another embodiment is a compound of Formula (II) wherein n is 2, m is 0, R₃ is F, Cl, Br, —CF₃, —CH₃, —OCF₃, or —OCH₃, and each R₁ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (II) wherein n is 2, m is 0, R₃ is F, Cl, Br, —CF₃, —CH₃, —OCF₃, or —OCH₃, and each R₁ is independently F, Cl, Br, —CF₃, —CH₃, —OCF₃, or —OCH₃. In another embodiment is a compound of Formula (II) wherein n is 2, m is 0, R₃ is F, Cl, Br, —CF₃, —CH₃, or —OCH₃, and each R₁ is independently F, Cl, Br, or —CF₃.

In another embodiment is a compound of Formula (II) wherein m is 1, n is 1, R₃ is F, Cl, Br, —CF₃, —CH₃, —OCF₃, or —OCH₃, and R₁ and R₂ are independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (II) wherein m is 1, n is 1, R₃ is F, Cl, Br, —CF₃, —CH₃, —OCF₃, or —OCH₃, and R₁ and R₂ are independently F, Cl, Br, —CF₃, —CH₃, —OCF₃, or —OCH₃. In another embodiment is a compound of Formula (II) wherein m is 1, n is 1, R₃ is F, Cl, Br, —CF₃, —CH₃, or —OCH₃, and R₁ and R₂ are independently F, Cl, Br, or —CF₃.

In another embodiment is a compound of Formula (II) wherein m is 0, n is 2, R₃ is F, Cl, Br, —CF₃, —CH₃, —OCF₃, or —OCH₃, and each R₁ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (II) wherein m is 0, n is 2, R₃ is F, Cl, Br, —CF₃, —CH₃, —OCF₃, or —OCH₃, and each R₁ is independently F, Cl, Br, —CF₃, —CH₃, —OCF₃, or —OCH₃. In another embodiment is a compound of Formula (II) wherein m is 0, n is 2, $R_3$ is F, Cl, Br, —$CF_3$, —$CH_3$, or —$OCH_3$, and each $R_1$ is independently F, Cl, Br, or —$CF_3$.

In some embodiments is a compound having the structure of Formula (III):

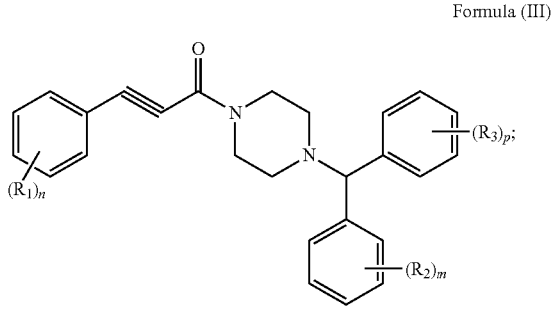

Formula (III)

wherein:
each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl; or two $R_1$ on adjacent carbon atoms are combined with the adjacent carbon atoms to form a —$OCH_2O$— ring;

each $R_2$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl;

each $R_3$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl;

each $R_4$ is independently H or $C_1$-$C_6$alkyl;
each $R_5$ is independently H or $C_1$-$C_6$alkyl;
m is an integer selected from 0-3;
n is an integer selected from 0-3; and
p is an integer selected from 0-3;
or a pharmaceutically acceptable salt, pharmaceutically acceptable solvate, or pharmaceutically acceptable prodrug thereof.

In some embodiments is a compound of Formula (III) wherein each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, aryl, or heteroaryl. In some embodiments is a compound of Formula (III) wherein each $R_1$ is independently F, Cl, Br, —$CF_3$, —$CH_3$, —$OCF_3$, or —$OCH_3$. In some embodiments is a compound of Formula (III) wherein each $R_1$ is F. In some embodiments is a compound of Formula (III) wherein each $R_1$ is Cl. In some embodiments is a compound of Formula (III) wherein each $R_1$ is Br. In some embodiments is a compound of Formula (III) wherein each $R_1$ is —$CF_3$. In some embodiments is a compound of Formula (III) wherein each $R_1$ is —$CH_3$. In some embodiments is a compound of Formula (III) wherein each $R_1$ is —$OCF_3$. In some embodiments is a compound of Formula (III) wherein each $R_1$ is —$OCH_3$.

In some embodiments is a compound of Formula (III) wherein each $R_2$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, aryl, or heteroaryl. In some embodiments is a compound of Formula (III) wherein each $R_2$ is independently F, Cl, Br, —$CF_3$, —$CH_3$, —$OCF_3$, or —$OCH_3$. In some embodiments is a compound of Formula (III) wherein each $R_2$ is F. In some embodiments is a compound of Formula (III) wherein each $R_2$ is Cl. In some embodiments is a compound of Formula (III) wherein each $R_2$ is Br. In some embodiments is a compound of Formula (III) wherein each $R_2$ is —$CF_3$. In some embodiments is a compound of Formula (III) wherein each $R_2$ is —$CH_3$. In some embodiments is a compound of Formula (III) wherein each $R_2$ is —$OCF_3$. In some embodiments is a compound of Formula (III) wherein each $R_2$ is —$OCH_3$.

In some embodiments is a compound of Formula (III) wherein each $R_3$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, aryl, or heteroaryl. In some embodiments is a compound of Formula (III) wherein each $R_3$ is independently F, Cl, Br, —$CF_3$, —$CH_3$, —$OCF_3$, or —$OCH_3$. In some embodiments is a compound of Formula (III) wherein each $R_3$ is F. In some embodiments is a compound of Formula (III) wherein each $R_3$ is Cl. In some embodiments is a compound of Formula (III) wherein each $R_3$ is Br. In some embodiments is a compound of Formula (III) wherein each $R_3$ is —$CF_3$. In some embodiments is a compound of Formula (III) wherein each $R_3$ is —$CH_3$. In some embodiments is a compound of Formula (III) wherein each $R_3$ is —$OCF_3$. In some embodiments is a compound of Formula (III) wherein each $R_3$ is —$OCH_3$.

In another embodiment is a compound of Formula (III) wherein m is 0, n is 0, and p is 0.

In another embodiment is a compound of Formula (III) wherein m is 0, n is 1, and p is 0. In another embodiment is a compound of Formula (III) wherein m is 0, n is 2, and p is 0. In another embodiment is a compound of Formula (III) wherein m is 1, n is 1, and p is 1. In another embodiment is a compound of Formula (III) wherein m is 1, n is 2, and p is 1.

In another embodiment is a compound of Formula (III) wherein m is 0, n is 1, p is 0, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (III) wherein m is 0, n is 1, p is 0, and $R_1$ is F, Cl, Br, —$CF_3$, —$CH_3$, —$OCF_3$, or —$OCH_3$. In another embodiment is a compound of Formula (III) wherein m is 0, n is 1, p is 0, and $R_1$ is F, Cl, Br, or —$CF_3$.

In another embodiment is a compound of Formula (III) wherein m is 0, n is 2, p is 0, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (III) wherein m is 0, n is 2, p is 0, and each $R_1$ is independently F, Cl, Br, —$CF_3$, —$CH_3$, —$OCF_3$, or —$OCH_3$. In another embodiment is a compound of Formula (III) wherein m is 0, n is 2, p is 0, and each $R_1$ is independently F, Cl, Br, or —$CF_3$. In another embodiment is a compound of Formula (III) wherein m is 0, n is 2, p is 0, and two $R_1$ on adjacent carbon atoms are combined with the adjacent carbon atoms to form a —$OCH_2O$— ring.

In another embodiment is a compound of Formula (III) wherein m is 1, n is 2, p is 1, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ and $R_3$ are independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (III) wherein m is 1, n is 2, p is 1, each $R_1$ is independently F, Cl, Br, —$CF_3$, —$CH_3$, —$OCF_3$, or —$OCH_3$, and $R_2$ and $R_3$ are independently F, Cl, Br, —$CF_3$, —$CH_3$, —$OCF_3$, or —$OCH_3$. In another embodiment is a compound of Formula (III) wherein m is 1, n is 2, p is 1, each $R_1$ is independently F, Cl, Br, —$CF_3$, —$CH_3$, or —$OCH_3$, and $R_2$ and $R_3$ are independently F, Cl, Br, or —$CF_3$.

In some embodiments is a compound having the structure of Formula (IV):

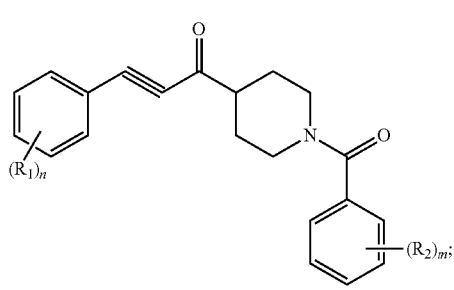

Formula (IV)

wherein:
  each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl; or two $R_1$ on adjacent carbon atoms are combined with the adjacent carbon atoms to form a —$OCH_2O$— ring;
  each $R_2$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, —C(=O)$C_1$-$C_6$alkyl, $CO_2H$, B(OH)$_2$, $PO_3H$, $C_3$-$C_8$cycloalkyl, $C_1$-$C_6$heteroalkyl, $C_1$-$C_6$haloalkyl, $C_2$-$C_8$heterocycloalkyl, aryl, or heteroaryl;
  each $R_4$ is independently H or $C_1$-$C_6$alkyl;
  each $R_5$ is independently H or $C_1$-$C_6$alkyl;
  m is an integer selected from 0-3; and
  n is an integer selected from 0-3;
or a pharmaceutically acceptable salt, pharmaceutically acceptable solvate, or pharmaceutically acceptable prodrug thereof.

In some embodiments is a compound of Formula (IV) wherein each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, aryl, or heteroaryl. In some embodiments is a compound of Formula (IV) wherein each $R_1$ is independently F, Cl, Br, —$CF_3$, —$CH_3$, —$OCF_3$, or —$OCH_3$. In some embodiments is a compound of Formula (IV) wherein each $R_1$ is F. In some embodiments is a compound of Formula (IV) wherein each $R_1$ is Cl. In some embodiments is a compound of Formula (IV) wherein each $R_1$ is Br. In some embodiments is a compound of Formula (IV) wherein each $R_1$ is —$CF_3$. In some embodiments is a compound of Formula (IV) wherein each $R_1$ is —$CH_3$. In some embodiments is a compound of Formula (IV) wherein each $R_1$ is —$OCF_3$. In some embodiments is a compound of Formula (IV) wherein each $R_1$ is —$OCH_3$.

In some embodiments is a compound of Formula (IV) wherein each $R_2$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, aryl, or heteroaryl. In some embodiments is a compound of Formula (IV) wherein each $R_2$ is independently F, Cl, Br, —$CF_3$, —$CH_3$, —$OCF_3$, or —$OCH_3$. In some embodiments is a compound of Formula (IV) wherein each $R_2$ is F. In some embodiments is a compound of Formula (IV) wherein each $R_2$ is Cl. In some embodiments is a compound of Formula (IV) wherein each $R_2$ is Br. In some embodiments is a compound of Formula (IV) wherein each $R_2$ is —$CF_3$. In some embodiments is a compound of Formula (IV) wherein each $R_2$ is —$CH_3$. In some embodiments is a compound of Formula (IV) wherein each $R_2$ is —$OCF_3$. In some embodiments is a compound of Formula (IV) wherein each $R_2$ is —$OCH_3$.

In another embodiment is a compound of Formula (IV) wherein m is 0 and n is 0.

In another embodiment is a compound of Formula (IV) wherein m is 0 and n is 1. In another embodiment is a compound of Formula (IV) wherein m is 1 and n is 0. In another embodiment is a compound of Formula (IV) wherein m is 0 and n is 2. In another embodiment is a compound of Formula (IV) wherein m is 2 and n is 0. In another embodiment is a compound of Formula (IV) wherein m is 1 and n is 1. In another embodiment is a compound of Formula (IV) wherein m is 1 and n is 2. In another embodiment is a compound of Formula (IV) wherein m is 2 and n is 2.

In another embodiment is a compound of Formula (IV) wherein m is 0, n is 1, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (IV) wherein m is 0, n is 1, and $R_1$ is F, Cl, Br, —$CF_3$, —$CH_3$, —$OCF_3$, or —$OCH_3$. In another embodiment is a compound of Formula (IV) wherein m is 0, n is 1, and $R_1$ is F, Cl, Br, or —$CF_3$.

In another embodiment is a compound of Formula (IV) wherein m is 0, n is 2, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (IV) wherein m is 0, n is 2, and each $R_1$ is independently F, Cl, Br, —$CF_3$, —$CH_3$, —$OCF_3$, or —$OCH_3$. In another embodiment is a compound of Formula (IV) wherein m is 0, n is 2, and each $R_1$ is independently F, Cl, Br, or —$CF_3$. In another embodiment is a compound of Formula (IV) wherein m is 0, n is 2, and two $R_1$ on adjacent carbon atoms are combined with the adjacent carbon atoms to form a —$OCH_2O$— ring.

In another embodiment is a compound of Formula (IV) wherein m is 1, n is 1, $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (IV) wherein m is 1, n is 1, $R_1$ is F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (IV) wherein m is 1, n is 1, $R_1$ is F, Cl, Br, —$CF_3$, —$CH_3$, or —$OCH_3$, and $R_2$ is independently F, Cl, Br, or —$CF_3$.

In another embodiment is a compound of Formula (IV) wherein m is 1, n is 2, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (IV) wherein m is 1, n is 2, each $R_1$ is independently F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (IV) wherein m is 1, n is 2, each $R_1$ is F, Cl, Br, —$CF_3$, —$CH_3$, or —$OCH_3$, and $R_2$ is independently F, Cl, Br, or —$CF_3$.

In another embodiment is a compound of Formula (IV) wherein m is 2, n is 1, $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (IV) wherein m is 2, n is 1, $R_1$ is F, Cl, Br, —$CF_3$, —CH₃, —OCF₃, or —OCH₃, and each R₂ is independently F, Cl, Br, —CF₃, —CH₃, —OCF₃, or —OCH₃. In another embodiment is a compound of Formula (IV) wherein m is 2, n is 1, R₁ is F, Cl, Br, —CF₃, —CH₃, or —OCH₃, and each R₂ is independently F, Cl, Br, or —CF₃.

In some embodiments is a compound having the structure of Formula (V):

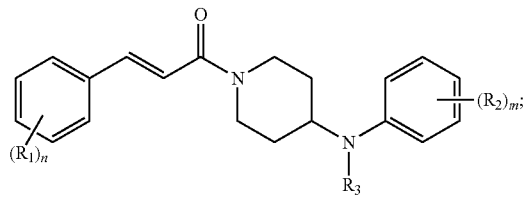

Formula (V)

wherein:
each $R_1$ is independently F, Cl, Br, I, —CN, —NR₄R₅, —NO₂, —OH, —CF₃, —OCF₃, —OC₁-C₆alkyl, C₁-C₆alkyl, C₃-C₈cycloalkyl, C₁-C₆heteroalkyl, C₁-C₆haloalkyl, C₂-C₈heterocycloalkyl, aryl, or heteroaryl; or two $R_1$ on adjacent carbon atoms are combined with the adjacent carbon atoms to form a —OCH₂O— ring;
each $R_2$ is independently F, Cl, Br, I, —CN, —NR₄R₅, —NO₂, —OH, —CF₃, —OCF₃, —OC₁-C₆alkyl, C₁-C₆alkyl, C₃-C₈cycloalkyl, C₁-C₆heteroalkyl, C₁-C₆haloalkyl, —C(=O)C₁-C₆alkyl, CO₂H, B(OH)₂, PO₃H, aryl, or heteroaryl;
$R_3$ is H, C₁-C₆alkyl, or aryl;
each $R_4$ is independently H or C₁-C₆alkyl;
each $R_5$ is independently H or C₁-C₆alkyl;
m is an integer selected from 0-3; and
n is an integer selected from 0-3;
or a pharmaceutically acceptable salt, pharmaceutically acceptable solvate, or pharmaceutically acceptable prodrug thereof.

In some embodiments is a compound of Formula (V) wherein $R_3$ is H. In some embodiments is a compound of Formula (V) wherein $R_3$ is C₁-C₆alkyl. In some embodiments is a compound of Formula (V) wherein $R_3$ is CH₃. In some embodiments is a compound of Formula (V) wherein $R_3$ is aryl. In some embodiments is a compound of Formula (V) wherein $R_3$ is phenyl.

In some embodiments is a compound of Formula (V) wherein each $R_1$ is independently F, Cl, Br, I, —CN, —NR₄R₅, —NO₂, —OH, —CF₃, —OCF₃, —OC₁-C₆alkyl, C₁-C₆alkyl, aryl, or heteroaryl. In some embodiments is a compound of Formula (V) wherein each $R_1$ is independently F, Cl, Br, —CF₃, —CH₃, —OCF₃, or —OCH₃. In some embodiments is a compound of Formula (V) wherein each $R_1$ is F. In some embodiments is a compound of Formula (V) wherein each $R_1$ is Cl. In some embodiments is a compound of Formula (V) wherein each $R_1$ is Br. In some embodiments is a compound of Formula (V) wherein each $R_1$ is —CF₃. In some embodiments is a compound of Formula (V) wherein each $R_1$ is —CH₃. In some embodiments is a compound of Formula (V) wherein each $R_1$ is —OCF₃. In some embodiments is a compound of Formula (V) wherein each $R_1$ is —OCH₃.

In some embodiments is a compound of Formula (V) wherein each $R_2$ is independently F, Cl, Br, I, —CN, —NR₄R₅, —NO₂, —OH, —CF₃, —OCF₃, —OC₁-C₆alkyl, C₁-C₆alkyl, aryl, or heteroaryl. In some embodiments is a compound of Formula (V) wherein each $R_2$ is independently F, Cl, Br, —CF₃, —CH₃, —OCF₃, or —OCH₃. In some embodiments is a compound of Formula (V) wherein each $R_2$ is F. In some embodiments is a compound of Formula (V) wherein each $R_2$ is Cl. In some embodiments is a compound of Formula (V) wherein each $R_2$ is Br. In some embodiments is a compound of Formula (V) wherein each $R_2$ is —CF₃. In some embodiments is a compound of Formula (V) wherein each $R_2$ is —CH₃. In some embodiments is a compound of Formula (V) wherein each $R_2$ is —OCF₃. In some embodiments is a compound of Formula (V) wherein each $R_2$ is —OCH₃.

In another embodiment is a compound of Formula (V) wherein m is 0 and n is 0.

In another embodiment is a compound of Formula (V) wherein m is 0 and n is 1. In another embodiment is a compound of Formula (V) wherein m is 1 and n is 0. In another embodiment is a compound of Formula (V) wherein m is 0 and n is 2. In another embodiment is a compound of Formula (V) wherein m is 2 and n is 0. In another embodiment is a compound of Formula (V) wherein m is 1 and n is 1. In another embodiment is a compound of Formula (V) wherein m is 1 and n is 2. In another embodiment is a compound of Formula (V) wherein m is 2 and n is 2.

In another embodiment is a compound of Formula (V) wherein m is 0, n is 1, $R_3$ is H, and $R_1$ is F, Cl, Br, —CN, —NR₄R₅, —NO₂, —CF₃, —OCF₃, —OH, —C₁-C₆alkyl, or —OC₁-C₆alkyl. In another embodiment is a compound of Formula (V) wherein m is 0, n is 1, $R_3$ is H, and $R_1$ is F, Cl, Br, —CF₃, —CH₃, —OCF₃, or —OCH₃. In another embodiment is a compound of Formula (V) wherein m is 0, n is 1, $R_3$ is H, and $R_1$ is F, Cl, Br, or —CF₃.

In another embodiment is a compound of Formula (V) wherein m is 0, n is 2, $R_3$ is H, and each $R_1$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (V) wherein m is 0, n is 2, $R_3$ is H, and each $R_1$ is independently F, Cl, Br, —CF₃, —CH₃, —OCF₃, or —OCH₃. In another embodiment is a compound of Formula (V) wherein m is 0, n is 2, $R_3$ is H, and each $R_1$ is independently F, Cl, Br, or —CF₃. In another embodiment is a compound of Formula (V) wherein m is 0, n is 2, $R_3$ is H, and two $R_1$ on adjacent carbon atoms are combined with the adjacent carbon atoms to form a —OCH₂O— ring.

In another embodiment is a compound of Formula (V) wherein m is 1, n is 1, $R_3$ is H, $R_1$ is F, Cl, Br, —CN, —NR₄R₅, —NO₂, —CF₃, —OCF₃, —OH, —C₁-C₆alkyl, or —OC₁-C₆alkyl, and $R_2$ is F, Cl, Br, —CN, —NR₄R₅, —NO₂, —CF₃, —OCF₃, —OH, —C₁-C₆alkyl, or —OC₁-C₆alkyl. In another embodiment is a compound of Formula (V) wherein m is 1, n is 1, $R_3$ is H, $R_1$ is F, Cl, Br, —CF₃, —CH₃, —OCF₃, or —OCH₃, and $R_2$ is F, Cl, Br, —CF₃, —CH₃, —OCF₃, or —OCH₃. In another embodiment is a compound of Formula (V) wherein m is 1, n is 1, $R_3$ is H, $R_1$ is F, Cl, Br, —CF₃, —CH₃, or —OCH₃, and $R_2$ is F, Cl, Br, or —CF₃.

In another embodiment is a compound of Formula (V) wherein m is 1, n is 2, $R_3$ is H, each $R_1$ is independently F, Cl, Br, —CN, —NR₄R₅, —NO₂, —CF₃, —OCF₃, —OH, —C₁-C₆alkyl, or —OC₁-C₆alkyl, and $R_2$ is F, Cl, Br, —CN, —NR₄R₅, —NO₂, —CF₃, —OCF₃, —OH, —C₁-C₆alkyl, or —OC₁-C₆alkyl. In another embodiment is a compound of Formula (V) wherein m is 1, n is 2, $R_3$ is H, each $R_1$ is independently F, Cl, Br, —CF₃, —CH₃, —OCF₃, or —OCH₃, and $R_2$ is F, Cl, Br, —CF₃, —CH₃, —OCF₃, or —OCH₃. In another embodiment is a compound of Formula (V) wherein m is 1, n is 2, $R_3$ is H, each $R_1$ is independently F, Cl, Br, —$CF_3$, —$CH_3$, or —$OCH_3$, and $R_2$ is F, Cl, Br, or —$CF_3$.

In another embodiment is a compound of Formula (V) wherein m is 2, n is 1, $R_3$ is H, $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (V) wherein m is 2, n is 1, $R_3$ is H, $R_1$ is F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (V) wherein m is 2, n is 1, $R_3$ is H, $R_1$ is F, Cl, Br, —$CF_3$, —$CH_3$, or —$OCH_3$, and each $R_2$ is independently F, Cl, Br, or —$CF_3$.

In another embodiment is a compound of Formula (V) wherein m is 0, n is 1, $R_3$ is —$CH_3$, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (V) wherein m is 0, n is 1, $R_3$ is —$CH_3$, and $R_1$ is F, Cl, Br, —$CF_3$, —$CH_3$, —$OCF_3$, or —$OCH_3$. In another embodiment is a compound of Formula (V) wherein m is 0, n is 1, $R_3$ is —$CH_3$, and $R_1$ is F, Cl, Br, or —$CF_3$.

In another embodiment is a compound of Formula (V) wherein m is 0, n is 2, $R_3$ is —$CH_3$, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (V) wherein m is 0, n is 2, $R_3$ is —$CH_3$, and each $R_1$ is independently F, Cl, Br, —$CF_3$, —$CH_3$, —$OCF_3$, or —$OCH_3$. In another embodiment is a compound of Formula (V) wherein m is 0, n is 2, $R_3$ is —$CH_3$, and each $R_1$ is independently F, Cl, Br, or —$CF_3$. In another embodiment is a compound of Formula (V) wherein m is 0, n is 2, $R_3$ is —$CH_3$, and two $R_1$ on adjacent carbon atoms are combined with the adjacent carbon atoms to form a —$OCH_2O$— ring.

In another embodiment is a compound of Formula (V) wherein m is 1, n is 1, $R_3$ is —$CH_3$, $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (V) wherein m is 1, n is 1, $R_3$ is —$CH_3$, $R_1$ is F, Cl, Br, —$CF_3$, —$CH_3$, —$OCF_3$, or —$OCH_3$, and $R_2$ is F, Cl, Br, —$CF_3$, —$CH_3$, —$OCF_3$, or —$OCH_3$. In another embodiment is a compound of Formula (V) wherein m is 1, n is 1, $R_3$ is —$CH_3$, $R_1$ is F, Cl, Br, —$CF_3$, —$CH_3$, or —$OCH_3$, and $R_2$ is F, Cl, Br, or —$CF_3$.

In another embodiment is a compound of Formula (V) wherein m is 1, n is 2, $R_3$ is —$CH_3$, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (V) wherein m is 1, n is 2, $R_3$ is —$CH_3$, each $R_1$ is independently F, Cl, Br, —$CF_3$, —$CH_3$, —$OCF_3$, or —$OCH_3$, and $R_2$ is F, Cl, Br, —$CF_3$, —$CH_3$, —$OCF_3$, or —$OCH_3$. In another embodiment is a compound of Formula (V) wherein m is 1, n is 2, $R_3$ is —$CH_3$, each $R_1$ is independently F, Cl, Br, —$CF_3$, —$CH_3$, or —$OCH_3$, and $R_2$ is F, Cl, Br, or —$CF_3$.

In another embodiment is a compound of Formula (V) wherein m is 2, n is 1, $R_3$ is —$CH_3$, $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (V) wherein m is 2, n is 1, $R_3$ is —$CH_3$, $R_1$ is F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (V) wherein m is 2, n is 1, $R_3$ is —$CH_3$, $R_1$ is F, Cl, Br, —$CF_3$, —$CH_3$, or —$OCH_3$, and each $R_2$ is independently F, Cl, Br, or —$CF_3$.

In some embodiments is a compound having the structure of Formula (VI):

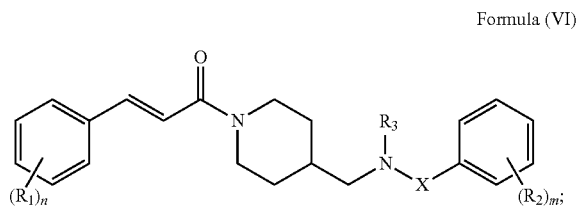

Formula (VI)

wherein:
X is a bond, —$CH_2$—, —C(H)(Ph)-, —C(=O)—, or —S(=O)$_2$—;
each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl; or two $R_1$ on adjacent carbon atoms are combined with the adjacent carbon atoms to form a —$OCH_2O$— ring;
each $R_2$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, $C_1$-$C_6$heteroalkyl, $C_1$-$C_6$haloalkyl, $C_2$-$C_8$heterocycloalkyl, —C(=O)$C_1$-$C_6$alkyl, $CO_2H$, $B(OH)_2$, $PO_3H$, aryl, or heteroaryl;
$R_3$ is H, $C_1$-$C_6$alkyl, or aryl;
each $R_4$ is independently H or $C_1$-$C_6$alkyl;
each $R_5$ is independently H or $C_1$-$C_6$alkyl;
m is an integer selected from 0-3; and
n is an integer selected from 0-3;
or a pharmaceutically acceptable salt, pharmaceutically acceptable solvate, or pharmaceutically acceptable prodrug thereof.

In some embodiments is a compound of Formula (VI) wherein $R_3$ is H. In some embodiments is a compound of Formula (VI) wherein $R_3$ is $C_1$-$C_6$alkyl. In some embodiments is a compound of Formula (VI) wherein $R_3$ is $CH_3$. In some embodiments is a compound of Formula (VI) wherein $R_3$ is aryl. In some embodiments is a compound of Formula (VI) wherein $R_3$ is phenyl.

In some embodiments is a compound of Formula (VI) wherein X is a bond. In another embodiment is a compound of Formula (VI) wherein X is —$CH_2$—. In another embodiment is a compound of Formula (VI) wherein X is —C(H)(Ph)-. In another embodiment is a compound of Formula (VI) wherein X is —C(=O)—. In another embodiment is a compound of Formula (VI) wherein X is —S(=O)$_2$—.

In some embodiments is a compound of Formula (VI) wherein each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, aryl, or heteroaryl. In some embodiments is a compound of Formula (VI) wherein each $R_1$ is independently F, Cl, Br, —$CF_3$, —$CH_3$, —$OCF_3$, or —$OCH_3$. In some embodiments is a compound of Formula (VI) wherein each $R_1$ is F. In some embodiments is a compound of Formula (VI) wherein each $R_1$ is Cl. In some embodiments is a compound of Formula (VI) wherein each $R_1$ is Br. In some embodiments is a compound of Formula (VI) wherein each $R_1$ is —$CF_3$. In some embodiments is a compound of Formula (VI) wherein each $R_1$ is —$CH_3$. In some embodiments is a compound of Formula (VI) wherein each $R_1$ is —$OCF_3$. In some embodiments is a compound of Formula (VI) wherein each $R_1$ is —$OCH_3$.

In some embodiments is a compound of Formula (VI) wherein each $R_2$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, aryl, or heteroaryl. In some embodiments is a compound of Formula (VI) wherein each $R_2$ is independently F, Cl, Br, —$CF_3$, —$CH_3$, —$OCF_3$, or —$OCH_3$. In some embodiments is a compound of Formula (VI) wherein each $R_2$ is F. In some embodiments is a compound of Formula (VI) wherein each $R_2$ is Cl. In some embodiments is a compound of Formula (VI) wherein each $R_2$ is Br. In some embodiments is a compound of Formula (VI) wherein each $R_2$ is —$CF_3$. In some embodiments is a compound of Formula (VI) wherein each $R_2$ is —$CH_3$. In some embodiments is a compound of Formula (VI) wherein each $R_2$ is —$OCF_3$. In some embodiments is a compound of Formula (VI) wherein each $R_2$ is —$OCH_3$.

In another embodiment is a compound of Formula (VI) wherein m is 0 and n is 0.

In another embodiment is a compound of Formula (VI) wherein m is 0 and n is 1. In another embodiment is a compound of Formula (VI) wherein m is 1 and n is 0. In another embodiment is a compound of Formula (VI) wherein m is 0 and n is 2. In another embodiment is a compound of Formula (VI) wherein m is 2 and n is 0. In another embodiment is a compound of Formula (VI) wherein m is 1 and n is 1. In another embodiment is a compound of Formula (VI) wherein m is 1 and n is 2. In another embodiment is a compound of Formula (VI) wherein m is 2 and n is 2.

In another embodiment is a compound of Formula (VI) wherein m is 0, n is 1, X is —$CH_2$—, $R_3$ is H, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VI) wherein m is 0, n is 1, X is —$CH_2$—, $R_3$ is H, and $R_1$ is F, Cl, Br, —$CF_3$, —$CH_3$, —$OCF_3$, or —$OCH_3$. In another embodiment is a compound of Formula (VI) wherein m is 0, n is 1, X is —$CH_2$—, $R_3$ is H, and $R_1$ is F, Cl, Br, or —$CF_3$.

In another embodiment is a compound of Formula (VI) wherein m is 0, n is 2, X is —$CH_2$—, $R_3$ is H, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VI) wherein m is 0, n is 2, X is —$CH_2$—, $R_3$ is H, and each $R_1$ is independently F, Cl, Br, —$CF_3$, —$CH_3$, —$OCF_3$, or —$OCH_3$. In another embodiment is a compound of Formula (VI) wherein m is 0, n is 2, X is —$CH_2$—, $R_3$ is H, and each $R_1$ is independently F, Cl, Br, or —$CF_3$. In another embodiment is a compound of Formula (VI) wherein m is 0, n is 2, X is —$CH_2$—, $R_3$ is H, and two $R_1$ on adjacent carbon atoms are combined with the adjacent carbon atoms to form a —$OCH_2O$— ring.

In another embodiment is a compound of Formula (VI) wherein m is 1, n is 1, X is —$CH_2$—, $R_3$ is H, $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VI) wherein m is 1, n is 1, X is —$CH_2$—, $R_3$ is H, $R_1$ is F, Cl, Br, —$CF_3$, —$CH_3$, —$OCF_3$, or —$OCH_3$, and $R_2$ is F, Cl, Br, —$CF_3$, —$CH_3$, —$OCF_3$, or —$OCH_3$. In another embodiment is a compound of Formula (VI) wherein m is 1, n is 1, X is —$CH_2$—, $R_3$ is H, $R_1$ is F, Cl, Br, —$CF_3$, —$CH_3$, —$OCF_3$, or —$OCH_3$, and $R_2$ is F, Cl, Br, or —$CF_3$.

In another embodiment is a compound of Formula (VI) wherein m is 1, n is 2, X is —$CH_2$—, $R_3$ is H, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VI) wherein m is 1, n is 2, X is —$CH_2$—, $R_3$ is H, each $R_1$ is independently F, Cl, Br, —$CF_3$, —$CH_3$, —$OCF_3$, or —$OCH_3$, and $R_2$ is F, Cl, Br, —$CF_3$, —$CH_3$, —$OCF_3$, or —$OCH_3$. In another embodiment is a compound of Formula (VI) wherein m is 1, n is 2, X is —$CH_2$—, $R_3$ is H, each $R_1$ is independently F, Cl, Br, —$CF_3$, —$CH_3$, or —$OCH_3$, and $R_2$ is F, Cl, Br, or —$CF_3$.

In another embodiment is a compound of Formula (VI) wherein m is 2, n is 1, X is —$CH_2$—, $R_3$ is H, $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VI) wherein m is 2, n is 1, X is —$CH_2$—, $R_3$ is H, $R_1$ is F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (VI) wherein m is 2, n is 1, X is —$CH_2$—, $R_3$ is H, $R_1$ is F, Cl, Br, —$CF_3$, —$CH_3$, or —$OCH_3$, and each $R_2$ is independently F, Cl, Br, or —$CF_3$.

In another embodiment is a compound of Formula (VI) wherein m is 0, n is 1, X is —C(=O)—, $R_3$ is H, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VI) wherein m is 0, n is 1, X is —C(=O)—, $R_3$ is H, and $R_1$ is F, Cl, Br, —$CF_3$, —$CH_3$, —$OCF_3$, or —$OCH_3$. In another embodiment is a compound of Formula (VI) wherein m is 0, n is 1, X is —C(=O)—, $R_3$ is H, and $R_1$ is F, Cl, Br, or —$CF_3$.

In another embodiment is a compound of Formula (VI) wherein m is 0, n is 2, X is —C(=O)—, $R_3$ is H, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VI) wherein m is 0, n is 2, X is —C(=O)—, $R_3$ is H, and each $R_1$ is independently F, Cl, Br, —$CF_3$, —$CH_3$, —$OCF_3$, or —$OCH_3$. In another embodiment is a compound of Formula (VI) wherein m is 0, n is 2, X is —C(=O)—, $R_3$ is H, and each $R_1$ is independently F, Cl, Br, or —$CF_3$. In another embodiment is a compound of Formula (VI) wherein m is 0, n is 2, X is —C(=O)—, $R_3$ is H, and two $R_1$ on adjacent carbon atoms are combined with the adjacent carbon atoms to form a —$OCH_2O$— ring.

In another embodiment is a compound of Formula (VI) wherein m is 1, n is 1, X is —C(=O)—, $R_3$ is H, $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VI) wherein m is 1, n is 1, X is —C(=O)—, $R_3$ is H, $R_1$ is F, Cl, Br, —$CF_3$, —$CH_3$, —$OCF_3$, or —$OCH_3$, and $R_2$ is F, Cl, Br, —$CF_3$, —$CH_3$, —$OCF_3$, or —$OCH_3$. In another embodiment is a compound of Formula (VI) wherein m is 1, n is 1, X is —C(=O)—, $R_3$ is H, $R_1$ is F, Cl, Br, —$CF_3$, —$CH_3$, or —$OCH_3$, and $R_2$ is F, Cl, Br, or —$CF_3$.

In another embodiment is a compound of Formula (VI) wherein m is 1, n is 2, X is —C(=O)—, $R_3$ is H, each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 1, n is 2, X is —C(=O)—, $R_3$ is H, each $R_1$ is independently F, Cl, Br, —CF$_3$, —CH$_3$, —OCF$_3$, or —OCH$_3$, and $R_2$ is F, Cl, Br, —CF$_3$, —CH$_3$, —OCF$_3$, or —OCH$_3$. In another embodiment is a compound of Formula (VI) wherein m is 1, n is 2, X is —C(=O)—, $R_3$ is H, each $R_1$ is independently F, Cl, Br, —CF$_3$, —CH$_3$, or —OCH$_3$, and $R_2$ is F, Cl, Br, or —CF$_3$.

In another embodiment is a compound of Formula (VI) wherein m is 2, n is 1, X is —C(=O)—, $R_3$ is H, $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 2, n is 1, X is —C(=O)—, $R_3$ is H, $R_1$ is F, Cl, Br, —CF$_3$, —CH$_3$, —OCF$_3$, or —OCH$_3$, and each $R_2$ is independently F, Cl, Br, —CF$_3$, —CH$_3$, —OCF$_3$, or —OCH$_3$. In another embodiment is a compound of Formula (VI) wherein m is 2, n is 1, X is —C(=O)—, $R_3$ is H, $R_1$ is F, Cl, Br, —CF$_3$, —CH$_3$, or —OCH$_3$, and each $R_2$ is independently F, Cl, Br, or —CF$_3$.

In another embodiment is a compound of Formula (VI) wherein m is 0, n is 1, X is —CH$_2$—, $R_3$ is —CH$_3$, and $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 0, n is 1, X is —CH$_2$—, $R_3$ is —CH$_3$, and $R_1$ is F, Cl, Br, —CF$_3$, —CH$_3$, —OCF$_3$, or —OCH$_3$. In another embodiment is a compound of Formula (VI) wherein m is 0, n is 1, X is —CH$_2$—, $R_3$ is —CH$_3$, and $R_1$ is F, Cl, Br, or —CF$_3$.

In another embodiment is a compound of Formula (VI) wherein m is 0, n is 2, X is —CH$_2$—, $R_3$ is —CH$_3$, and each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 0, n is 2, X is —CH$_2$—, $R_3$ is —CH$_3$, and each $R_1$ is independently F, Cl, Br, —CF$_3$, —CH$_3$, —OCF$_3$, or —OCH$_3$. In another embodiment is a compound of Formula (VI) wherein m is 0, n is 2, X is —CH$_2$—, $R_3$ is —CH$_3$, and each $R_1$ is independently F, Cl, Br, or —CF$_3$. In another embodiment is a compound of Formula (VI) wherein m is 0, n is 2, X is —CH$_2$—, $R_3$ is —CH$_3$, and two $R_1$ on adjacent carbon atoms are combined with the adjacent carbon atoms to form a —OCH$_2$O— ring.

In another embodiment is a compound of Formula (VI) wherein m is 1, n is 1, X is —CH$_2$—, $R_3$ is —CH$_3$, $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 1, n is 1, X is —CH$_2$—, $R_3$ is —CH$_3$, $R_1$ is F, Cl, Br, —CF$_3$, —CH$_3$, —OCF$_3$, or —OCH$_3$, and $R_2$ is F, Cl, Br, —CF$_3$, —CH$_3$, —OCF$_3$, or —OCH$_3$. In another embodiment is a compound of Formula (VI) wherein m is 1, n is 1, X is —CH$_2$—, $R_3$ is —CH$_3$, $R_1$ is F, Cl, Br, —CF$_3$, —CH$_3$, or —OCH$_3$, and $R_2$ is F, Cl, Br, or —CF$_3$.

In another embodiment is a compound of Formula (VI) wherein m is 1, n is 2, X is —CH$_2$—, $R_3$ is —CH$_3$, each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 1, n is 2, X is —CH$_2$—, $R_3$ is —CH$_3$, each $R_1$ is independently F, Cl, Br, —CF$_3$, —CH$_3$, —OCF$_3$, or —OCH$_3$, and $R_2$ is F, Cl, Br, —CF$_3$, —CH$_3$, —OCF$_3$, or —OCH$_3$. In another embodiment is a compound of Formula (VI) wherein m is 1, n is 2, X is —CH$_2$—, $R_3$ is —CH$_3$, each $R_1$ is independently F, Cl, Br, —CF$_3$, —CH$_3$, or —OCH$_3$, and $R_2$ is F, Cl, Br, or —CF$_3$.

In another embodiment is a compound of Formula (VI) wherein m is 2, n is 1, X is —CH$_2$—, $R_3$ is —CH$_3$, $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 2, n is 1, X is —CH$_2$—, $R_3$ is —CH$_3$, $R_1$ is F, Cl, Br, —CF$_3$, —CH$_3$, —OCF$_3$, or —OCH$_3$, and each $R_2$ is independently F, Cl, Br, —CF$_3$, —CH$_3$, —OCF$_3$, or —OCH$_3$. In another embodiment is a compound of Formula (VI) wherein m is 2, n is 1, X is —CH$_2$—, $R_3$ is —CH$_3$, $R_1$ is F, Cl, Br, —CF$_3$, —CH$_3$, or —OCH$_3$, and each $R_2$ is independently F, Cl, Br, or —CF$_3$.

In another embodiment is a compound of Formula (VI) wherein m is 0, n is 1, X is —C(=O)—, $R_3$ is —CH$_3$, and $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 0, n is 1, X is —C(=O)—, $R_3$ is —CH$_3$, and $R_1$ is F, Cl, Br, —CF$_3$, —CH$_3$, —OCF$_3$, or —OCH$_3$. In another embodiment is a compound of Formula (VI) wherein m is 0, n is 1, X is —C(=O)—, $R_3$ is —CH$_3$, and $R_1$ is F, Cl, Br, or —CF$_3$.

In another embodiment is a compound of Formula (VI) wherein m is 0, n is 2, X is —C(=O)—, $R_3$ is —CH$_3$, and each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 0, n is 2, X is —C(=O)—, $R_3$ is —CH$_3$, and each $R_1$ is independently F, Cl, Br, —CF$_3$, —CH$_3$, —OCF$_3$, or —OCH$_3$. In another embodiment is a compound of Formula (VI) wherein m is 0, n is 2, X is —C(=O)—, $R_3$ is —CH$_3$, and each $R_1$ is independently F, Cl, Br, or —CF$_3$. In another embodiment is a compound of Formula (VI) wherein m is 0, n is 2, X is —C(=O)—, $R_3$ is —CH$_3$, and two $R_1$ on adjacent carbon atoms are combined with the adjacent carbon atoms to form a —OCH$_2$O— ring.

In another embodiment is a compound of Formula (VI) wherein m is 1, n is 1, X is —C(=O)—, $R_3$ is —CH$_3$, $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 1, n is 1, X is —C(=O)—, $R_3$ is —CH$_3$, $R_1$ is F, Cl, Br, —CF$_3$, —CH$_3$, —OCF$_3$, or —OCH$_3$, and $R_2$ is F, Cl, Br, —CF$_3$, —CH$_3$, —OCF$_3$, or —OCH$_3$. In another embodiment is a compound of Formula (VI) wherein m is 1, n is 1, X is —C(=O)—, $R_3$ is —CH$_3$, $R_1$ is F, Cl, Br, —CF$_3$, —CH$_3$, or —OCH$_3$, and $R_2$ is F, Cl, Br, or —CF$_3$.

In another embodiment is a compound of Formula (VI) wherein m is 1, n is 2, X is —C(=O)—, $R_3$ is —CH$_3$, each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI)

wherein m is 1, n is 2, X is —C(═O)—, $R_3$ is —CH$_3$, each $R_1$ is independently F, Cl, Br, —CF$_3$, —CH$_3$, —OCF$_3$, or —OCH$_3$, and $R_2$ is F, Cl, Br, —CF$_3$, —CH$_3$, —OCF$_3$, or —OCH$_3$. In another embodiment is a compound of Formula (VI) wherein m is 1, n is 2, X is —C(═O)—, $R_3$ is —CH$_3$, each $R_1$ is independently F, Cl, Br, —CF$_3$, —CH$_3$, or —OCH$_3$, and $R_2$ is F, Cl, Br, or —CF$_3$.

In another embodiment is a compound of Formula (VI) wherein m is 2, n is 1, X is —C(═O)—, $R_3$ is —CH$_3$, $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VI) wherein m is 2, n is 1, X is —C(═O)—, $R_3$ is —CH$_3$, $R_1$ is F, Cl, Br, —CF$_3$, —CH$_3$, —OCF$_3$, or —OCH$_3$, and each $R_2$ is independently F, Cl, Br, —CF$_3$, —CH$_3$, —OCF$_3$, or —OCH$_3$. In another embodiment is a compound of Formula (VI) wherein m is 2, n is 1, X is —C(═O)—, $R_3$ is —CH$_3$, $R_1$ is F, Cl, Br, —CF$_3$, —CH$_3$, or —OCH$_3$, and each $R_2$ is independently F, Cl, Br, or —CF$_3$.

In some embodiments is a compound having the structure of Formula (VII):

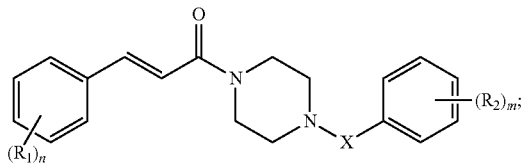

Formula (VII)

wherein:
X is a bond, —CH$_2$—, —C(H)(Ph)-, or —S(═O)$_2$—;
each $R_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl; or two $R_1$ on adjacent carbon atoms are combined with the adjacent carbon atoms to form a —OCH$_2$O— ring;
each $R_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, —C(═O)C$_1$-C$_6$alkyl, CO$_2$H, B(OH)$_2$, PO$_3$H, C$_3$-C$_8$cycloalkyl, C$_1$-C$_6$heteroalkyl, C$_1$-C$_6$haloalkyl, C$_2$-C$_8$heterocycloalkyl, aryl, or heteroaryl;
each $R_4$ is independently H or C$_1$-C$_6$alkyl;
each $R_5$ is independently H or C$_1$-C$_6$alkyl;
m is an integer selected from 0-3; and
n is an integer selected from 0-3;
or a pharmaceutically acceptable salt, pharmaceutically acceptable solvate, or pharmaceutically acceptable prodrug thereof.

In some embodiments is a compound of Formula (VII) wherein X is a bond. In another embodiment is a compound of Formula (VII) wherein X is —CH$_2$—. In another embodiment is a compound of Formula (VII) wherein X is —C(H)(Ph)-. In another embodiment is a compound of Formula (VII) wherein X is —S(═O)$_2$—.

In some embodiments is a compound of Formula (VII) wherein each $R_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, aryl, or heteroaryl. In some embodiments is a compound of Formula (VII) wherein each $R_1$ is independently F, Cl, Br, —CF$_3$, —CH$_3$, —OCF$_3$, or —OCH$_3$. In some embodiments is a compound of Formula (VII) wherein each $R_1$ is F. In some embodiments is a compound of Formula (VII) wherein each $R_1$ is Cl. In some embodiments is a compound of Formula (VII) wherein each $R_1$ is Br. In some embodiments is a compound of Formula (VII) wherein each $R_1$ is —CF$_3$. In some embodiments is a compound of Formula (VII) wherein each $R_1$ is —CH$_3$. In some embodiments is a compound of Formula (VII) wherein each $R_1$ is —OCF$_3$. In some embodiments is a compound of Formula (VII) wherein each $R_1$ is —OCH$_3$.

In some embodiments is a compound of Formula (VII) wherein each $R_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, aryl, or heteroaryl. In some embodiments is a compound of Formula (VII) wherein each $R_2$ is independently F, Cl, Br, —CF$_3$, —CH$_3$, —OCF$_3$, or —OCH$_3$. In some embodiments is a compound of Formula (VII) wherein each $R_2$ is F. In some embodiments is a compound of Formula (VII) wherein each $R_2$ is Cl. In some embodiments is a compound of Formula (VII) wherein each $R_2$ is Br. In some embodiments is a compound of Formula (VII) wherein each $R_2$ is —CF$_3$. In some embodiments is a compound of Formula (VII) wherein each $R_2$ is —CH$_3$. In some embodiments is a compound of Formula (VII) wherein each $R_2$ is —OCF$_3$. In some embodiments is a compound of Formula (VII) wherein each $R_2$ is —OCH$_3$.

In another embodiment is a compound of Formula (VII) wherein m is 0 and n is 0.

In another embodiment is a compound of Formula (VII) wherein m is 0 and n is 1. In another embodiment is a compound of Formula (VII) wherein m is 1 and n is 0. In another embodiment is a compound of Formula (VII) wherein m is 0 and n is 2. In another embodiment is a compound of Formula (VII) wherein m is 2 and n is 0. In another embodiment is a compound of Formula (VII) wherein m is 1 and n is 1. In another embodiment is a compound of Formula (VII) wherein m is 1 and n is 2. In another embodiment is a compound of Formula (VII) wherein m is 2 and n is 2.

In another embodiment is a compound of Formula (VII) wherein m is 0, n is 1, X is a bond, and $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VII) wherein m is 0, n is 1, X is a bond, and $R_1$ is F, Cl, Br, —CF$_3$, —CH$_3$, —OCF$_3$, or —OCH$_3$. In another embodiment is a compound of Formula (VII) wherein m is 0, n is 1, X is a bond, and $R_1$ is F, Cl, Br, or —CF$_3$.

In another embodiment is a compound of Formula (VII) wherein m is 0, n is 2, X is a bond, and each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VII) wherein m is 0, n is 2, X is a bond, and each $R_1$ is independently F, Cl, Br, —CF$_3$, —CH$_3$, —OCF$_3$, or —OCH$_3$. In another embodiment is a compound of Formula (VII) wherein m is 0, n is 2, X is a bond, and each $R_1$ is independently F, Cl, Br, or —CF$_3$. In another embodiment is a compound of Formula (VII) wherein m is 0, n is 2, X is a bond, and two $R_1$ on adjacent carbon atoms are combined with the adjacent carbon atoms to form a —OCH$_2$O— ring.

In another embodiment is a compound of Formula (VII) wherein m is 1, n is 1, X is a bond, $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VII) wherein m is 1, n is 1, X is a bond, $R_1$ is F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VII) wherein m is 1, n is 1, X is a bond, $R_1$ is F, Cl, Br, —$CF_3$, —$CH_3$, or —$OCH_3$, and $R_2$ is independently F, Cl, Br, or —$CF_3$.

In another embodiment is a compound of Formula (VII) wherein m is 1, n is 2, X is a bond, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 1, n is 2, X is a bond, each $R_1$ is independently F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VII) wherein m is 1, n is 2, X is a bond, each $R_1$ is independently F, Cl, Br, —$CF_3$, —$CH_3$, or —$OCH_3$, and $R_2$ is independently F, Cl, Br, or —$CF_3$.

In another embodiment is a compound of Formula (VII) wherein m is 2, n is 1, X is a bond, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 2, n is 1, X is a bond, $R_1$ is independently F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (VII) wherein m is 2, n is 1, X is a bond, $R_1$ is independently F, Cl, Br, —$CF_3$, —$CH_3$, or —$OCH_3$, and each $R_2$ is independently F, Cl, Br, or —$CF_3$.

In another embodiment is a compound of Formula (VII) wherein m is 0, n is 1, X is —$CH_2$—, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 0, n is 1, X is —$CH_2$—, and $R_1$ is F, Cl, Br, —$CF_3$, —$CH_3$, —$OCF_3$, or —$OCH_3$. In another embodiment is a compound of Formula (VII) wherein m is 0, n is 1, X is —$CH_2$—, and $R_1$ is F, Cl, Br, or —$CF_3$.

In another embodiment is a compound of Formula (VII) wherein m is 0, n is 2, X is —$CH_2$—, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 0, n is 2, X is —$CH_2$—, and each $R_1$ is independently F, Cl, Br, —$CF_3$, —$CH_3$, —$OCF_3$, or —$OCH_3$. In another embodiment is a compound of Formula (VII) wherein m is 0, n is 2, X is —$CH_2$—, and each $R_1$ is independently F, Cl, Br, or —$CF_3$. In another embodiment is a compound of Formula (VII) wherein m is 0, n is 2, X is —$CH_2$—, and two $R_1$ on adjacent carbon atoms are combined with the adjacent carbon atoms to form a —$OCH_2O$— ring.

In another embodiment is a compound of Formula (VII) wherein m is 1, n is 1, X is —$CH_2$—, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 1, n is 1, X is —$CH_2$—, $R_1$ is F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VII) wherein m is 1, n is 1, X is —$CH_2$—, $R_1$ is F, Cl, Br, —$CF_3$, —$CH_3$, or —$OCH_3$, and $R_2$ is independently F, Cl, Br, or —$CF_3$.

In another embodiment is a compound of Formula (VII) wherein m is 1, n is 2, X is —$CH_2$—, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 1, n is 2, X is —$CH_2$—, each $R_1$ is independently F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VII) wherein m is 1, n is 2, X is —$CH_2$—, each $R_1$ is independently F, Cl, Br, —$CF_3$, —$CH_3$, or —$OCH_3$, and $R_2$ is independently F, Cl, Br, or —$CF_3$.

In another embodiment is a compound of Formula (VII) wherein m is 2, n is 1, X is —$CH_2$—, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 2, n is 1, X is —$CH_2$—, $R_1$ is independently F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (VII) wherein m is 2, n is 1, X is —$CH_2$—, $R_1$ is independently F, Cl, Br, —$CF_3$, —$CH_3$, or —$OCH_3$, and each $R_2$ is independently F, Cl, Br, or —$CF_3$.

In another embodiment is a compound of Formula (VII) wherein m is 0, n is 1, X is —C(H)(Ph)-, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 0, n is 1, X is —C(H)(Ph)-, and $R_1$ is F, Cl, Br, —$CF_3$, —$CH_3$, —$OCF_3$, or —$OCH_3$. In another embodiment is a compound of Formula (VII) wherein m is 0, n is 1, X is —C(H)(Ph)-, and $R_1$ is F, Cl, Br, or —$CF_3$.

In another embodiment is a compound of Formula (VII) wherein m is 0, n is 2, X is —C(H)(Ph)-, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 0, n is 2, X is —C(H)(Ph)-, and each $R_1$ is independently F, Cl, Br, —$CF_3$, —$CH_3$, —$OCF_3$, or —$OCH_3$. In another embodiment is a compound of Formula (VII) wherein m is 0, n is 2, X is —C(H)(Ph)-, and each $R_1$ is independently F, Cl, Br, or —$CF_3$. In another embodiment is a compound of Formula (VII) wherein m is 0, n is 2, X is —C(H)(Ph)-, and two $R_1$ on adjacent carbon atoms are combined with the adjacent carbon atoms to form a —$OCH_2O$— ring.

In another embodiment is a compound of Formula (VII) wherein m is 1, n is 1, X is —C(H)(Ph)-, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 1, n is 1, X is —C(H)(Ph)-, $R_1$ is F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VII) wherein m is 1, n is 1, X is —C(H)(Ph)-, $R_1$ is F, Cl, Br, —$CF_3$, —$CH_3$, or —$OCH_3$, and $R_2$ is independently F, Cl, Br, or —$CF_3$.

In another embodiment is a compound of Formula (VII) wherein m is 1, n is 2, X is —C(H)(Ph)-, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 1, n is 2, X is —C(H)(Ph)-, each $R_1$ is independently F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VII) wherein m is 1, n is 2, X is —C(H)(Ph)-, each $R_1$ is independently F, Cl, Br, —$CF_3$, —$CH_3$, or —$OCH_3$, and $R_2$ is independently F, Cl, Br, or —$CF_3$.

In another embodiment is a compound of Formula (VII) wherein m is 2, n is 1, X is —C(H)(Ph)-, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 2, n is 1, X is —C(H)(Ph)-, $R_1$ is independently F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (VII) wherein m is 2, n is 1, X is —C(H)(Ph)-, $R_1$ is independently F, Cl, Br, —$CF_3$, —$CH_3$, or —$OCH_3$, and each $R_2$ is independently F, Cl, Br, or —$CF_3$.

In another embodiment is a compound of Formula (VII) wherein m is 0, n is 1, X is —S(=O)$_2$—, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 0, n is 1, X is —S(=O)$_2$—, and $R_1$ is F, Cl, Br, —$CF_3$, —$CH_3$, —$OCF_3$, or —$OCH_3$. In another embodiment is a compound of Formula (VII) wherein m is 0, n is 1, X is —S(=O)$_2$—, and $R_1$ is F, Cl, Br, or —$CF_3$.

In another embodiment is a compound of Formula (VII) wherein m is 0, n is 2, X is —S(=O)$_2$—, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 0, n is 2, X is —S(=O)$_2$—, and each $R_1$ is independently F, Cl, Br, —$CF_3$, —$CH_3$, —$OCF_3$, or —$OCH_3$. In another embodiment is a compound of Formula (VII) wherein m is 0, n is 2, X is —S(=O)$_2$—, and each $R_1$ is independently F, Cl, Br, or —$CF_3$. In another embodiment is a compound of Formula (VII) wherein m is 0, n is 2, X is —S(=O)$_2$—, and two $R_1$ on adjacent carbon atoms are combined with the adjacent carbon atoms to form a —$OCH_2O$— ring.

In another embodiment is a compound of Formula (VII) wherein m is 1, n is 1, X is —S(=O)$_2$—, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 1, n is 1, X is —S(=O)$_2$—, $R_1$ is F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VII) wherein m is 1, n is 1, X is —S(=O)$_2$—, $R_1$ is F, Cl, Br, —$CF_3$, —$CH_3$, or —$OCH_3$, and $R_2$ is independently F, Cl, Br, or —$CF_3$.

In another embodiment is a compound of Formula (VII) wherein m is 1, n is 2, X is —S(=O)$_2$—, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 1, n is 2, X is —S(=O)$_2$—, each $R_1$ is independently F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VII) wherein m is 1, n is 2, X is —S(=O)$_2$—, each $R_1$ is independently F, Cl, Br, —$CF_3$, —$CH_3$, or —$OCH_3$, and $R_2$ is independently F, Cl, Br, or —$CF_3$.

In another embodiment is a compound of Formula (VII) wherein m is 2, n is 1, X is —S(=O)$_2$—, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VII) wherein m is 2, n is 1, X is —S(=O)$_2$—, $R_1$ is independently F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (VII) wherein m is 2, n is 1, X is —S(=O)$_2$—, $R_1$ is independently F, Cl, Br, —$CF_3$, —$CH_3$, or —$OCH_3$, and each $R_2$ is independently F, Cl, Br, or —$CF_3$.

In another embodiment, provided herein is a pharmaceutical composition comprising a compound of Formula (VII), or a pharmaceutically acceptable salt, solvate, prodrug, or N-oxide thereof, and a pharmaceutically acceptable excipient. In another embodiment, the pharmaceutical composition comprising the compound of Formula (VII), or a pharmaceutically acceptable salt, pharmaceutically acceptable solvate, pharmaceutically acceptable prodrug, or N-oxide thereof, is formulated for a route of administration selected from oral administration, parenteral administration, buccal administration, nasal administration, topical administration, or rectal administration.

In another aspect is a method for treating an autoimmune disease or condition comprising administering to an individual in need a therapeutically effective amount of a compound of Formula (VII), or a pharmaceutically acceptable salt, pharmaceutically acceptable solvate, pharmaceutically acceptable prodrug, or N-oxide thereof. In some embodiments, the autoimmune disease is selected from type-1-diabetes, multiple sclerosis, rheumatoid arthritis and lupus. In another embodiment is a method for treating type-1-diabetes comprising administering to an individual in need a therapeutically effective amount of a compound of Formula (VII), or a pharmaceutically acceptable salt, pharmaceutically acceptable solvate, pharmaceutically acceptable prodrug, or N-oxide thereof. In another embodiment is a method for treating multiple sclerosis comprising administering to an individual in need a therapeutically effective amount of a compound of Formula (VII), or a pharmaceutically acceptable salt, pharmaceutically acceptable solvate, pharmaceutically acceptable prodrug, or N-oxide thereof. In another embodiment is a method for treating rheumatoid arthritis comprising administering to an individual in need a therapeutically effective amount of a compound of Formula (VII), or a pharmaceutically acceptable salt, pharmaceutically acceptable solvate, pharmaceutically acceptable prodrug, or N-oxide thereof. In another embodiment is a method for treating lupus comprising administering to an individual in need a therapeutically effective amount of a compound of Formula (VII), or a pharmaceutically acceptable salt, pharmaceutically acceptable solvate, pharmaceutically acceptable prodrug, or N-oxide thereof.

In another aspect is a method for treating a cardiovascular disease or condition comprising administering to an individual in need a therapeutically effective amount of a compound of Formula (VII), or a pharmaceutically acceptable salt, pharmaceutically acceptable solvate, pharmaceutically acceptable prodrug, or N-oxide thereof. In one embodiment, the cardiovascular disease is atherosclerosis.

In another aspect is a method of treating a viral infection comprising administering to an individual in need a therapeutically effective amount of a compound of Formula (VII), or a pharmaceutically acceptable salt, pharmaceutically acceptable solvate, pharmaceutically acceptable prodrug, or N-oxide thereof. In some embodiments, the viral infection is an Epstein-Barr viral infection.

In another aspect is a method of treating cancer comprising administering to an individual in need a therapeutically effective amount of a compound of Formula (VII) or a pharmaceutically acceptable salt, pharmaceutically acceptable solvate, pharmaceutically acceptable prodrug, or N-oxide thereof. In one embodiment, the cancer is blood, brain, breast, colorectal, gastrointestinal, liver, lung, ovarian, pancreatic, prostate, skin or uterine cancer. In some embodiments, the cancer produces molecules involved in Epstein-Barr virus (EBV)-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

In another aspect, described herein is a method of treating a disease, disorder or condition mediated by EBI2 in a subject in need thereof, which method comprises administering to the subject a therapeutically effective amount of a compound of Formula (VII), or a pharmaceutically acceptable salt thereof. In another aspect, described herein is a method of treating a disease in a subject mediated by EBI2, which method comprises administering to the subject a pharmaceutical composition comprising a compound of Formula (VII), or a pharmaceutically acceptable salt thereof. In some embodiments, the disease, disorder or condition is an autoimmune disease or condition. In some embodiments, the autoimmune disease or condition is selected from type-1-diabetes, multiple sclerosis, rheumatoid arthritis and lupus. In some embodiments, the disease, disorder or condition is a cardiovascular disease or condition. In some embodiments, the cardiovascular disease or condition is atherosclerosis. In some embodiments, the disease, disorder or condition is a viral infection. In some embodiments, the viral infection is an Epstein-Barr viral infection. In some embodiments, the disease, disorder or condition is cancer. In some embodiments, the cancer is blood, brain, breast, colorectal, gastrointestinal, liver, lung, ovarian, pancreatic, prostate, skin or uterine cancer. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

Also provided is the use a compound of Formula (VII), or a pharmaceutically acceptable salt, pharmaceutically acceptable solvate, pharmaceutically acceptable prodrug, or N-oxide thereof for the treatment of an autoimmune disease or condition in a human. In some embodiments is the use a compound of Formula (VII), or a pharmaceutically acceptable salt, pharmaceutically acceptable solvate, pharmaceutically acceptable prodrug, or N-oxide thereof for the treatment of an autoimmune disease or condition in a human, wherein the autoimmune disease or condition is selected from type-1-diabetes, multiple sclerosis, rheumatoid arthritis and lupus.

Further provided is the use a compound of Formula (VII), or a pharmaceutically acceptable salt, pharmaceutically acceptable solvate, pharmaceutically acceptable prodrug, or N-oxide thereof for the treatment of a cardiovascular disease or condition in a human. In some embodiments is the use a compound of Formula (VII), or a pharmaceutically acceptable salt, pharmaceutically acceptable solvate, pharmaceutically acceptable prodrug, or N-oxide thereof for the treatment of atherosclerosis in a human.

Further provided is the use a compound of Formula (VII), or a pharmaceutically acceptable salt, pharmaceutically acceptable solvate, pharmaceutically acceptable prodrug, or N-oxide thereof for the treatment of a viral infection in a human. In some embodiments is the use a compound of Formula (VII), or a pharmaceutically acceptable salt, pharmaceutically acceptable solvate, pharmaceutically acceptable prodrug, or N-oxide thereof for the treatment of an Epstein-Barr viral infection in a human.

Further provided is the use of a compound of Formula (VII), or a pharmaceutically acceptable salt, pharmaceutically acceptable solvate, pharmaceutically acceptable prodrug, or N-oxide thereof for the treatment of cancer in a human. In some embodiments is the use of a compound of Formula (VII), or a pharmaceutically acceptable salt, pharmaceutically acceptable solvate, pharmaceutically acceptable prodrug, or N-oxide thereof for the treatment of a blood, brain, breast, colorectal, gastrointestinal, liver, lung, ovarian, pancreatic, prostate, skin or uterine cancer in a human. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

Also provided is the use a compound of Formula (VII), or a pharmaceutically acceptable salt, pharmaceutically acceptable solvate, pharmaceutically acceptable prodrug, or N-oxide thereof for the manufacture of a medicament for the treatment of an autoimmune disease or condition in a human. In some embodiments is the use a compound of Formula (VII), or a pharmaceutically acceptable salt, pharmaceutically acceptable solvate, pharmaceutically acceptable prodrug, or N-oxide thereof for the manufacture of a medicament for the treatment of an autoimmune disease or condition in a human, wherein the autoimmune disease or condition is selected from type-1-diabetes, multiple sclerosis, rheumatoid arthritis and lupus.

Further provided is the use a compound of Formula (VII), or a pharmaceutically acceptable salt, pharmaceutically acceptable solvate, pharmaceutically acceptable prodrug, or N-oxide thereof for the manufacture of a medicament for the treatment of a cardiovascular disease or condition in a human. In some embodiments is the use a compound of Formula (VII), or a pharmaceutically acceptable salt, pharmaceutically acceptable solvate, pharmaceutically acceptable prodrug, or N-oxide thereof for the manufacture of a medicament for the treatment of atherosclerosis in a human.

Further provided is the use a compound of Formula (VII), or a pharmaceutically acceptable salt, pharmaceutically acceptable solvate, pharmaceutically acceptable prodrug, or N-oxide thereof for the manufacture of a medicament for the treatment of a viral infection in a human. In some embodiments is the use a compound of Formula (VII), or a pharmaceutically acceptable salt, pharmaceutically acceptable solvate, pharmaceutically acceptable prodrug, or N-oxide thereof for the manufacture of a medicament for the treatment of an Epstein-Barr viral infection in a human.

Further provided is the use of a compound of Formula (VII), or a pharmaceutically acceptable salt, pharmaceutically acceptable solvate, pharmaceutically acceptable prodrug, or N-oxide thereof for the manufacture of a medicament for the treatment of cancer in a human. In some embodiments is the use of a compound of Formula (VII), or a pharmaceutically acceptable salt, pharmaceutically acceptable solvate, pharmaceutically acceptable prodrug, or N-oxide thereof for the manufacture of a medicament for the treatment of a blood, brain, breast, colorectal, gastrointestinal, liver, lung, ovarian, pancreatic, prostate, skin or uterine cancer in a human. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

In any of the aforementioned aspects are further embodiments in which: (a) the effective amount of the compound of Formula (VII), is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (VII), or a pharmaceutically acceptable salt thereof, to a subject are further embodiments comprising administering at least one additional agent in addition to the administration of a compound having the structure of Formula (VII), or a pharmaceutically acceptable salt thereof. In various embodiments, the compound of Formula (VII), and the additional agent are administered in any order, including simultaneously. In some embodiments, the compound of Formula (VII), and the additional agent are administered to the subject in the same pharmaceutical composition or in separate pharmaceutical compositions.

In some embodiments is a compound having the structure of Formula (VIII):

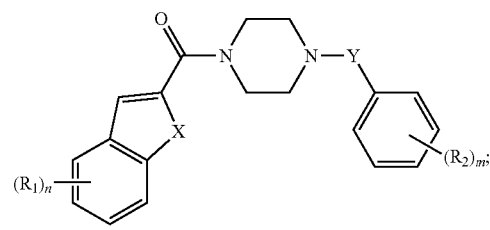

Formula (VIII)

wherein:
X is —N(H)—, —N($R_3$)—, —O—, or —S—;
Y is a bond, —$CH_2$—, —C(H)(Ph)-, —C(=O)—, or —S(=O)$_2$—;

each $R_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl; or two $R_1$ on adjacent carbon atoms are combined with the adjacent carbon atoms to form a —OCH$_2$O— ring;

each $R_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, —C(=O)C$_1$-C$_6$alkyl, CO$_2$H, B(OH)$_2$, PO$_3$H, C$_3$-C$_8$cycloalkyl, C$_1$-C$_6$heteroalkyl, C$_1$-C$_6$haloalkyl, C$_2$-C$_8$heterocycloalkyl, aryl, or heteroaryl;

$R_3$ is C$_1$-C$_6$alkyl;

each $R_4$ is independently H or C$_1$-C$_6$alkyl;

each $R_5$ is independently H or C$_1$-C$_6$alkyl;

m is an integer selected from 0-3; and n is an integer selected from 0-3;

or a pharmaceutically acceptable salt, pharmaceutically acceptable solvate, or pharmaceutically acceptable prodrug thereof.

In some embodiments is a compound of Formula (VIII) wherein X is —N(H)—. In another embodiment is a compound of Formula (VIII) wherein X is —N(R$_3$)—. In another embodiment is a compound of Formula (VIII) wherein X is —N(CH$_3$)—. In another embodiment is a compound of Formula (VIII) wherein X is —O—. In another embodiment is a compound of Formula (VIII) wherein X is —S—.

In some embodiments is a compound of Formula (VIII) wherein Y is a bond. In another embodiment is a compound of Formula (VIII) wherein Y is —CH$_2$—. In another embodiment is a compound of Formula (VIII) wherein Y is —C(H)(Ph)-. In another embodiment is a compound of Formula (VIII) wherein Y is —C(=O)—. In another embodiment is a compound of Formula (VIII) wherein Y is —S(=O)$_2$—.

In some embodiments is a compound of Formula (VIII) wherein each $R_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, aryl, or heteroaryl. In some embodiments is a compound of Formula (VIII) wherein each $R_1$ is independently F, Cl, Br, —CF$_3$, —CH$_3$, —OCF$_3$, or —OCH$_3$. In some embodiments is a compound of Formula (VIII) wherein each $R_1$ is F. In some embodiments is a compound of Formula (VIII) wherein each $R_1$ is Cl. In some embodiments is a compound of Formula (VIII) wherein each $R_1$ is Br. In some embodiments is a compound of Formula (VIII) wherein each $R_1$ is —CF$_3$. In some embodiments is a compound of Formula (VIII) wherein each $R_1$ is —CH$_3$. In some embodiments is a compound of Formula (VIII) wherein each $R_1$ is —OCF$_3$. In some embodiments is a compound of Formula (VIII) wherein each $R_1$ is —OCH$_3$.

In some embodiments is a compound of Formula (VIII) wherein each $R_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, aryl, or heteroaryl. In some embodiments is a compound of Formula (VIII) wherein each $R_2$ is independently F, Cl, Br, —CF$_3$, —CH$_3$, —OCF$_3$, or —OCH$_3$. In some embodiments is a compound of Formula (VIII) wherein each $R_2$ is F. In some embodiments is a compound of Formula (VIII) wherein each $R_2$ is Cl. In some embodiments is a compound of Formula (VIII) wherein each $R_2$ is Br. In some embodiments is a compound of Formula (VIII) wherein each $R_2$ is —CF$_3$. In some embodiments is a compound of Formula (VIII) wherein each $R_2$ is —CH$_3$. In some embodiments is a compound of Formula (VIII) wherein each $R_2$ is —OCF$_3$. In some embodiments is a compound of Formula (VIII) wherein each $R_2$ is —OCH$_3$.

In another embodiment is a compound of Formula (VIII) wherein m is 0 and n is 0.

In another embodiment is a compound of Formula (VIII) wherein m is 0 and n is 1. In another embodiment is a compound of Formula (VIII) wherein m is 1 and n is 0. In another embodiment is a compound of Formula (VIII) wherein m is 0 and n is 2. In another embodiment is a compound of Formula (VIII) wherein m is 2 and n is 0. In another embodiment is a compound of Formula (VIII) wherein m is 1 and n is 1. In another embodiment is a compound of Formula (VIII) wherein m is 1 and n is 2. In another embodiment is a compound of Formula (VIII) wherein m is 2 and n is 2.

In another embodiment is a compound of Formula (VIII) wherein m is 0, n is 1, X is —N(H)—, Y is a bond, and $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 1, Y is a bond, and $R_1$ is F, Cl, Br, —CF$_3$, —CH$_3$, —OCF$_3$, or —OCH$_3$. In another embodiment is a compound of Formula (VIII) wherein m is 0, n is 1, Y is a bond, and $R_1$ is F, Cl, Br, or —CF$_3$.

In another embodiment is a compound of Formula (VIII) wherein m is 0, n is 2, X is —N(H)—, Y is a bond, and each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 2, X is —N(H)—, Y is a bond, and each $R_1$ is independently F, Cl, Br, —CF$_3$, —CH$_3$, —OCF$_3$, or —OCH$_3$. In another embodiment is a compound of Formula (VIII) wherein m is 0, n is 2, X is —N(H)—, Y is a bond, and each $R_1$ is independently F, Cl, Br, or —CF$_3$. In another embodiment is a compound of Formula (VIII) wherein m is 0, n is 2, X is —N(H)—, Y is a bond, and two $R_1$ on adjacent carbon atoms are combined with the adjacent carbon atoms to form a —OCH$_2$O— ring.

In another embodiment is a compound of Formula (VIII) wherein m is 1, n is 1, X is —N(H)—, Y is a bond, $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 1, X is —N(H)—, Y is a bond, $R_1$ is F, Cl, Br, —CF$_3$, —CH$_3$, —OCF$_3$, or —OCH$_3$, and $R_2$ is independently F, Cl, Br, —CF$_3$, —CH$_3$, —OCF$_3$, or —OCH$_3$. In another embodiment is a compound of Formula (VIII) wherein m is 1, n is 1, X is —N(H)—, Y is a bond, $R_1$ is F, Cl, Br, —CF$_3$, —CH$_3$, or —OCH$_3$, and $R_2$ is independently F, Cl, Br, or —CF$_3$.

In another embodiment is a compound of Formula (VIII) wherein m is 1, n is 2, X is —N(H)—, Y is a bond, each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 2, X is —N(H)—, Y is a bond, each $R_1$ is independently F, Cl, Br, —CF$_3$, —CH$_3$, —OCF$_3$, or —OCH$_3$, and $R_2$ is independently F, Cl, Br, —CF$_3$, —CH$_3$, —OCF$_3$, or —OCH$_3$. In another embodiment is a compound of Formula (VIII) wherein m is 1, n is 2, X is —N(H)—, Y is a bond, each $R_1$ is independently F, Cl, Br, —CF$_3$, —CH$_3$, or —OCH$_3$, and $R_2$ is independently F, Cl, Br, or —CF$_3$.

In another embodiment is a compound of Formula (VIII) wherein m is 2, n is 1, X is —N(H)—, Y is a bond, $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 2, n is 1, X is —N(H)—, Y is a bond, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (VIII) wherein m is 2, n is 1, X is —N(H)—, Y is a bond, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (VIII) wherein m is 0, n is 1, X is —N(H)—, Y is —CH$_2$—, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 1, X is —N(H)—, Y is —CH$_2$—, and R$_1$ is F, Cl, Br, —CF$_3$, —CH$_3$, —OCF$_3$, or —OCH$_3$. In another embodiment is a compound of Formula (VIII) wherein m is 0, n is 1, X is —N(H)—, Y is —CH$_2$—, and R$_1$ is F, Cl, Br, or —CF$_3$.

In another embodiment is a compound of Formula (VIII) wherein m is 0, n is 2, X is —N(H)—, Y is —CH$_2$—, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 2, X is —N(H)—, Y is —CH$_2$—, and each R$_1$ is independently F, Cl, Br, —CF$_3$, —CH$_3$, —OCF$_3$, or —OCH$_3$. In another embodiment is a compound of Formula (VIII) wherein m is 0, n is 2, X is —N(H)—, Y is —CH$_2$—, and each R$_1$ is independently F, Cl, Br, or —CF$_3$. In another embodiment is a compound of Formula (VIII) wherein m is 0, n is 2, X is —N(H)—, Y is —CH$_2$—, and two R$_1$ on adjacent carbon atoms are combined with the adjacent carbon atoms to form a —OCH$_2$O— ring.

In another embodiment is a compound of Formula (VIII) wherein m is 1, n is 1, X is —N(H)—, Y is —CH$_2$—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 1, X is —N(H)—, Y is —CH$_2$—, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 1, X is —N(H)—, Y is —CH$_2$—, R$_1$ is F, Cl, Br, —CF$_3$, —CH$_3$, or —OCH$_3$, and R$_2$ is independently F, Cl, Br, or —CF$_3$.

In another embodiment is a compound of Formula (VIII) wherein m is 1, n is 2, X is —N(H)—, Y is —CH$_2$—, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 2, X is —N(H)—, Y is —CH$_2$—, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 2, X is —N(H)—, Y is —CH$_2$—, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (VIII) wherein m is 2, n is 1, X is —N(H)—, Y is —CH$_2$—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 2, n is 1, X is —N(H)—, Y is —CH$_2$—, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (VIII) wherein m is 2, n is 1, X is —N(H)—, Y is —CH$_2$—, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (VIII) wherein m is 0, n is 1, X is —N(H)—, Y is —C(H)(Ph)-, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 1, X is —N(H)—, Y is —C(H)(Ph)-, and R$_1$ is F, Cl, Br, —CF$_3$, —CH$_3$, —OCF$_3$, or —OCH$_3$. In another embodiment is a compound of Formula (VIII) wherein m is 0, n is 1, X is —N(H)—, Y is —C(H)(Ph)-, and R$_1$ is F, Cl, Br, or —CF$_3$.

In another embodiment is a compound of Formula (VIII) wherein m is 0, n is 2, X is —N(H)—, Y is —C(H)(Ph)-, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 2, X is —N(H)—, Y is —C(H)(Ph)-, and each R$_1$ is independently F, Cl, Br, —CF$_3$, —CH$_3$, —OCF$_3$, or —OCH$_3$. In another embodiment is a compound of Formula (VIII) wherein m is 0, n is 2, X is —N(H)—, Y is —C(H)(Ph)-, and each R$_1$ is independently F, Cl, Br, or —CF$_3$. In another embodiment is a compound of Formula (VIII) wherein m is 0, n is 2, X is —N(H)—, Y is —C(H)(Ph)-, and two R$_1$ on adjacent carbon atoms are combined with the adjacent carbon atoms to form a —OCH$_2$O— ring.

In another embodiment is a compound of Formula (VIII) wherein m is 1, n is 1, X is —N(H)—, Y is —C(H)(Ph)-, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 1, X is —N(H)—, Y is —C(H)(Ph)-, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 1, X is —N(H)—, Y is —C(H)(Ph)-, R$_1$ is F, Cl, Br, —CF$_3$, —CH$_3$, or —OCH$_3$, and R$_2$ is independently F, Cl, Br, or —CF$_3$.

In another embodiment is a compound of Formula (VIII) wherein m is 1, n is 2, X is —N(H)—, Y is —C(H)(Ph)-, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 2, X is —N(H)—, Y is —C(H)(Ph)-, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 2, X is —N(H)—, Y is —C(H)(Ph)-, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (VIII) wherein m is 2, n is 1, X is —N(H)—, Y is —C(H)(Ph)-, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 2, n is 1, X is —N(H)—, Y is —C(H)(Ph)-, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (VIII) wherein m is 2, n is 1, X is —N(H)—, Y is —C(H)(Ph)-, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (VIII) wherein m is 0, n is 1, X is —N(H)—, Y is —C(=O)—, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 1, X is —N(H)—, Y is —C(=O)—, and R$_1$ is F, Cl, Br, —CF$_3$, —CH$_3$, —OCF$_3$, or —OCH$_3$. In another embodiment is a compound of Formula (VIII) wherein m is 0, n is 1, X is —N(H)—, Y is —C(=O)—, and R$_1$ is F, Cl, Br, or —CF$_3$.

In another embodiment is a compound of Formula (VIII) wherein m is 0, n is 2, X is —N(H)—, Y is —C(=O)—, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 2, X is —N(H)—, Y is —C(=O)—, and each R$_1$ is independently F, Cl, Br, —CF$_3$, —CH$_3$, —OCF$_3$, or —OCH$_3$. In another embodiment is a compound of Formula (VIII) wherein m is 0, n is 2, X is —N(H)—, Y is —C(=O)—, and each R$_1$ is independently F, Cl, Br, or —CF$_3$. In another embodiment is a compound of Formula (VIII) wherein m is 0, n is 2, X is —N(H)—, Y is —C(=O)—, and two R$_1$ on adjacent carbon atoms are combined with the adjacent carbon atoms to form a —OCH$_2$O— ring.

In another embodiment is a compound of Formula (VIII) wherein m is 1, n is 1, X is —N(H)—, Y is —C(=O)—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 1, X is —N(H)—, Y is —C(=O)—, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 1, X is —N(H)—, Y is —C(=O)—, R$_1$ is F, Cl, Br, —CF$_3$, —CH$_3$, or —OCH$_3$, and R$_2$ is independently F, Cl, Br, or —CF$_3$.

In another embodiment is a compound of Formula (VIII) wherein m is 1, n is 2, X is —N(H)—, Y is —C(=O)—, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 2, X is —N(H)—, Y is —C(=O)—, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 2, X is —N(H)—, Y is —C(=O)—, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (VIII) wherein m is 2, n is 1, X is —N(H)—, Y is —C(=O)—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 2, n is 1, X is —N(H)—, Y is —C(=O)—, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (VIII) wherein m is 2, n is 1, X is —N(H)—, Y is —C(=O)—, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (VIII) wherein m is 0, n is 1, X is —N(H)—, Y is —S(=O)$_2$—, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 1, X is —N(H)—, Y is —S(=O)$_2$—, and R$_1$ is F, Cl, Br, —CF$_3$, —CH$_3$, —OCF$_3$, or —OCH$_3$. In another embodiment is a compound of Formula (VIII) wherein m is 0, n is 1, X is —N(H)—, Y is —S(=O)$_2$—, and R$_1$ is F, Cl, Br, or —CF$_3$.

In another embodiment is a compound of Formula (VIII) wherein m is 0, n is 2, X is —N(H)—, Y is —S(=O)$_2$—, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 2, X is —N(H)—, Y is —S(=O)$_2$—, and each R$_1$ is independently F, Cl, Br, —CF$_3$, —CH$_3$, —OCF$_3$, or —OCH$_3$. In another embodiment is a compound of Formula (VIII) wherein m is 0, n is 2, X is —N(H)—, Y is —S(=O)$_2$—, and each R$_1$ is independently F, Cl, Br, or —CF$_3$. In another embodiment is a compound of Formula (VIII) wherein m is 0, n is 2, X is —N(H)—, Y is —S(=O)$_2$—, and two R$_1$ on adjacent carbon atoms are combined with the adjacent carbon atoms to form a —OCH$_2$O— ring.

In another embodiment is a compound of Formula (VIII) wherein m is 1, n is 1, X is —N(H)—, Y is —S(=O)$_2$—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 1, X is —N(H)—, Y is —S(=O)$_2$—, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 1, X is —N(H)—, Y is —S(=O)$_2$—, R$_1$ is F, Cl, Br, —CF$_3$, —CH$_3$, or —OCH$_3$, and R$_2$ is independently F, Cl, Br, or —CF$_3$.

In another embodiment is a compound of Formula (VIII) wherein m is 1, n is 2, X is —N(H)—, Y is —S(=O)$_2$—, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 2, X is —N(H)—, Y is —S(=O)$_2$—, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 2, X is —N(H)—, Y is —S(=O)₂—, each $R_1$ is independently F, Cl, Br, —CF₃, —CH₃, or —OCH₃, and $R_2$ is independently F, Cl, Br, or —CF₃.

In another embodiment is a compound of Formula (VIII) wherein m is 2, n is 1, X is —N(H)—, Y is —S(=O)₂—, $R_1$ is independently F, Cl, Br, —CN, —NR₄R₅, —NO₂, —CF₃, —OCF₃, —OH, —C₁-C₆alkyl, or —OC₁-C₆alkyl, and each $R_2$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 2, n is 1, X is —N(H)—, Y is —S(=O)₂—, $R_1$ is independently F, Cl, Br, —CF₃, —CH₃, —OCF₃, or —OCH₃, and each $R_2$ is independently F, Cl, Br, —CF₃, —CH₃, —OCF₃, or —OCH₃. In another embodiment is a compound of Formula (VIII) wherein m is 2, n is 1, X is —N(H)—, Y is —S(=O)₂—, $R_1$ is independently F, Cl, Br, —CF₃, —CH₃, or —OCH₃, and each $R_2$ is independently F, Cl, Br, or —CF₃.

In another embodiment is a compound of Formula (VIII) wherein m is 0, n is 1, X is —O—, Y is a bond, and $R_1$ is F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 0, n is 1, X is —O—, Y is a bond, and $R_1$ is F, Cl, Br, —CF₃, —CH₃, —OCF₃, or —OCH₃. In another embodiment is a compound of Formula (VIII) wherein m is 0, n is 1, X is —O—, Y is a bond, and $R_1$ is F, Cl, Br, or —CF₃.

In another embodiment is a compound of Formula (VIII) wherein m is 0, n is 2, X is —O—, Y is a bond, and each $R_1$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 0, n is 2, X is —O—, Y is a bond, and each $R_1$ is independently F, Cl, Br, —CF₃, —CH₃, —OCF₃, or —OCH₃. In another embodiment is a compound of Formula (VIII) wherein m is 0, n is 2, X is —O—, Y is a bond, and each $R_1$ is independently F, Cl, Br, or —CF₃. In another embodiment is a compound of Formula (VIII) wherein m is 0, n is 2, X is —O—, Y is a bond, and two $R_1$ on adjacent carbon atoms are combined with the adjacent carbon atoms to form a —OCH₂O— ring.

In another embodiment is a compound of Formula (VIII) wherein m is 1, n is 1, X is —O—, Y is a bond, $R_1$ is independently F, Cl, Br, —CN, —NR₄R₅, —NO₂, —CF₃, —OCF₃, —OH, —C₁-C₆alkyl, or —OC₁-C₆alkyl, and $R_2$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 1, n is 1, X is —O—, Y is a bond, $R_1$ is F, Cl, Br, —CF₃, —CH₃, —OCF₃, or —OCH₃, and $R_2$ is independently F, Cl, Br, —CF₃, —CH₃, —OCF₃, or —OCH₃. In another embodiment is a compound of Formula (VIII) wherein m is 1, n is 1, X is —O—, Y is a bond, $R_1$ is F, Cl, Br, —CF₃, —CH₃, or —OCH₃, and $R_2$ is independently F, Cl, Br, or —CF₃.

In another embodiment is a compound of Formula (VIII) wherein m is 1, n is 2, X is —O—, Y is a bond, each $R_1$ is independently F, Cl, Br, —CN, —NR₄R₅, —NO₂, —CF₃, —OCF₃, —OH, —C₁-C₆alkyl, or —OC₁-C₆alkyl, and $R_2$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 1, n is 2, X is —O—, Y is a bond, each $R_1$ is independently F, Cl, Br, —CF₃, —CH₃, —OCF₃, or —OCH₃, and $R_2$ is independently F, Cl, Br, —CF₃, —CH₃, —OCF₃, or —OCH₃. In another embodiment is a compound of Formula (VIII) wherein m is 1, n is 2, X is —O—, Y is a bond, each $R_1$ is independently F, Cl, Br, —CF₃, —CH₃, or —OCH₃, and $R_2$ is independently F, Cl, Br, or —CF₃.

In another embodiment is a compound of Formula (VIII) wherein m is 2, n is 1, X is —O—, Y is a bond, $R_1$ is independently F, Cl, Br, —CN, —NR₄R₅, —NO₂, —CF₃, —OCF₃, —OH, —C₁-C₆alkyl, or —OC₁-C₆alkyl, and each $R_2$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 2, n is 1, X is —O—, Y is a bond, $R_1$ is independently F, Cl, Br, —CF₃, —CH₃, —OCF₃, or —OCH₃, and each $R_2$ is independently F, Cl, Br, —CF₃, —CH₃, —OCF₃, or —OCH₃. In another embodiment is a compound of Formula (VIII) wherein m is 2, n is 1, X is —O—, Y is a bond, $R_1$ is independently F, Cl, Br, —CF₃, —CH₃, or —OCH₃, and each $R_2$ is independently F, Cl, Br, or —CF₃.

In another embodiment is a compound of Formula (VIII) wherein m is 0, n is 1, X is —O—, Y is —CH₂—, and $R_1$ is F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 0, n is 1, X is —O—, Y is —CH₂—, and $R_1$ is F, Cl, Br, —CF₃, —CH₃, —OCF₃, or —OCH₃. In another embodiment is a compound of Formula (VIII) wherein m is 0, n is 1, X is —O—, Y is —CH₂—, and $R_1$ is F, Cl, Br, or —CF₃.

In another embodiment is a compound of Formula (VIII) wherein m is 0, n is 2, X is —O—, Y is —CH₂—, and each $R_1$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 0, n is 2, X is —O—, Y is —CH₂—, and each $R_1$ is independently F, Cl, Br, —CF₃, —CH₃, —OCF₃, or —OCH₃. In another embodiment is a compound of Formula (VIII) wherein m is 0, n is 2, X is —O—, Y is —CH₂—, and each $R_1$ is independently F, Cl, Br, or —CF₃. In another embodiment is a compound of Formula (VIII) wherein m is 0, n is 2, X is —O—, Y is —CH₂—, and two $R_1$ on adjacent carbon atoms are combined with the adjacent carbon atoms to form a —OCH₂O— ring.

In another embodiment is a compound of Formula (VIII) wherein m is 1, n is 1, X is —O—, Y is —CH₂—, $R_1$ is independently F, Cl, Br, —CN, —NR₄R₅, —NO₂, —CF₃, —OCF₃, —OH, —C₁-C₆alkyl, or —OC₁-C₆alkyl, and $R_2$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 1, n is 1, X is —O—, Y is —CH₂—, $R_1$ is F, Cl, Br, —CF₃, —CH₃, —OCF₃, or —OCH₃, and $R_2$ is independently F, Cl, Br, —CF₃, —CH₃, —OCF₃, or —OCH₃. In another embodiment is a compound of Formula (VIII) wherein m is 1, n is 1, X is —O—, Y is —CH₂—, $R_1$ is F, Cl, Br, —CF₃, —CH₃, or —OCH₃, and $R_2$ is independently F, Cl, Br, or —CF₃.

In another embodiment is a compound of Formula (VIII) wherein m is 1, n is 2, X is —O—, Y is —CH₂—, each $R_1$ is independently F, Cl, Br, —CN, —NR₄R₅, —NO₂, —CF₃, —OCF₃, —OH, —C₁-C₆alkyl, or —OC₁-C₆alkyl, and $R_2$ is independently F, Cl, Br, —CN, —NR₄R₅, —NO₂, —CF₃, —OCF₃, —OH, —C₁-C₆alkyl, or —OC₁-C₆alkyl. In another embodiment is a compound of Formula (VIII) wherein m is 1, n is 2, X is —O—, Y is —CH₂—, each $R_1$ is independently F, Cl, Br, —CF₃, —CH₃, —OCF₃, or —OCH₃, and $R_2$ is independently F, Cl, Br, —CF₃, —CH₃, —OCF₃, or —OCH₃. In another embodiment is a compound of Formula (VIII) wherein m is 1, n is 2, X is —O—, Y is —CH$_2$—, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (VIII) wherein m is 2, n is 1, X is —O—, Y is —CH$_2$—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 2, n is 1, X is —O—, Y is —CH$_2$—, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (VIII) wherein m is 2, n is 1, X is —O—, Y is —CH$_2$—, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (VIII) wherein m is 0, n is 1, X is —O—, Y is —C(H)(Ph)-, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 1, X is —O—, Y is —C(H)(Ph)-, and R$_1$ is F, Cl, Br, —CF$_3$, —CH$_3$, —OCF$_3$, or —OCH$_3$. In another embodiment is a compound of Formula (VIII) wherein m is 0, n is 1, X is —O—, Y is —C(H)(Ph)-, and R$_1$ is F, Cl, Br, or —CF$_3$.

In another embodiment is a compound of Formula (VIII) wherein m is 0, n is 2, X is —O—, Y is —C(H)(Ph)-, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 2, X is —O—, Y is —C(H)(Ph)-, and each R$_1$ is independently F, Cl, Br, —CF$_3$, —CH$_3$, —OCF$_3$, or —OCH$_3$. In another embodiment is a compound of Formula (VIII) wherein m is 0, n is 2, X is —O—, Y is —C(H)(Ph)-, and each R$_1$ is independently F, Cl, Br, or —CF$_3$. In another embodiment is a compound of Formula (VIII) wherein m is 0, n is 2, X is —O—, Y is —C(H)(Ph)-, and two R$_1$ on adjacent carbon atoms are combined with the adjacent carbon atoms to form a —OCH$_2$O— ring.

In another embodiment is a compound of Formula (VIII) wherein m is 1, n is 1, X is —O—, Y is —C(H)(Ph)-, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 1, X is —O—, Y is —C(H)(Ph)-, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 1, X is —O—, Y is —C(H)(Ph)-, R$_1$ is F, Cl, Br, —CF$_3$, —CH$_3$, or —OCH$_3$, and R$_2$ is independently F, Cl, Br, or —CF$_3$.

In another embodiment is a compound of Formula (VIII) wherein m is 1, n is 2, X is —O—, Y is —C(H)(Ph)-, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 2, X is —O—, Y is —C(H)(Ph)-, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 2, X is —O—, Y is —C(H)(Ph)-, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (VIII) wherein m is 2, n is 1, X is —O—, Y is —C(H)(Ph)-, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 2, n is 1, X is —O—, Y is —C(H)(Ph)-, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (VIII) wherein m is 2, n is 1, X is —O—, Y is —C(H)(Ph)-, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (VIII) wherein m is 0, n is 1, X is —O—, Y is —C(=O)—, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 1, X is —O—, Y is —C(=O)—, and R$_1$ is F, Cl, Br, —CF$_3$, —CH$_3$, —OCF$_3$, or —OCH$_3$. In another embodiment is a compound of Formula (VIII) wherein m is 0, n is 1, X is —O—, Y is —C(=O)—, and R$_1$ is F, Cl, Br, or —CF$_3$.

In another embodiment is a compound of Formula (VIII) wherein m is 0, n is 2, X is —O—, Y is —C(=O)—, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 2, X is —O—, Y is —C(=O)—, and each R$_1$ is independently F, Cl, Br, —CF$_3$, —CH$_3$, —OCF$_3$, or —OCH$_3$. In another embodiment is a compound of Formula (VIII) wherein m is 0, n is 2, X is —O—, Y is —C(=O)—, and each R$_1$ is independently F, Cl, Br, or —CF$_3$. In another embodiment is a compound of Formula (VIII) wherein m is 0, n is 2, X is —O—, Y is —C(=O)—, and two R$_1$ on adjacent carbon atoms are combined with the adjacent carbon atoms to form a —OCH$_2$O— ring.

In another embodiment is a compound of Formula (VIII) wherein m is 1, n is 1, X is —O—, Y is —C(=O)—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 1, X is —O—, Y is —C(=O)—, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 1, X is —O—, Y is —C(=O)—, R$_1$ is F, Cl, Br, —CF$_3$, —CH$_3$, or —OCH$_3$, and R$_2$ is independently F, Cl, Br, or —CF$_3$.

In another embodiment is a compound of Formula (VIII) wherein m is 1, n is 2, X is —O—, Y is —C(=O)—, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 2, X is —O—, Y is —C(=O)—, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (VIII) wherein m is 1, n is 2, X is —O—, Y is —C(=O)—, each $R_1$ is independently F, Cl, Br, —CF$_3$, —CH$_3$, or —OCH$_3$, and $R_2$ is independently F, Cl, Br, or —CF$_3$.

In another embodiment is a compound of Formula (VIII) wherein m is 2, n is 1, X is —O—, Y is —C(=O)—, $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 2, n is 1, X is —O—, Y is —C(=O)—, $R_1$ is independently F, Cl, Br, —CF$_3$, —CH$_3$, —OCF$_3$, or —OCH$_3$, and each $R_2$ is independently F, Cl, Br, —CF$_3$, —CH$_3$, —OCF$_3$, or —OCH$_3$. In another embodiment is a compound of Formula (VIII) wherein m is 2, n is 1, X is —O—, Y is —C(=O)—, $R_1$ is independently F, Cl, Br, —CF$_3$, —CH$_3$, or —OCH$_3$, and each $R_2$ is independently F, Cl, Br, or —CF$_3$.

In another embodiment is a compound of Formula (VIII) wherein m is 0, n is 1, X is —O—, Y is —S(=O)$_2$—, and $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 1, X is —O—, Y is —S(=O)$_2$—, and $R_1$ is F, Cl, Br, —CF$_3$, —CH$_3$, —OCF$_3$, or —OCH$_3$. In another embodiment is a compound of Formula (VIII) wherein m is 0, n is 1, X is —O—, Y is —S(=O)$_2$—, and $R_1$ is F, Cl, Br, or —CF$_3$.

In another embodiment is a compound of Formula (VIII) wherein m is 0, n is 2, X is —O—, Y is —S(=O)$_2$—, and each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 2, X is —O—, Y is —S(=O)$_2$—, and each $R_1$ is independently F, Cl, Br, —CF$_3$, —CH$_3$, —OCF$_3$, or —OCH$_3$. In another embodiment is a compound of Formula (VIII) wherein m is 0, n is 2, X is —O—, Y is —S(=O)$_2$—, and each $R_1$ is independently F, Cl, Br, or —CF$_3$. In another embodiment is a compound of Formula (VIII) wherein m is 0, n is 2, X is —O—, Y is —S(=O)$_2$—, and two $R_1$ on adjacent carbon atoms are combined with the adjacent carbon atoms to form a —OCH$_2$O— ring.

In another embodiment is a compound of Formula (VIII) wherein m is 1, n is 1, X is —O—, Y is —S(=O)$_2$—, $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 1, X is —O—, Y is —S(=O)$_2$—, $R_1$ is F, Cl, Br, —CF$_3$, —CH$_3$, —OCF$_3$, or —OCH$_3$, and $R_2$ is independently F, Cl, Br, —CF$_3$, —CH$_3$, —OCF$_3$, or —OCH$_3$. In another embodiment is a compound of Formula (VIII) wherein m is 1, n is 1, X is —O—, Y is —S(=O)$_2$—, $R_1$ is F, Cl, Br, —CF$_3$, —CH$_3$, or —OCH$_3$, and $R_2$ is independently F, Cl, Br, or —CF$_3$.

In another embodiment is a compound of Formula (VIII) wherein m is 1, n is 2, X is —O—, Y is —S(=O)$_2$—, each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 2, X is —O—, Y is —S(=O)$_2$—, each $R_1$ is independently F, Cl, Br, —CF$_3$, —CH$_3$, —OCF$_3$, or —OCH$_3$, and $R_2$ is independently F, Cl, Br, —CF$_3$, —CH$_3$, —OCF$_3$, or —OCH$_3$. In another embodiment is a compound of Formula (VIII) wherein m is 1, n is 2, X is —O—, Y is —S(=O)$_2$—, each $R_1$ is independently F, Cl, Br, —CF$_3$, —CH$_3$, or —OCH$_3$, and $R_2$ is independently F, Cl, Br, or —CF$_3$.

In another embodiment is a compound of Formula (VIII) wherein m is 2, n is 1, X is —O—, Y is —S(=O)$_2$—, $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 2, n is 1, X is —O—, Y is —S(=O)$_2$—, $R_1$ is independently F, Cl, Br, —CF$_3$, —CH$_3$, —OCF$_3$, or —OCH$_3$, and each $R_2$ is independently F, Cl, Br, —CF$_3$, —CH$_3$, —OCF$_3$, or —OCH$_3$. In another embodiment is a compound of Formula (VIII) wherein m is 2, n is 1, X is —O—, Y is —S(=O)$_2$—, $R_1$ is independently F, Cl, Br, —CF$_3$, —CH$_3$, or —OCH$_3$, and each $R_2$ is independently F, Cl, Br, or —CF$_3$.

In another embodiment is a compound of Formula (VIII) wherein m is 0, n is 1, X is —S—, Y is a bond, and $R_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 1, X is —S—, Y is a bond, and $R_1$ is F, Cl, Br, —CF$_3$, —CH$_3$, —OCF$_3$, or —OCH$_3$. In another embodiment is a compound of Formula (VIII) wherein m is 0, n is 1, X is —S—, Y is a bond, and $R_1$ is F, Cl, Br, or —CF$_3$.

In another embodiment is a compound of Formula (VIII) wherein m is 0, n is 2, X is —S—, Y is a bond, and each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 0, n is 2, X is —S—, Y is a bond, and each $R_1$ is independently F, Cl, Br, —CF$_3$, —CH$_3$, —OCF$_3$, or —OCH$_3$. In another embodiment is a compound of Formula (VIII) wherein m is 0, n is 2, X is —S—, Y is a bond, and each $R_1$ is independently F, Cl, Br, or —CF$_3$. In another embodiment is a compound of Formula (VIII) wherein m is 0, n is 2, X is —S—, Y is a bond, and two $R_1$ on adjacent carbon atoms are combined with the adjacent carbon atoms to form a —OCH$_2$O— ring.

In another embodiment is a compound of Formula (VIII) wherein m is 1, n is 1, X is —S—, Y is a bond, $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 1, X is —S—, Y is a bond, $R_1$ is F, Cl, Br, —CF$_3$, —CH$_3$, —OCF$_3$, or —OCH$_3$, and $R_2$ is independently F, Cl, Br, —CF$_3$, —CH$_3$, —OCF$_3$, or —OCH$_3$. In another embodiment is a compound of Formula (VIII) wherein m is 1, n is 1, X is —S—, Y is a bond, $R_1$ is F, Cl, Br, —CF$_3$, —CH$_3$, or —OCH$_3$, and $R_2$ is independently F, Cl, Br, or —CF$_3$.

In another embodiment is a compound of Formula (VIII) wherein m is 1, n is 2, X is —S—, Y is a bond, each $R_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and $R_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 1, n is 2, X is —S—, Y is a bond, each $R_1$ is independently F, Cl, Br, —CF$_3$, —CH$_3$, —OCF$_3$, or —OCH$_3$, and $R_2$ is independently F, Cl, Br, —CF$_3$, —CH$_3$, —OCF$_3$, or —OCH$_3$. In another embodiment is a compound of Formula (VIII) wherein m is 1, n is 2, X is —S—, Y is a bond, each $R_1$ is independently F, Cl, Br, —$CF_3$, —$CH_3$, or —$OCH_3$, and $R_2$ is independently F, Cl, Br, or —$CF_3$.

In another embodiment is a compound of Formula (VIII) wherein m is 2, n is 1, X is —S—, Y is a bond, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 2, n is 1, X is —S—, Y is a bond, $R_1$ is independently F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (VIII) wherein m is 2, n is 1, X is —S—, Y is a bond, $R_1$ is independently F, Cl, Br, —$CF_3$, —$CH_3$, or —$OCH_3$, and each $R_2$ is independently F, Cl, Br, or —$CF_3$.

In another embodiment is a compound of Formula (VIII) wherein m is 0, n is 1, X is —S—, Y is —$CH_2$—, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 0, n is 1, X is —S—, Y is —$CH_2$—, and $R_1$ is F, Cl, Br, —$CF_3$, —$CH_3$, —$OCF_3$, or —$OCH_3$. In another embodiment is a compound of Formula (VIII) wherein m is 0, n is 1, X is —S—, Y is —$CH_2$—, and $R_1$ is F, Cl, Br, or —$CF_3$.

In another embodiment is a compound of Formula (VIII) wherein m is 0, n is 2, X is —S—, Y is —$CH_2$—, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 0, n is 2, X is —S—, Y is —$CH_2$—, and each $R_1$ is independently F, Cl, Br, —$CF_3$, —$CH_3$, —$OCF_3$, or —$OCH_3$. In another embodiment is a compound of Formula (VIII) wherein m is 0, n is 2, X is —S—, Y is —$CH_2$—, and each $R_1$ is independently F, Cl, Br, or —$CF_3$. In another embodiment is a compound of Formula (VIII) wherein m is 0, n is 2, X is —S—, Y is —$CH_2$—, and two $R_1$ on adjacent carbon atoms are combined with the adjacent carbon atoms to form a —$OCH_2O$— ring.

In another embodiment is a compound of Formula (VIII) wherein m is 1, n is 1, X is —S—, Y is —$CH_2$—, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 1, n is 1, X is —S—, Y is —$CH_2$—, $R_1$ is F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VIII) wherein m is 1, n is 1, X is —S—, Y is —$CH_2$—, $R_1$ is F, Cl, Br, —$CF_3$, —$CH_3$, or —$OCH_3$, and $R_2$ is independently F, Cl, Br, or —$CF_3$.

In another embodiment is a compound of Formula (VIII) wherein m is 1, n is 2, X is —S—, Y is —$CH_2$—, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 1, n is 2, X is —S—, Y is —$CH_2$—, each $R_1$ is independently F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VIII) wherein m is 1, n is 2, X is —S—, Y is —$CH_2$—, each $R_1$ is independently F, Cl, Br, —$CF_3$, —$CH_3$, or —$OCH_3$, and $R_2$ is independently F, Cl, Br, or —$CF_3$.

In another embodiment is a compound of Formula (VIII) wherein m is 2, n is 1, X is —S—, Y is —$CH_2$—, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 2, n is 1, X is —S—, Y is —$CH_2$—, $R_1$ is independently F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (VIII) wherein m is 2, n is 1, X is —S—, Y is —$CH_2$—, $R_1$ is independently F, Cl, Br, —$CF_3$, —$CH_3$, or —$OCH_3$, and each $R_2$ is independently F, Cl, Br, or —$CF_3$.

In another embodiment is a compound of Formula (VIII) wherein m is 0, n is 1, X is —S—, Y is —C(H)(Ph)-, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 0, n is 1, X is —S—, Y is —C(H)(Ph)-, and $R_1$ is F, Cl, Br, —$CF_3$, —$CH_3$, —$OCF_3$, or —$OCH_3$. In another embodiment is a compound of Formula (VIII) wherein m is 0, n is 1, X is —S—, Y is —C(H)(Ph)-, and $R_1$ is F, Cl, Br, or —$CF_3$.

In another embodiment is a compound of Formula (VIII) wherein m is 0, n is 2, X is —S—, Y is —C(H)(Ph)-, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 0, n is 2, X is —S—, Y is —C(H)(Ph)-, and each $R_1$ is independently F, Cl, Br, —$CF_3$, —$CH_3$, —$OCF_3$, or —$OCH_3$. In another embodiment is a compound of Formula (VIII) wherein m is 0, n is 2, X is —S—, Y is —C(H)(Ph)-, and each $R_1$ is independently F, Cl, Br, or —$CF_3$. In another embodiment is a compound of Formula (VIII) wherein m is 0, n is 2, X is —S—, Y is —C(H)(Ph)-, and two $R_1$ on adjacent carbon atoms are combined with the adjacent carbon atoms to form a —$OCH_2O$— ring.

In another embodiment is a compound of Formula (VIII) wherein m is 1, n is 1, X is —S—, Y is —C(H)(Ph)-, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 1, n is 1, X is —S—, Y is —C(H)(Ph)-, $R_1$ is F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VIII) wherein m is 1, n is 1, X is —S—, Y is —C(H)(Ph)-, $R_1$ is F, Cl, Br, —$CF_3$, —$CH_3$, or —$OCH_3$, and $R_2$ is independently F, Cl, Br, or —$CF_3$.

In another embodiment is a compound of Formula (VIII) wherein m is 1, n is 2, X is —S—, Y is —C(H)(Ph)-, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 1, n is 2, X is —S—, Y is —C(H)(Ph)-, each $R_1$ is independently F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VIII) wherein m is 1, n is 2, X is —S—, Y is —C(H)(Ph)-, each $R_1$ is independently F, Cl, Br, —$CF_3$, —$CH_3$, or —$OCH_3$, and $R_2$ is independently F, Cl, Br, or —$CF_3$.

In another embodiment is a compound of Formula (VIII) wherein m is 2, n is 1, X is —S—, Y is —C(H)(Ph)-, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 2, n is 1, X is —S—, Y is —C(H)(Ph)-, $R_1$ is independently F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (VIII) wherein m is 2, n is 1, X is —S—, Y is —C(H)(Ph)-, $R_1$ is independently F, Cl, Br, —$CF_3$, —$CH_3$, or —$OCH_3$, and each $R_2$ is independently F, Cl, Br, or —$CF_3$.

In another embodiment is a compound of Formula (VIII) wherein m is 0, n is 1, X is —S—, Y is —C(=O)—, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 0, n is 1, X is —S—, Y is —C(=O)—, and $R_1$ is F, Cl, Br, —$CF_3$, —$CH_3$, —$OCF_3$, or —$OCH_3$. In another embodiment is a compound of Formula (VIII) wherein m is 0, n is 1, X is —S—, Y is —C(=O)—, and $R_1$ is F, Cl, Br, or —$CF_3$.

In another embodiment is a compound of Formula (VIII) wherein m is 0, n is 2, X is —S—, Y is —C(=O)—, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 0, n is 2, X is —S—, Y is —C(=O)—, and each $R_1$ is independently F, Cl, Br, —$CF_3$, —$CH_3$, —$OCF_3$, or —$OCH_3$. In another embodiment is a compound of Formula (VIII) wherein m is 0, n is 2, X is —S—, Y is —C(=O)—, and each $R_1$ is independently F, Cl, Br, or —$CF_3$. In another embodiment is a compound of Formula (VIII) wherein m is 0, n is 2, X is —S—, Y is —C(=O)—, and two $R_1$ on adjacent carbon atoms are combined with the adjacent carbon atoms to form a —$OCH_2O$— ring.

In another embodiment is a compound of Formula (VIII) wherein m is 1, n is 1, X is —S—, Y is —C(=O)—, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 1, n is 1, X is —S—, Y is —C(=O)—, $R_1$ is F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VIII) wherein m is 1, n is 1, X is —S—, Y is —C(=O)—, $R_1$ is F, Cl, Br, —$CF_3$, —$CH_3$, or —$OCH_3$, and $R_2$ is independently F, Cl, Br, or —$CF_3$.

In another embodiment is a compound of Formula (VIII) wherein m is 1, n is 2, X is —S—, Y is —C(=O)—, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 1, n is 2, X is —S—, Y is —C(=O)—, each $R_1$ is independently F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VIII) wherein m is 1, n is 2, X is —S—, Y is —C(=O)—, each $R_1$ is independently F, Cl, Br, —$CF_3$, —$CH_3$, or —$OCH_3$, and $R_2$ is independently F, Cl, Br, or —$CF_3$.

In another embodiment is a compound of Formula (VIII) wherein m is 2, n is 1, X is —S—, Y is —C(=O)—, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 2, n is 1, X is —S—, Y is —C(=O)—, $R_1$ is independently F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (VIII) wherein m is 2, n is 1, X is —S—, Y is —C(=O)—, $R_1$ is independently F, Cl, Br, —$CF_3$, —$CH_3$, or —$OCH_3$, and each $R_2$ is independently F, Cl, Br, or —$CF_3$.

In another embodiment is a compound of Formula (VIII) wherein m is 0, n is 1, X is —S—, Y is —S(=O)$_2$—, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 0, n is 1, X is —S—, Y is —S(=O)$_2$—, and $R_1$ is F, Cl, Br, —$CF_3$, —$CH_3$, —$OCF_3$, or —$OCH_3$. In another embodiment is a compound of Formula (VIII) wherein m is 0, n is 1, X is —S—, Y is —S(=O)$_2$—, and $R_1$ is F, Cl, Br, or —$CF_3$.

In another embodiment is a compound of Formula (VIII) wherein m is 0, n is 2, X is —S—, Y is —S(=O)$_2$—, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 0, n is 2, X is —S—, Y is —S(=O)$_2$—, and each $R_1$ is independently F, Cl, Br, —$CF_3$, —$CH_3$, —$OCF_3$, or —$OCH_3$. In another embodiment is a compound of Formula (VIII) wherein m is 0, n is 2, X is —S—, Y is —S(=O)$_2$—, and each $R_1$ is independently F, Cl, Br, or —$CF_3$. In another embodiment is a compound of Formula (VIII) wherein m is 0, n is 2, X is —S—, Y is —S(=O)$_2$—, and two $R_1$ on adjacent carbon atoms are combined with the adjacent carbon atoms to form a —$OCH_2O$— ring.

In another embodiment is a compound of Formula (VIII) wherein m is 1, n is 1, X is —S—, Y is —S(=O)$_2$—, $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 1, n is 1, X is —S—, Y is —S(=O)$_2$—, $R_1$ is F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VIII) wherein m is 1, n is 1, X is —S—, Y is —S(=O)$_2$—, $R_1$ is F, Cl, Br, —$CF_3$, —$CH_3$, or —$OCH_3$, and $R_2$ is independently F, Cl, Br, or —$CF_3$.

In another embodiment is a compound of Formula (VIII) wherein m is 1, n is 2, X is —S—, Y is —S(=O)$_2$—, each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl, and $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (VIII) wherein m is 1, n is 2, X is —S—, Y is —S(=O)$_2$—, each $R_1$ is independently F, Cl, Br, —$CF_3$, —$CH_3$, —$OCF_3$, or —$OCH_3$, and $R_2$ is independently F, Cl, Br, —$CF_3$, —$CH_3$, —$OCF_3$, or —$OCH_3$. In another embodiment is a compound of Formula (VIII) wherein m is 1, n is 2, X is —S—, Y is —S(=O)$_2$—, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (VIII) wherein m is 2, n is 1, X is —S—, Y is —S(=O)$_2$—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (VIII) wherein m is 2, n is 1, X is —S—, Y is —S(=O)$_2$—, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (VIII) wherein m is 2, n is 1, X is —S—, Y is —S(=O)$_2$—, R$_1$ is independently F, Cl, Br, —CF$_3$, —CH$_3$, or —OCH$_3$, and each R$_2$ is independently F, Cl, Br, or —CF$_3$.

In another embodiment, provided herein is a pharmaceutical composition comprising a compound of Formula (VIII), or a pharmaceutically acceptable salt, solvate, prodrug, or N-oxide thereof, and a pharmaceutically acceptable excipient. In another embodiment, the pharmaceutical composition comprising the compound of Formula (VIII), or a pharmaceutically acceptable salt, pharmaceutically acceptable solvate, pharmaceutically acceptable prodrug, or N-oxide thereof, is formulated for a route of administration selected from oral administration, parenteral administration, buccal administration, nasal administration, topical administration, or rectal administration.

In another aspect is a method for treating an autoimmune disease or condition comprising administering to an individual in need a therapeutically effective amount of a compound of Formula (VIII), or a pharmaceutically acceptable salt, pharmaceutically acceptable solvate, pharmaceutically acceptable prodrug, or N-oxide thereof. In some embodiments, the autoimmune disease is selected from type-1-diabetes, multiple sclerosis, rheumatoid arthritis and lupus. In another embodiment is a method for treating type-1-diabetes comprising administering to an individual in need a therapeutically effective amount of a compound of Formula (VIII), or a pharmaceutically acceptable salt, pharmaceutically acceptable solvate, pharmaceutically acceptable prodrug, or N-oxide thereof. In another embodiment is a method for treating multiple sclerosis comprising administering to an individual in need a therapeutically effective amount of a compound of Formula (VIII), or a pharmaceutically acceptable salt, pharmaceutically acceptable solvate, pharmaceutically acceptable prodrug, or N-oxide thereof. In another embodiment is a method for treating rheumatoid arthritis comprising administering to an individual in need a therapeutically effective amount of a compound of Formula (VIII), or a pharmaceutically acceptable salt, pharmaceutically acceptable solvate, pharmaceutically acceptable prodrug, or N-oxide thereof. In another embodiment is a method for treating lupus comprising administering to an individual in need a therapeutically effective amount of a compound of Formula (VIII), or a pharmaceutically acceptable salt, pharmaceutically acceptable solvate, pharmaceutically acceptable prodrug, or N-oxide thereof.

In another aspect is a method for treating a cardiovascular disease or condition comprising administering to an individual in need a therapeutically effective amount of a compound of Formula (VIII), or a pharmaceutically acceptable salt, pharmaceutically acceptable solvate, pharmaceutically acceptable prodrug, or N-oxide thereof. In one embodiment, the cardiovascular disease is atherosclerosis.

In another aspect is a method of treating a viral infection comprising administering to an individual in need a therapeutically effective amount of a compound of Formula (VIII), or a pharmaceutically acceptable salt, pharmaceutically acceptable solvate, pharmaceutically acceptable prodrug, or N-oxide thereof. In some embodiments, the viral infection is an Epstein-Barr viral infection.

In another aspect is a method of treating cancer comprising administering to an individual in need a therapeutically effective amount of a compound of Formula (VIII), or a pharmaceutically acceptable salt, pharmaceutically acceptable solvate, pharmaceutically acceptable prodrug, or N-oxide thereof. In one embodiment, the cancer is blood, brain, breast, colorectal, gastrointestinal, liver, lung, ovarian, pancreatic, prostate, skin or uterine cancer. In some embodiments, the cancer produces molecules involved in Epstein-Barr virus (EBV)-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

In another aspect, described herein is a method of treating a disease, disorder or condition mediated by EBI2 in a subject in need thereof, which method comprises administering to the subject a therapeutically effective amount of a compound of Formula (VIII), or a pharmaceutically acceptable salt thereof. In another aspect, described herein is a method of treating a disease in a subject mediated by EBI2, which method comprises administering to the subject a pharmaceutical composition comprising a compound of Formula (VIII), or a pharmaceutically acceptable salt thereof. In some embodiments, the disease, disorder or condition is an autoimmune disease or condition. In some embodiments, the autoimmune disease or condition is selected from type-1-diabetes, multiple sclerosis, rheumatoid arthritis and lupus. In some embodiments, the disease, disorder or condition is a cardiovascular disease or condition. In some embodiments, the cardiovascular disease or condition is atherosclerosis. In some embodiments, the disease, disorder or condition is a viral infection. In some embodiments, the viral infection is an Epstein-Barr viral infection. In some embodiments, the disease, disorder or condition is cancer. In some embodiments, the cancer is blood, brain, breast, colorectal, gastrointestinal, liver, lung, ovarian, pancreatic, prostate, skin or uterine cancer. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

Also provided is the use a compound of Formula (VIII), or a pharmaceutically acceptable salt, pharmaceutically acceptable solvate, pharmaceutically acceptable prodrug, or N-oxide thereof for the treatment of an autoimmune disease or condition in a human. In some embodiments is the use a compound of Formula (VIII), or a pharmaceutically acceptable salt, pharmaceutically acceptable solvate, pharmaceutically acceptable prodrug, or N-oxide thereof for the treatment of an autoimmune disease or condition in a human, wherein the autoimmune disease or condition is selected from type-1-diabetes, multiple sclerosis, rheumatoid arthritis and lupus.

Further provided is the use a compound of Formula (VIII), or a pharmaceutically acceptable salt, pharmaceutically acceptable solvate, pharmaceutically acceptable prodrug, or N-oxide thereof for the treatment of a cardiovascular disease or condition in a human. In some embodiments is the use a compound of Formula (VIII), or a pharmaceutically acceptable salt, pharmaceutically acceptable solvate, pharmaceutically acceptable prodrug, or N-oxide thereof for the treatment of atherosclerosis in a human.

Further provided is the use a compound of Formula (VIII), or a pharmaceutically acceptable salt, pharmaceutically acceptable solvate, pharmaceutically acceptable prodrug, or N-oxide thereof for the treatment of a viral infection in a human. In some embodiments is the use a compound of Formula (VIII), or a pharmaceutically acceptable salt, pharmaceutically acceptable solvate, pharmaceutically acceptable prodrug, or N-oxide thereof for the treatment of an Epstein-Barr viral infection in a human.

Further provided is the use of a compound of Formula (VIII), or a pharmaceutically acceptable salt, pharmaceutically acceptable solvate, pharmaceutically acceptable prodrug, or N-oxide thereof for the treatment of cancer in a human. In some embodiments is the use of a compound of Formula (VIII), or a pharmaceutically acceptable salt, pharmaceutically acceptable solvate, pharmaceutically acceptable prodrug, or N-oxide thereof for the treatment of a blood, brain, breast, colorectal, gastrointestinal, liver, lung, ovarian, pancreatic, prostate, skin or uterine cancer in a human. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

Also provided is the use a compound of Formula (VIII), or a pharmaceutically acceptable salt, pharmaceutically acceptable solvate, pharmaceutically acceptable prodrug, or N-oxide thereof for the manufacture of a medicament for the treatment of an autoimmune disease or condition in a human. In some embodiments is the use a compound of Formula (VIII), or a pharmaceutically acceptable salt, pharmaceutically acceptable solvate, pharmaceutically acceptable prodrug, or N-oxide thereof for the manufacture of a medicament for the treatment of an autoimmune disease or condition in a human, wherein the autoimmune disease or condition is selected from type-1-diabetes, multiple sclerosis, rheumatoid arthritis and lupus.

Further provided is the use a compound of Formula (VIII), or a pharmaceutically acceptable salt, pharmaceutically acceptable solvate, pharmaceutically acceptable prodrug, or N-oxide thereof for the manufacture of a medicament for the treatment of a cardiovascular disease or condition in a human. In some embodiments is the use a compound of Formula (VIII), or a pharmaceutically acceptable salt, pharmaceutically acceptable solvate, pharmaceutically acceptable prodrug, or N-oxide thereof for the manufacture of a medicament for the treatment of atherosclerosis in a human.

Further provided is the use of a compound of Formula (VIII), or a pharmaceutically acceptable salt, pharmaceutically acceptable solvate, pharmaceutically acceptable prodrug, or N-oxide thereof for the manufacture of a medicament for the treatment of a viral infection in a human. In some embodiments is the use a compound of Formula (VIII), or a pharmaceutically acceptable salt, pharmaceutically acceptable solvate, pharmaceutically acceptable prodrug, or N-oxide thereof for the manufacture of a medicament for the treatment of an Epstein-Barr viral infection in a human.

Further provided is the use of a compound of Formula (VIII), or a pharmaceutically acceptable salt, pharmaceutically acceptable solvate, pharmaceutically acceptable prodrug, or N-oxide thereof for the manufacture of a medicament for the treatment of cancer in a human. In some embodiments is the use of a compound of Formula (VIII), or a pharmaceutically acceptable salt, pharmaceutically acceptable solvate, pharmaceutically acceptable prodrug, or N-oxide thereof for the manufacture of a medicament for the treatment of a blood, brain, breast, colorectal, gastrointestinal, liver, lung, ovarian, pancreatic, prostate, skin or uterine cancer in a human. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

In any of the aforementioned aspects are further embodiments in which: (a) the effective amount of the compound of Formula (VIII), is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration;

and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (VIII), or a pharmaceutically acceptable salt thereof, to a subject are further embodiments comprising administering at least one additional agent in addition to the administration of a compound having the structure of Formula (VIII), or a pharmaceutically acceptable salt thereof. In various embodiments, the compound of Formula (VIII), and the additional agent are administered in any order, including simultaneously. In some embodiments, the compound of Formula (VIII), and the additional agent are administered to the subject in the same pharmaceutical composition or in separate pharmaceutical compositions.

In some embodiments is a compound having the structure of Formula (IX):

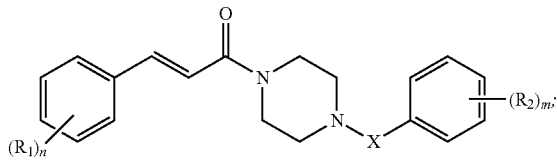

Formula (IX)

wherein:

X is —C(=O)—;

each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, $C_3$-$C_8$cycloalkyl, $C_1$-$C_6$heteroalkyl, $C_1$-$C_6$haloalkyl, $C_2$-$C_8$heterocycloalkyl, aryl, or heteroaryl; or two $R_1$ on adjacent carbon atoms are combined with the adjacent carbon atoms to form a —$OCH_2O$— ring;

each $R_2$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, —C(=O)$C_1$-$C_6$alkyl, $CO_2H$, $B(OH)_2$, $PO_3H$, $C_3$-$C_8$cycloalkyl, $C_1$-$C_6$heteroalkyl, $C_1$-$C_6$haloalkyl, $C_2$-$C_8$heterocycloalkyl, aryl, or heteroaryl;

each $R_4$ is independently H or $C_1$-$C_6$alkyl;

each $R_5$ is independently H or $C_1$-$C_6$alkyl;

m is an integer selected from 0-3; and n is an integer selected from 0-3;

or a pharmaceutically acceptable salt, pharmaceutically acceptable solvate, or pharmaceutically acceptable prodrug thereof.

In some embodiments is a compound of Formula (IX) wherein each $R_1$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, aryl, or heteroaryl. In some embodiments is a compound of Formula (IX) wherein each $R_1$ is independently F, Cl, Br, —$CF_3$, —$CH_3$, —$OCF_3$, or —$OCH_3$. In some embodiments is a compound of Formula (IX) wherein each $R_1$ is F. In some embodiments is a compound of Formula (IX) wherein each $R_1$ is Cl. In some embodiments is a compound of Formula (IX) wherein each $R_1$ is Br. In some embodiments is a compound of Formula (IX) wherein each $R_1$ is —$CF_3$. In some embodiments is a compound of Formula (IX) wherein each $R_1$ is —$CH_3$. In some embodiments is a compound of Formula (IX) wherein each $R_1$ is —$OCF_3$. In some embodiments is a compound of Formula (IX) wherein each $R_1$ is —$OCH_3$.

In some embodiments is a compound of Formula (IX) wherein each $R_2$ is independently F, Cl, Br, I, —CN, —$NR_4R_5$, —$NO_2$, —OH, —$CF_3$, —$OCF_3$, —$OC_1$-$C_6$alkyl, $C_1$-$C_6$alkyl, aryl, or heteroaryl. In some embodiments is a compound of Formula (IX) wherein each $R_2$ is independently F, Cl, Br, —$CF_3$, —$CH_3$, —$OCF_3$, or —$OCH_3$. In some embodiments is a compound of Formula (IX) wherein each $R_2$ is F. In some embodiments is a compound of Formula (IX) wherein each $R_2$ is Cl. In some embodiments is a compound of Formula (IX) wherein each $R_2$ is Br. In some embodiments is a compound of Formula (IX) wherein each $R_2$ is —$CF_3$. In some embodiments is a compound of Formula (IX) wherein each $R_2$ is —$CH_3$. In some embodiments is a compound of Formula (IX) wherein each $R_2$ is —$OCF_3$. In some embodiments is a compound of Formula (IX) wherein each $R_2$ is —$OCH_3$.

In another embodiment is a compound of Formula (IX) wherein m is 0 and n is 0.

In another embodiment is a compound of Formula (IX) wherein m is 0 and n is 1. In another embodiment is a compound of Formula (IX) wherein m is 1 and n is 0. In another embodiment is a compound of Formula (IX) wherein m is 0 and n is 2. In another embodiment is a compound of Formula (IX) wherein m is 2 and n is 0. In another embodiment is a compound of Formula (IX) wherein m is 1 and n is 1. In another embodiment is a compound of Formula (IX) wherein m is 1 and n is 2. In another embodiment is a compound of Formula (IX) wherein m is 2 and n is 2.

In another embodiment is a compound of Formula (IX) wherein m is 0, n is 1, and $R_1$ is F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (IX) wherein m is 0, n is 1, and $R_1$ is F, Cl, Br, —$CF_3$, —$CH_3$, —$OCF_3$, or —$OCH_3$. In another embodiment is a compound of Formula (IX) wherein m is 0, n is 1, and $R_1$ is F, Cl, Br, or —$CF_3$.

In another embodiment is a compound of Formula (IX) wherein m is 0, n is 2, and each $R_1$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (IX) wherein m is 0, n is 2, and each $R_1$ is independently F, Cl, Br, —$CF_3$, —$CH_3$, —$OCF_3$, or —$OCH_3$. In another embodiment is a compound of Formula (IX) wherein m is 0, n is 2, and each $R_1$ is independently F, Cl, Br, or —CF$_3$. In another embodiment is a compound of Formula (IX) wherein m is 0, n is 2, X is a bond, and two R$_1$ on adjacent carbon atoms are combined with the adjacent carbon atoms to form a —OCH$_2$O— ring.

In another embodiment is a compound of Formula (IX) wherein m is 1, n is 1, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (IX) wherein m is 1, n is 1, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (IX) wherein m is 1, n is 1, R$_1$ is F, Cl, Br, —CF$_3$, —CH$_3$, or —OCH$_3$, and R$_2$ is independently F, Cl, Br, or —CF$_3$.

In another embodiment is a compound of Formula (IX) wherein m is 1, n is 2, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (IX) wherein m is 1, n is 2, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (IX) wherein m is 1, n is 2, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (IX) wherein m is 2, n is 1, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (IX) wherein m is 2, n is 1, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (IX) wherein m is 2, n is 1, R$_1$ is independently F, Cl, Br, —CF$_3$, —CH$_3$, or —OCH$_3$, and each R$_2$ is independently F, Cl, Br, or —CF$_3$.

In another embodiment, provided herein is a pharmaceutical composition comprising a compound of Formula (IX), or a pharmaceutically acceptable salt, solvate, prodrug, or N-oxide thereof, and a pharmaceutically acceptable excipient. In another embodiment, the pharmaceutical composition comprising the compound of Formula (IX), or a pharmaceutically acceptable salt, pharmaceutically acceptable solvate, pharmaceutically acceptable prodrug, or N-oxide thereof, is formulated for a route of administration selected from oral administration, parenteral administration, buccal administration, nasal administration, topical administration, or rectal administration.

In another aspect is a method for treating an autoimmune disease or condition comprising administering to an individual in need a therapeutically effective amount of a compound of Formula (IX), or a pharmaceutically acceptable salt, pharmaceutically acceptable solvate, pharmaceutically acceptable prodrug, or N-oxide thereof. In some embodiments, the autoimmune disease is selected from type-1-diabetes, multiple sclerosis, rheumatoid arthritis and lupus. In another embodiment is a method for treating type-1-diabetes comprising administering to an individual in need a therapeutically effective amount of a compound of Formula (IX), or a pharmaceutically acceptable salt, pharmaceutically acceptable solvate, pharmaceutically acceptable prodrug, or N-oxide thereof. In another embodiment is a method for treating multiple sclerosis comprising administering to an individual in need a therapeutically effective amount of a compound of Formula (IX), or a pharmaceutically acceptable salt, pharmaceutically acceptable solvate, pharmaceutically acceptable prodrug, or N-oxide thereof. In another embodiment is a method for treating rheumatoid arthritis comprising administering to an individual in need a therapeutically effective amount of a compound of Formula (IX), or a pharmaceutically acceptable salt, pharmaceutically acceptable solvate, pharmaceutically acceptable prodrug, or N-oxide thereof. In another embodiment is a method for treating lupus comprising administering to an individual in need a therapeutically effective amount of a compound of Formula (IX), or a pharmaceutically acceptable salt, pharmaceutically acceptable solvate, pharmaceutically acceptable prodrug, or N-oxide thereof.

In another aspect is a method for treating a cardiovascular disease or condition comprising administering to an individual in need a therapeutically effective amount of a compound of Formula (IX), or a pharmaceutically acceptable salt, pharmaceutically acceptable solvate, pharmaceutically acceptable prodrug, or N-oxide thereof. In one embodiment, the cardiovascular disease is atherosclerosis.

In another aspect is a method of treating a viral infection comprising administering to an individual in need a therapeutically effective amount of a compound of Formula (IX), or a pharmaceutically acceptable salt, pharmaceutically acceptable solvate, pharmaceutically acceptable prodrug, or N-oxide thereof. In some embodiments, the viral infection is an Epstein-Barr viral infection.

In another aspect is a method of treating cancer comprising administering to an individual in need a therapeutically effective amount of a compound of Formula (IX), or a pharmaceutically acceptable salt, pharmaceutically acceptable solvate, pharmaceutically acceptable prodrug, or N-oxide thereof. In one embodiment, the cancer is blood, brain, breast, colorectal, gastrointestinal, liver, lung, ovarian, pancreatic, prostate, skin or uterine cancer. In some embodiments, the cancer produces molecules involved in Epstein-Barr virus (EBV)-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

In another aspect, described herein is a method of treating a disease, disorder or condition mediated by EBI2 in a subject in need thereof, which method comprises administering to the subject a therapeutically effective amount of a compound of Formula (IX), or a pharmaceutically acceptable salt thereof. In another aspect, described herein is a method of treating a disease in a subject mediated by EBI2, which method comprises administering to the subject a pharmaceutical composition comprising a compound of Formula (IX), or a pharmaceutically acceptable salt thereof. In some embodiments, the disease, disorder or condition is an autoimmune disease or condition. In some embodiments, the autoimmune disease or condition is selected from type-1-diabetes, multiple sclerosis, rheumatoid arthritis and lupus. In some embodiments, the disease, disorder or condition is a cardiovascular disease or condition. In some embodiments, the cardiovascular disease or condition is atherosclerosis. In some embodiments, the disease, disorder or condition is a viral infection. In some embodiments, the viral infection is an Epstein-Barr viral infection. In some embodiments, the disease, disorder or condition is cancer. In some embodiments, the cancer is blood, brain, breast, colorectal, gastrointestinal, liver, lung, ovarian, pancreatic, prostate, skin or uterine cancer. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

Also provided is the use a compound of Formula (IX), or a pharmaceutically acceptable salt, pharmaceutically acceptable solvate, pharmaceutically acceptable prodrug, or N-oxide thereof for the treatment of an autoimmune disease or condition in a human. In some embodiments is the use a compound of Formula (IX), or a pharmaceutically acceptable salt, pharmaceutically acceptable solvate, pharmaceutically acceptable prodrug, or N-oxide thereof for the treatment of an autoimmune disease or condition in a human, wherein the autoimmune disease or condition is selected from type-1-diabetes, multiple sclerosis, rheumatoid arthritis and lupus.

Further provided is the use a compound of Formula (IX), or a pharmaceutically acceptable salt, pharmaceutically acceptable solvate, pharmaceutically acceptable prodrug, or N-oxide thereof for the treatment of a cardiovascular disease or condition in a human. In some embodiments is the use a compound of Formula (IX), or a pharmaceutically acceptable salt, pharmaceutically acceptable solvate, pharmaceutically acceptable prodrug, or N-oxide thereof for the treatment of atherosclerosis in a human.

Further provided is the use a compound of Formula (IX), or a pharmaceutically acceptable salt, pharmaceutically acceptable solvate, pharmaceutically acceptable prodrug, or N-oxide thereof for the treatment of a viral infection in a human. In some embodiments is the use a compound of Formula (IX), or a pharmaceutically acceptable salt, pharmaceutically acceptable solvate, pharmaceutically acceptable prodrug, or N-oxide thereof for the treatment of an Epstein-Barr viral infection in a human.

Also provided is the use a compound of Formula (IX), or a pharmaceutically acceptable salt, pharmaceutically acceptable solvate, pharmaceutically acceptable prodrug, or N-oxide thereof for the manufacture of a medicament for the treatment of an autoimmune disease or condition in a human. In some embodiments is the use a compound of Formula (IX), or a pharmaceutically acceptable salt, pharmaceutically acceptable solvate, pharmaceutically acceptable prodrug, or N-oxide thereof for the manufacture of a medicament for the treatment of an autoimmune disease or condition in a human, wherein the autoimmune disease or condition is selected from type-1-diabetes, multiple sclerosis, rheumatoid arthritis and lupus.

Further provided is the use a compound of Formula (IX), or a pharmaceutically acceptable salt, pharmaceutically acceptable solvate, pharmaceutically acceptable prodrug, or N-oxide thereof for the manufacture of a medicament for the treatment of a cardiovascular disease or condition in a human. In some embodiments is the use a compound of Formula (IX), or a pharmaceutically acceptable salt, pharmaceutically acceptable solvate, pharmaceutically acceptable prodrug, or N-oxide thereof for the manufacture of a medicament for the treatment of atherosclerosis in a human.

Further provided is the use a compound of Formula (IX), or a pharmaceutically acceptable salt, pharmaceutically acceptable solvate, pharmaceutically acceptable prodrug, or N-oxide thereof for the manufacture of a medicament for the treatment of a viral infection in a human. In some embodiments is the use a compound of Formula (IX), or a pharmaceutically acceptable salt, pharmaceutically acceptable solvate, pharmaceutically acceptable prodrug, or N-oxide thereof for the manufacture of a medicament for the treatment of an Epstein-Barr viral infection in a human.

In any of the aforementioned aspects are further embodiments in which: (a) the effective amount of the compound of Formula (IX), is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (IX), or a pharmaceutically acceptable salt thereof, to a subject are further embodiments comprising administering at least one additional agent in addition to the administration of a compound having the structure of Formula (IX), or a pharmaceutically acceptable salt thereof. In various embodiments, the compound of Formula (IX), and the additional agent are administered in any order, including simultaneously. In some embodiments, the compound of Formula (IX), and the additional agent are administered to the subject in the same pharmaceutical composition or in separate pharmaceutical compositions.

In some embodiments is a compound having the structure of Formula (X):

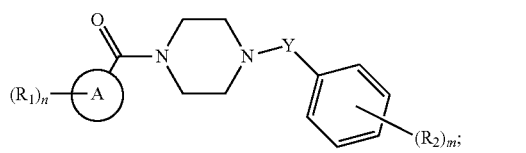

Formula (X)

wherein:

A is a bicyclic heteroaryl;

Y is a bond, —CH$_2$—, —C(H)(Ph)-, —C(=O)—, or —S(=O)$_2$—;

each R$_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, C$_3$-C$_8$cycloalkyl, C$_1$-C$_6$heteroalkyl, C$_1$-C$_6$haloalkyl, C$_2$-C$_8$heterocycloalkyl, aryl, or heteroaryl; or two R$_1$ on adjacent carbon atoms are combined with the adjacent carbon atoms to form a —OCH$_2$O— ring;

each R$_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, —C(=O)C$_1$-C$_6$alkyl, CO$_2$H, B(OH)$_2$, PO$_3$H, C$_3$-C$_8$cycloalkyl, C$_1$-C$_6$heteroalkyl, C$_1$-C$_6$haloalkyl, C$_2$-C$_8$heterocycloalkyl, aryl, or heteroaryl;

R$_3$ is C$_1$-C$_6$alkyl;

each R$_4$ is independently H or C$_1$-C$_6$alkyl;

each R$_5$ is independently H or C$_1$-C$_6$alkyl;

m is an integer selected from 0-3; and n is an integer selected from 0-3;

or a pharmaceutically acceptable salt, pharmaceutically acceptable solvate, or pharmaceutically acceptable prodrug thereof.

In some embodiments is a compound of Formula (X) wherein Y is a bond. In another embodiment is a compound of Formula (X) wherein Y is —CH$_2$—. In another embodiment is a compound of Formula (X) wherein Y is —C(H)(Ph)-. In another embodiment is a compound of Formula (X) wherein Y is —C(=O)—. In another embodiment is a compound of Formula (X) wherein Y is —S(=O)$_2$—.

In some embodiments is a compound of Formula (X) wherein each R$_1$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, aryl, or heteroaryl. In some embodiments is a compound of Formula (X) wherein each R$_1$ is independently F, Cl, Br, —CF$_3$, —CH$_3$, —OCF$_3$, or —OCH$_3$. In some embodiments is a compound of Formula (X) wherein each R$_1$ is F. In some embodiments is a compound of Formula (X) wherein each R$_1$ is Cl. In some embodiments is a compound of Formula (X) wherein each R$_1$ is Br. In some embodiments is a compound of Formula (X) wherein each R$_1$ is —CF$_3$. In some embodiments is a compound of Formula (X) wherein each R$_1$ is —CH$_3$. In some embodiments is a compound of Formula (X) wherein each R$_1$ is —OCF$_3$. In some embodiments is a compound of Formula (X) wherein each R$_1$ is —OCH$_3$.

In some embodiments is a compound of Formula (X) wherein each R$_2$ is independently F, Cl, Br, I, —CN, —NR$_4$R$_5$, —NO$_2$, —OH, —CF$_3$, —OCF$_3$, —OC$_1$-C$_6$alkyl, C$_1$-C$_6$alkyl, aryl, or heteroaryl. In some embodiments is a compound of Formula (X) wherein each R$_2$ is independently F, Cl, Br, —CF$_3$, —CH$_3$, —OCF$_3$, or —OCH$_3$. In some embodiments is a compound of Formula (X) wherein each R$_2$ is F. In some embodiments is a compound of Formula (X) wherein each R$_2$ is Cl. In some embodiments is a compound of Formula (X) wherein each R$_2$ is Br. In some embodiments is a compound of Formula (X) wherein each R$_2$ is —CF$_3$. In some embodiments is a compound of Formula (X) wherein each R$_2$ is —CH$_3$. In some embodiments is a compound of Formula (X) wherein each R$_2$ is —OCF$_3$. In some embodiments is a compound of Formula (X) wherein each R$_2$ is —OCH$_3$.

In another embodiment is a compound of Formula (X) wherein m is 0 and n is 0.

In another embodiment is a compound of Formula (X) wherein m is 0 and n is 1. In another embodiment is a compound of Formula (X) wherein m is 1 and n is 0. In another embodiment is a compound of Formula (X) wherein m is 0 and n is 2. In another embodiment is a compound of Formula (X) wherein m is 2 and n is 0. In another embodiment is a compound of Formula (X) wherein m is 1 and n is 1. In another embodiment is a compound of Formula (X) wherein m is 1 and n is 2. In another embodiment is a compound of Formula (X) wherein m is 2 and n is 2.

In another embodiment is a compound of Formula (X) wherein m is 0, n is 1, Y is a bond, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 1, Y is a bond, and R$_1$ is F, Cl, Br, —CF$_3$, —CH$_3$, —OCF$_3$, or —OCH$_3$. In another embodiment is a compound of Formula (X) wherein m is 0, n is 1, Y is a bond, and R$_1$ is F, Cl, Br, or —CF$_3$.

In another embodiment is a compound of Formula (X) wherein m is 0, n is 2, Y is a bond, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 2, Y is a bond, and each R$_1$ is independently F, Cl, Br, —CF$_3$, —CH$_3$, —OCF$_3$, or —OCH$_3$. In another embodiment is a compound of Formula (X) wherein m is 0, n is 2, Y is a bond, and each R$_1$ is independently F, Cl, Br, or —CF$_3$. In another embodiment is a compound of Formula (X) wherein m is 0, n is 2, Y is a bond, and two R$_1$ on adjacent carbon atoms are combined with the adjacent carbon atoms to form a —OCH$_2$O— ring.

In another embodiment is a compound of Formula (X) wherein m is 1, n is 1, Y is a bond, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 1, Y is a bond, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 1, Y is a bond, R$_1$ is F, Cl, Br, —CF$_3$, —CH$_3$, or —OCH$_3$, and R$_2$ is independently F, Cl, Br, or —CF$_3$.

In another embodiment is a compound of Formula (X) wherein m is 1, n is 2, Y is a bond, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 2, Y is a bond, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 2, Y is a bond, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (X) wherein m is 2, n is 1, Y is a bond, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 2, n is 1, X is —N(H)—, Y is a bond, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (X) wherein m is 2, n is 1, X is —N(H)—, Y is a bond, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (X) wherein m is 0, n is 1, Y is —CH$_2$—, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 1, Y is —CH$_2$—, and R$_1$ is F, Cl, Br, —CF$_3$, —CH$_3$, —OCF$_3$, or —OCH$_3$. In another embodiment is a compound of Formula (X) wherein m is 0, n is 1, Y is —CH$_2$—, and R$_1$ is F, Cl, Br, or —CF$_3$.

In another embodiment is a compound of Formula (X) wherein m is 0, n is 2, Y is —CH$_2$—, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 2, Y is —CH$_2$—, and each R$_1$ is independently F, Cl, Br, —CF$_3$, —CH$_3$, —OCF$_3$, or —OCH$_3$. In another embodiment is a compound of Formula (X) wherein m is 0, n is 2, Y is —CH$_2$—, and each R$_1$ is independently F, Cl, Br, or —CF$_3$. In another embodiment is a compound of Formula (X) wherein m is 0, n is 2, Y is —CH$_2$—, and two R$_1$ on adjacent carbon atoms are combined with the adjacent carbon atoms to form a —OCH$_2$O— ring.

In another embodiment is a compound of Formula (X) wherein m is 1, n is 1, Y is —CH$_2$—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 1, Y is —CH$_2$—, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 1, Y is —CH$_2$—, R$_1$ is F, Cl, Br, —CF$_3$, —CH$_3$, or —OCH$_3$, and R$_2$ is independently F, Cl, Br, or —CF$_3$.

In another embodiment is a compound of Formula (X) wherein m is 1, n is 2, Y is —CH$_2$—, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 2, Y is —CH$_2$—, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 2, Y is —CH$_2$—, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (X) wherein m is 2, n is 1, Y is —CH$_2$—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 2, n is 1, Y is —CH$_2$—, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (X) wherein m is 2, n is 1, Y is —CH$_2$—, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (X) wherein m is 0, n is 1, Y is —C(H)(Ph)-, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 1, Y is —C(H)(Ph)-, and R$_1$ is F, Cl, Br, —CF$_3$, —CH$_3$, —OCF$_3$, or —OCH$_3$. In another embodiment is a compound of Formula (X) wherein m is 0, n is 1, Y is —C(H)(Ph)-, and R$_1$ is F, Cl, Br, or —CF$_3$.

In another embodiment is a compound of Formula (X) wherein m is 0, n is 2, Y is —C(H)(Ph)-, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 2, Y is —C(H)(Ph)-, and each R$_1$ is independently F, Cl, Br, —CF$_3$, —CH$_3$, —OCF$_3$, or —OCH$_3$. In another embodiment is a compound of Formula (X) wherein m is 0, n is 2, Y is —C(H)(Ph)-, and each R$_1$ is independently F, Cl, Br, or —CF$_3$. In another embodiment is a compound of Formula (X) wherein m is 0, n is 2, Y is —C(H)(Ph)-, and two R$_1$ on adjacent carbon atoms are combined with the adjacent carbon atoms to form a —OCH$_2$O— ring.

In another embodiment is a compound of Formula (X) wherein m is 1, n is 1, Y is —C(H)(Ph)-, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 1, Y is —C(H)(Ph)-, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 1, Y is —C(H)(Ph)-, R$_1$ is F, Cl, Br, —CF$_3$, —CH$_3$, or —OCH$_3$, and R$_2$ is independently F, Cl, Br, or —CF$_3$.

In another embodiment is a compound of Formula (X) wherein m is 1, n is 2, Y is —C(H)(Ph)-, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 2, Y is —C(H)(Ph)-, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 2, Y is —C(H)(Ph)-, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (X) wherein m is 2, n is 1, Y is —C(H)(Ph)-, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 2, n is 1, Y is —C(H)(Ph)-, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (X) wherein m is 2, n is 1, Y is —C(H)(Ph)-, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (X) wherein m is 0, n is 1, Y is —C(=O)—, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 1, Y is —C(=O)—, and R$_1$ is F, Cl, Br, —CF$_3$, —CH$_3$, —OCF$_3$, or —OCH$_3$. In another embodiment is a compound of Formula (X) wherein m is 0, n is 1, Y is —C(=O)—, and R$_1$ is F, Cl, Br, or —CF$_3$.

In another embodiment is a compound of Formula (X) wherein m is 0, n is 2, Y is —C(=O)—, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 2, Y is —C(=O)—, and each R$_1$ is independently F, Cl, Br, —CF$_3$, —CH$_3$, —OCF$_3$, or —OCH$_3$. In another embodiment is a compound of Formula (X) wherein m is 0, n is 2, Y is —C(=O)—, and each R$_1$ is independently F, Cl, Br, or —CF$_3$. In another embodiment is a compound of Formula (X) wherein m is 0, n is 2, Y is —C(=O)—, and two R$_1$ on adjacent carbon atoms are combined with the adjacent carbon atoms to form a —OCH$_2$O— ring.

In another embodiment is a compound of Formula (X) wherein m is 1, n is 1, Y is —C(=O)—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 1, Y is —C(=O)—, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 1, Y is —C(=O)—, R$_1$ is F, Cl, Br, —CF$_3$, —CH$_3$, or —OCH$_3$, and R$_2$ is independently F, Cl, Br, or —CF$_3$.

In another embodiment is a compound of Formula (X) wherein m is 1, n is 2, Y is —C(=O)—, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 2, Y is —C(=O)—, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 2, Y is —C(=O)—, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (X) wherein m is 2, n is 1, Y is —C(=O)—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and each R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 2, n is 1, Y is —C(=O)—, R$_1$ is independently F, Cl, Br, —CF$_3$, —CH$_3$, —OCF$_3$, or —OCH$_3$, and each R$_2$ is independently F, Cl, Br, —CF$_3$, —CH$_3$, —OCF$_3$, or —OCH$_3$. In another embodiment is a compound of Formula (X) wherein m is 2, n is 1, Y is —C(=O)—, R$_1$ is independently F, Cl, Br, —CF$_3$, —CH$_3$, or —OCH$_3$, and each R$_2$ is independently F, Cl, Br, or —CF$_3$.

In another embodiment is a compound of Formula (X) wherein m is 0, n is 1, Y is —S(=O)$_2$—, and R$_1$ is F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 1, Y is —S(=O)$_2$—, and R$_1$ is F, Cl, Br, —CF$_3$, —CH$_3$, —OCF$_3$, or —OCH$_3$. In another embodiment is a compound of Formula (X) wherein m is 0, n is 1, Y is —S(=O)$_2$—, and R$_1$ is F, Cl, Br, or —CF$_3$.

In another embodiment is a compound of Formula (X) wherein m is 0, n is 2, Y is —S(=O)$_2$—, and each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 0, n is 2, Y is —S(=O)$_2$—, and each R$_1$ is independently F, Cl, Br, —CF$_3$, —CH$_3$, —OCF$_3$, or —OCH$_3$. In another embodiment is a compound of Formula (X) wherein m is 0, n is 2, Y is —S(=O)$_2$—, and each R$_1$ is independently F, Cl, Br, or —CF$_3$. In another embodiment is a compound of Formula (X) wherein m is 0, n is 2, Y is —S(=O)$_2$—, and two R$_1$ on adjacent carbon atoms are combined with the adjacent carbon atoms to form a —OCH$_2$O— ring.

In another embodiment is a compound of Formula (X) wherein m is 1, n is 1, Y is —S(=O)$_2$—, R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 1, Y is —S(=O)$_2$—, R$_1$ is F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 1, Y is —S(=O)$_2$—, R$_1$ is F, Cl, Br, —CF$_3$, —CH$_3$, or —OCH$_3$, and R$_2$ is independently F, Cl, Br, or —CF$_3$.

In another embodiment is a compound of Formula (X) wherein m is 1, n is 2, Y is —S(=O)$_2$—, each R$_1$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl, and R$_2$ is independently F, Cl, Br, —CN, —NR$_4$R$_5$, —NO$_2$, —CF$_3$, —OCF$_3$, —OH, —C$_1$-C$_6$alkyl, or —OC$_1$-C$_6$alkyl. In another embodiment is a compound of Formula (X) wherein m is 1, n is 2, Y is —S(=O)$_2$—, each R$_1$ is independently F, Cl, Br, —CF$_3$, —CH$_3$, —OCF$_3$, or —OCH$_3$, and R$_2$ is independently F, Cl, Br, —CF$_3$, —CH$_3$, —OCF$_3$, or —OCH$_3$. In another embodiment is a compound of Formula (X) wherein m is 1, n is 2, Y is —S(=O)$_2$—, each R$_1$ is independently F, Cl, Br, —CF$_3$, —CH$_3$, or —OCH$_3$, and R$_2$ is independently F, Cl, Br, or —CF$_3$.

In another embodiment is a compound of Formula (X) wherein m is 2, n is 1, Y is —S(=O)$_2$—, R$_1$ is independently F, Cl, Br, —CN, —NR$_4$R$_5$, —NO$_2$, —CF$_3$, —OCF$_3$, —OH, —$C_1$-$C_6$alkyl, or —$OC_1$-$C_6$alkyl, and each $R_2$ is independently F, Cl, Br, —CN, —$NR_4R_5$, —$NO_2$, —$CF_3$, —$OCF_3$, —OH, —$C_1$-$C_6$alkyl, or —$OC_1$-$C_6$alkyl. In another embodiment is a compound of Formula (X) wherein m is 2, n is 1, Y is —S(=O)$_2$—, $R_1$ is independently F, Cl, Br, —$CF_3$, —$CH_3$, —$OCF_3$, or —$OCH_3$, and each $R_2$ is independently F, Cl, Br, —$CF_3$, —$CH_3$, —$OCF_3$, or —$OCH_3$. In another embodiment is a compound of Formula (X) wherein m is 2, n is 1, Y is —S(=O)$_2$—, $R_1$ is independently F, Cl, Br, —$CF_3$, —$CH_3$, or —$OCH_3$, and each $R_2$ is independently F, Cl, Br, or —$CF_3$.

In another embodiment, provided herein is a pharmaceutical composition comprising a compound of Formula (X), or a pharmaceutically acceptable salt, solvate, prodrug, or N-oxide thereof, and a pharmaceutically acceptable excipient. In another embodiment, the pharmaceutical composition comprising the compound of Formula (X), or a pharmaceutically acceptable salt, pharmaceutically acceptable solvate, pharmaceutically acceptable prodrug, or N-oxide thereof, is formulated for a route of administration selected from oral administration, parenteral administration, buccal administration, nasal administration, topical administration, or rectal administration.

In another aspect is a method for treating an autoimmune disease or condition comprising administering to an individual in need a therapeutically effective amount of a compound of Formula (X), or a pharmaceutically acceptable salt, pharmaceutically acceptable solvate, pharmaceutically acceptable prodrug, or N-oxide thereof. In some embodiments, the autoimmune disease is selected from type-1-diabetes, multiple sclerosis, rheumatoid arthritis and lupus. In another embodiment is a method for treating type-1-diabetes comprising administering to an individual in need a therapeutically effective amount of a compound of Formula (X), or a pharmaceutically acceptable salt, pharmaceutically acceptable solvate, pharmaceutically acceptable prodrug, or N-oxide thereof. In another embodiment is a method for treating multiple sclerosis comprising administering to an individual in need a therapeutically effective amount of a compound of Formula (X), or a pharmaceutically acceptable salt, pharmaceutically acceptable solvate, pharmaceutically acceptable prodrug, or N-oxide thereof. In another embodiment is a method for treating rheumatoid arthritis comprising administering to an individual in need a therapeutically effective amount of a compound of Formula (X), or a pharmaceutically acceptable salt, pharmaceutically acceptable solvate, pharmaceutically acceptable prodrug, or N-oxide thereof. In another embodiment is a method for treating lupus comprising administering to an individual in need a therapeutically effective amount of a compound of Formula (X), or a pharmaceutically acceptable salt, pharmaceutically acceptable solvate, pharmaceutically acceptable prodrug, or N-oxide thereof.

In another aspect is a method for treating a cardiovascular disease or condition comprising administering to an individual in need a therapeutically effective amount of a compound of Formula (X), or a pharmaceutically acceptable salt, pharmaceutically acceptable solvate, pharmaceutically acceptable prodrug, or N-oxide thereof. In one embodiment, the cardiovascular disease is atherosclerosis.

In another aspect is a method of treating a viral infection comprising administering to an individual in need a therapeutically effective amount of a compound of Formula (X), or a pharmaceutically acceptable salt, pharmaceutically acceptable solvate, pharmaceutically acceptable prodrug, or N-oxide thereof. In some embodiments, the viral infection is an Epstein-Barr viral infection.

In another aspect is a method of treating cancer comprising administering to an individual in need a therapeutically effective amount of a compound of Formula (X), or a pharmaceutically acceptable salt, pharmaceutically acceptable solvate, pharmaceutically acceptable prodrug, or N-oxide thereof. In one embodiment, the cancer is blood, brain, breast, colorectal, gastrointestinal, liver, lung, ovarian, pancreatic, prostate, skin or uterine cancer. In some embodiments, the cancer produces molecules involved in Epstein-Barr virus (EBV)-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

In another aspect, described herein is a method of treating a disease, disorder or condition mediated by EBI2 in a subject in need thereof, which method comprises administering to the subject a therapeutically effective amount of a compound of Formula (X), or a pharmaceutically acceptable salt thereof. In another aspect, described herein is a method of treating a disease in a subject mediated by EBI2, which method comprises administering to the subject a pharmaceutical composition comprising a compound of Formula (X), or a pharmaceutically acceptable salt thereof. In some embodiments, the disease, disorder or condition is an autoimmune disease or condition. In some embodiments, the autoimmune disease or condition is selected from type-1-diabetes, multiple sclerosis, rheumatoid arthritis and lupus. In some embodiments, the disease, disorder or condition is a cardiovascular disease or condition. In some embodiments, the cardiovascular disease or condition is atherosclerosis. In some embodiments, the disease, disorder or condition is a viral infection. In some embodiments, the viral infection is an Epstein-Barr viral infection. In some embodiments, the disease, disorder or condition is cancer. In some embodiments, the cancer is blood, brain, breast, colorectal, gastrointestinal, liver, lung, ovarian, pancreatic, prostate, skin or uterine cancer. In some embodiments, the cancer produces molecules involved in Epstein-Barr virus-induced G-protein coupled receptor 2 (EBI2) mediated signaling. In some embodiments, the molecules are EBI2 receptor. In some embodiments, the cancer is associated with EBV or other herpes virus infections. In some embodiments, the cancer is a hematopoietic tumor. In some embodiments, the hematopoietic tumor is a tumor of myeloid or lymphoid tissues. In some embodiments, the cancer is a brain cancer. In some embodiments, the EBI2 receptor is mutated or its expression level altered. In some embodiments, the molecules are oxysterols. In some embodiments, the oxysterol is an EBI2 ligand. In some embodiments, the oxysterol level is altered. In some embodiments, the molecule is an enzyme involved in metabolism of oxysterols. In some embodiments, the enzyme is mutated or its expression level altered.

Also provided is the use a compound of Formula (X), or a pharmaceutically acceptable salt, pharmaceutically acceptable solvate, pharmaceutically acceptable prodrug, or N-oxide thereof for the treatment of an autoimmune disease or condition in a human. In some embodiments is the use a compound of Formula (X), or a pharmaceutically acceptable salt, pharmaceutically acceptable solvate, pharmaceutically acceptable prodrug, or N-oxide thereof for the treatment of an autoimmune disease or condition in a human, wherein the autoimmune disease or condition is selected from type-1-diabetes, multiple sclerosis, rheumatoid arthritis and lupus.

Further provided is the use a compound of Formula (X), or a pharmaceutically acceptable salt, pharmaceutically acceptable solvate, pharmaceutically acceptable prodrug, or N-oxide thereof for the treatment of a cardiovascular disease or condition in a human. In some embodiments is the use a compound of Formula (X), or a pharmaceutically acceptable salt, pharmaceutically acceptable solvate, pharmaceutically acceptable prodrug, or N-oxide thereof for the treatment of atherosclerosis in a human.

Further provided is the use a compound of Formula (X), or a pharmaceutically acceptable salt, pharmaceutically acceptable solvate, pharmaceutically acceptable prodrug, or N-oxide thereof for the treatment of a viral infection in a human. In some embodiments is the use a compound of Formula (X), or a pharmaceutically acceptable salt, pharmaceutically acceptable solvate, pharmaceutically acceptable prodrug, or N-oxide thereof for the treatment of an Epstein-Barr viral infection in a human.

Also provided is the use a compound of Formula (X), or a pharmaceutically acceptable salt, pharmaceutically acceptable solvate, pharmaceutically acceptable prodrug, or N-oxide thereof for the manufacture of a medicament for the treatment of an autoimmune disease or condition in a human. In some embodiments is the use a compound of Formula (X), or a pharmaceutically acceptable salt, pharmaceutically acceptable solvate, pharmaceutically acceptable prodrug, or N-oxide thereof for the manufacture of a medicament for the treatment of an autoimmune disease or condition in a human, wherein the autoimmune disease or condition is selected from type-1-diabetes, multiple sclerosis, rheumatoid arthritis and lupus.

Further provided is the use a compound of Formula (X), or a pharmaceutically acceptable salt, pharmaceutically acceptable solvate, pharmaceutically acceptable prodrug, or N-oxide thereof for the manufacture of a medicament for the treatment of a cardiovascular disease or condition in a human. In some embodiments is the use a compound of Formula (X), or a pharmaceutically acceptable salt, pharmaceutically acceptable solvate, pharmaceutically acceptable prodrug, or N-oxide thereof for the manufacture of a medicament for the treatment of atherosclerosis in a human.

Further provided is the use a compound of Formula (X), or a pharmaceutically acceptable salt, pharmaceutically acceptable solvate, pharmaceutically acceptable prodrug, or N-oxide thereof for the manufacture of a medicament for the treatment of a viral infection in a human. In some embodiments is the use a compound of Formula (X), or a pharmaceutically acceptable salt, pharmaceutically acceptable solvate, pharmaceutically acceptable prodrug, or N-oxide thereof for the manufacture of a medicament for the treatment of an Epstein-Barr viral infection in a human.

In any of the aforementioned aspects are further embodiments in which: (a) the effective amount of the compound of Formula (X), is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (X), or a pharmaceutically acceptable salt thereof, to a subject are further embodiments comprising administering at least one additional agent in addition to the administration of a compound having the structure of Formula (X), or a pharmaceutically acceptable salt thereof. In various embodiments, the compound of Formula (X), and the additional agent are administered in any order, including simultaneously. In some embodiments, the compound of Formula (X), and the additional agent are administered to the subject in the same pharmaceutical composition or in separate pharmaceutical compositions.

In another embodiment is a compound having the structure of Formula (XI):

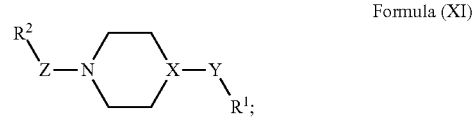

Formula (XI)

wherein:
$R^1$ and $R^2$ are independently selected from the group consisting of optionally substituted phenyl, optionally substituted 5- or 6-membered heteroaryl, or optionally substituted cycloalkyl;
Y and Z are independently a bond, O, —C(O)—N($R^3$)—, —C(O)—O—, —N($R^4$)—, —C($R^5$)($R^6$)—, SO$_2$, S, C(O)=CH—, C(O)=C$R^7$—, spiroalkyl, spiroheteroalkyl;
X is CH— or N—;
$R^3$-$R^7$ are independently selected from the group consisting of optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

$R^{10}$ and $R^{11}$ are independently selected from the group consisting of hydrogen, halogen, —CN, —S(O)$R^{12}$—C(O)—N($R^{13}$)—$R^{14}$, —C(O)—O—$R^{15}$, —SO$_2$N($R^{16}$)($R^{17}$) optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

or a pharmaceutically acceptable salt, polymorph, solvate, tautomer, or N-oxide thereof.

In another embodiment is a compound of Formula (XI) wherein the compound is a selective EBI2 antagonist or inverse agonist.

In another aspect, provided herein is a pharmaceutical composition comprising a compound of Formula (XI) or a pharmaceutically acceptable salt thereof, and a pharmaceutically acceptable excipient.

In another aspect is a method of treating a disease in a subject mediated by EBI2 comprising administering to a subject a pharmaceutical composition comprising a compound of Formula (XI) or a pharmaceutically acceptable salt thereof, and a pharmaceutically acceptable excipient.

In another embodiment is a compound having the structure of Formula (XII):

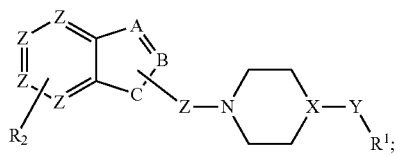

Formula (XII)

wherein:

$R^1$ and $R^2$ are independently selected from the group consisting of optionally substituted phenyl, optionally substituted 5- or 6-membered heteroaryl, or optionally substituted cycloalkyl;

Y and Z are independently a bond, O, —C(O)—N($R^3$)—, —C(O)—O—, —N($R^4$)—, —C($R^5$)($R^6$)—, SO$_2$, S, C(O)=CH—, C(O)=C$R^7$—, spiroalkyl, spiroheteroalkyl;

Z is independently C$R^8$ or N;

X is CH— or N—;

A, B and C are independently N, O, S, C$R^9$;

$R^3$-$R^9$ are independently selected from the group consisting of optionally substituted alkyl, optionally substituted cycloalkyl, optionally substituted heterocycloalkyl, optionally substituted alkoxy, haloalkyl, haloalkoxy, optionally substituted phenyl, and optionally substituted 5- or 6-membered heteroaryl;

or a pharmaceutically acceptable salt, polymorph, solvate, tautomer, or N-oxide thereof.

In another embodiment is a compound of Formula (XII) wherein the compound is a selective EBI2 antagonist or inverse agonist.

In another aspect, provided herein is a pharmaceutical composition comprising a compound of Formula (XII) or a pharmaceutically acceptable salt thereof, and a pharmaceutically acceptable excipient.

In another aspect is a method of treating a disease in a subject mediated by EBI2 comprising administering to a subject a pharmaceutical composition comprising a compound of Formula (XII) or a pharmaceutically acceptable salt thereof, and a pharmaceutically acceptable excipient.

In another embodiment is a compound selected from:

(2E)-3-(4-bromophenyl)-1-{4-[(4-chlorophenyl)carbonyl]piperazinyl}prop-2-en-1-one
(2E)-3-(4-bromophenyl)-1-{4-[(4-methoxyphenyl)carbonyl]piperazinyl}prop-2-en-1-one
(E)-(4-(4-(3-(4-bromophenyl)acryloyl)piperazine-1-carbonyl)phenyl)phosphonic acid
(2E)-3-(4-bromophenyl)-1-(4-{[4-(trifluoromethyl)phenyl]carbonyl}piperazinyl)prop-2-en-1-one
(2E)-3-(3,4-dichlorophenyl)-1-[4-(diphenylmethyl)piperazinyl]prop-2-en-1-one
(2E)-3-(3,4-dichlorophenyl)-1-(4-{[4-(trifluoromethyl)phenyl]carbonyl}piperazinyl)prop-2-en-1-one
3-(4-chlorophenyl)-1-{4-[(4-methoxyphenyl)carbonyl]piperazinyl}prop-2-yn-1-one
1-{4-[(4-methoxyphenyl)carbonyl]piperazinyl}-3-(4-methylphenyl)prop-2-yn-1-one
1-{4-[(4-methoxyphenyl)carbonyl]piperazinyl}-3-[4-(trifluoromethyl)phenyl]prop-2-yn-1-one
3-(4-bromophenyl)-1-{4-[(4-methoxyphenyl)carbonyl]piperazinyl}prop-2-yn-1-one
3-(3,4-dichlorophenyl)-1-{4-[(4-methoxyphenyl)carbonyl]piperazinyl}prop-2-en-1-one
3-(3,4-dichlorophenyl)-1-{4-[(4-methoxyphenyl)carbonyl]piperazinyl}prop-2-yn-1-one
(2E)-3-(4-bromophenyl)-1-[4-(phenylamino)piperidyl]prop-2-en-1-one
(2E)-3-(4-bromophenyl)-1-[4-(phenylcarbonyl)piperazinyl]prop-2-en-1-one
(2E)-1-{4-[(3,5-difluorophenyl)amino]piperidyl}-3-(4-bromophenyl)prop-2-en-1-one
3-(4-chlorophenyl)-1-{4-[(4-chlorophenyl)carbonyl]piperazinyl}prop-2-yn-1-one
(2E)-1-[4-(diphenylmethyl)piperazinyl]-3-(4-methoxyphenyl)prop-2-en-1-one
3-(2,3-dichlorophenyl)-1-{4-[(4-fluorophenyl)carbonyl]piperazinyl}prop-2-yn-1-one
1-{4-[(4-bromophenyl)carbonyl]piperazinyl}-3-(4-chlorophenyl)prop-2-yn-1-one (2E)-3-(3,4-dichlorophenyl)-1-{4-[(4-fluorophenyl)carbonyl]piperazinyl}prop-2-en-1-one
(2E)-1-[4-(diphenylmethyl)piperazinyl]-3-(4-ethoxyphenyl)prop-2-en-1-one
(2E)-1-[4-(2-3,4-dihydronaphthylsulfonyl)piperazinyl]-3-(4-fluorophenyl)prop-2-en-1-one
(2E)-3-(3,4-dichlorophenyl)-1-{4-[(4-chlorophenyl)carbonyl]piperazinyl}prop-2-en-1-one
(2E)-1-[4-(diphenylmethyl)piperazinyl]-3-(4-bromo-2-fluorophenyl)prop-2-en-1-one
3-(2,3-dichlorophenyl)-1-[4-(diphenylmethyl)piperazinyl]prop-2-yn-1-one
(2E)-3-(4-bromophenyl)-1-{4-[(4-chlorophenyl)amino]piperidyl}prop-2-en-1-one
(2E)-1-[4-(diphenylmethyl)piperazinyl]-3-(4-bromophenyl)prop-2-en-1-one
3-(4-chlorophenyl)-1-{4-[(4-fluorophenyl)carbonyl]piperazinyl}prop-2-yn-1-one
(2E)-1-[4-(diphenylmethyl)piperazinyl]-3-[4-(trifluoromethyl)phenyl]prop-2-en-1-one
3-(2,3-dichlorophenyl)-1-{4-[(4-chlorophenyl)carbonyl]piperazinyl}prop-2-yn-1-one
(2E)-1-{4-[(3,5-difluorophenyl)methyl]piperazinyl}-3-(4-bromophenyl)prop-2-en-1-one
(2E)-3-(4-bromophenyl)-1-{4-[(4-fluoro-3-methylphenyl)methyl]piperazinyl}prop-2-en-1-one
1-{4-[(4-chlorophenyl)carbonyl]piperazinyl}-3-(4-methylphenyl)prop-2-yn-1-one
3-(3-chlorophenyl)-1-{4-[(4-chlorophenyl)carbonyl]piperazinyl}prop-2-yn-1-one
3-(3-chlorophenyl)-1-{4-[(4-fluorophenyl)carbonyl]piperazinyl}prop-2-yn-1-one
4-(diphenylmethyl)piperazinyl 5-chlorobenzo[b]thiophen-2-yl ketone
(2E)-3-(4-bromophenyl)-1-{4-[(4-bromophenyl)sulfonyl]piperazinyl}prop-2-en-1-one
1-{4-[(4-fluorophenyl)carbonyl]piperazinyl}-3-(4-methylphenyl)prop-2-yn-1-one
(2E)-1-{4-[(3,4-dichlorophenyl)methyl]piperazinyl}-3-(4-bromophenyl)prop-2-en-1-one
2E)-1-[4-(diphenylmethyl)piperazinyl]-3-(4-chloro-2-fluorophenyl)prop-2-en-1-one
(2E)-3-(4-bromophenyl)-1-{4-[(4-methylphenyl)methyl]piperazinyl}prop-2-en-1-one
(2E)-1-[4-(diphenylmethyl)piperazinyl]-3-phenylprop-2-en-1-one
4-(diphenylmethyl)piperazinyl 5-bromoindol-2-yl ketone
(2E)-3-(4-bromophenyl)-1-(4-{[4-(trifluoromethyl)phenyl]carbonyl}piperazinyl)prop-2-en-1-one
4-(diphenylmethyl)piperazinyl 6-chlorobenzo[b]thiophen-2-yl ketone
(2E)-1-{4-[(2,4-difluorophenyl)carbonyl]piperazinyl}-3-(4-bromophenyl)prop-2-en-1-one
(2E)-3-(4-bromophenyl)-1-[4-({[(4-fluorophenyl)methyl]amino}methyl)piperidyl]prop-2-en-1-one
4-[((1E)-2-phenylvinyl)sulfonyl]piperazinyl 5-methylindol-2-yl ketone
(2E)-3-(4-bromophenyl)-1-(4-butylpiperazinyl)prop-2-en-1-one
1-[4-(diphenylmethyl)piperazinyl]-3-(4-bromophenyl)prop-2-yn-1-one
3-(3,4-dichlorophenyl)-1-{4-[(4-chlorophenyl)carbonyl]piperazinyl}prop-2-yn-1-one
(2E)-3-(4-bromophenyl)-1-[4-(methylpropyl)piperazinyl]prop-2-en-1-one
3-(4-methylphenyl)-1-(4-{[4-(trifluoromethyl)phenyl]carbonyl}piperazinyl)prop-2-yn-1-one
(2E)-1-[4-({[(3,5-difluorophenyl)methyl]amino}methyl)piperidyl]-3-(4-bromophenyl)prop-2-en-1-one
3-(4-bromophenyl)-1-{4-[(4-chlorophenyl)carbonyl]piperazinyl}prop-2-yn-1-one
4-(diphenylmethyl)piperazinyl 5-chloroindol-2-yl ketone
5-methylindol-2-yl 4-[(2-phenylethyl)sulfonyl]piperazinyl ketone
1-[4-(diphenylmethyl)piperazinyl]-3-(4-methylphenyl)prop-2-yn-1-one
3-(3-chlorophenyl)-1-{4-[(4-methoxyphenyl)carbonyl]piperazinyl}prop-2-yn-1-one
1-{4-[(4-chlorophenyl)carbonyl]piperazinyl}-3-[4-(trifluoromethyl)phenyl]prop-2-yn-1-one
3-(4-bromophenyl)-1-{4-[(4-bromophenyl)carbonyl]piperazinyl}prop-2-yn-1-one
methyl 4-({4-[(5-chloroindol-2-yl)carbonyl]piperazinyl}carbonyl)benzoate
(2E)-1-[4-(diphenylmethyl)piperazinyl]-3-(4-nitrophenyl)prop-2-en-1-one
4-[(4-chlorophenyl)carbonyl]piperazinyl 5-(trifluoromethyl)indol-2-yl ketone
1-{4-[(4-bromophenyl)carbonyl]piperazinyl}-3-phenylprop-2-yn-1-one
1-[4-(diphenylmethyl)piperazinyl]-3-[4-(trifluoromethyl)phenyl]prop-2-yn-1-one
(2E)-3-(4-bromophenyl)-1-{4-[(4-chlorophenyl)methyl]piperazinyl}prop-2-en-1-one
(2E)-1-[4-(diphenylmethyl)piperazinyl]-3-(4-fluorophenyl)prop-2-en-1-one
1-{4-[(4-chlorophenyl)carbonyl]piperazinyl}-3-(4-fluorophenyl)prop-2-yn-1-one
3-(4-bromophenyl)-1-{4-[(4-fluorophenyl)carbonyl]piperazinyl}prop-2-yn-1-one
4-(diphenylmethyl)piperazinyl indol-2-yl ketone
(2E)-1-{4-[(3,5-dimethoxyphenyl)methyl]piperazinyl}-3-(4-bromophenyl)prop-2-en-1-one 3-(4-chlorophenyl)-1-(4-{[4-(trifluoromethyl)phenyl]carbonyl}piperazinyl)prop-2-yn-1-one
(2E)-3-(4-bromophenyl)-1-[4-({[(4-chlorophenyl)methyl]amino}methyl)piperidyl]prop-2-en-1-one
3-(4-fluorophenyl)-1-{4-[(4-methoxyphenyl)carbonyl]piperazinyl}prop-2-yn-1-one
1-{4-[(4-fluorophenyl)carbonyl]piperazinyl}-3-[4-(trifluoromethyl)phenyl]prop-2-yn-1-one
3-(3,4-dichlorophenyl)-1-[4-(diphenylmethyl)piperazinyl]prop-2-yn-1-one
(2E)-3-(4-bromophenyl)-1-[4-(2-methylbutanoyl)piperazinyl]prop-2-en-1-one
4-(diphenylmethyl)piperazinyl 5-(trifluoromethyl)indol-2-yl ketone
(2E)-3-(4-bromophenyl)-1-(4-heptanoylpiperazinyl)prop-2-en-1-one
methyl 4-({4-[(5-bromoindol-2-yl)carbonyl]piperazinyl}carbonyl)benzoate
(2E)-3-(4-bromophenyl)-1-[4-(cyclopentylcarbonyl)piperazinyl]prop-2-en-1-one
potassium (E)-5-(4-(4-(3-(4-bromophenyl)acryloyl)piperazine-1-carbonyl)phenyl)tetrazol-1-ide
3-[4-(trifluoromethyl)phenyl]-1-(4-{[4-(trifluoromethyl)phenyl]carbonyl}piperazinyl)prop-2-yn-1-one
5-bromoindol-2-yl 4-[(4-chlorophenyl)carbonyl]piperazinyl ketone
4-(diphenylmethyl)piperazinyl 7-fluoro(3-quinolyl) ketone
benzo[d]furan-2-yl 4-(diphenylmethyl)piperazinyl ketone
5-chloroindol-2-yl 4-[(2-phenylethyl)sulfonyl]piperazinyl ketone
5-chloroindol-2-yl 4-[(4-chlorophenyl)carbonyl]piperazinyl ketone
3-(2,3-dichlorophenyl)-1-(4-{[4-fluoro-2-(trifluoromethyl)phenyl]carbonyl}piperazinyl)prop-2-yn-1-one
(2E)-3-(4-bromophenyl)-1-(4-{[4-chloro-2-(trifluoromethyl)phenyl]methyl}piperazinyl)prop-2-en-1-one
1-[4-(diphenylmethyl)piperazinyl]-3-(3-chlorophenyl)prop-2-yn-1-one
3-(3,4-dichlorophenyl)-1-{4-[(4-fluorophenyl)carbonyl]piperazinyl}prop-2-yn-1-one
4-(diphenylmethyl)piperazinyl 5-fluorobenzo[b]thiophen-2-yl ketone
(2E)-1-{4-[(((1E)-2-phenylvinyl)sulfonyl]piperazinyl}-3-(4-fluorophenyl)prop-2-en-1-one
(2E)-1-{4-[(4-chlorophenyl)sulfonyl]piperazinyl}-3-(4-fluorophenyl)prop-2-en-1-one
4-(diphenylmethyl)piperazinyl 5-methoxyindol-2-yl ketone
(2E)-3-(4-bromophenyl)-1-(4-pentanoylpiperazinyl)prop-2-en-1-one
(2E)-1-[4-((2E)-3-phenylprop-2-enoyl)piperazinyl]-3-phenylprop-2-en-1-one
(2E)-1-{4-[(2-bromophenyl)sulfonyl]piperazinyl}-3-(4-fluorophenyl)prop-2-en-1-one
4-(diphenylmethyl)piperazinyl 2-naphthyl ketone
4-[(4-{[5-(trifluoromethyl)indol-2-yl]carbonyl}piperazinyl)carbonyl]benzenecarbonitrile
(2E)-3-(4-bromophenyl)-1-(4-{[4-(methylethyl)phenyl]methyl}piperazinyl)prop-2-en-1-one
4-(diphenylmethyl)piperazinyl 6-chloroindol-2-yl ketone
1,5-dimethylindol-2-yl 4-(diphenylmethyl)piperazinyl ketone
(2E)-3-(3,4-difluorophenyl)-1-[4-(diphenylmethyl)piperazinyl]prop-2-en-1-one
1-[4-(diphenylmethyl)piperazinyl]-3-(4-bromo-2-fluorophenyl)prop-2-yn-1-one
4-(diphenylmethyl)piperazinyl 6-bromoindol-2-yl ketone
(2E)-1-{4-[(3,5-dimethylphenyl)methyl]piperazinyl}-3-(4-bromophenyl)prop-2-en-1-one
4-(diphenylmethyl)piperazinyl 6-quinolyl ketone
4-(2H-benzo[d]1,3-dioxolan-5-ylmethyl)piperazinyl 5-methylindol-2-yl ketone
3-(2H-benzo[3,4-d]1,3-dioxolen-5-yl)-1-{1-[(4-fluorophenyl)carbonyl](4-piperidyl)}prop-2-yn-1-one
(2E)-1-[4-(diphenylmethyl)piperazinyl]-3-(2-fluorophenyl)prop-2-en-1-one
3-(2H-benzo[3,4-d]1,3-dioxolen-5-yl)-1-{4-[(4-chlorophenyl)carbonyl]piperazinyl}prop-2-yn-1-one
5-chloroindol-2-yl 4-[(4-iodophenyl)carbonyl]piperazinyl ketone
1-{4-[(4-fluorophenyl)carbonyl]piperazinyl}-3-phenylprop-2-yn-1-one
3-(3-chlorophenyl)-1-(4-{[4-(trifluoromethyl)phenyl]carbonyl}piperazinyl)prop-2-yn-1-one
(2E)-3-(4-bromophenyl)-1-[4-(3-methylbutanoyl)piperazinyl]prop-2-en-1-one
5-chloroindol-2-yl 4-[(4-fluorophenyl)carbonyl]piperazinyl ketone
3-(2H-benzo[3,4-d]1,3-dioxolen-5-yl)-1-{4-[(4-bromophenyl)carbonyl]piperazinyl}prop-2-yn-1-one
(2E)-3-(4-bromophenyl)-1-{4-[({[3-fluoro-4-(trifluoromethyl)phenyl]methyl}amino)methyl]piperidyl}prop-2-en-1-one
1-{4-[(4-fluorophenyl)methyl]piperazinyl}-3-(4-methylphenyl)prop-2-yn-1-one
benzo[b]thiophen-2-yl 4-(diphenylmethyl)piperazinyl ketone
(2E)-3-(4-fluorophenyl)-1-{4-[(4-methylphenyl)sulfonyl]piperazinyl}prop-2-en-1-one
4-(diphenylmethyl)piperazinyl 3-quinolyl ketone
4-(diphenylmethyl)piperazinyl 5-fluoroindol-2-yl ketone
4-[(3-chlorophenyl)carbonyl]piperazinyl 5-(trifluoromethyl)indol-2-yl ketone
3-(4-fluorophenyl)-1-{4-[(4-fluorophenyl)carbonyl]piperazinyl}prop-2-yn-1-one
3-(3-chlorophenyl)-1-{4-[(4-fluorophenyl)methyl]piperazinyl}prop-2-yn-1-one
(2E)-3-(4-bromophenyl)-1-{4-[(4-chloro-2- fluorophenyl)methyl]piperazinyl}prop-2-en-1-one
(2E)-3-(4-bromophenyl)-1-(4-{[4-fluoro-2-
(trifluoromethyl)phenyl]methyl}piperazinyl)prop-2-en-1-one
3-(2,3-dichlorophenyl)-1-(4-{[4-
(trifluoromethyl)phenyl]carbonyl}piperazinyl)prop-2-yn-1-one
5-(trifluoromethyl)indol-2-yl 4-{[4-(trifluoromethyl)phenyl]carbonyl}piperazinyl
ketone
piperazinyl 5-nitroindol-2-yl ketone
5-bromoindol-2-yl 4-[(4-fluorophenyl)carbonyl]piperazinyl ketone
N-({1-[(2E)-3-(4-bromophenyl)prop-2-enoyl](4-piperidyl)}methyl)(4-
fluorophenyl)carboxamide
1-{4-[(4-chlorophenyl)methyl]piperazinyl}-3-[4-(trifluoromethyl)phenyl]prop-2-
yn-1-one
(2E)-1-{4-[(3-chlorophenyl)sulfonyl]piperazinyl}-3-(4-fluorophenyl)prop-2-en-
1-one
1-[4-(diphenylmethyl)piperazinyl]-3-phenylprop-2-yn-1-one
5-bromoindol-2-yl 4-{[(trifluoromethyl)phenyl]carbonyl}piperazinyl ketone
3-(2,3-dichlorophenyl)-1-(4-{[4-fluoro-2-
(trifluoromethyl)phenyl]methyl}piperazinyl)prop-2-yn-1-one
4-(diphenylmethyl)piperazinyl 5-(trifluoromethyl)benzo[b]thiophen-2-yl ketone
4-[(4-bromophenyl)sulfonyl]piperazinyl 5-methylindol-2-yl ketone
(2E)-1-(4-{[4-(tert-butyl)phenyl]methyl}piperazinyl)-3-(4-bromophenyl)prop-2-
en-1-one
(2E)-3-(4-bromophenyl)-1-(4-propanoylpiperazinyl)prop-2-en-1-one
(2E)-1-{4-[(4-bromophenyl)sulfonyl]piperazinyl}-3-(4-methoxyphenyl)prop-2-
en-1-one
(2E)-1-[4-(diphenylmethyl)piperazinyl]-3-(3,4,5-trifluorophenyl)prop-2-en-1-one
5-methylindol-2-yl 4-(phenylethyl)piperazinyl ketone
3-(4-bromophenyl)-1-{4-[(4-(5H-1,2,3,4-tetraazol-5-
yl)phenyl)carbonyl]piperazinyl}prop-2-yn-1-one
(2E)-1-(4-{[4-(tert-butyl)phenyl]sulfonyl}piperazinyl)-3-(4-bromophenyl)prop-2-
en-1-one
6-chloroindol-2-yl 4-[(4-methoxyphenyl)carbonyl]piperazinyl ketone
(2E)-3-(4-bromophenyl)-1-{4-[(4-(1H-1,2,3,4-tetraazol-5-
yl)phenyl)carbonyl]piperazinyl}prop-2-en-1-one
(E)-(4-(4-(3-(4-bromophenyl)acryloyl)piperazine-1-carbonyl)phenyl)boronic
acid
(2E)-3-(4-bromophenyl)-1-{4-[({[4-
(trifluoromethyl)phenyl]methyl}amino)methyl]piperidyl}prop-2-en-1-one
1-[4-(diphenylmethyl)piperazinyl]-3-bromo-3-(4-bromophenyl)prop-2-en-1-one
4-(diphenylmethyl)piperazinyl 5-fluorobenzo[b]thiophen-2-yl ketone
3-(3-chlorophenyl)-1-(4-{[4-fluoro-2-
(trifluoromethyl)phenyl]carbonyl}piperazinyl)prop-2-yn-1-one
[4-(diphenylmethyl)piperazinyl](5-methylindol-2-yl)methane-1-thione
1-[4-(diphenylmethyl)piperazinyl]-3-(4-fluorophenyl)prop-2-yn-1-one
4-(4-(3-(4-bromophenyl)propioloyl)piperazine-1-carbonyl)phenylboronic acid
(2E)-1-{4-[(4-nitrophenyl)methyl]piperazinyl}-3-phenylprop-2-en-1-one
N-[1-(diphenylmethyl)(4-piperidyl)](5-methylindol-2-yl)carboxamide
5-chloroindol-2-yl 4-(pyrrol-3-ylcarbonyl)piperazinyl ketone
4-bromophenyl 4-{[4-fluoro-2-(trifluoromethyl)phenyl]methyl}piperazinyl
ketone
4-bromophenyl 4-[(4-fluorophenyl)methyl]piperazinyl ketone
3-(2,4-difluorophenyl)-1-(4-{[4-
(trifluoromethyl)phenyl]carbonyl}piperazinyl)prop-2-yn-1-one
3-(2H-benzo[3,4-d]1,3-dioxolan-5-yl)-1-(4-{[4-
(trifluoromethyl)phenyl]methyl}piperazinyl)prop-2-en-1-one
benzothiazol-2-yl 4-(diphenylmethyl)piperazinyl ketone
3-[2-(trifluoromethyl)phenyl]-1-(4-{[4-
(trifluoromethyl)phenyl]carbonyl}piperazinyl)prop-2-yn-1-one
4-[(4-chlorophenyl)methyl]piperazinyl 2-(trifluoromethyl)benzimidazol-5-yl
ketone
3-(3,4-dichlorophenyl)-1-(4-{[4-
(trifluoromethyl)phenyl]methyl}piperazinyl)prop-2-yn-1-one
5-chloroindol-2-yl 4-{[4-(4-chlorophenyl)phenyl]sulfonyl}piperazinyl ketone
4-(diphenylmethyl)piperazinyl 6-methylthiopheno[3,2-d]pyrrol-5-yl ketone
(2E)-3-(5-bromo-2-fluorophenyl)-1-{4-[(4-
bromophenyl)sulfonyl]piperazinyl}prop-2-en-1-one
4-[(4-chlorophenyl)methyl]piperazinyl 3-quinolyl ketone
4-bromophenyl 4-{[4-(methylethyl)phenyl]methyl}piperazinyl ketone
4-({4-[(5-chloroindol-2-yl)carbonyl]piperazinyl}methyl)benzoic acid
4-(diphenylmethyl)piperazinyl 7-nitroindol-2-yl ketone
3-(4-fluorophenyl)-1-(4-{[4-fluoro-2-
(trifluoromethyl)phenyl]methyl}piperazinyl)prop-2-yn-1-one
6-bromoindol-2-yl 4-[(4-bromophenyl)methyl]piperazinyl ketone
[4-({4-[(5-chloroindol-2-yl)carbonyl]piperazinyl}methyl)phenyl]-N-(4-
fluorophenyl)carboxamide
5-chloroindol-2-yl 4-(2-pyridyl)piperazinyl ketone
5-chloroindol-2-yl 4-{[2-(trifluoromethyl)benzimidazol-5-yl]carbonyl}piperazinyl
ketone N-{1-[(5-chloroindol-2-yl)carbonyl](4-piperidyl)}(4-chlorophenyl)carboxamide
4-(diphenylmethyl)piperazinyl 3-methylbenzo[b]thiophen-2-yl ketone
3-(2H-benzo[3,4-d]1,3-dioxolan-5-yl)-1-(4-{[4-fluoro-2-(trifluoromethyl)phenyl]methyl}piperazinyl)prop-2-en-1-one
[3-({4-[(5-chloroindol-2-yl)carbonyl]piperazinyl}methyl)phenyl]-N-(4-fluorophenyl)carboxamide
3-({4-[(5-chloroindol-2-yl)carbonyl]piperazinyl}methyl)benzoic acid
6-fluoroindol-2-yl 4-{[4-fluoro-2-(trifluoromethyl)phenyl]carbonyl}piperazinyl ketone
(2E)-1-(4-{[4-(tert-butyl)phenyl]sulfonyl}piperazinyl)-3-(2-fluorophenyl)prop-2-en-1-one
(2E)-3-phenyl-1-[4-(2-pyridylmethyl)piperazinyl]prop-2-en-1-one
(2E)-1-[4-(diphenylmethyl)(1,4-diazaperhydroepinyl)]-3-(4-fluorophenyl)prop-2-en-1-one
4-(diphenylmethyl)piperazinyl pyrrolo[4,5-b]pyridin-2-yl ketone
5-chloroindol-2-yl 4-[(4-phosphonophenyl)carbonyl]piperazinyl ketone
3-(3,5-difluorophenyl)-1-(4-{[4-(trifluoromethyl)phenyl]methyl}piperazinyl)prop-2-yn-1-one
(2E)-3-(2-methylphenyl)-1-[4-(phenylsulfonyl)piperazinyl]prop-2-en-1-one
3-(3,5-difluorophenyl)-1-{4-[(4-fluorophenyl)methyl]piperazinyl}prop-2-yn-1-one
(2E)-1-{4-[((1E)-2-phenylvinyl)sulfonyl](1,4-diazaperhydroepinyl)}-3-(4-fluorophenyl)prop-2-en-1-one
5-chloroindol-2-yl 4-morpholin-4-ylpiperidyl ketone
4-{[3-fluoro-4-(trifluoromethyl)phenyl]carbonyl}piperazinyl 5-(trifluoromethyl)indol-2-yl ketone
(2E)-1-{4-[(3-methylphenyl)methyl]piperazinyl}-3-phenylprop-2-en-1-one
(2E)-1-(4-{[4-(tert-butyl)phenyl]sulfonyl}piperazinyl)-3-(4-fluorophenyl)prop-2-en-1-one
(2E)-1-{4-[(4-bromophenyl)methyl]piperazinyl}-3-phenylprop-2-en-1-one
5-chloroindol-2-yl 4-[(4-(1H-1,2,3,4-tetraazol-5-yl)phenyl)carbonyl]piperazinyl ketone
(2E)-3-(4-fluorophenyl)-1-[4-(phenylsulfonyl)piperazinyl]prop-2-en-1-one
(2E)-3-(4-fluorophenyl)-1-{4-[(4-nitrophenyl)sulfonyl]piperazinyl}prop-2-en-1-one
4-(diphenylmethyl)piperazinyl 5-bromobenzo[b]thiophen-2-yl ketone
5-bromoindol-2-yl 4-{[4-fluoro-2-(trifluoromethyl)phenyl]carbonyl}piperazinyl ketone
(2E)-1-{4-[(3-bromophenyl)sulfonyl]piperazinyl}-3-(4-fluorophenyl)prop-2-en-1-one
(2E)-3-(3,4-dichlorophenyl)-1-{4-[(4-fluorophenyl)methyl]piperazinyl}prop-2-en-1-one
4-[(4-fluorophenyl)methyl]piperazinyl 5-(trifluoromethyl)indol-2-yl ketone
(2E)-3-(4-fluorophenyl)-1-{4-[(3-fluorophenyl)sulfonyl]piperazinyl}prop-2-en-1-one
(2E)-1-{4-[(4-bromophenyl)sulfonyl]piperazinyl}-3-(4-ethoxyphenyl)prop-2-en-1-one
(2E)-3-(3,4-dichlorophenyl)-1-{4-[(4-chlorophenyl)methyl]piperazinyl}prop-2-en-1-one
4-(diphenylmethyl)piperazinyl 6-fluoroindol-2-yl ketone
3-(2H-benzo[3,4-d]1,3-dioxolen-5-yl)-1-{4-[(4-fluorophenyl)carbonyl]piperazinyl}prop-2-en-1-one
4-(diphenylmethyl)piperazinyl 5-phenylindol-2-yl ketone
(2E)-1-{4-[(5-chloroindol-2-yl)carbonyl]piperazinyl}-3-[4-(trifluoromethyl)phenyl]prop-2-en-1-one
4-[(4-fluorophenyl)methyl]piperazinyl 5-methylindol-2-yl ketone
4-(diphenylmethyl)piperazinyl 5-(4-methoxyphenyl)indol-2-yl ketone
(2E)-3-(4-fluorophenyl)-1-[4-(2-naphthylsulfonyl)piperazinyl]prop-2-en-1-one
(2E)-3-(4-bromophenyl)-1-(4-ethylpiperazinyl)prop-2-en-1-one
6-amino(2-naphthyl) 4-(diphenylmethyl)piperazinyl ketone
1-(4-{[4-fluoro-2-(trifluoromethyl)phenyl]carbonyl}piperazinyl)-3-(4-methylphenyl)prop-2-yn-1-one
(2E)-1-{4-[(2,5-dichlorophenyl)sulfonyl]piperazinyl}-3-(4-fluorophenyl)prop-2-en-1-one
5-chloroindol-2-yl 4-[(4-fluorophenyl)amino]piperidyl ketone
4-(diphenylmethyl)piperazinyl 6-fluoro(3-quinolyl) ketone
4-(diphenylmethyl)piperazinyl 2-methylthiopheno[2,3-d]pyrrol-5-yl ketone
5-chloroindol-2-yl 4-(phenylcarbonyl)piperidyl ketone
(2E)-3-(3,4-dichlorophenyl)-1-[4-(phenylsulfonyl)piperazinyl]prop-2-en-1-one
1-{4-[(4-fluorophenyl)methyl]piperazinyl}-3-[4-(trifluoromethyl)phenyl]prop-2-yn-1-one
4-{[4-(diethylamino)phenyl]carbonyl}piperazinyl 5-chloroindol-2-yl ketone
(2E)-3-[4-(dimethylamino)phenyl]-1-[4-(diphenylmethyl)piperazinyl]prop-2-en-1-one
3-(2H-benzo[3,4-d]1,3-dioxolan-5-yl)-1-{4-[(4-bromophenyl)carbonyl]piperazinyl}prop-2-en-1-one
(2E)-3-(4-fluorophenyl)-1-{4-[(4-fluorophenyl)sulfonyl]piperazinyl}prop-2-en-1-one
1-{4-[(4-methoxyphenyl)methyl]piperazinyl}-3-(4-methylphenyl)prop-2-yn-1-one (2E)-3-(4-fluorophenyl)-1-{4-[(2-fluorophenyl)sulfonyl]piperazinyl}prop-2-en-1-one
3-(2H-benzo[3,4-d]1,3-dioxolen-5-yl)-1-{4-[(4-chlorophenyl)carbonyl]piperazinyl}prop-2-en-1-one
6-bromoindol-2-yl 4-[(4-chlorophenyl)carbonyl]piperazinyl ketone
(2E)-1-{4-[(3-fluorophenyl)methyl]piperazinyl}-3-phenylprop-2-en-1-one
(2E)-1-[4-(diphenylmethyl)piperazinyl]-3-(2-methylphenyl)prop-2-en-1-one
4-(diphenylmethyl)piperazinyl 1-methylindol-2-yl ketone
5-chloroindol-2-yl 4-(phenylcarbonyl)piperazinyl ketone
4-{[4-(tert-butyl)phenyl]methyl}piperazinyl 5-methylindol-2-yl ketone
1-{4-[(4-chlorophenyl)methyl]piperazinyl}-3-(4-methylphenyl)prop-2-yn-1-one
4-[(2,4-dichlorophenyl)carbonyl]piperazinyl 5-(trifluoromethyl)indol-2-yl ketone
benzo[b]thiophen-5-yl 4-(diphenylmethyl)piperazinyl ketone
(2E)-1-{4-[(4-fluorophenyl)methyl]piperazinyl}-3-phenylprop-2-en-1-one
3-(3,4-dichlorophenyl)-1-(4-{[4-(trifluoromethyl)phenyl]carbonyl}piperazinyl)prop-2-yn-1-one
4,6-dichloroindol-2-yl 4-(diphenylmethyl)piperazinyl ketone
4-[(3,5-difluorophenyl)methyl]piperazinyl 5-(trifluoromethyl)indol-2-yl ketone
5-chloroindol-2-yl 4-[(3-fluorophenyl)amino]piperidyl ketone
3-(4-fluorophenyl)-1-(4-{[4-(trifluoromethyl)phenyl]carbonyl}piperazinyl)prop-2-yn-1-one
5-chloroindol-2-yl 4-[(4-(3-pyridyl)phenyl)carbonyl]piperazinyl ketone
6-chloroindol-2-yl 4-[(4-chlorophenyl)carbonyl]piperazinyl ketone
3-(2H-benzo[3,4-d]1,3-dioxolen-5-yl)-1-{4-[(4-methoxyphenyl)carbonyl]piperazinyl}prop-2-en-1-one
4-(diphenylmethyl)piperazinyl 6-chloro(3-quinolyl) ketone
4-[(2,4-difluorophenyl)amino]piperidyl 5-chloroindol-2-yl ketone
(2E)-3-(4-fluorophenyl)-1-{4-[(4-propylphenyl)sulfonyl]piperazinyl}prop-2-en-1-one
2E)-1-{4-[(4-methylphenyl)methyl]piperazinyl}-3-phenylprop-2-en-1-one
(2E)-3-(4-fluorophenyl)-1-(4-{[4-(methylethyl)phenyl]sulfonyl}piperazinyl)prop-2-en-1-one
3-(2,3-dichlorophenyl)-1-{4-[(4-fluorophenyl)methyl]piperazinyl}prop-2-yn-1-one
4,6-difluoroindol-2-yl 4-(diphenylmethyl)piperazinyl ketone
6-bromoindol-2-yl 4-[(4-bromophenyl)carbonyl]piperazinyl ketone
(2E)-1-[4-(diphenylmethyl)piperazinyl]-3-[3-(trifluoromethyl)phenyl]prop-2-en-1-one
3-(2H-benzo[3,4-d]1,3-dioxolen-5-yl)-1-(4-{[4-(trifluoromethyl)phenyl]carbonyl}piperazinyl)prop-2-yn-1-one
(E)-(3-(4-(3-(4-bromophenyl)acryloyl)piperazine-1-carbonyl)phenyl)boronic acid
6-chloroindol-2-yl 4-[(4-fluorophenyl)carbonyl]piperazinyl ketone
(2E)-3-(4-bromophenyl)-1-{4-[(2-fluorophenyl)methyl]piperazinyl}prop-2-en-1-one
(2E)-1-{4-[2-(4-chlorophenyl)ethyl]piperazinyl}-3-phenylprop-2-en-1-one
5-(trifluoromethyl)indol-2-yl 4-{[3-(trifluoromethyl)phenyl]carbonyl}piperazinyl ketone
5-chloroindol-2-yl 4-(3-chlorophenoxy)piperidyl ketone
4-[(3,5-difluorophenyl)amino]piperidyl 5-chloroindol-2-yl ketone
3-(4-bromophenyl)-1-{4-[(4-methoxyphenyl)methyl]piperazinyl}prop-2-yn-1-one
3-(2,3-dichlorophenyl)-1-{4-[(4-chlorophenyl)methyl]piperazinyl}prop-2-yn-1-one
4-(diphenylmethyl)piperazinyl quinoxalin-2-yl ketone
(2E)-1-{4-[(4-bromophenyl)sulfonyl]piperazinyl}-3-[2-(trifluoromethyl)phenyl]prop-2-en-1-one
5-chloroindol-2-yl 4-(8-hydropyrazolo[1,5-a]pyridin-2-ylcarbonyl)piperazinyl ketone
5-chloroindol-2-yl 4-(4-hydroimidazo[1,2-a]pyridin-2-ylcarbonyl)piperazinyl ketone
5,6-dimethoxyindol-2-yl 4-(diphenylmethyl)piperazinyl ketone
3-(2,3-dichlorophenyl)-1-(4-{[4-(trifluoromethyl)phenyl]methyl}piperazinyl)prop-2-yn-1-one
4-({4-[(5-chloroindol-2-yl)carbonyl]piperazinyl}carbonyl)benzamide
2-(difluoromethyl)benzimidazol-5-yl 4-(diphenylmethyl)piperazinyl ketone
3-(3,4-dichlorophenyl)-1-{4-[(4-fluorophenyl)methyl]piperazinyl}prop-2-yn-1-one
4-[(2-chloro(3-pyridyl))carbonyl]piperazinyl 5-chloroindol-2-yl ketone
tert-butyl 4-[(1-methylindol-2-yl)carbonyl]piperazinecarboxylate
3-(4-fluorophenyl)-1-(4-{[4-fluoro-2-(trifluoromethyl)phenyl]carbonyl}piperazinyl)prop-2-yn-1-one
4-(benzimidazol-2-ylcarbonyl)piperazinyl 5-chloroindol-2-yl ketone
5-chloroindol-2-yl 4-(2-pyridyloxy)piperidyl ketone
benzo[b]thiophen-3-yl 4-(diphenylmethyl)piperazinyl ketone
3-(3,4-dichlorophenyl)-1-{4-[(4-chlorophenyl)methyl]piperazinyl}prop-2-yn-1-one
6-fluoroindol-2-yl 4-{[4-(trifluoromethyl)phenyl]carbonyl}piperazinyl ketone
6-bromoindol-2-yl 4-[(4-fluorophenyl)methyl]piperazinyl ketone
3-(3,5-difluorophenyl)-1-{4-[(4-chlorophenyl)methyl]piperazinyl}prop-2-yn-1-one 5-chloroindol-2-yl 4-ethylpiperazinyl ketone
benzimidazol-5-yl 4-(diphenylmethyl)piperazinyl ketone
3-(2H-benzo[3,4-d]1,3-dioxolan-5-yl)-1-{4-[(4-chlorophenyl)methyl]piperazinyl}prop-2-en-1-one
3-(2H-benzo[3,4-d]1,3-dioxolan-5-yl)-1-{4-[(4-bromophenyl)methyl]piperazinyl}prop-2-en-1-one
4-(diphenylmethyl)piperazinyl 2-(trifluoromethyl)benzimidazol-5-yl ketone
(2E)-3-(4-chloro-2-fluorophenyl)-1-{4-[(5-chloroindol-2-yl)carbonyl]piperazinyl}prop-2-en-1-one
2-anthryl 4-(diphenylmethyl)piperazinyl ketone
3-(3-chlorophenyl)-1-(4-{[4-fluoro-2-(trifluoromethyl)phenyl]methyl}piperazinyl)prop-2-yn-1-one
5-bromoindol-2-yl 4-[(4-chlorophenyl)methyl]piperazinyl ketone
4-(diphenylmethyl)piperazinyl 6-methoxyindol-2-yl ketone
(2E)-3-(4-aminophenyl)-1-[4-(diphenylmethyl)piperazinyl]prop-2-en-1-one
4-{[(4-bromophenyl)sulfonyl]amino}piperidyl 5-chloroindol-2-yl ketone
4-({4-[(2E)-3-(4-ethoxyphenyl)prop-2-enoyl]piperazinyl}sulfonyl)-1-acetylbenzene
(2E)-1-[4-(naphthylmethyl)piperazinyl]-3-phenylprop-2-en-1-one
1-{4-[(4-chlorophenyl)carbonyl]piperazinyl}-3-[2-(trifluoromethyl)phenyl]prop-2-yn-1-one
6-bromoindol-2-yl 4-[(4-(1H-1,2,3,4-tetraazol-5-yl)phenyl)carbonyl]piperazinyl ketone
[4-(diphenylmethyl)piperazinyl]-3-quinolylmethane-1-thione
(2E)-1-(4-butylpiperazinyl)-3-phenylprop-2-en-1-one
(2E)-3-(4-ethoxyphenyl)-1-[4-(phenylsulfonyl)piperazinyl]prop-2-en-1-one
(2E)-3-(4-fluorophenyl)-1-{4-[(3-methoxyphenyl)sulfonyl]piperazinyl}prop-2-en-1-one
5-chloroindol-2-yl 4-(4-fluorophenoxy)piperidyl ketone
3-(3-chlorophenyl)-1-{4-[(4-chlorophenyl)methyl]piperazinyl}prop-2-yn-1-one
5-chloroindol-2-yl 4-(4-chlorophenoxy)piperidyl ketone
(2E)-1-{4-[(2,5-dimethoxyphenyl)sulfonyl]piperazinyl}-3-(4-fluorophenyl)prop-2-en-1-one
5-chloroindol-2-yl 4-[(4-fluorophenyl)methyl]piperazinyl ketone
(2E)-1-[4-(diphenylmethyl)piperazinyl]-3-(2-chlorophenyl)prop-2-en-1-one
1-(4-{[4-fluoro-2-(trifluoromethyl)phenyl]carbonyl}piperazinyl)-3-phenylprop-2-yn-1-one
4-[(3,4-dimethylphenyl)amino]piperidyl 5-chloroindol-2-yl ketone
(2E)-3-(4-fluorophenyl)-1-{4-[benzylsulfonyl]piperazinyl}prop-2-en-1-one
methyl 4-({4-[(5-chloroindol-2-yl)carbonyl]piperazinyl}methyl)benzoate
1-(4-{[4-fluoro-2-(trifluoromethyl)phenyl]carbonyl}piperazinyl)-3-[4-(trifluoromethyl)phenyl]prop-2-yn-1-one
4-{3-[4-(diphenylmethyl)piperazinyl]-3-oxoprop-1-ynyl}benzenecarbonitrile
5-chloroindol-2-yl 4-[(4-phenylphenyl)methyl]piperazinyl ketone
4-[(3,4-dichlorophenyl)methyl]piperazinyl 5-methylindol-2-yl ketone
6-bromoindol-2-yl 4-{[3-fluoro-4-(trifluoromethyl)phenyl]carbonyl}piperazinyl ketone
4-{[3,5-bis(trifluoromethyl)phenyl]carbonyl}piperazinyl 5-(trifluoromethyl)indol-2-yl ketone
5-chloroindol-2-yl 4-{[4-(trifluoromethyl)phenyl]methyl}piperazinyl ketone
(2E)-1-{4-[(4-methoxyphenyl)methyl]piperazinyl}-3-phenylprop-2-en-1-one
4-[(4-bromophenyl)sulfonyl]piperazinyl 5-chloroindol-2-yl ketone
(2E)-3-(3,4-dichlorophenyl)-1-(4-{[4-(tert-butyl)phenyl]sulfonyl}piperazinyl)prop-2-en-1-one
4-{[4-((2E)-3-phenylprop-2-enoyl)piperazinyl]methyl}benzenecarbonitrile
3-(4-bromophenyl)-1-(4-{[4-fluoro-2-(trifluoromethyl)phenyl]carbonyl}piperazinyl)prop-2-yn-1-one
(2E)-3-phenyl-1-[4-benzylpiperazinyl]prop-2-en-1-one
4-(diphenylmethyl)piperazinyl 5-(methylethyl)indol-2-yl ketone
4-[(4-chlorophenyl)methyl]piperazinyl 5-methylindol-2-yl ketone
(2E)-1-{4-[(3,5-dimethylphenyl)methyl]piperazinyl}-3-phenylprop-2-en-1-one
2-({4-[(2E)-3-(4-fluorophenyl)prop-2-enoyl]piperazinyl}sulfonyl)benzenecarbonitrile
3-(4-bromophenyl)-1-{4-[(4-chlorophenyl)methyl]piperazinyl}prop-2-yn-1-one
3-(3,5-difluorophenyl)-1-{4-[(4-chlorophenyl)carbonyl]piperazinyl}prop-2-yn-1-one
(2E)-1-{4-[(2-bromophenyl)methyl]piperazinyl}-3-phenylprop-2-en-1-one
(2E)-3-(4-fluorophenyl)-1-[4-(naphthylsulfonyl)piperazinyl]prop-2-en-1-one
3-(4-methylphenyl)-1-(4-{[4-(trifluoromethyl)phenyl]methyl}piperazinyl)prop-2-yn-1-one
indol-2-yl 4-(phenylethyl)piperazinyl ketone
4-(diphenylmethyl)piperazinyl 5-hydroxyindol-2-yl ketone
3-(2,4-difluorophenyl)-1-{4-[(4-chlorophenyl)carbonyl]piperazinyl}prop-2-yn-1-one
(2E)-1-{4-[(2,5-difluorophenyl)methyl]piperazinyl}-3-phenylprop-2-en-1-one
4-(diphenylmethyl)piperazinyl 2-quinolyl ketone
1-{4-[(4-methoxyphenyl)methyl]piperazinyl}-3-[4-(trifluoromethyl)phenyl]prop-2-yn-1-one
3-(3-chlorophenyl)-1-(4-{[4-(trifluoromethyl)phenyl]methyl}piperazinyl)prop-2-yn-1-one (2E)-1-{4-[(4-chlorophenyl)methyl]piperazinyl}-3-phenylprop-2-en-1-one
(2E)-1-{4-[((1E)-2-phenylvinyl)sulfonyl](1,4-diazaperhydroepinyl)}-3-(4-bromophenyl)prop-2-en-1-one
3-(4-chlorophenyl)-1-(4-{[4-(trifluoromethyl)phenyl]methyl}piperazinyl)prop-2-yn-1-one
5-chloroindol-2-yl 4-(4-fluoro-2-methylphenoxy)piperidyl ketone
methyl 3-({4-[(5-chloroindol-2-yl)carbonyl]piperazinyl}methyl)benzoate
4-[(3,5-dimethylphenyl)methyl]piperazinyl 5-methylindol-2-yl ketone
4-{[2-fluoro-4-(trifluoromethyl)phenyl]carbonyl}piperazinyl 5-(trifluoromethyl)indol-2-yl ketone
(2E)-1-{4-[2-(2-fluorophenyl)ethyl]piperazinyl}-3-phenylprop-2-en-1-one
(2E)-1-[4-(2-(1,3-dihydroisobenzofuran-5-yl)ethyl)piperazinyl]-3-phenylprop-2-en-1-one
methyl 3-({4-[(5-chloroindol-2-yl)carbonyl]piperazinyl}carbonyl)benzoate
3-(4-bromophenyl)-1-{4-[(4-bromophenyl)methyl]piperazinyl}prop-2-yn-1-one
(2E)-1-{4-[(3-chlorophenyl)methyl]piperazinyl}-3-phenylprop-2-en-1-one
4-[(4-chlorophenyl)carbonyl]piperazinyl 6-fluoroindol-2-yl ketone
(2E)-3-(4-fluorophenyl)-1-[4-(2-thienylsulfonyl)piperazinyl]prop-2-en-1-one
4-butylpiperazinyl 5-chloroindol-2-yl ketone
3-(4-chlorophenyl)-1-{4-[(4-fluorophenyl)methyl]piperazinyl}prop-2-yn-1-one
4-(diphenylmethyl)piperazinyl indol-6-yl ketone
5-bromoindol-2-yl 4-{[4-(trifluoromethyl)phenyl]methyl}piperazinyl ketone
3-(4-chlorophenyl)-1-{4-[(4-methoxyphenyl)methyl]piperazinyl}prop-2-yn-1-one
1-{4-[(4-methoxyphenyl)carbonyl]piperazinyl}-3-[2-(trifluoromethyl)phenyl]prop-2-yn-1-one
(2E)-1-{4-[(2-chlorophenyl)methyl]piperazinyl}-3-phenylprop-2-en-1-one
6-bromoindol-2-yl 4-{[4-(trifluoromethyl)phenyl]carbonyl}piperazinyl ketone
5-methylindol-2-yl 4-benzylpiperazinyl ketone
(2E)-3-(4-bromo-2-fluorophenyl)-1-{4-[(4-bromophenyl)sulfonyl]piperazinyl}prop-2-en-1-one
4-[(2,4-difluorophenyl)carbonyl]piperazinyl 5-chloroindol-2-yl ketone
(2E)-1-{4-[(3-methoxyphenyl)methyl]piperazinyl}-3-phenylprop-2-en-1-one
4-(diphenylmethyl)piperazinyl thiopheno[2,3-d]pyrrol-5-yl ketone
4-bromophenyl 4-(2-naphthylcarbonyl)piperazinyl ketone
4-(4-(6-bromo-1H-indole-2-carbonyl)piperazine-1-carbonyl)phenylboronic acid
1-{4-[(4-bromophenyl)methyl]piperazinyl}-3-(4-chlorophenyl)prop-2-yn-1-one
3-(4-chlorophenyl)-1-{4-[(4-chlorophenyl)methyl]piperazinyl}prop-2-yn-1-one
(2E)-1-(4-{[4-(tert-butyl)phenyl]sulfonyl}piperazinyl)-3-(4-methoxyphenyl)prop-2-en-1-one
4-(diphenylmethyl)piperazinyl 8-fluoro(3-quinolyl) ketone
(2E)-1-{4-[(3-nitrophenyl)methyl]piperazinyl}-3-phenylprop-2-en-1-one
(2E)-1-{4-[(4-bromophenyl)sulfonyl]piperazinyl}-3-(4-chloro-2-fluorophenyl)prop-2-en-1-one
4-{[3-fluoro-4-(trifluoromethyl)phenyl]methyl}piperazinyl 5-(trifluoromethyl)indol-2-yl ketone
5-chloroindol-2-yl 4-[4-(trifluoromethyl)phenoxy]piperidyl ketone
6-chloroindol-2-yl 4-{[4-(trifluoromethyl)phenyl]carbonyl}piperazinyl ketone
(2E)-1-[4-(methylpropyl)piperazinyl]-3-phenylprop-2-en-1-one
1-{4-[(4-fluorophenyl)carbonyl]piperazinyl}-3-[2-(trifluoromethyl)phenyl]prop-2-yn-1-one
(2E)-1-{4-[(2-methylphenyl)methyl]piperazinyl}-3-phenylprop-2-en-1-one
3-({4-[(5-chloroindol-2-yl)carbonyl]piperazinyl}carbonyl)benzenecarbonitrile
{1-[(5-chloroindol-2-yl)carbonyl](4-piperidyl)}-N-(3-chlorophenyl)carboxamide
4-({4-[(5-chloroindol-2-yl)carbonyl]piperazinyl}carbonyl)benzaldehyde
3-(3,5-difluorophenyl)-1-(4-{[4-(trifluoromethyl)phenyl]carbonyl}piperazinyl)prop-2-yn-1-one
3-(4-chlorophenyl)-1-(4-{[4-fluoro-2-(trifluoromethyl)phenyl]carbonyl}piperazinyl)prop-2-yn-1-one
4-(2,3-dimethylphenyl)piperazinyl 5-chloroindol-2-yl ketone
3-(4-bromophenyl)-1-{4-[(4-fluorophenyl)methyl]piperazinyl}prop-2-yn-1-one
5-chloroindol-2-yl 4-{[3-fluoro-4-(trifluoromethyl)phenyl]methyl}piperazinyl ketone
5-chloroindol-2-yl 4-[(3-phenylphenyl)methyl]piperazinyl ketone
(2E)-3-(4-bromo-2-fluorophenyl)-1-[4-(phenylsulfonyl)piperazinyl]prop-2-en-1-one
benzo[d]furan-2-yl 4-(phenylethyl)piperazinyl ketone
1-{4-[((1E)-2-phenylvinyl)sulfonyl]piperazinyl}-3-(4-fluorophenyl)propan-1-one
(2E)-1-{4-[2-(2,4-dichlorophenoxy)ethyl]piperazinyl}-3-phenylprop-2-en-1-one
3-(4-bromophenyl)-1-(4-{[4-(trifluoromethyl)phenyl]methyl}piperazinyl)prop-2-yn-1-one
4-(4-(5-chloro-1H-indole-2-carbonyl)piperazine-1-carbonyl)phenylboronic acid
3-(3,5-difluorophenyl)-1-{4-[(4-fluorophenyl)carbonyl]piperazinyl}prop-2-yn-1-one
3-[4-(trifluoromethyl)phenyl]-1-(4-{[4-(trifluoromethyl)phenyl]methyl}piperazinyl)prop-2-yn-1-one
4-[(2,4-difluorophenyl)methyl]piperazinyl 5-(trifluoromethyl)indol-2-yl ketone
5-chloroindol-2-yl 4-phenoxypiperidyl ketone
tert-butyl 4-(indol-2-ylcarbonyl)piperazinecarboxylate 4-{[4-fluoro-3-(trifluoromethyl)phenyl]methyl}piperazinyl 5-(trifluoromethyl)indol-2-yl ketone
phenyl 4-[(5-chloroindol-2-yl)carbonyl]piperazinecarboxylate
{1-[(5-chloroindol-2-yl)carbonyl](4-piperidyl)}-N-(3-fluorophenyl)carboxamide
4-{[4-fluoro-2-(trifluoromethyl)phenyl]methyl}piperazinyl 5-(trifluoromethyl)indol-2-yl ketone
3-(3,5-difluorophenyl)-1-[4-(diphenylmethyl)piperazinyl]prop-2-yn-1-one
5-chloroindol-2-yl 4-{[4-fluoro-3-(trifluoromethyl)phenyl]methyl}piperazinyl ketone
5-chloroindol-2-yl 4-{[4-(4-methoxyphenyl)phenyl]sulfonyl}piperazinyl ketone
3-(3,5-difluorophenyl)-1-(4-{[4-fluoro-2-(trifluoromethyl)phenyl]methyl}piperazinyl)prop-2-yn-1-one
4-{[3,5-bis(trifluoromethyl)phenyl]methyl}piperazinyl 5-chloroindol-2-yl ketone
3-(2,4-difluorophenyl)-1-{4-[(4-fluorophenyl)carbonyl]piperazinyl}prop-2-yn-1-one
6-fluoroindol-2-yl 4-[(4-fluorophenyl)carbonyl]piperazinyl ketone
5-chloroindol-2-yl 4-{[4-fluoro-2-(trifluoromethyl)phenyl]methyl}piperazinyl ketone
4-[(2,4-difluorophenyl)methyl]piperazinyl 5-chloroindol-2-yl ketone
5-chloroindol-2-yl 4-{[4-chloro-2-(trifluoromethyl)phenyl]methyl}piperazinyl ketone
{4-[(5-chloroindol-2-yl)carbonyl]piperazinyl}-N-(4-chlorophenyl)carboxamide
3-(2H-benzo[3,4-d]1,3-dioxolen-5-yl)-1-(4-{[4-(trifluoromethyl)phenyl]carbonyl}piperazinyl)prop-2-en-1-one
4-(diphenylmethyl)piperazinyl pyrrolo[2,3-c]pyridin-2-yl ketone
1-(4-{[4-fluoro-2-(trifluoromethyl)phenyl]methyl}piperazinyl)-3-[4-(trifluoromethyl)phenyl]prop-2-yn-1-one
4-(diphenylmethyl)piperazinyl 1-methylindol-5-yl ketone
4-(2,4-difluorophenyl)piperazinyl 5-chloroindol-2-yl ketone
3-(4-chlorophenyl)-1-(4-{[4-fluoro-2-(trifluoromethyl)phenyl]methyl}piperazinyl)prop-2-yn-1-one
4-(diphenylmethyl)piperazinyl 4-bromopyrrol-2-yl ketone
3-(3,4-dichlorophenyl)-1-(4-{[4-fluoro-2-(trifluoromethyl)phenyl]carbonyl}piperazinyl)prop-2-yn-1-one
1-{4-[(4-fluorophenyl)methyl]piperazinyl}-3-[2-(trifluoromethyl)phenyl]prop-2-yn-1-one
(2E)-3-(4-chloro-2-fluorophenyl)-1-[4-(phenylsulfonyl)piperazinyl]prop-2-en-1-one
3-(4-(5-chloro-1H-indole-2-carbonyl)piperazine-1-carbonyl)phenylboronic acid
(2E)-1-[4-(diphenylmethyl)piperazinyl]-3-(5-bromo-2-fluorophenyl)prop-2-en-1-one
(2E)-1-{4-[(4-bromophenyl)sulfonyl]piperazinyl}-3-(2-methylphenyl)prop-2-en-1-one
1-[4-(diphenylmethyl)piperazinyl]-3-[2-(trifluoromethyl)phenyl]prop-2-yn-1-one
(2E)-3-phenyl-1-piperazinylprop-2-en-1-one
N-(4-bromophenyl){4-[(5-chloroindol-2-yl)carbonyl]piperazinyl}carboxamide
3-(4-fluorophenyl)-1-{4-[(4-fluorophenyl)methyl]piperazinyl}prop-2-yn-1-one
6-chloroindol-2-yl 4-{[4-fluoro-2-(trifluoromethyl)phenyl]carbonyl}piperazinyl ketone
(2E)-1-(4-{[4-(tert-butyl)phenyl]sulfonyl}piperazinyl)-3-(4-chloro-2-fluorophenyl)prop-2-en-1-one
5-chloroindol-2-yl 4-(cyclopentylamino)piperidyl ketone
{4-[(5-chloroindol-2-yl)carbonyl]piperazinyl}-N-[4-fluoro-3-(trifluoromethyl)phenyl]carboxamide
{4-[(5-chloroindol-2-yl)carbonyl]piperazinyl}-N-(3-fluorophenyl)carboxamide
4-(2H-benzo[d]1,3-dioxolan-5-ylmethyl)piperazinyl benzo[d]furan-2-yl ketone
(2E)-1-[4-(diphenylmethyl)piperazinyl]-3-(4-methylphenyl)prop-2-en-1-one
5-chloroindol-2-yl 4-[(4-phenylphenyl)sulfonyl]piperazinyl ketone
(2E)-1-{4-[(4-bromophenyl)sulfonyl]piperazinyl}-3-(2-fluorophenyl)prop-2-en-1-one
{4-[(5-chloroindol-2-yl)carbonyl]piperazinyl}-N-[4-(trifluoromethyl)phenyl]carboxamide
3-(2H-benzo[3,4-d]1,3-dioxolan-5-yl)-1-{4-[(4-(1H-1,2,3,4-tetraazol-5-yl)phenyl)carbonyl]piperazinyl}prop-2-en-1-one
5-methylindol-2-yl 4-(3-pyridylmethyl)piperazinyl ketone
1-(4-{[4-fluoro-2-(trifluoromethyl)phenyl]methyl}piperazinyl)-3-(4-methylphenyl)prop-2-yn-1-one
4-({4-[(5-chloroindol-2-yl)carbonyl]piperazinyl}carbonyl)benzoic acid
1-{4-[(4-chlorophenyl)methyl]piperazinyl}-3-(4-fluorophenyl)prop-2-yn-1-one
{1-[(5-chloroindol-2-yl)carbonyl](4-piperidyl)}(4-chlorophenyl)
3-(2H-benzo[3,4-d]1,3-dioxolan-5-yl)-1-{4-[(4-fluorophenyl)methyl]piperazinyl}prop-2-en-1-one
4-[(4-chlorophenyl)methyl]piperazinyl 3-quinolyl ketone
4-(diphenylmethyl)piperazinyl 2-methylbenzimidazol-5-yl ketone
(2E)-3-phenyl-1-[4-(4-pyridylmethyl)piperazinyl]prop-2-en-1-one
3-(3,5-difluorophenyl)-1-{4-[(4-methoxyphenyl)carbonyl]piperazinyl}prop-2-yn-1-one
4-(diphenylmethyl)piperazinyl 3-isoquinolyl ketone -continued 1-{4-[(4-chlorophenyl)methyl]piperazinyl}-3-[2-(trifluoromethyl)phenyl]prop-2-yn-1-one
5-chloroindol-2-yl 4-(4-fluorophenyl)piperazinyl ketone
6-bromoindol-2-yl 4-[(4-chlorophenyl)methyl]piperazinyl ketone
4-bromophenyl 4-[(4-chlorophenyl)methyl]piperazinyl ketone
3-(3-chlorophenyl)-1-{4-[(4-methoxyphenyl)methyl]piperazinyl}prop-2-yn-1-one
{4-[(5-chloroindol-2-yl)carbonyl]piperazinyl}-N-(3-iodophenyl)carboxamide
3-[2-(trifluoromethyl)phenyl]-1-(4-{[4-(trifluoromethyl)phenyl]methyl}piperazinyl)prop-2-yn-1-one
5-chloroindol-2-yl 4-(2-fluorophenyl)piperazinyl ketone
N-(2,4-difluorophenyl){4-[(5-chloroindol-2-yl)carbonyl]piperazinyl}carboxamide
4-(diphenylmethyl)piperazinyl 8-hydropyrazolo[1,5-a]pyridin-2-yl ketone
3-(2H-benzo[3,4-d]1,3-dioxolan-5-yl)-1-(4-{[4-fluoro-2-(trifluoromethyl)phenyl]carbonyl}piperazinyl)prop-2-en-1-one
(2E)-1-(4-{[4-(tert-butyl)phenyl]sulfonyl}piperazinyl)-3-(2-methylphenyl)prop-2-en-1-one
(2E)-3-(4-bromophenyl)-1-{4-[(4-chlorophenyl)methyl]piperazinyl}prop-2-en-1-one
(E)-1-(4-(2-fluorobenzyl)piperazin-1-yl)-3-phenylprop-2-en-1-one
(E)-3-(3,4-dichlorophenyl)-1-(4-(4-(trifluoromethyl)benzyl)piperazin-1-yl)prop-2-en-1-one
(E)-3-(4-bromophenyl)-1-(4-(mesitylsulfonyl)piperazin-1-yl)prop-2-en-1-one
(E)-1-(4-((4-bromophenyl)sulfonyl)piperazin-1-yl)-3-(4-fluorophenyl)prop-2-en-1-one
(E)-3-(4-fluorophenyl)-1-(4-(phenethylsulfonyl)piperazin-1-yl)prop-2-en-1-one
(E)-3-(4-methoxyphenyl)-1-(4-(phenylsulfonyl)piperazin-1-yl)prop-2-en-1-one
(E)-1-(4-((4-acetylphenyl)sulfonyl)piperazin-1-yl)-3-(4-bromo-2-fluorophenyl)prop-2-en-1-one
(E)-3-(4-bromophenyl)-1-(4-(((4-(trifluoromethyl)benzyl)amino)methyl)piperidin-1-yl)prop-2-en-1-one
(E)-N-((1-(3-(4-bromophenyl)acryloyl)piperidin-4-yl)methyl)-4-(trifluoromethyl)benzamide In another embodiment is a compound selected from:

| Name |
| --- |
| (2E)-1-{4-[(2-fluorophenyl)methyl]piperazinyl}-3-phenylprop-2-en-1-one |
| (2E)-1-{4-[(3-fluorophenyl)methyl]piperazinyl}-3-phenylprop-2-en-1-one |
| (2E)-1-{4-[(4-fluorophenyl)methyl]piperazinyl}-3-phenylprop-2-en-1-one |
| (2E)-1-{4-[(3-methoxyphenyl)methyl]piperazinyl}-3-phenylprop-2-en-1-one |
| (2E)-1-{4-[(2-chlorophenyl)methyl]piperazinyl}-3-phenylprop-2-en-1-one |
| (2E)-1-{4-[(3-chlorophenyl)methyl]piperazinyl}-3-phenylprop-2-en-1-one |
| (2E)-1-{4-[(4-chlorophenyl)methyl]piperazinyl}-3-phenylprop-2-en-1-one |
| (2E)-1-{4-[(3-nitrophenyl)methyl]piperazinyl}-3-phenylprop-2-en-1-one |
| (2E)-1-{4-[(4-nitrophenyl)methyl]piperazinyl}-3-phenylprop-2-en-1-one |
| (2E)-1-{4-[(4-bromophenyl)methyl]piperazinyl}-3-phenylprop-2-en-1-one |
| (2E)-1-{4-[(2-bromophenyl)methyl]piperazinyl}-3-phenylprop-2-en-1-one |
| (2E)-1-{4-[(4-methylphenyl)methyl]piperazinyl}-3-phenylprop-2-en-1-one |
| (2E)-1-{4-[(3-methylphenyl)methyl]piperazinyl}-3-phenylprop-2-en-1-one |
| (2E)-1-{4-[(2-methylphenyl)methyl]piperazinyl}-3-phenylprop-2-en-1-one |
| 4-{[4-((2E)-3-phenylprop-2-enoyl)piperazinyl]methyl}benzenecarbonitrile |
| (2E)-1-{4-[(4-methoxyphenyl)methyl]piperazinyl}-3-phenylprop-2-en-1-one |
| (2E)-1-[4-((2E)-3-phenylprop-2-enoyl)piperazinyl]-3-phenylprop-2-en-1-one |
| (2E)-1-[4-(diphenylmethyl)piperazinyl]-3-phenylprop-2-en-1-one |
| (2E)-3-phenyl-1-piperazinylprop-2-en-1-one |
| (2E)-3-phenyl-1-[4-benzylpiperazinyl]prop-2-en-1-one |
| (2E)-1-[4-(naphthylmethyl)piperazinyl]-3-phenylprop-2-en-1-one |
| (2E)-3-phenyl-1-[4-(2-pyridylmethyl)piperazinyl]prop-2-en-1-one |
| (2E)-1-{4-[(2,5-difluorophenyl)methyl]piperazinyl}-3-phenylprop-2-en-1-one |
| (2E)-3-phenyl-1-[4-(4-pyridylmethyl)piperazinyl]prop-2-en-1-one |
| (2E)-1-{4-[(3,5-dimethylphenyl)methyl]piperazinyl}-3-phenylprop-2-en-1-one |
| (2E)-1-{4-[2-(2-fluorophenyl)ethyl]piperazinyl}-3-phenylprop-2-en-1-one |
| (2E)-1-{4-[2-(4-chlorophenyl)ethyl]piperazinyl}-3-phenylprop-2-en-1-one |
| (2E)-1-{4-[2-(2,4-dichlorophenoxy)ethyl]piperazinyl}-3-phenylprop-2-en-1-one |
| (2E)-1-[4-(methylpropyl)piperazinyl]-3-phenylprop-2-en-1-one |
| (2E)-1-(4-butylpiperazinyl)-3-phenylprop-2-en-1-one |
| (2E)-1-[4-(2-(1,3-dihydroisobenzofuran-5-yl)ethyl)piperazinyl]-3-phenylprop-2-en-1-one |
| (2E)-3-(4-fluorophenyl)-1-{4-[benzylsulfonyl]piperazinyl}prop-2-en-1-one |
| (2E)-1-{4-[(4-bromophenyl)sulfonyl]piperazinyl}-3-(4-fluorophenyl)prop-2-en-1-one |
| (2E)-1-{4-[(4-chlorophenyl)sulfonyl]piperazinyl}-3-(4-fluorophenyl)prop-2-en-1-one |
| (2E)-3-(4-fluorophenyl)-1-{4-[(4-methylphenyl)sulfonyl]piperazinyl}prop-2-en-1-one |
| (2E)-3-(4-fluorophenyl)-1-{4-[(4-nitrophenyl)sulfonyl]piperazinyl}prop-2-en-1-one |

| Name |
| --- |
| (2E)-1-(4-{[4-(tert-butyl)phenyl]sulfonyl}piperazinyl)-3-(4-fluorophenyl)prop-2-en-1-one |
| (2E)-3-(4-fluorophenyl)-1-[4-(phenylsulfonyl)piperazinyl]prop-2-en-1-one |
| (2E)-3-(4-fluorophenyl)-1-{4-[(4-fluorophenyl)sulfonyl]piperazinyl}prop-2-en-1-one |
| 1-[((1E)-2-phenylvinyl)sulfonyl]-4-(diphenylmethyl)piperazine |
| (2E)-1-[4-(2-3,4-dihydronaphthylsulfonyl)piperazinyl]-3-(4-fluorophenyl)prop-2-en-1-one |
| (2E)-3-(4-fluorophenyl)-1-{4-[(2-fluorophenyl)sulfonyl]piperazinyl}prop-2-en-1-one |
| (2E)-3-(4-fluorophenyl)-1-{4-[(4-methoxyphenyl)sulfonyl]piperazinyl}prop-2-en-1-one |
| (2E)-3-(4-fluorophenyl)-1-{4-[(3-fluorophenyl)sulfonyl]piperazinyl}prop-2-en-1-one |
| (2E)-1-{4-[(3-chlorophenyl)sulfonyl]piperazinyl}-3-(4-fluorophenyl)prop-2-en-1-one |
| (2E)-1-{4-[(2-bromophenyl)sulfonyl]piperazinyl}-3-(4-fluorophenyl)prop-2-en-1-one |
| (2E)-3-(4-fluorophenyl)-1-{4-[(3-methoxyphenyl)sulfonyl]piperazinyl}prop-2-en-1-one |
| (2E)-3-(4-fluorophenyl)-1-{4-[(4-propylphenyl)sulfonyl]piperazinyl}prop-2-en-1-one |
| (2E)-1-{4-[(2,5-dimethoxyphenyl)sulfonyl]piperazinyl}-3-(4-fluorophenyl)prop-2-en-1-one |
| (2E)-3-(4-fluorophenyl)-1-(4-{[4-(methylethyl)phenyl]sulfonyl}piperazinyl)prop-2-en-1-one |
| (2E)-1-{4-[(2,5-dichlorophenyl)sulfonyl]piperazinyl}-3-(4-fluorophenyl)prop-2-en-1-one |
| (2E)-1-{4-[(3-bromophenyl)sulfonyl]piperazinyl}-3-(4-fluorophenyl)prop-2-en-1-one |
| 2-({4-[(2E)-3-(4-fluorophenyl)prop-2-enoyl]piperazinyl}sulfonyl)benzenecarbonitrile |
| (2E)-3-(4-fluorophenyl)-1-[4-(2-naphthylsulfonyl)piperazinyl]prop-2-en-1-one |
| (2E)-3-(4-fluorophenyl)-1-[4-(naphthylsulfonyl)piperazinyl]prop-2-en-1-one |
| (2E)-3-(4-fluorophenyl)-1-[4-(2-thienylsulfonyl)piperazinyl]prop-2-en-1-one |
| 4-(diphenylmethyl)piperazinyl 5-methyl(3-pyridyl) ketone |
| 4-(diphenylmethyl)piperazinyl 3-bromophenyl ketone |
| 4-(diphenylmethyl)piperazinyl 5-chloro(3-pyridyl) ketone |
| 4-(diphenylmethyl)piperazinyl 5-bromo(3-pyridyl) ketone |
| 4-(diphenylmethyl)piperazinyl 3-methylphenyl ketone |
| 1-{4-[((1E)-2-phenylvinyl)sulfonyl]piperazinyl}-3-(4-fluorophenyl)propan-1-one |
| (2E)-3-(4-fluorophenyl)-1-{4-[(2-phenylethyl)sulfonyl]piperazinyl}prop-2-en-1-one |
| (2E)-3-(4-bromophenyl)-1-{4-[(4-bromophenyl)sulfonyl]piperazinyl}prop-2-en-1-one |
| (2E)-3-(4-bromophenyl)-1-{4-[(2,4,6-trimethylphenyl)sulfonyl]piperazinyl}prop-2-en-1-one |
| (2E)-1-(4-{[4-(tert-butyl)phenyl]sulfonyl}piperazinyl)-3-(4-bromophenyl)prop-2-en-1-one |
| (2E)-1-[4-(diphenylmethyl)piperazinyl]-3-(4-nitrophenyl)prop-2-en-1-one |
| (2E)-1-[4-(diphenylmethyl)piperazinyl]-3-(2-chlorophenyl)prop-2-en-1-one |
| 3-(4-aminophenyl)-1-[4-(diphenylmethyl)piperazinyl]propan-1-one |
| (2E)-3-(4-bromophenyl)-1-{4-[(4-chlorophenyl)methyl]piperazinyl}prop-2-en-1-one |
| (2E)-3-(4-bromophenyl)-1-{4-[(3-fluorophenyl)methyl]piperazinyl}prop-2-en-1-one |
| (2E)-3-(4-bromophenyl)-1-{4-[(4-methylphenyl)methyl]piperazinyl}prop-2-en-1-one |
| (2E)-3-(4-bromophenyl)-1-(4-{[4-(methylethyl)phenyl]methyl}piperazinyl)prop-2-en-1-one |
| (2E)-1-{4-[(3,5-dimethylphenyl)methyl]piperazinyl}-3-(4-bromophenyl)prop-2-en-1-one |
| (2E)-1-{4-[(3,4-dichlorophenyl)methyl]piperazinyl}-3-(4-bromophenyl)prop-2-en-1-one |
| (2E)-1-{4-[(3,5-dimethoxyphenyl)methyl]piperazinyl}-3-(4-bromophenyl)prop-2-en-1-one |
| (2E)-1-(4-{[4-(tert-butyl)phenyl]methyl}piperazinyl)-3-(4-bromophenyl)prop-2-en-1-one |
| (2E)-1-{4-[(3,5-difluorophenyl)methyl]piperazinyl}-3-(4-bromophenyl)prop-2-en-1-one |
| (2E)-3-(4-bromophenyl)-1-{4-[(4-fluoro-3-methylphenyl)methyl]piperazinyl}prop-2-en-1-one |
| (2E)-3-(4-bromophenyl)-1-{4-[(4-chloro-2-fluorophenyl)methyl]piperazinyl}prop-2-en-1-one |
| (2E)-3-(4-bromophenyl)-1-(4-{[4-fluoro-2-(trifluoromethyl)phenyl]methyl}piperazinyl)prop-2-en-1-one |
| (2E)-3-(4-aminophenyl)-1-[4-(diphenylmethyl)piperazinyl]prop-2-en-1-one |
| (2E)-3-(4-bromophenyl)-1-(4-{[4-chloro-2-(trifluoromethyl)phenyl]methyl}piperazinyl)prop-2-en-1-one |
| (2E)-3-(4-bromophenyl)-1-{4-[(2-fluorophenyl)methyl]piperazinyl}prop-2-en-1-one |
| (2E)-1-[4-(diphenylmethyl)piperazinyl]-3-(4-methylphenyl)prop-2-en-1-one |
| (2E)-1-{4-[((1E)-2-phenylvinyl)sulfonyl](1,4-diazaperhydroepinyl)}-3-(4-bromophenyl)prop-2-en-1-one |
| (2E)—N-(2-{[((1E)-2-phenylvinyl)sulfonyl]amino}ethyl)-3-(4-bromophenyl)prop-2-enamide |
| (2E)—N-(3-{[((1E)-2-phenylvinyl)sulfonyl]amino}propyl)-3-(4-bromophenyl)prop-2-enamide |
| (2E)—N-(2-{[((1E)-2-phenylvinyl)sulfonyl]amino}ethyl)-3-(4-bromophenyl)-N-methylprop-2-enamide |

| Name |
| --- |
| (2E)—N-(2-{[((1E)-2-phenylvinyl)sulfonyl]amino}ethyl)-3-(4-fluorophenyl)-N-methylprop-2-enamide |
| (2E)—N-(2-{[((1E)-2-phenylvinyl)sulfonyl]amino}ethyl)-3-(4-fluorophenyl)prop-2-enamide |
| (2E)—N-(3-{[((1E)-2-phenylvinyl)sulfonyl]amino}propyl)-3-(4-fluorophenyl)prop-2-enamide |
| (2E)-1-{4-[((1E)-2-phenylvinyl)sulfonyl](1,4-diazaperhydroepinyl)}-3-(4-fluorophenyl)prop-2-en-1-one |
| (2E)-1-[4-(diphenylmethyl)(1,4-diazaperhydroepinyl)]-3-(4-fluorophenyl)prop-2-en-1-one |
| (2E)-1-[4-(diphenylmethyl)piperazinyl]-3-[3-(trifluoromethyl)phenyl]prop-2-en-1-one |
| (2E)-1-[4-(diphenylmethyl)piperazinyl]-3-(4-bromophenyl)prop-2-en-1-one |
| (2E)-3-(4-bromophenyl)-1-(4-ethylpiperazinyl)prop-2-en-1-one |
| 4-(diphenylmethyl)piperazinyl 1-methylindol-5-yl ketone |
| (2E)-3-(4-bromophenyl)-1-(4-butylpiperazinyl)prop-2-en-1-one |
| (2E)-3-(4-bromophenyl)-1-[4-(methylpropyl)piperazinyl]prop-2-en-1-one |
| (2E)-1-(4,4-dimethylpiperazinyl)-3-(4-bromophenyl)prop-2-en-1-one |
| (2E)-1-[4-(diphenylmethyl)piperazinyl]-3-(3,4,5-trifluorophenyl)prop-2-en-1-one |
| (2E)-3-(3,4-dichlorophenyl)-1-[4-(diphenylmethyl)piperazinyl]prop-2-en-1-one |
| (2E)-1-[4-(diphenylmethyl)piperazinyl]-3-(4-chloro-2-fluorophenyl)prop-2-en-1-one |
| (2E)-1-[4-(diphenylmethyl)piperazinyl]-3-(4-methoxyphenyl)prop-2-en-1-one |
| (2E)-1-[4-(diphenylmethyl)piperazinyl]-3-(4-ethoxyphenyl)prop-2-en-1-one |
| (2E)-1-[4-(diphenylmethyl)piperazinyl]-3-(2-fluorophenyl)prop-2-en-1-one |
| (2E)-1-[4-(diphenylmethyl)piperazinyl]-3-(2-methylphenyl)prop-2-en-1-one |
| (2E)-1-[4-(diphenylmethyl)piperazinyl]-3-(5-bromo-2-fluorophenyl)prop-2-en-1-one |
| (2E)-1-[4-(diphenylmethyl)piperazinyl]-3-(4-bromo-2-fluorophenyl)prop-2-en-1-one |
| (2E)-3-(2,4-difluorophenyl)-1-[4-(diphenylmethyl)piperazinyl]prop-2-en-1-one |
| (2E)-3-(3,4-difluorophenyl)-1-[4-(diphenylmethyl)piperazinyl]prop-2-en-1-one |
| (2E)-1-[4-(diphenylmethyl)piperazinyl]-3-[4-(trifluoromethyl)phenyl]prop-2-en-1-one |
| (2E)-1-[4-(diphenylmethyl)piperazinyl]-3-[2,4-bis(trifluoromethyl)phenyl]prop-2-en-1-one |
| (2E)-3-(2,5-dichlorophenyl)-1-[4-(diphenylmethyl)piperazinyl]prop-2-en-1-one |
| (2E)-1-[4-(diphenylmethyl)piperazinyl]-3-(6-chloro-2-fluorophenyl)prop-2-en-1-one |
| (2E)-1-{4-[(4-bromophenyl)sulfonyl]piperazinyl}-3-(2-fluorophenyl)prop-2-en-1-one |
| (2E)-3-(2-fluorophenyl)-1-[4-(phenylsulfonyl)piperazinyl]prop-2-en-1-one |
| (2E)-1-(4-{[4-(tert-butyl)phenyl]sulfonyl}piperazinyl)-3-(2-fluorophenyl)prop-2-en-1-one |
| (2E)-3-(3,4-dichlorophenyl)-1-[4-(phenylsulfonyl)piperazinyl]prop-2-en-1-one |
| (2E)-3-(3,4-dichlorophenyl)-1-(4-{[4-(tert-butyl)phenyl]sulfonyl}piperazinyl)prop-2-en-1-one |
| (2E)-3-(4-chloro-2-fluorophenyl)-1-[4-(phenylsulfonyl)piperazinyl]prop-2-en-1-one |
| (2E)-1-{4-[(4-bromophenyl)sulfonyl]piperazinyl}-3-(4-chloro-2-fluorophenyl)prop-2-en-1-one |
| (2E)-1-(4-{[4-(tert-butyl)phenyl]sulfonyl}piperazinyl)-3-(4-chloro-2-fluorophenyl)prop-2-en-1-one |
| (2E)-1-(4-{[4-(tert-butyl)phenyl]sulfonyl}piperazinyl)-3-(4-methoxyphenyl)prop-2-en-1-one |
| (2E)-3-(4-methoxyphenyl)-1-[4-(phenylsulfonyl)piperazinyl]prop-2-en-1-one |
| (2E)-1-{4-[(4-bromophenyl)sulfonyl]piperazinyl}-3-(4-methoxyphenyl)prop-2-en-1-one |
| (2E)-3-(2-methylphenyl)-1-[4-(phenylsulfonyl)piperazinyl]prop-2-en-1-one |
| (2E)-1-(4-{[4-(tert-butyl)phenyl]sulfonyl}piperazinyl)-3-(2-methylphenyl)prop-2-en-1-one |
| (2E)-1-{4-[(4-bromophenyl)sulfonyl]piperazinyl}-3-(2-methylphenyl)prop-2-en-1-one |
| (2E)-1-{4-[(4-bromophenyl)sulfonyl]piperazinyl}-3-[2-(trifluoromethyl)phenyl]prop-2-en-1-one |
| (2E)-1-[4-(phenylsulfonyl)piperazinyl]-3-[2-(trifluoromethyl)phenyl]prop-2-en-1-one |
| (2E)-3-(4-bromo-2-fluorophenyl)-1-{4-[(4-bromophenyl)sulfonyl]piperazinyl}prop-2-en-1-one |
| (2E)-3-(4-bromo-2-fluorophenyl)-1-[4-(phenylsulfonyl)piperazinyl]prop-2-en-1-one |
| 4-({4-[(2E)-3-(4-bromo-2-fluorophenyl)prop-2-enoyl]piperazinyl}sulfonyl)-1-acetylbenzene |
| 4-({4-[(2E)-3-(4-ethoxyphenyl)prop-2-enoyl]piperazinyl}sulfonyl)-1-acetylbenzene |
| (2E)-1-{4-[(4-bromophenyl)sulfonyl]piperazinyl}-3-(4-ethoxyphenyl)prop-2-en-1-one |
| (2E)-3-(4-ethoxyphenyl)-1-[4-(phenylsulfonyl)piperazinyl]prop-2-en-1-one |
| 4-({4-[(2E)-3-(5-bromo-2-fluorophenyl)prop-2-enoyl]piperazinyl}sulfonyl)-1-acetylbenzene |
| (2E)-3-(5-bromo-2-fluorophenyl)-1-{4-[(4-bromophenyl)sulfonyl]piperazinyl}prop-2-en-1-one |
| (2E)-3-(5-bromo-2-fluorophenyl)-1-[4-(phenylsulfonyl)piperazinyl]prop-2-en-1-one |
| (2E)-3-(4-bromophenyl)-1-{4-[(4-methoxyphenyl)carbonyl]piperazinyl}prop-2-en-1-one |
| (2E)-3-(4-bromophenyl)-1-[4-(phenylcarbonyl)piperazinyl]prop-2-en-1-one |
| (2E)-3-(4-bromophenyl)-1-(4-{[4-(trifluoromethyl)phenyl]carbonyl}piperazinyl)prop-2-en-1-one |
| (2E)-3-(4-bromophenyl)-1-[4-(cyclopentylcarbonyl)piperazinyl]prop-2-en-1-one |
| (2E)-3-(4-bromophenyl)-1-(4-pentanoylpiperazinyl)prop-2-en-1-one |

| Name |
| --- |
| (2E)-3-(4-bromophenyl)-1-[4-(3-methylbutanoyl)piperazinyl]prop-2-en-1-one |
| 4-({4-[(2E)-3-(4-bromophenyl)prop-2-enoyl]piperazinyl}carbonyl)benzenecarbonitrile |
| (2E)-3-(4-bromophenyl)-1-[4-(2-methylbutanoyl)piperazinyl]prop-2-en-1-one |
| (2E)-3-(4-bromophenyl)-1-(4-heptanoylpiperazinyl)prop-2-en-1-one |
| (2E)-3-(4-bromophenyl)-1-{4-[(4-methylphenyl)carbonyl]piperazinyl}prop-2-en-1-one |
| (2E)-1-{4-[(2,4-difluorophenyl)carbonyl]piperazinyl}-3-(4-bromophenyl)prop-2-en-1-one |
| (2E)-3-(4-bromophenyl)-1-(4-propanoylpiperazinyl)prop-2-en-1-one |
| (2E)-3-(4-bromophenyl)-1-{4-[(4-fluorophenyl)amino]piperidyl}prop-2-en-1-one |
| (2E)-1-{4-[(3,5-difluorophenyl)amino]piperidyl}-3-(4-bromophenyl)prop-2-en-1-one |
| (2E)-3-(4-bromophenyl)-1-{4-[(4-chlorophenyl)carbonyl]piperazinyl}prop-2-en-1-one |
| (2E)-3-(4-bromophenyl)-1-[4-(phenylamino)piperidyl]prop-2-en-1-one |
| (2E)-3-(4-bromophenyl)-1-{4-[(4-chlorophenyl)amino]piperidyl}prop-2-en-1-one |
| N-({1-[(2E)-3-(4-bromophenyl)prop-2-enoyl](4-piperidyl)}methyl)(4-fluorophenyl)carboxamide |
| (E)-(4-(4-(3-(4-bromophenyl)acryloyl)piperazine-1-carbonyl)phenyl)boronic acid |
| (2E)-3-(4-bromophenyl)-1-{4-[(4-(1H-1,2,3,4-tetraazol-5-yl)phenyl]carbonyl]piperazinyl}prop-2-en-1-one |
| potassium (E)-5-(4-(4-(3-(4-bromophenyl)acryloyl)piperazine-1-carbonyl)phenyl)tetrazol-1-ide |
| (2E)-3-(4-bromophenyl)-1-{4-[({[4-(trifluoromethyl)phenyl]methyl}amino)methyl]piperidyl}prop-2-en-1-one |
| (2E)-3-(4-bromophenyl)-1-[4-({[(4-fluorophenyl)methyl]amino}methyl)piperidyl]prop-2-en-1-one |
| (2E)-3-(4-bromophenyl)-1-{4-[({[3-fluoro-4-(trifluoromethyl)phenyl]methyl}amino)methyl]piperidyl}prop-2-en-1-one |
| (2E)-3-(4-bromophenyl)-1-[4-({[(4-chlorophenyl)methyl]amino}methyl)piperidyl]prop-2-en-1-one |
| N-({1-[(2E)-3-(4-bromophenyl)prop-2-enoyl](4-piperidyl)}methyl)[4-(trifluoromethyl)phenyl]carboxamide |
| (2E)-1-[4-({[(3,5-difluorophenyl)methyl]amino}methyl)piperidyl]-3-(4-bromophenyl)prop-2-en-1-one |
| (2E)-3-(4-bromophenyl)-1-{4-[(4-chlorophenyl)methyl]piperazinyl}prop-2-en-1-one |
| 2-(4-bromophenyl)-1-{4-[(4-fluorophenyl)carbonyl]piperazinyl}ethan-1-one |
| 2-(4-bromophenyl)-1-{4-[(4-chlorophenyl)carbonyl]piperazinyl}ethan-1-one |
| 2-(4-bromophenyl)-1-{4-[(4-chlorophenyl)methyl]piperazinyl}ethan-1-one |
| 2-(4-bromophenyl)-1-{4-[(4-fluorophenyl)methyl]piperazinyl}ethan-1-one |
| 2-(4-bromophenyl)-1-(4-{[4-fluoro-2-(trifluoromethyl)phenyl]methyl}piperazinyl)ethan-1-one |
| 1-{4-[(3,4-dichlorophenyl)methyl]piperazinyl}-2-(4-bromophenyl)ethan-1-one |
| 2-(4-bromophenyl)-1-(4-{[4-(trifluoromethyl)phenyl]methyl}piperazinyl)ethan-1-one |
| 2-(4-bromophenyl)-1-{4-[(4-methylphenyl)methyl]piperazinyl}ethan-1-one |
| 2-(4-bromophenyl)-1-(4-{[4-(methylethyl)phenyl]methyl}piperazinyl)ethan-1-one |

In another embodiment is a compound selected from:

| Name |
| --- |
| 4-(diphenylmethyl)piperazinyl 3-quinolyl ketone |
| indol-3-yl 4-methyl-4-(phenylethyl)piperazinyl ketone |
| tert-butyl 4-(indol-3-ylcarbonyl)piperazinecarboxylate |
| tert-butyl 4-(indol-2-ylcarbonyl)piperazinecarboxylate |
| 4-(diphenylmethyl)piperazinyl indol-3-yl ketone |
| 4-(diphenylmethyl)piperazinyl indol-2-yl ketone |
| 1,5-dimethylindol-2-yl 4-(diphenylmethyl)piperazinyl ketone |
| 4-(diphenylmethyl)piperazinyl 1-methylindol-2-yl ketone |
| indol-2-yl 4-(phenylethyl)piperazinyl ketone |
| indol-3-yl 4-(phenylethyl)piperazinyl ketone |
| tert-butyl 4-[(1-methylindol-3-yl)carbonyl]piperazinecarboxylate |
| tert-butyl 4-[(1-methylindol-2-yl)carbonyl]piperazinecarboxylate |
| benzo[d]furan-2-yl 4-(phenylethyl)piperazinyl ketone |
| 4-(2H-benzo[d]1,3-dioxolan-5-ylmethyl)piperazinyl benzo[d]furan-2-yl ketone |
| 4-(2H-benzo[d]1,3-dioxolan-5-ylmethyl)piperazinyl indol-3-yl ketone |
| 4-(phenylethyl)piperazinyl 3-quinolyl ketone |
| 5-methylindol-2-yl 4-(phenylethyl)piperazinyl ketone |
| [4-(diphenylmethyl)piperazinyl]-3-quinolylmethane-1-thione |
| 4-(diphenylmethyl)piperazinyl 2-quinolyl ketone |
| 4-(2H-benzo[3,4-d]1,3-dioxolen-5-ylmethyl)piperazinyl 2-quinolyl ketone |
| 1-methylindol-3-yl 4-(phenylethyl)piperazinyl ketone |
| 4-(2H-benzo[d]1,3-dioxolan-5-ylmethyl)piperazinyl 3-quinolyl ketone |
| 4-(2H-benzo[d]1,3-dioxolan-5-ylmethyl)piperazinyl 5-methylindol-2-yl ketone |
| 4-(diphenylmethyl)piperazinyl 5-chloroindol-2-yl ketone |
| [4-(diphenylmethyl)piperazinyl](5-methylindol-2-yl)methane-1-thione |

| Name |
| --- |
| 4-(diphenylmethyl)piperazinyl 5-phenylindol-2-yl ketone |
| benzimidazol-2-yl 4-(diphenylmethyl)piperazinyl ketone |
| 5-methylindol-2-yl 4-benzylpiperazinyl ketone |
| 4-(diphenylmethyl)piperazinyl 5-(4-methoxyphenyl)indol-2-yl ketone |
| 4-(diphenylmethyl)piperazinyl 4-bromopyrrol-2-yl ketone |
| 4-{[4-(tert-butyl)phenyl]methyl}piperazinyl 5-methylindol-2-yl ketone |
| 4-[(4-fluorophenyl)methyl]piperazinyl 5-methylindol-2-yl ketone |
| 4-(diphenylmethyl)piperazinyl 2-naphthyl ketone |
| 4-[((1E)-2-phenylvinyl)sulfonyl]piperazinyl 5-methylindol-2-yl ketone |
| 4-[(4-bromophenyl)sulfonyl]piperazinyl 5-methylindol-2-yl ketone |
| 4-(diphenylmethyl)piperazinyl 5-methyl(3-pyridyl) ketone |
| 4-(diphenylmethyl)piperazinyl 3-bromophenyl ketone |
| 4-(diphenylmethyl)piperazinyl 5-chloro(3-pyridyl) ketone |
| 4-(diphenylmethyl)piperazinyl 5-bromo(3-pyridyl) ketone |
| benzo[b]thiophen-2-yl 4-(diphenylmethyl)piperazinyl ketone |
| 4-(diphenylmethyl)piperazinyl 3-methylphenyl ketone |
| N-[1-(diphenylmethyl)(4-piperidyl)](5-methylindol-2-yl)carboxamide |
| 4-(diphenylmethyl)piperazinyl indol-7-yl ketone |
| 4-(diphenylmethyl)piperazinyl 5-bromoindol-2-yl ketone |
| 4-(diphenylmethyl)piperazinyl 4-quinolyl ketone |
| 4-(diphenylmethyl)piperazinyl 4,5,6,7-tetrahydrobenzo[b]thiophen-2-yl ketone |
| 4-(diphenylmethyl)piperazinyl 5-fluoroindol-2-yl ketone |
| 4-(diphenylmethyl)piperazinyl 6-bromoindol-2-yl ketone |
| 4-(diphenylmethyl)piperazinyl quinoxalin-2-yl ketone |
| 4-(diphenylmethyl)piperazinyl 6-chloroindol-2-yl ketone |
| 4-(diphenylmethyl)piperazinyl 5-nitroindol-2-yl ketone |
| 4-(diphenylmethyl)piperazinyl 5-hydroxyindol-2-yl ketone |
| 4-(diphenylmethyl)piperazinyl 8-hydropyrazolo[1,5-a]pyridin-2-yl ketone |
| 4-(diphenylmethyl)piperazinyl 6-fluoroindol-2-yl ketone |
| 1H-indazol-3-yl 4-(diphenylmethyl)piperazinyl ketone |
| 4-(diphenylmethyl)piperazinyl pyrrolo[4,5-b]pyridin-2-yl ketone |
| 5-methylindol-2-yl 4-[(2-phenylethyl)sulfonyl]piperazinyl ketone |
| 4-(diphenylmethyl)piperazinyl 5-(trifluoromethyl)indol-2-yl ketone |
| 5-methylindol-2-yl 4-benzylpiperazinyl ketone |
| 4-(diphenylmethyl)piperazinyl indol-4-yl ketone |
| benzo[b]thiophen-3-yl 4-(diphenylmethyl)piperazinyl ketone |
| 4-(diphenylmethyl)piperazinyl 3-methylbenzo[b]thiophen-2-yl ketone |
| 4-(diphenylmethyl)piperazinyl 3-isoquinolyl ketone |
| 4,6-difluoroindol-2-yl 4-(diphenylmethyl)piperazinyl ketone |
| 4,6-dichloroindol-2-yl 4-(diphenylmethyl)piperazinyl ketone |
| 4-(diphenylmethyl)piperazinyl 5-methoxyindol-2-yl ketone |
| 5-methylindol-2-yl 4-(phenylamino)piperidyl ketone |
| 5,6-dimethoxyindol-2-yl 4-(diphenylmethyl)piperazinyl ketone |
| 4-(diphenylmethyl)piperazinyl 6-fluoro(2-naphthyl) ketone |
| 4-(diphenylmethyl)piperazinyl 7-nitroindol-2-yl ketone |
| 4-[(4-chlorophenyl)methyl]piperazinyl 5-methylindol-2-yl ketone |
| 4-[(3,5-dimethylphenyl)methyl]piperazinyl 5-methylindol-2-yl ketone |
| 4-[(3,4-dichlorophenyl)methyl]piperazinyl 5-methylindol-2-yl ketone |
| 4-(diphenylmethyl)piperazinyl 4-hydroimidazo[1,2-a]pyridin-2-yl ketone |
| 5-methylindol-2-yl 4-(2-pyridylmethyl)piperazinyl ketone |
| 5-methylindol-2-yl 4-(3-pyridylmethyl)piperazinyl ketone |
| 4-(diphenylmethyl)piperazinyl pyrrolo[2,3-c]pyridin-2-yl ketone |
| 3-{[4-(diphenylmethyl)piperazinyl]carbonyl}-8-fluorohydroquinolin-4-one |
| 4-(diphenylmethyl)piperazinyl 6-quinolyl ketone |
| 4-(diphenylmethyl)piperazinyl 2-methylbenzimidazol-5-yl ketone |
| benzimidazol-5-yl 4-(diphenylmethyl)piperazinyl ketone |
| 4-(diphenylmethyl)piperazinyl 6-methylthiopheno[3,2-d]pyrrol-5-yl ketone |
| 4-(diphenylmethyl)piperazinyl indol-6-yl ketone |
| 4-(diphenylmethyl)piperazinyl 6-ethylthiopheno[3,2-d]pyrrol-5-yl ketone |
| 4-(diphenylmethyl)piperazinyl 5-fluorobenzo[b]thiophen-2-yl ketone |
| 6-amino(2-naphthyl) 4-(diphenylmethyl)piperazinyl ketone |
| benzo[b]thiophen-5-yl 4-(diphenylmethyl)piperazinyl ketone |
| 4-(diphenylmethyl)piperazinyl 1-methylindol-5-yl ketone |
| 4-(diphenylmethyl)piperazinyl 4-methoxyindol-2-yl ketone |
| 4-(diphenylmethyl)piperazinyl 6-methoxyindol-2-yl ketone |
| 4-(diphenylmethyl)piperazinyl 5-(phenylmethoxy)indol-2-yl ketone |
| 4-(diphenylmethyl)piperazinyl 2-chloro(3-quinolyl) ketone |
| 5-(tert-butyl)-3-methylindol-2-yl 4-(diphenylmethyl)piperazinyl ketone |
| 5-chloroindol-2-yl 4-[(4-fluorophenyl)methyl]piperazinyl ketone |
| 5-chloroindol-2-yl 4-{[4-chloro-2-(trifluoromethyl)phenyl]methyl}piperazinyl ketone |
| 5-chloroindol-2-yl 4-{[4-fluoro-3-(trifluoromethyl)phenyl]methyl}piperazinyl ketone |
| 5-chloroindol-2-yl 4-{[3-fluoro-4-(trifluoromethyl)phenyl]methyl}piperazinyl ketone |
| 5-chloroindol-2-yl 4-{[4-fluoro-2-(trifluoromethyl)phenyl]methyl}piperazinyl ketone |
| 4-[(2,4-difluorophenyl)methyl]piperazinyl 5-chloroindol-2-yl ketone |
| 4-{[3,5-bis(trifluoromethyl)phenyl]methyl}piperazinyl 5-chloroindol-2-yl ketone |
| 4-(diphenylmethyl)piperazinyl 5-(methylethyl)indol-2-yl ketone |
| 4-(diphenylmethyl)piperazinyl 7-chloro-2-methyl(3-quinolyl) ketone |

| Name |
| --- |
| benzothiazol-2-yl 4-(diphenylmethyl)piperazinyl ketone |
| 5-(tert-butyl)indol-2-yl 4-(diphenylmethyl)piperazinyl ketone |
| 4-(diphenylmethyl)piperazinyl 5-bromobenzo[b]thiophen-2-yl ketone |
| 4-(diphenylmethyl)piperazinyl thiopheno[2,3-d]pyrrol-5-yl ketone |
| 4-(diphenylmethyl)piperazinyl 5-(trifluoromethyl)benzo[b]thiophen-2-yl ketone |
| 4-(diphenylmethyl)piperazinyl 6-chlorobenzo[b]thiophen-2-yl ketone |
| 4-[(4-fluorophenyl)methyl]piperazinyl 5-(trifluoromethyl)indol-2-yl ketone |
| 4-(diphenylmethyl)piperazinyl 8-fluoro(3-quinolyl) ketone |
| 3-{[4-(diphenylmethyl)piperazinyl]carbonyl}chromen-2-one |
| 5-chloroindol-2-yl 2-1,2,3,4-tetrahydroisoquinolyl ketone |
| 5-chloroindol-2-yl 3-phenylimidazo[2,1-c]piperazin-7-yl ketone |
| 5-chloroindol-2-yl 4,5,6,7-tetrahydroimidazo[5,4-c]pyridin-5-yl ketone |
| 5-chloroindol-2-yl 3-phenyl(1,2,4-triazolo[3,4-c]piperazin-7-yl) ketone |
| 4-{[3-fluoro-4-(trifluoromethyl)phenyl]methyl}piperazinyl 5-(trifluoromethyl)indol-2-yl ketone |
| 4-[(2,4-difluorophenyl)methyl]piperazinyl 5-(trifluoromethyl)indol-2-yl ketone |
| 4-{[4-fluoro-3-(trifluoromethyl)phenyl]methyl}piperazinyl 5-(trifluoromethyl)indol-2-yl ketone |
| 4-{[4-fluoro-2-(trifluoromethyl)phenyl]methyl}piperazinyl 5-(trifluoromethyl)indol-2-yl ketone |
| 4-[(3,5-difluorophenyl)methyl]piperazinyl 5-(trifluoromethyl)indol-2-yl ketone |
| 4-(diphenylmethyl)piperazinyl 5-chlorobenzo[b]thiophen-2-yl ketone |
| 4-(diphenylmethyl)piperazinyl 5-fluorobenzo[b]thiophen-2-yl ketone |
| 2,8-diazabicyclo[4.3.0]non-8-yl 5-chloroindol-2-yl ketone |
| 5-chloroindol-2-yl 2-ethyl-2,8-diazabicyclo[4.3.0]non-8-yl ketone |
| 5-chloroindol-2-yl 4-morpholin-4-ylpiperidyl ketone |
| 5-chloroindol-2-yl 4-phenoxypiperidyl ketone |
| 4-[(2,4-difluorophenyl)amino]piperidyl 5-chloroindol-2-yl ketone |
| 4-[(3,5-difluorophenyl)amino]piperidyl 5-chloroindol-2-yl ketone |
| 5-chloroindol-2-yl 4-[(3-fluorophenyl)amino]piperidyl ketone |
| 4-[(3,4-dimethylphenyl)amino]piperidyl 5-chloroindol-2-yl ketone |
| 5-chloroindol-2-yl 4-[(4-fluorophenyl)amino]piperidyl ketone |
| 5-chloroindol-2-yl 4-pyrrolidinylpiperidyl ketone |
| 5-chloroindol-2-yl 4-(cyclopentylamino)piperidyl ketone |
| 5-chloroindol-2-yl 4-ethylpiperazinyl ketone |
| 4-butylpiperazinyl 5-chloroindol-2-yl ketone |
| 5-methylindol-2-yl piperazinyl ketone |
| 3-azabicyclo[4.4.0]dec-3-yl 5-chloroindol-2-yl ketone |
| 5-chloroindol-2-yl 2-[(4-fluorophenyl)methyl]-2,8-diazabicyclo[4.3.0]non-8-yl ketone |
| 4-(diphenylmethyl)piperazinyl 2-methylthiopheno[2,3-d]pyrrol-5-yl ketone |
| 5-chloroindol-2-yl 3-methyl-4-(phenylcarbonyl)piperazinyl ketone |
| 4-(diphenylmethyl)piperazinyl 2-(trifluoromethyl)benzimidazol-5-yl ketone |
| 5-chloroindol-2-yl 4-(phenylcarbonyl)piperazinyl ketone |
| 5-chloroindol-2-yl 4-[(4-fluorophenyl)carbonyl]piperazinyl ketone |
| 5-chloroindol-2-yl 4-[(4-iodophenyl)carbonyl]piperazinyl ketone |
| 4-{[4-(diethylamino)phenyl]carbonyl}piperazinyl 5-chloroindol-2-yl ketone |
| 4-({4-[(5-chloroindol-2-yl)carbonyl]piperazinyl}carbonyl)benzaldehyde |
| 4-(2,3-dimethylphenyl)piperazinyl 5-chloroindol-2-yl ketone |
| 5-chloroindol-2-yl 4-(2-fluorophenyl)piperazinyl ketone |
| 4-(2,4-difluorophenyl)piperazinyl 5-chloroindol-2-yl ketone |
| 5-chloroindol-2-yl 4-(2-pyridyl)piperazinyl ketone |
| 5-chloroindol-2-yl 4-[(5-chloroindol-2-yl)carbonyl]piperazinyl ketone |
| 5-chloroindol-2-yl 4-(4-pyridyl)piperazinyl ketone |
| 5-chloroindol-2-yl 4-{[4-(trifluoromethyl)phenyl]methyl}piperazinyl ketone |
| 4-[(4-chlorophenyl)methyl]piperazinyl 2-(trifluoromethyl)benzimidazol-5-yl ketone |
| 5-chloroindol-2-yl 4-(4-fluorophenyl)piperazinyl ketone |
| 5-chloroindol-2-yl 1,2,3,4-tetrahydropyridino[4,3-b]indol-2-yl ketone |
| 5-chloroindol-2-yl 4-[4-(trifluoromethyl)phenoxy]piperidyl ketone |
| 5-chloroindol-2-yl 4-(4-fluorophenoxy)piperidyl ketone |
| 3-({4-[(5-chloroindol-2-yl)carbonyl]piperazinyl}carbonyl)benzenecarbonitrile |
| 5-chloroindol-2-yl 4-[(3-phenylphenyl)methyl]piperazinyl ketone |
| 5-chloroindol-2-yl 4-[(4-phenylphenyl)methyl]piperazinyl ketone |
| 5-chloroindol-2-yl 4-(3-chlorophenoxy)piperidyl ketone |
| 5-chloroindol-2-yl 4-(4-fluoro-2-methylphenoxy)piperidyl ketone |
| 5-chloroindol-2-yl 4-(4-chlorophenoxy)piperidyl ketone |
| 5-(trifluoromethyl)indol-2-yl 4-{[4-(trifluoromethyl)phenyl]carbonyl}piperazinyl ketone |
| 5-(trifluoromethyl)indol-2-yl 4-{[3-(trifluoromethyl)phenyl]carbonyl}piperazinyl ketone |
| 4-{[3,5-bis(trifluoromethyl)phenyl]carbonyl}piperazinyl 5-(trifluoromethyl)indol-2-yl ketone |
| 4-[(2,4-dichlorophenyl)carbonyl]piperazinyl 5-(trifluoromethyl)indol-2-yl ketone |
| 4-[(3-chlorophenyl)carbonyl]piperazinyl 5-(trifluoromethyl)indol-2-yl ketone |
| 4-[(4-{[5-(trifluoromethyl)indol-2-yl]carbonyl}piperazinyl)carbonyl]benzenecarbonitrile |
| 4-[(4-chlorophenyl)carbonyl]piperazinyl 5-(trifluoromethyl)indol-2-yl ketone |
| 2-(difluoromethyl)benzimidazol-5-yl 4-(diphenylmethyl)piperazinyl ketone |
| 2-anthryl 4-(diphenylmethyl)piperazinyl ketone |
| 1-[4-(diphenylmethyl)piperazinyl]-2-(5-chlorobenzimidazol-2-yl)ethan-1-one |

| Name |
| --- |
| 4-{[3-fluoro-4-(trifluoromethyl)phenyl]carbonyl}piperazinyl 5-(trifluoromethyl)indol-2-yl ketone |
| 4-{[2-fluoro-4-(trifluoromethyl)phenyl]carbonyl}piperazinyl 5-(trifluoromethyl)indol-2-yl ketone |
| 5-chloroindol-2-yl 4-[(4-(1H-1,2,3,4-tetraazol-5-yl)phenyl)carbonyl]piperazinyl ketone |
| 5-chloroindol-2-yl 4-[(4-chlorophenyl)carbonyl]piperazinyl ketone |
| 4-[(2,4-difluorophenyl)carbonyl]piperazinyl 5-chloroindol-2-yl ketone |
| N-({1-[(2E)-3-(4-bromophenyl)prop-2-enoyl](4-piperidyl)}methyl)(4-fluorophenyl)carboxamide |
| (E)-(4-(4-(3-(4-bromophenyl)acryloyl)piperazine-1-carbonyl)phenyl)boronic acid |
| (2E)-3-(4-bromophenyl)-1-{4-[(4-(1H-1,2,3,4-tetraazol-5-yl)phenyl)carbonyl]piperazinyl}prop-2-en-1-one |
| potassium (E)-5-(4-(4-(3-(4-bromophenyl)acryloyl)piperazine-1-carbonyl)phenyl)tetrazol-1-ide |
| methyl 4-({4-[(5-chloroindol-2-yl)carbonyl]piperazinyl}carbonyl)benzoate |
| methyl 4-({4-[(5-chloroindol-2-yl)carbonyl]piperazinyl}methyl)benzoate |
| methyl 3-({4-[(5-chloroindol-2-yl)carbonyl]piperazinyl}methyl)benzoate |
| 4-({4-[(5-chloroindol-2-yl)carbonyl]piperazinyl}carbonyl)benzoic acid |
| 4-({4-[(5-chloroindol-2-yl)carbonyl]piperazinyl}methyl)benzoic acid |
| 5-chloroindol-2-yl 4-[(4-(3-pyridyl)phenyl)carbonyl]piperazinyl ketone |
| methyl 3-({4-[(5-chloroindol-2-yl)carbonyl]piperazinyl}carbonyl)benzoate |
| 3-({4-[(5-chloroindol-2-yl)carbonyl]piperazinyl}methyl)benzoic acid |
| N-(2,4-difluorophenyl){4-[(5-chloroindol-2-yl)carbonyl]piperazinyl}carboxamide |
| 5-chloroindol-2-yl 4-{[4-(4-chlorophenyl)phenyl]sulfonyl}piperazinyl ketone |
| 5-chloroindol-2-yl 4-{[4-(4-methoxyphenyl)phenyl]sulfonyl}piperazinyl ketone |
| [4-({4-[(5-chloroindol-2-yl)carbonyl]piperazinyl}methyl)phenyl]-N-(4-fluorophenyl)carboxamide |
| [3-({4-[(5-chloroindol-2-yl)carbonyl]piperazinyl}methyl)phenyl]-N-(4-fluorophenyl)carboxamide |
| {4-[(5-chloroindol-2-yl)carbonyl]piperazinyl}-N-[4-fluoro-3-(trifluoromethyl)phenyl]carboxamide |
| {4-[(5-chloroindol-2-yl)carbonyl]piperazinyl}-N-(3-fluorophenyl)carboxamide |
| {4-[(5-chloroindol-2-yl)carbonyl]piperazinyl}-N-(4-chlorophenyl)carboxamide |
| {4-[(5-chloroindol-2-yl)carbonyl]piperazinyl}-N-[4-(trifluoromethyl)phenyl]carboxamide |
| N-(4-bromophenyl){4-[(5-chloroindol-2-yl)carbonyl]piperazinyl}carboxamide |
| {4-[(5-chloroindol-2-yl)carbonyl]piperazinyl}-N-(3-iodophenyl)carboxamide |
| 4-[(4-bromophenyl)sulfonyl]piperazinyl 5-chloroindol-2-yl ketone |
| 5-chloroindol-2-yl 4-[(2-phenylethyl)sulfonyl]piperazinyl ketone |
| N-{1-[(5-chloroindol-2-yl)carbonyl](4-piperidyl)}(4-chlorophenyl)carboxamide |
| {1-[(5-chloroindol-2-yl)carbonyl](4-piperidyl)}(4-chlorophenyl) |
| 4-{[(4-bromophenyl)sulfonyl]amino}piperidyl 5-chloroindol-2-yl ketone |
| 5-chloroindol-2-yl 4-(2-pyridyloxy)piperidyl ketone |

In another embodiment is a compound having the structure:

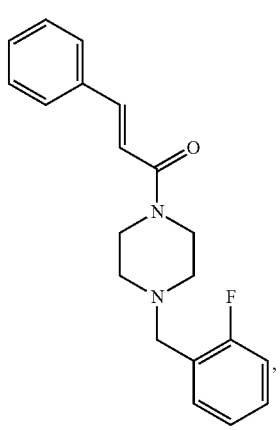

,

-continued

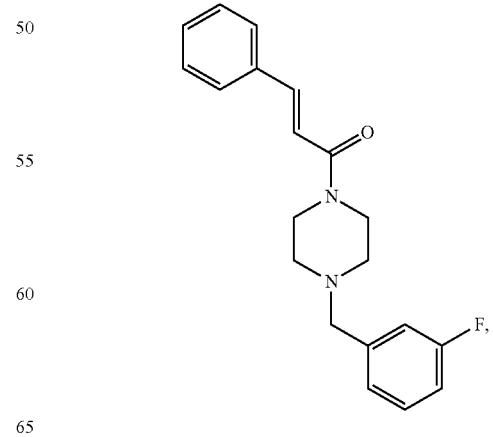

,

111
-continued
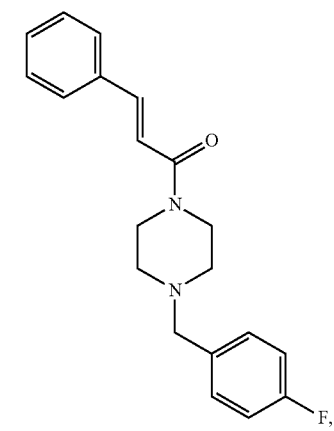
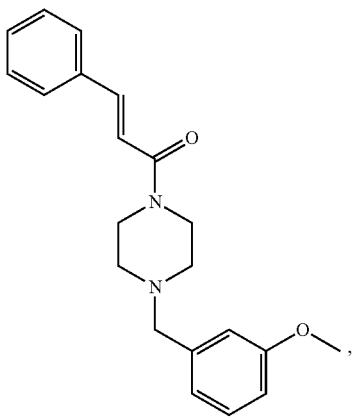
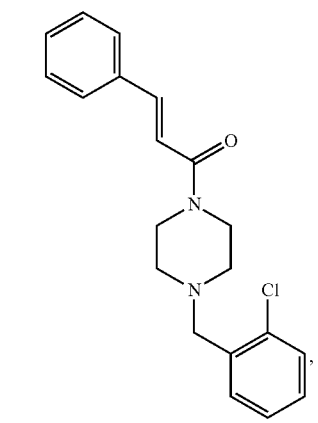
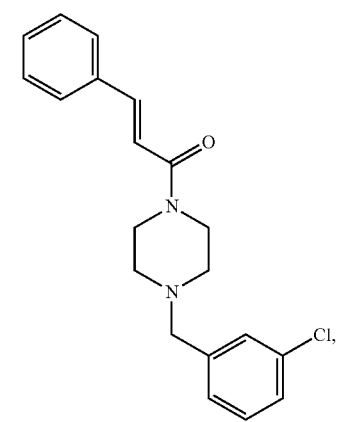
112
-continued
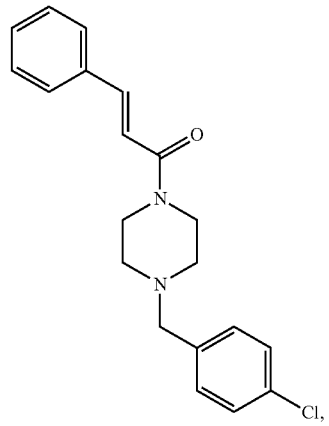
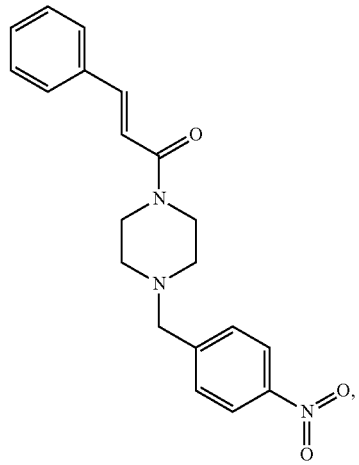
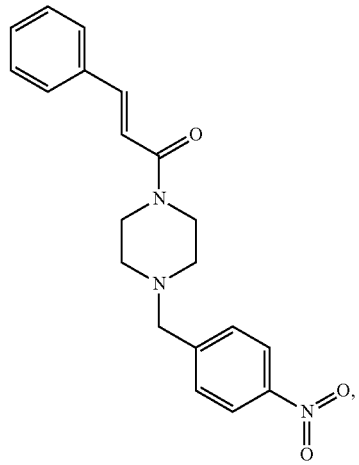
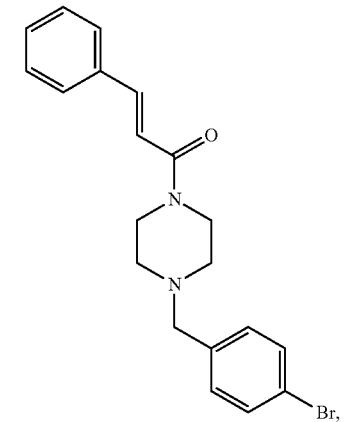

-continued
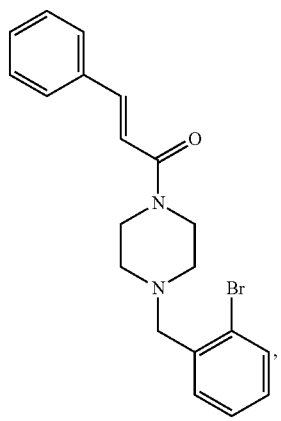
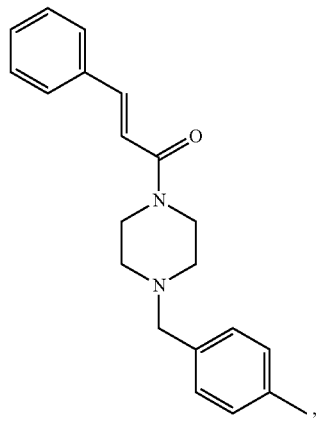
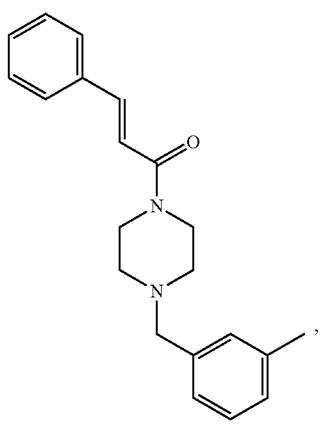
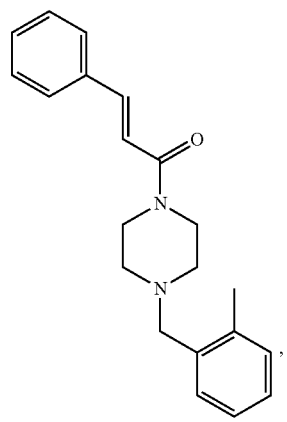
-continued
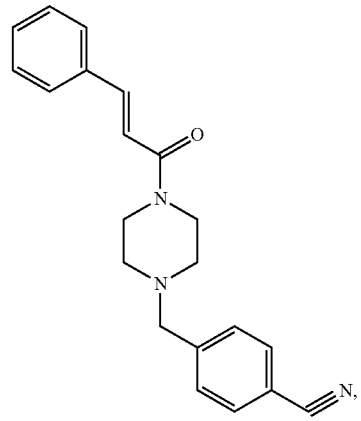
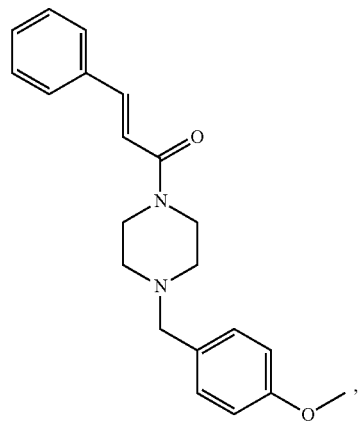
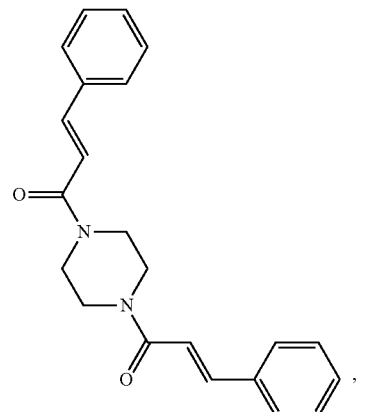
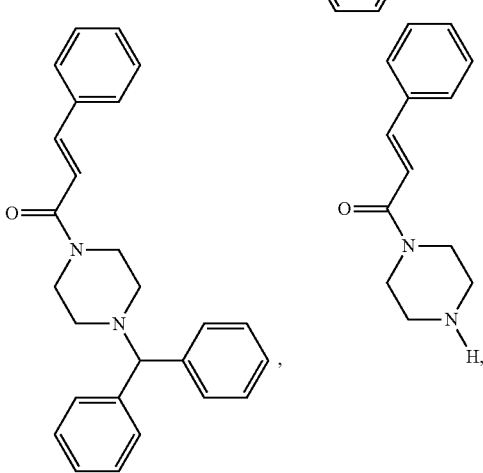

115
-continued
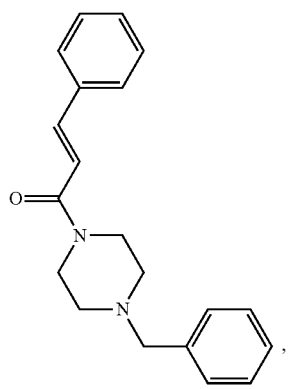
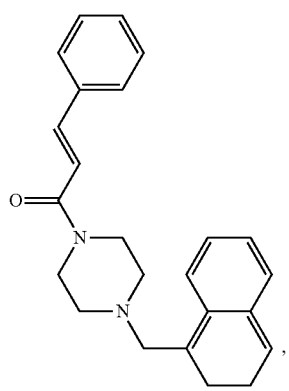
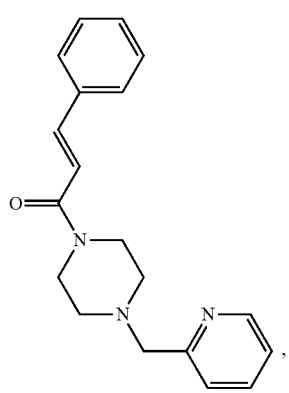
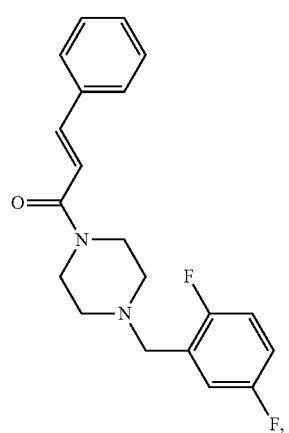
116
-continued
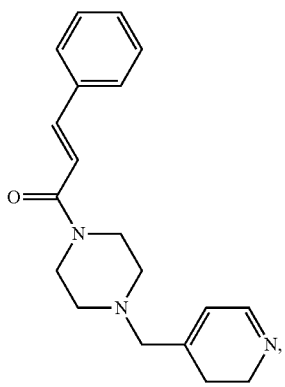
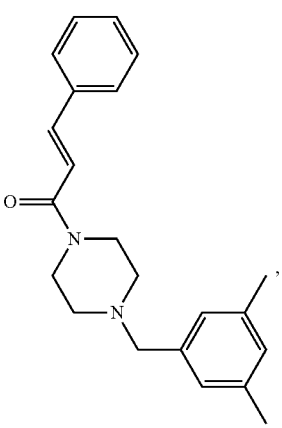
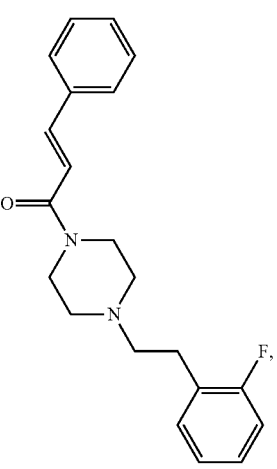

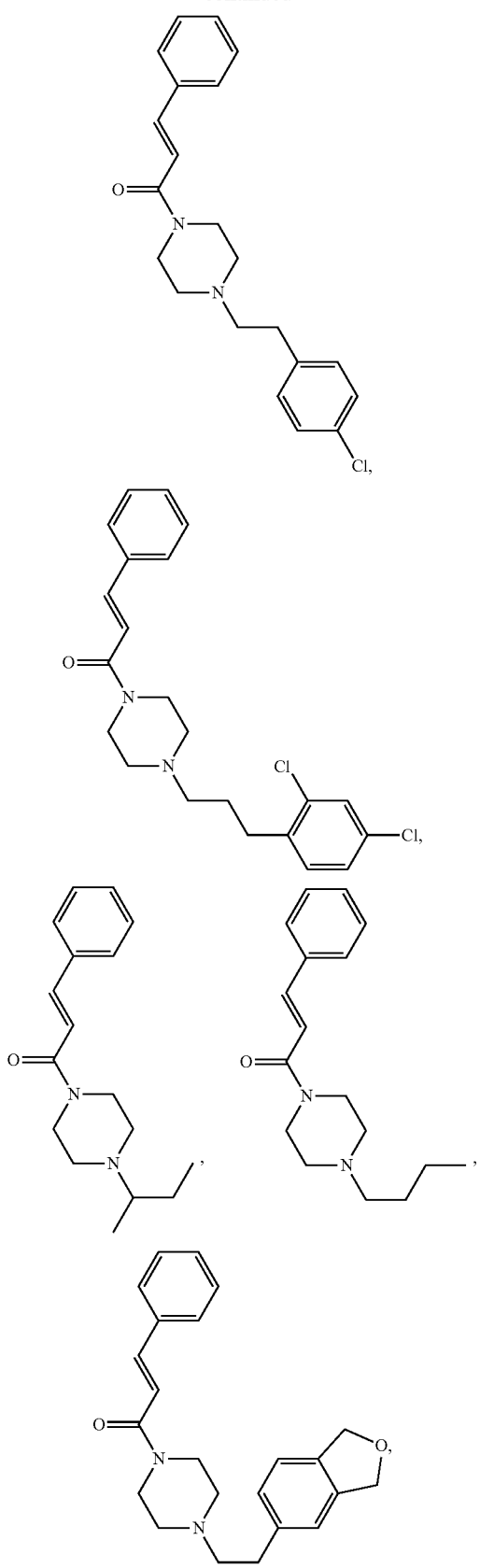

-continued
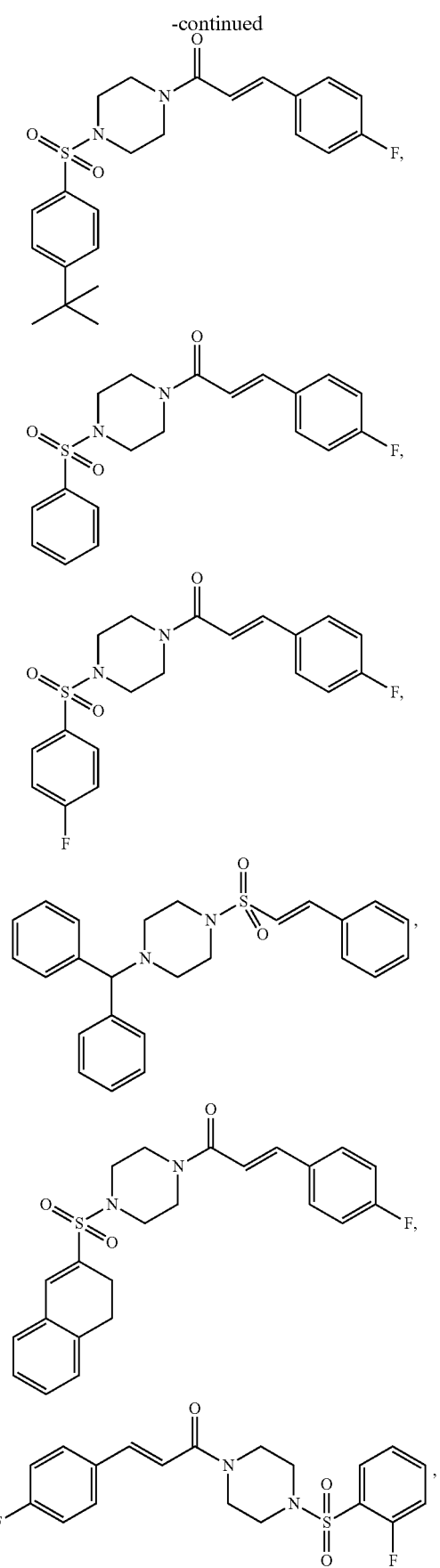
-continued
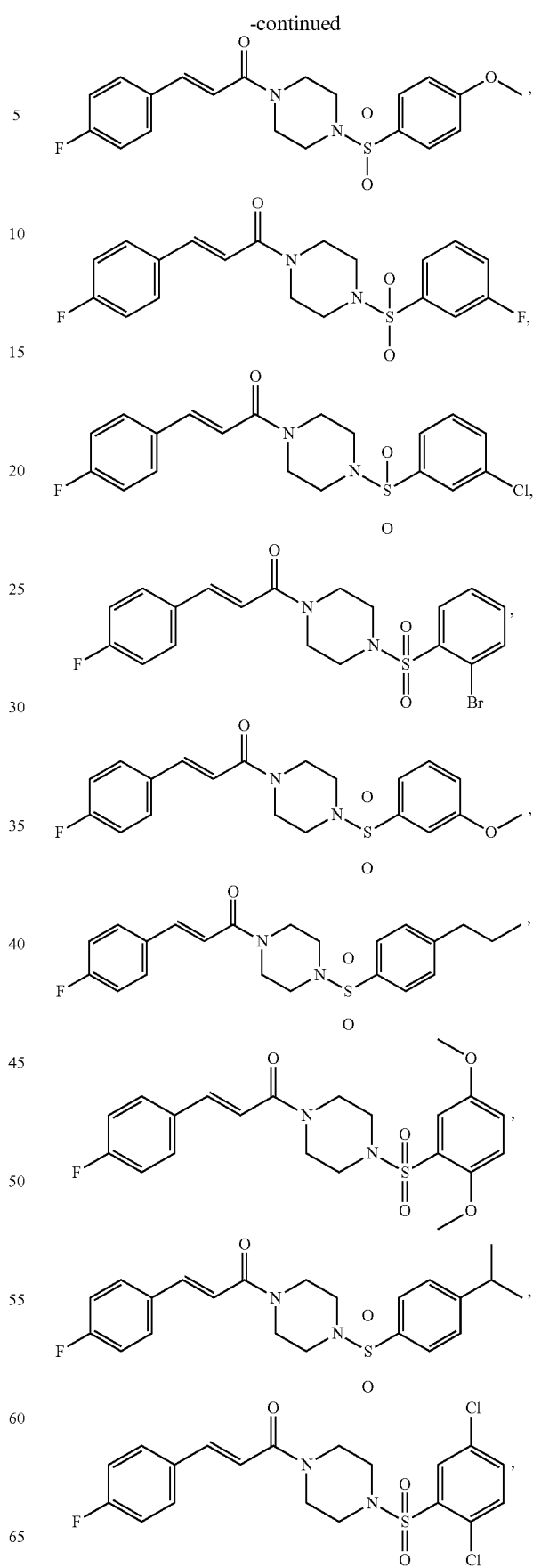

121
-continued
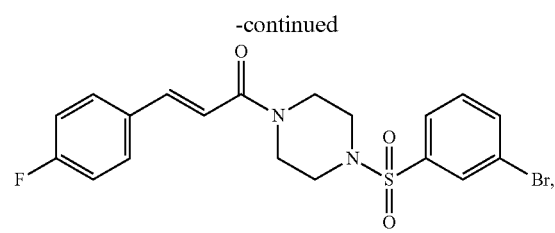
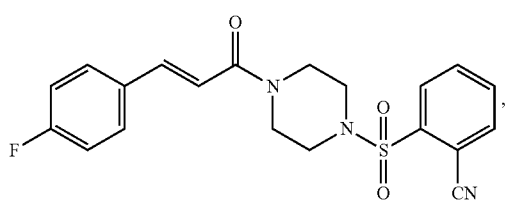
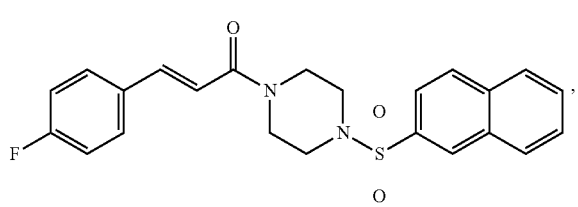
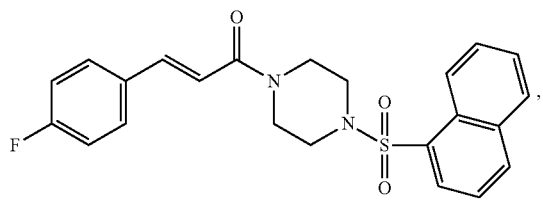
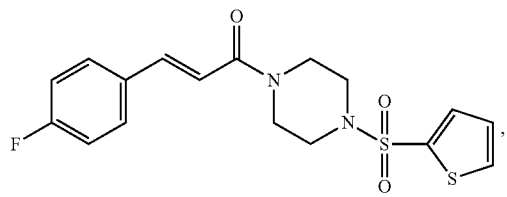
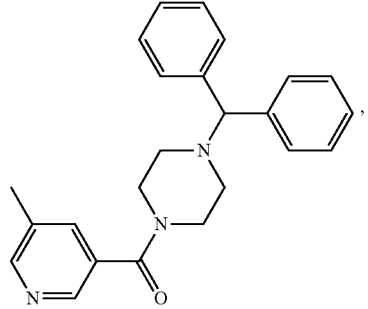
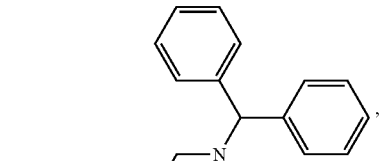
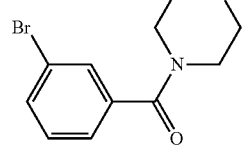
122
-continued
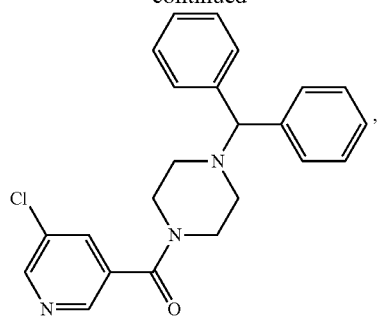
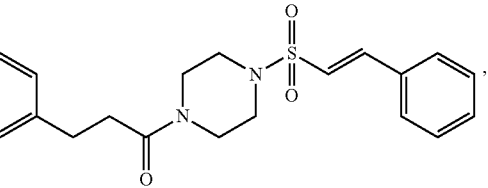
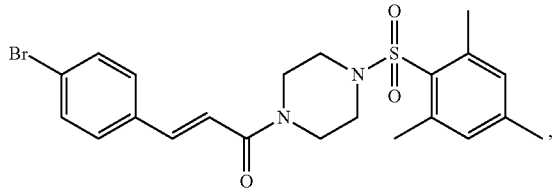

123
-continued
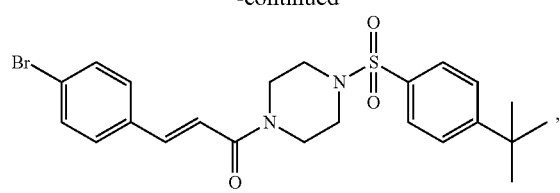
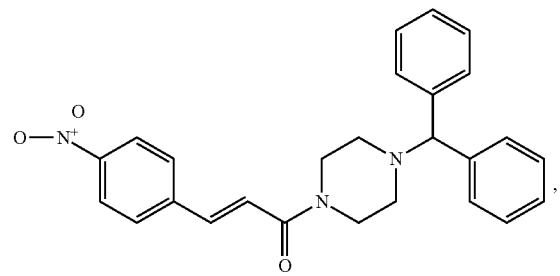
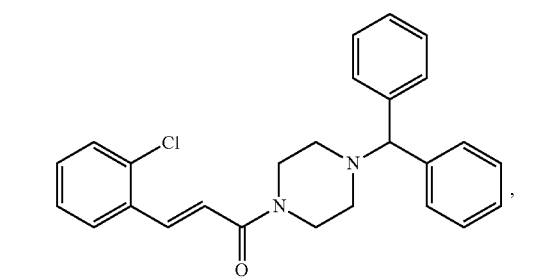
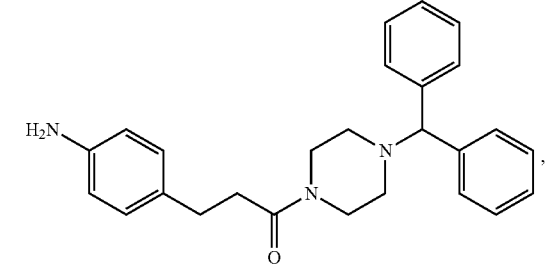
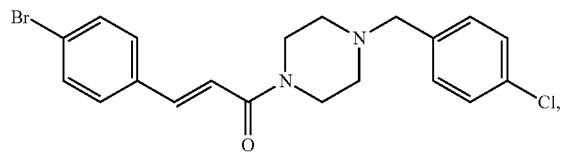
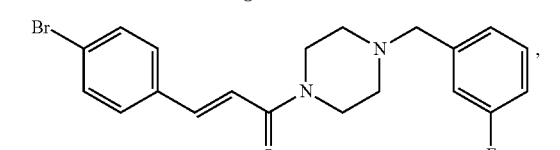
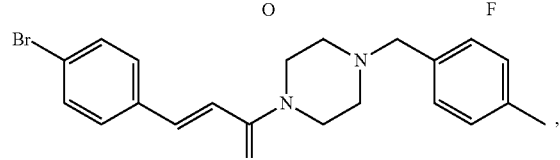
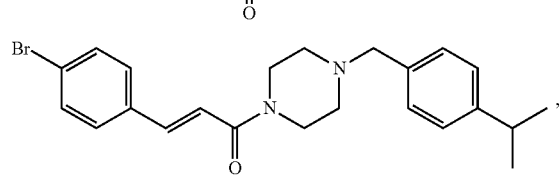
124
-continued
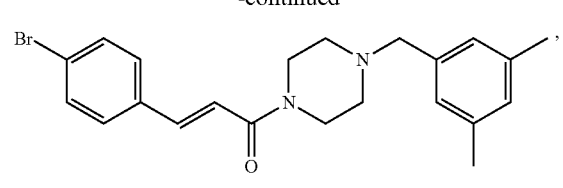
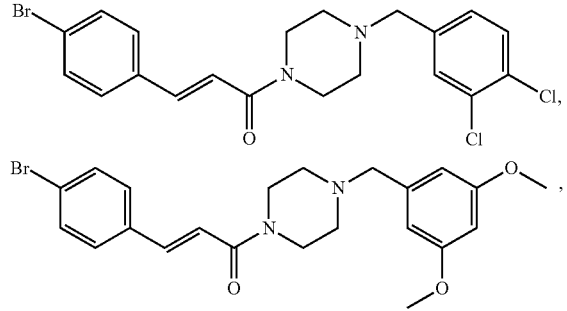
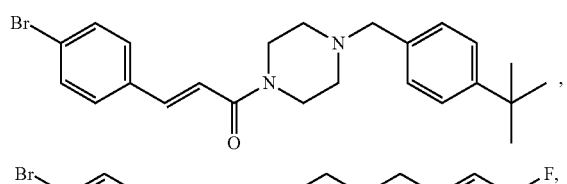
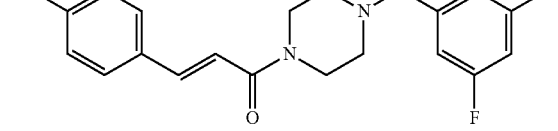
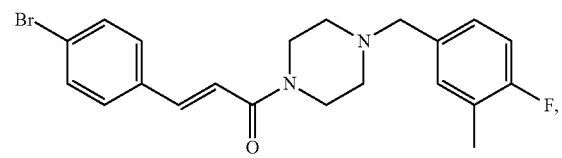
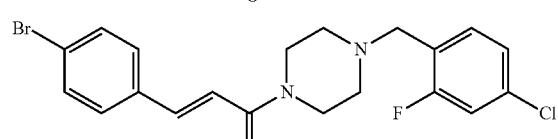
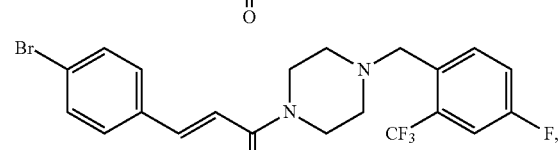
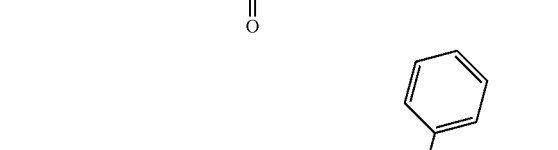
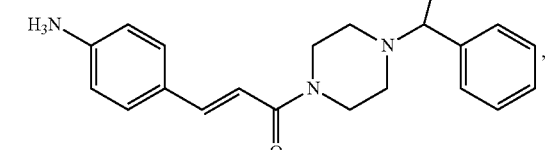
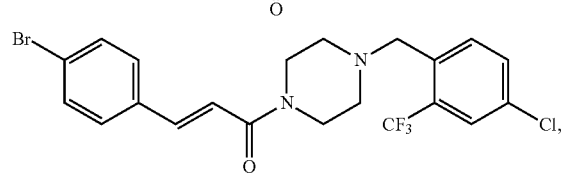

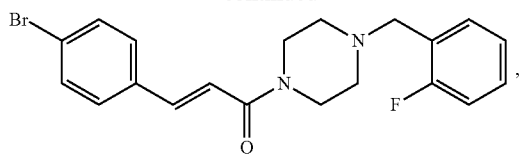
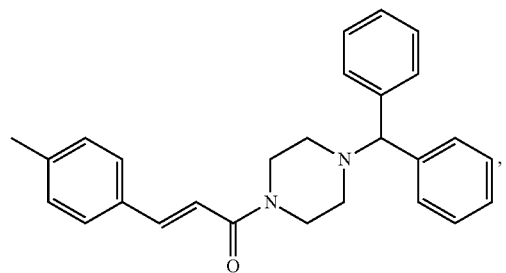
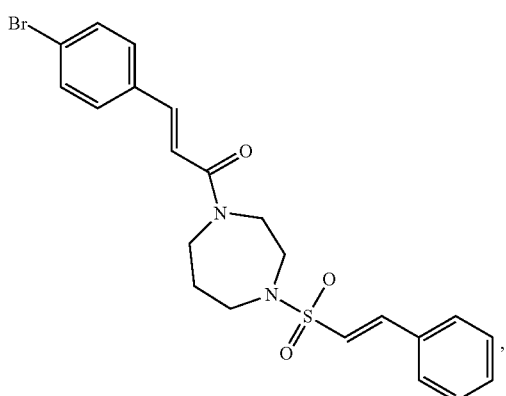
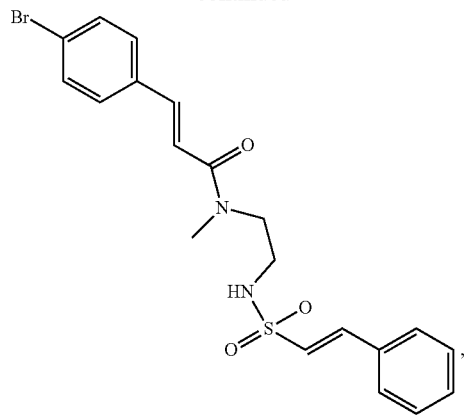

127
-continued
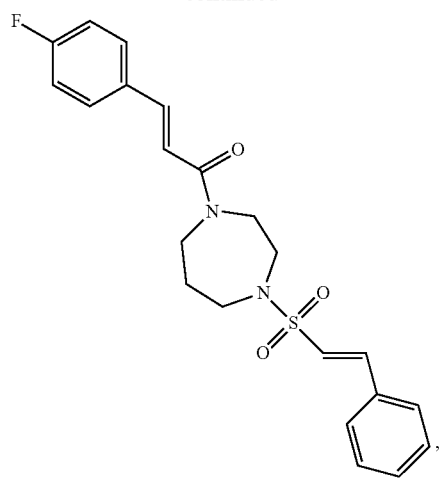
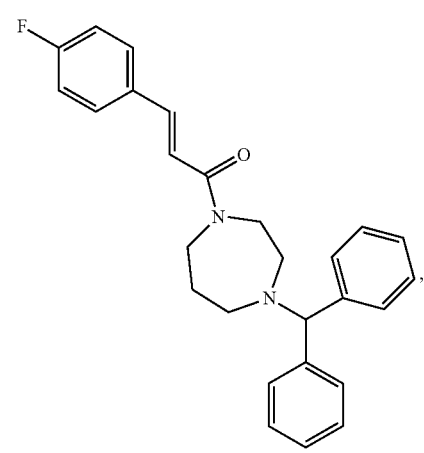
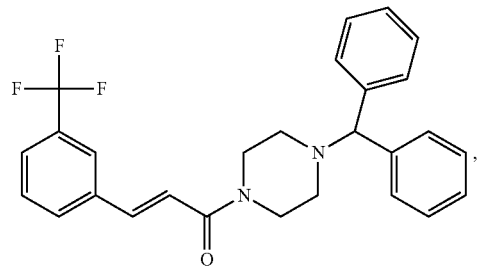
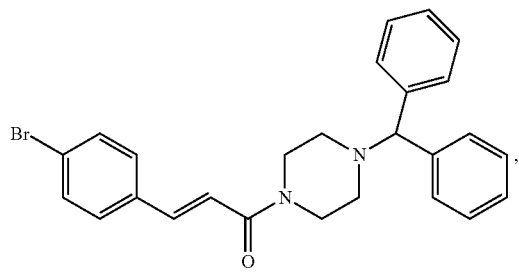
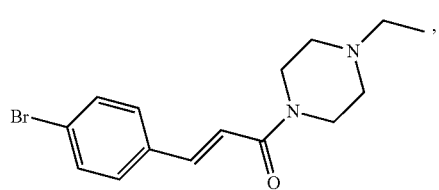
128
-continued
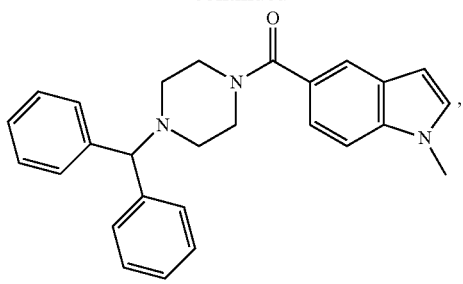
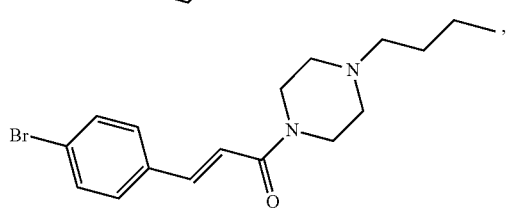
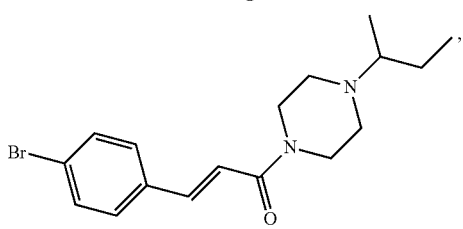
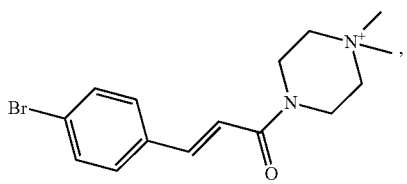
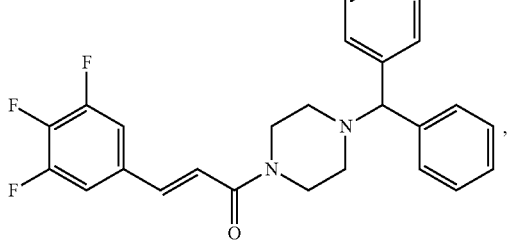
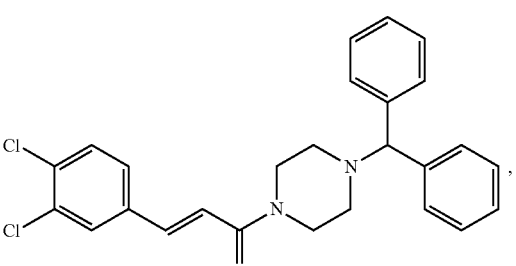
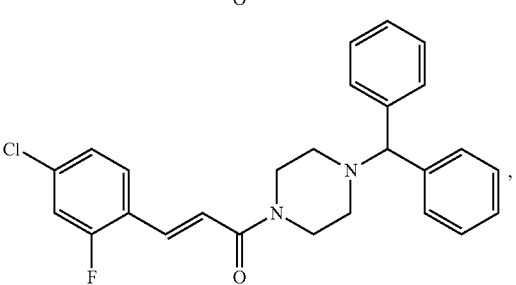

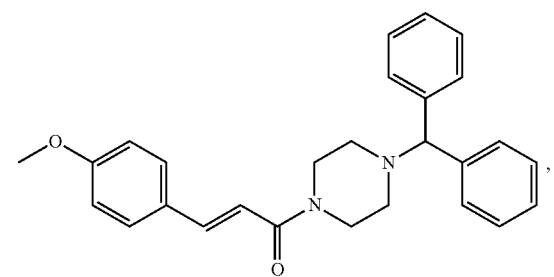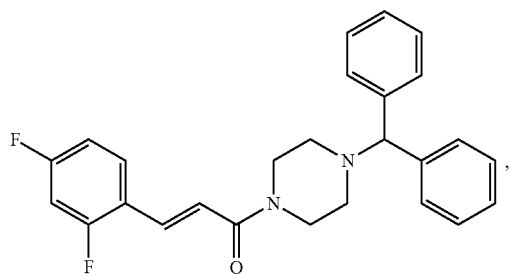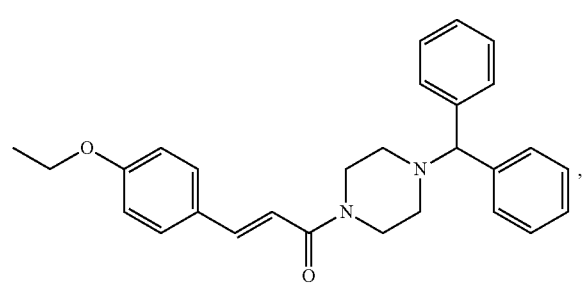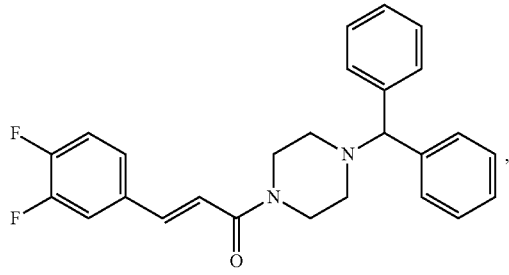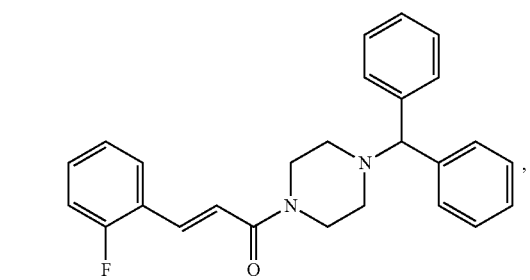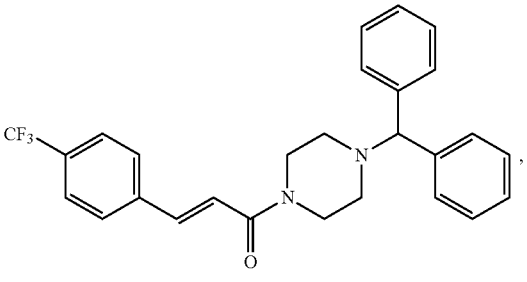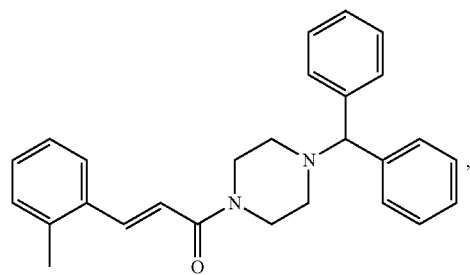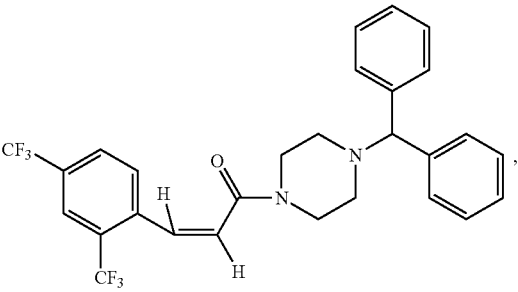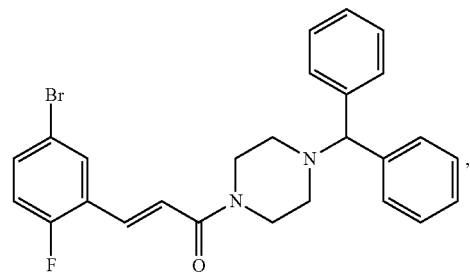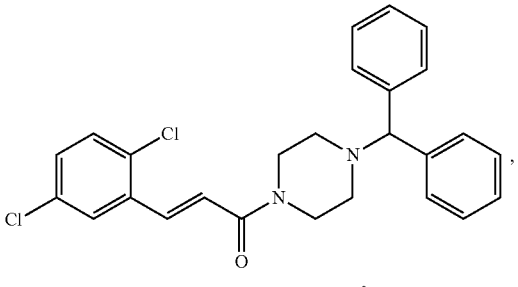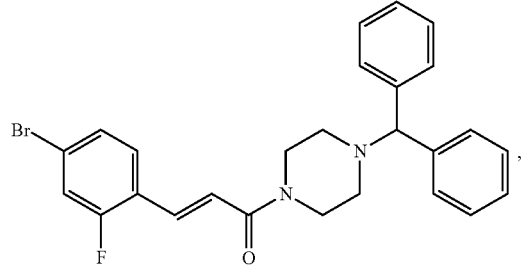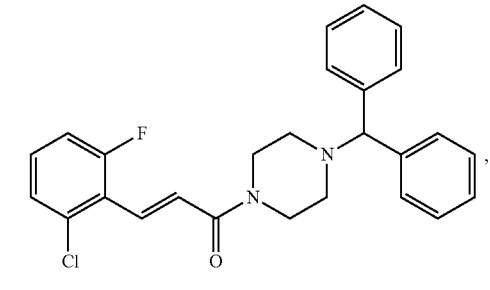

131
-continued
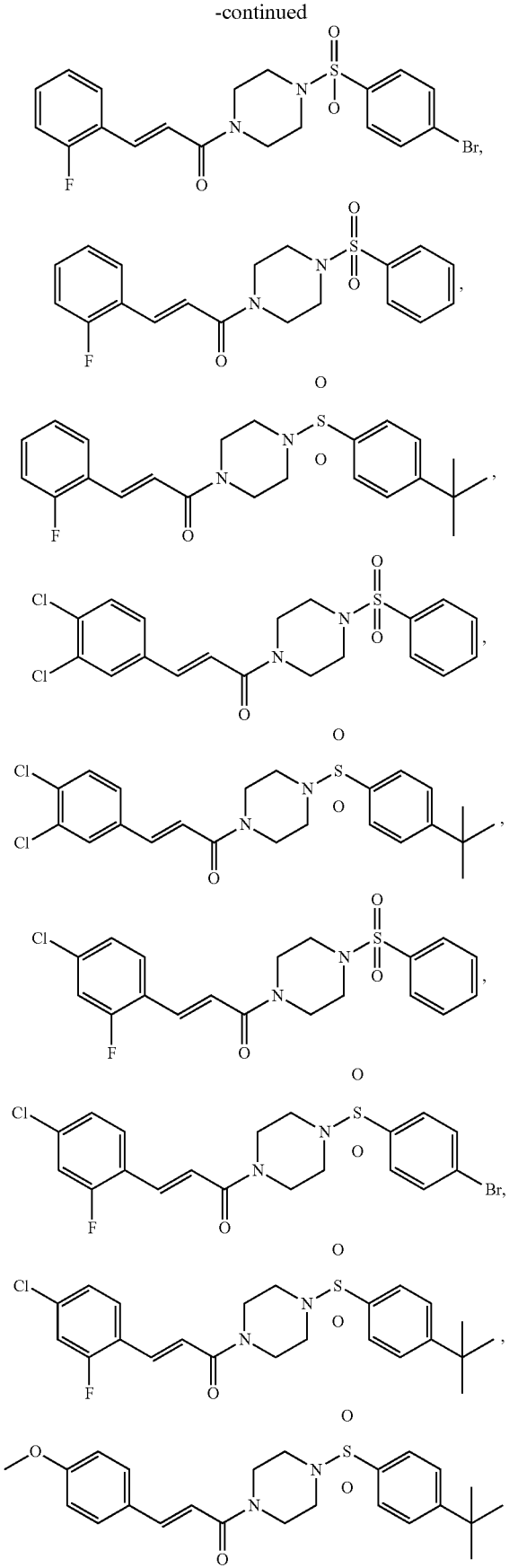
132
-continued
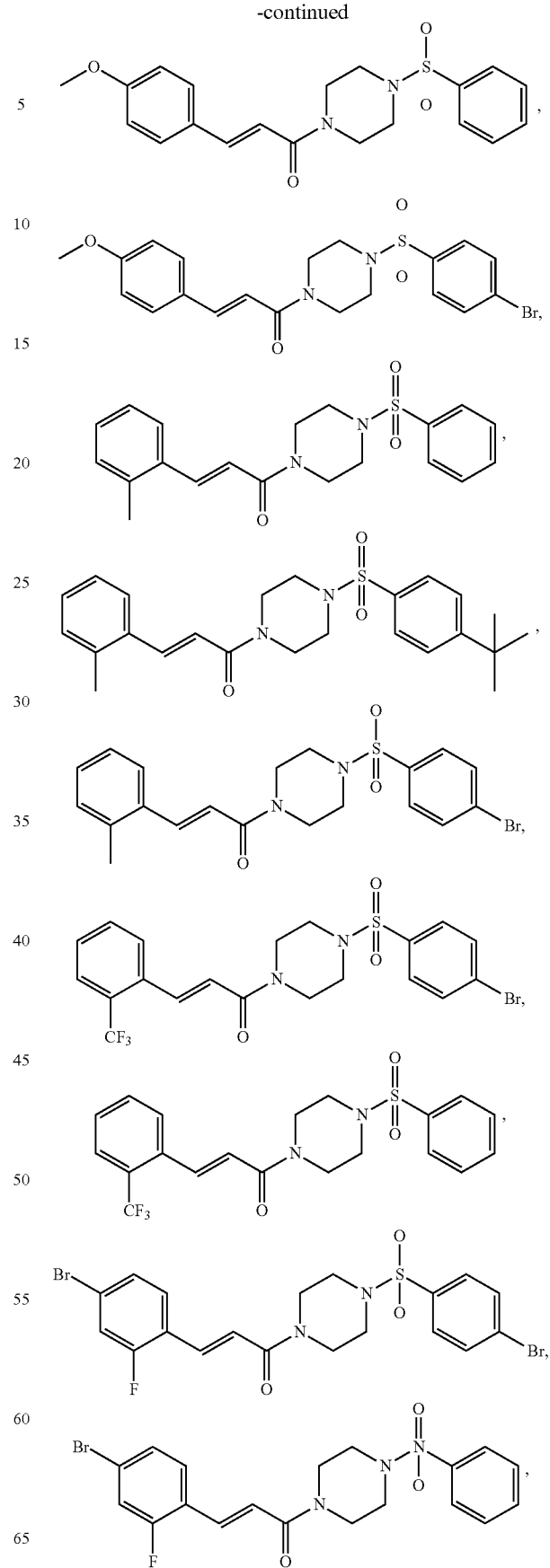

-continued
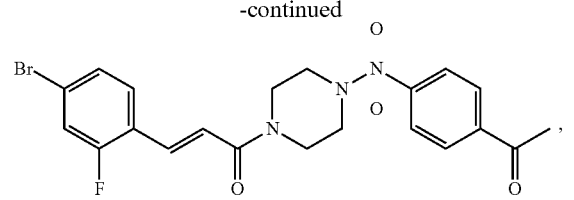
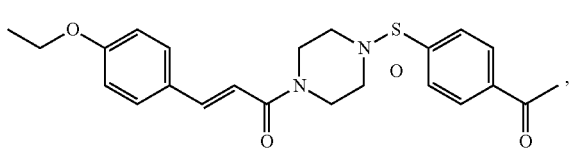
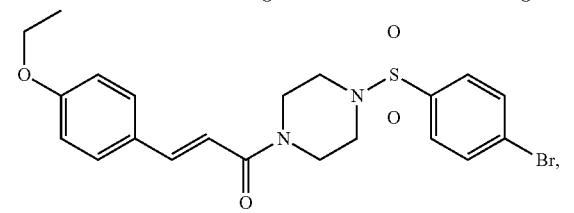
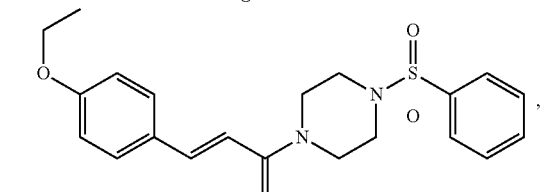
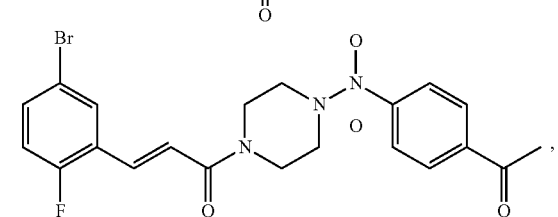
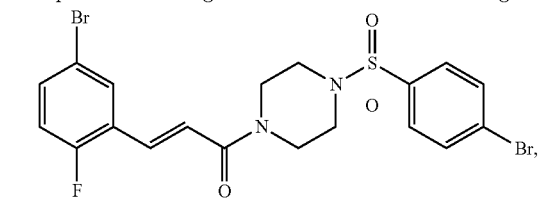
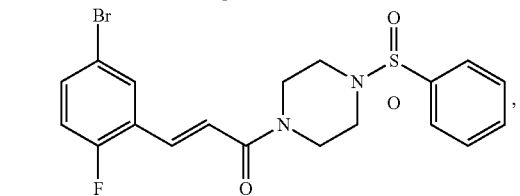
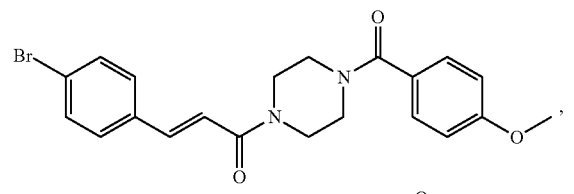
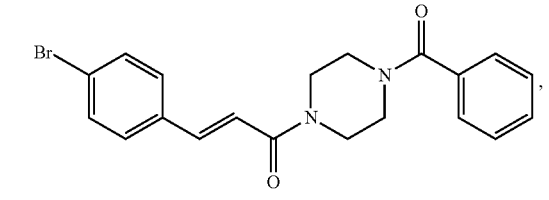
-continued
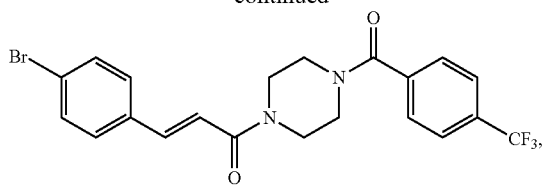
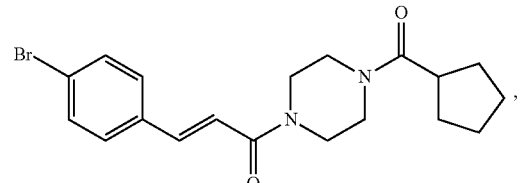
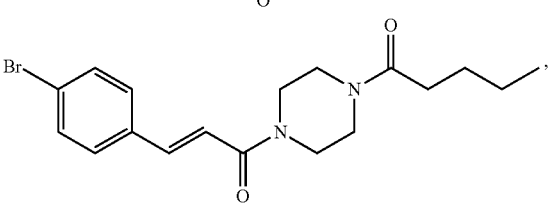
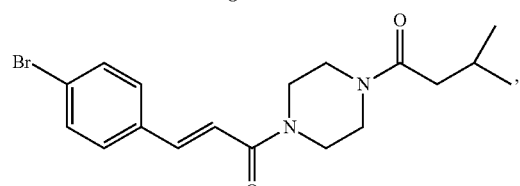
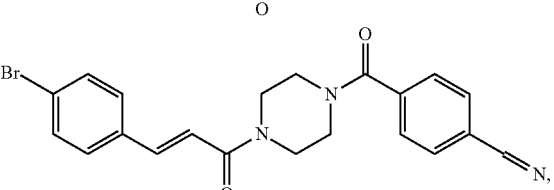
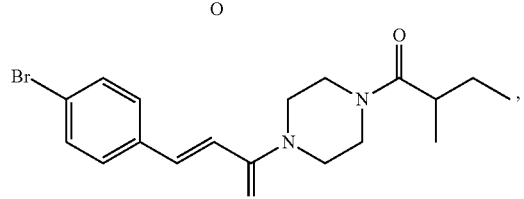
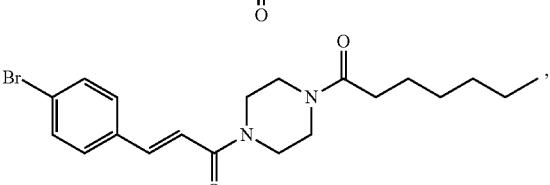
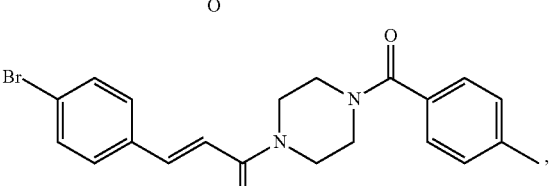
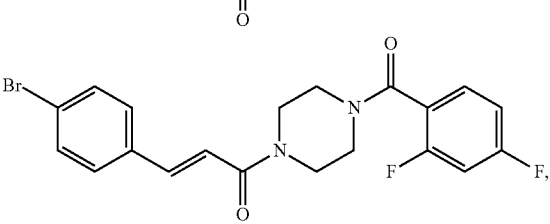

135
-continued
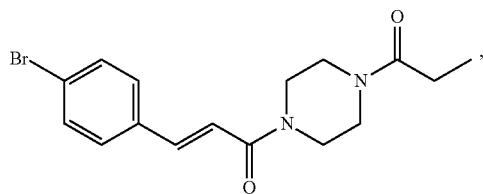
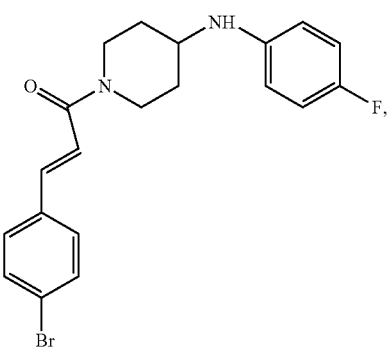
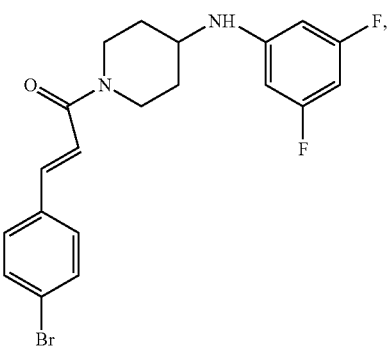
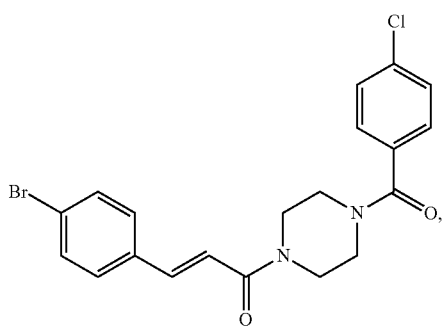
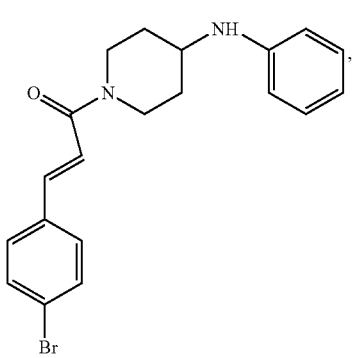
136
-continued
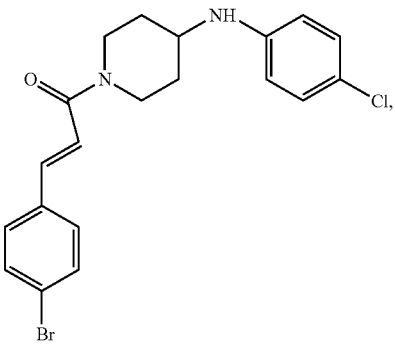
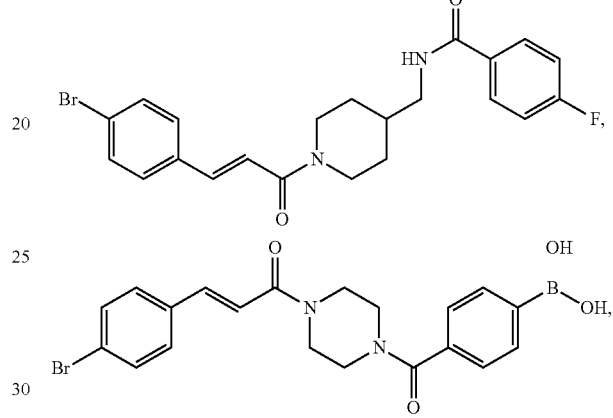
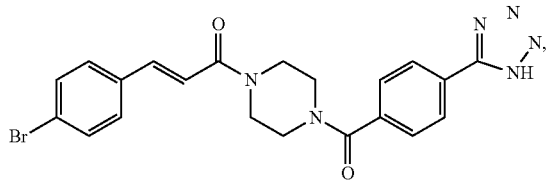
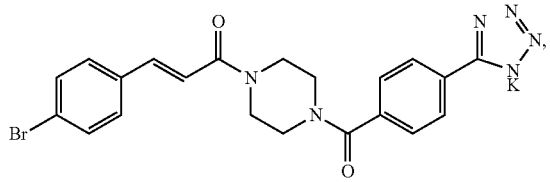
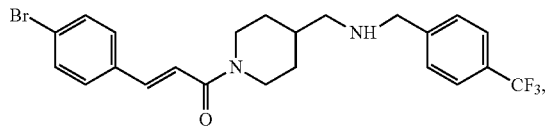
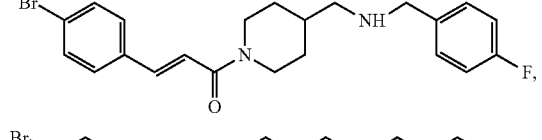
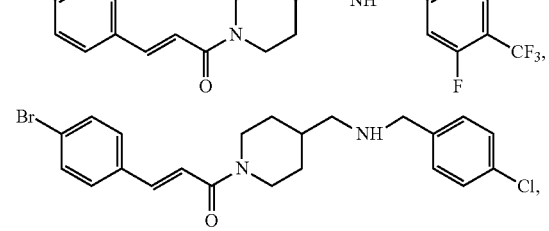

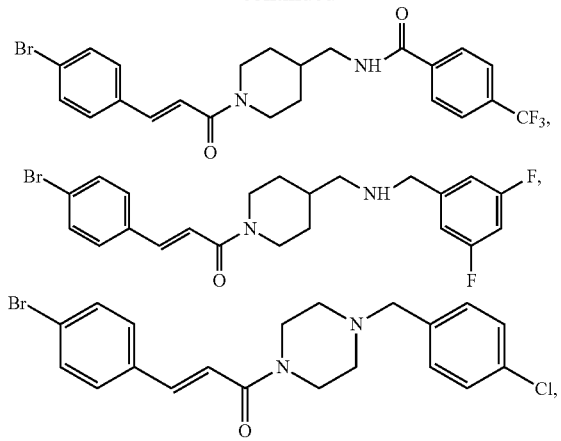
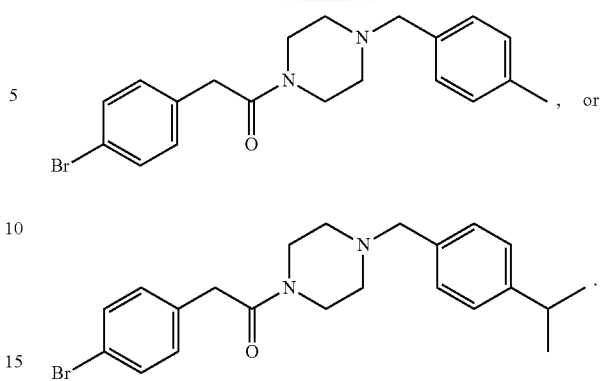
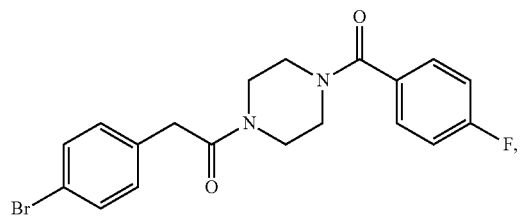
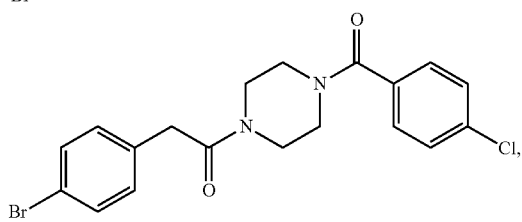
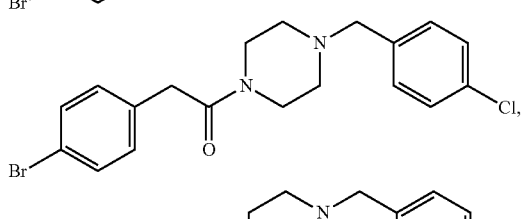
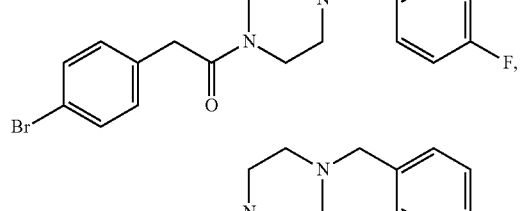
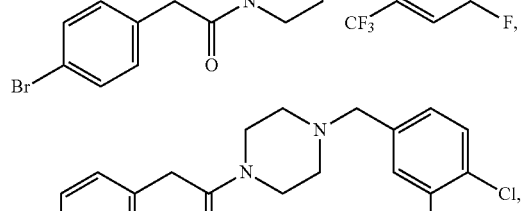
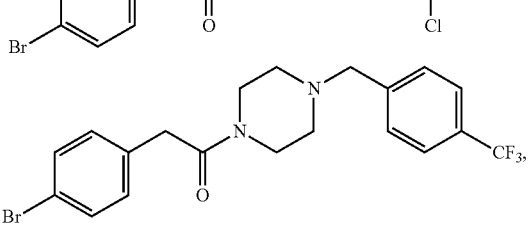
In another embodiment is a compound having the structure:
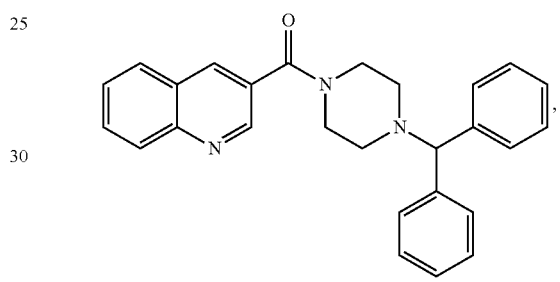
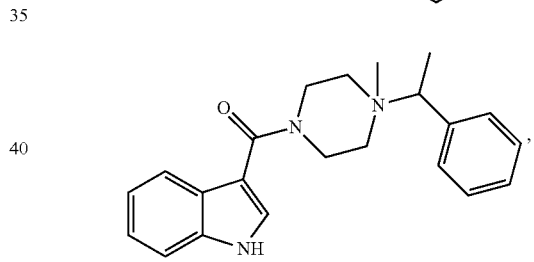
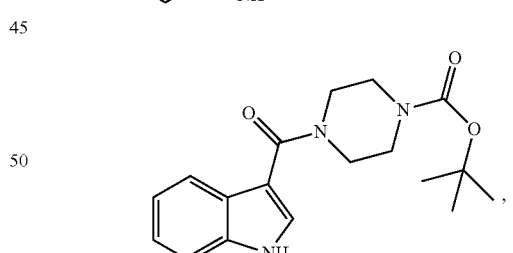
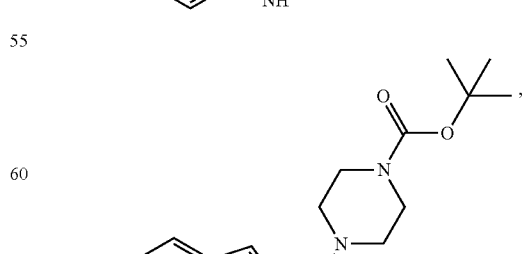
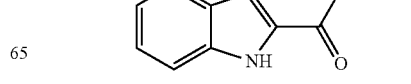

139
-continued
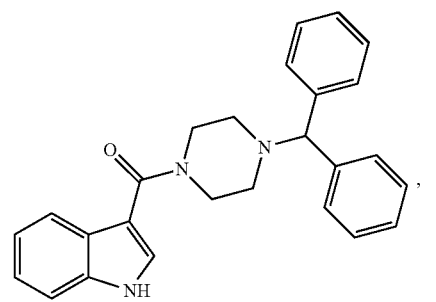
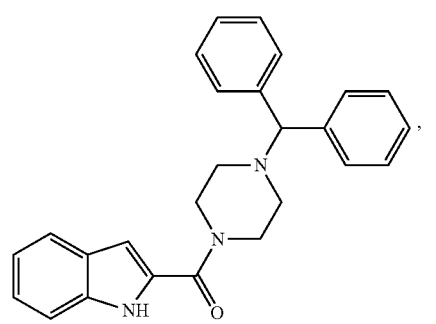
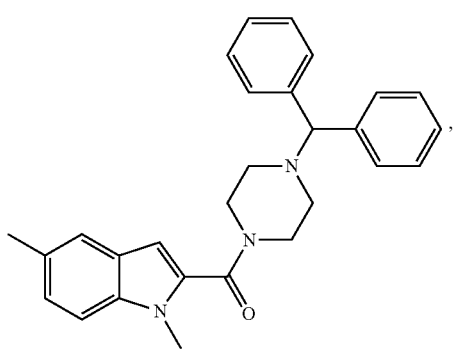
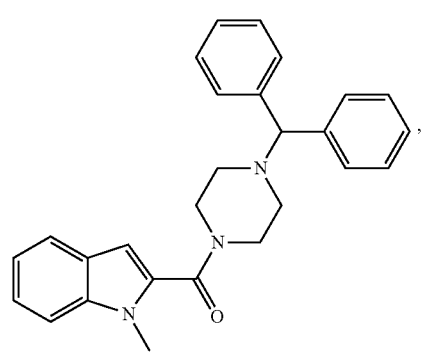
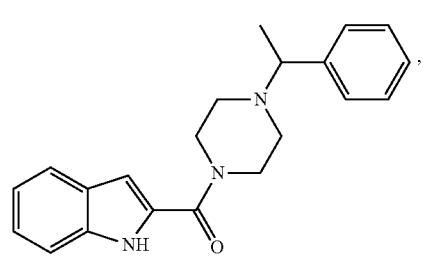
140
-continued
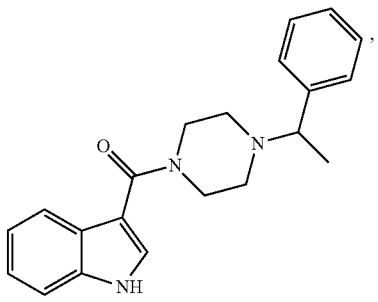
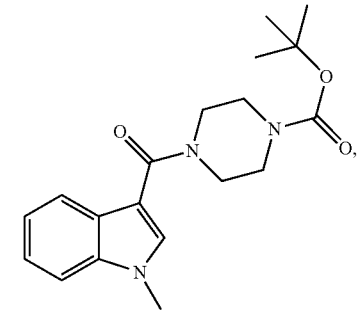
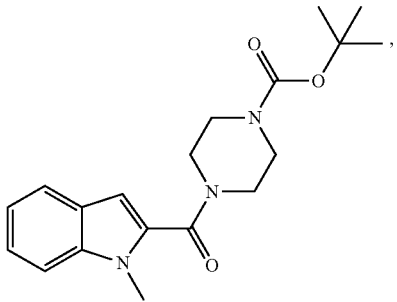
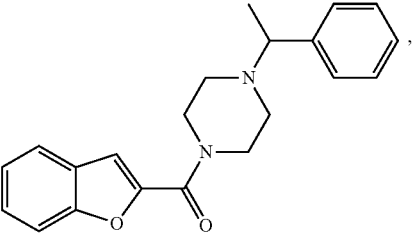
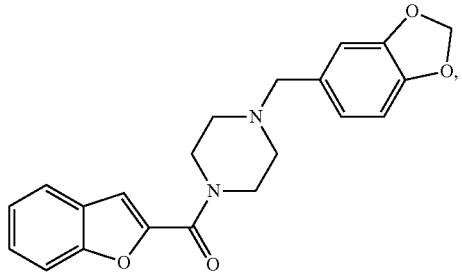
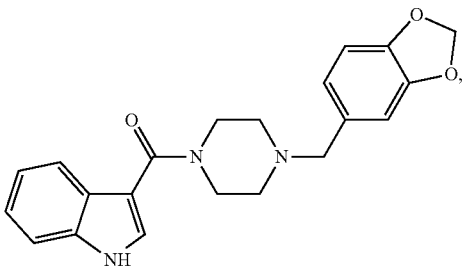

141
-continued
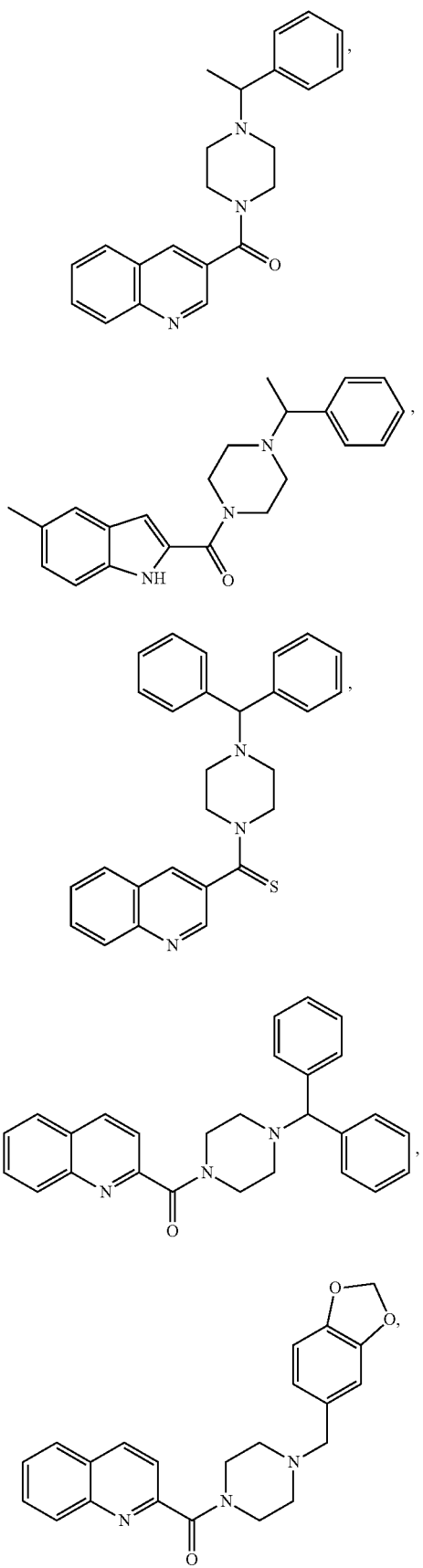
142
-continued
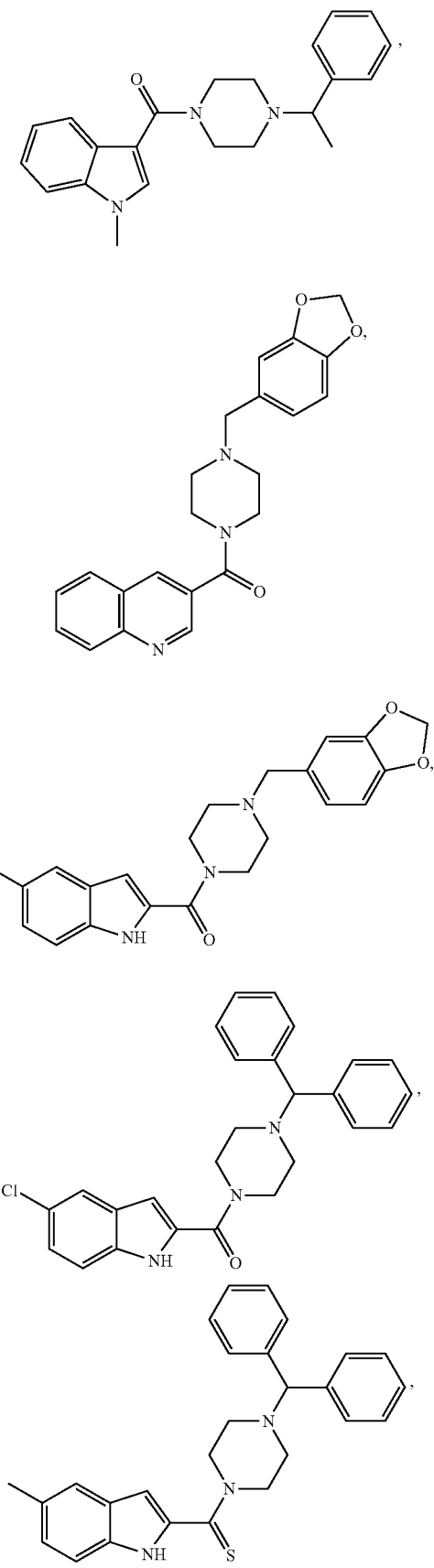

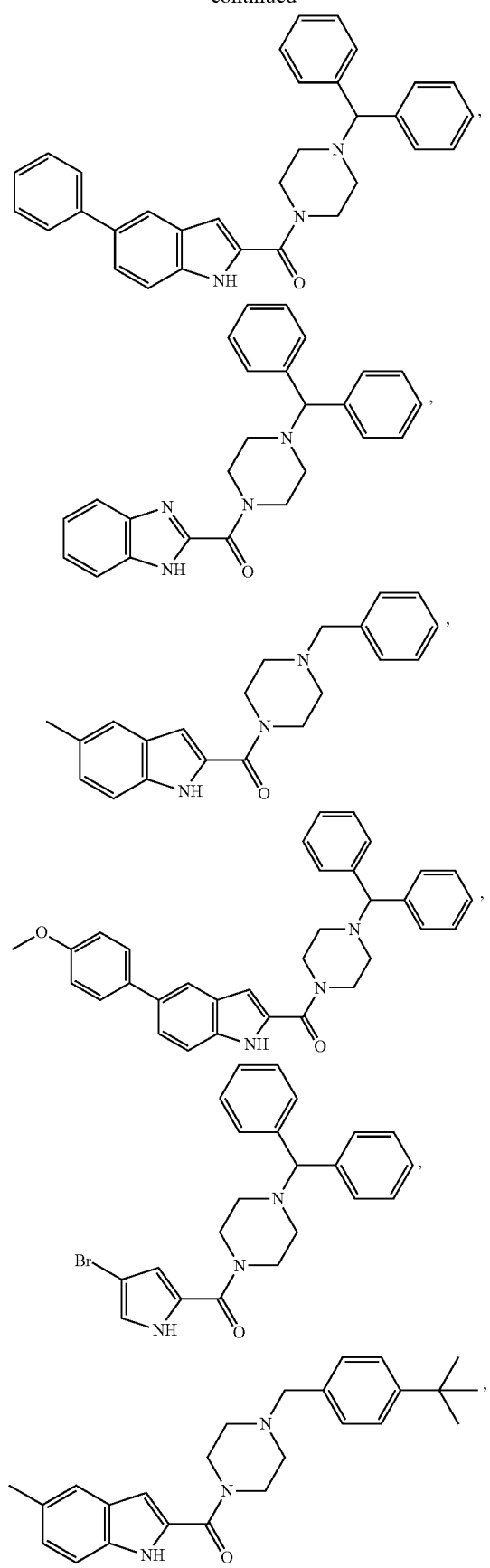
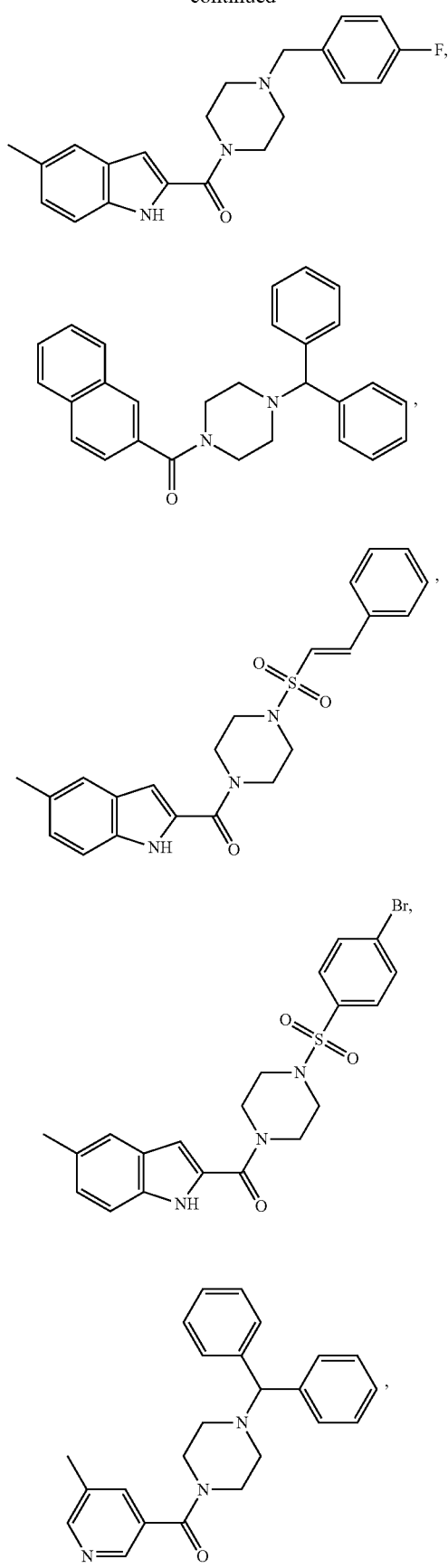

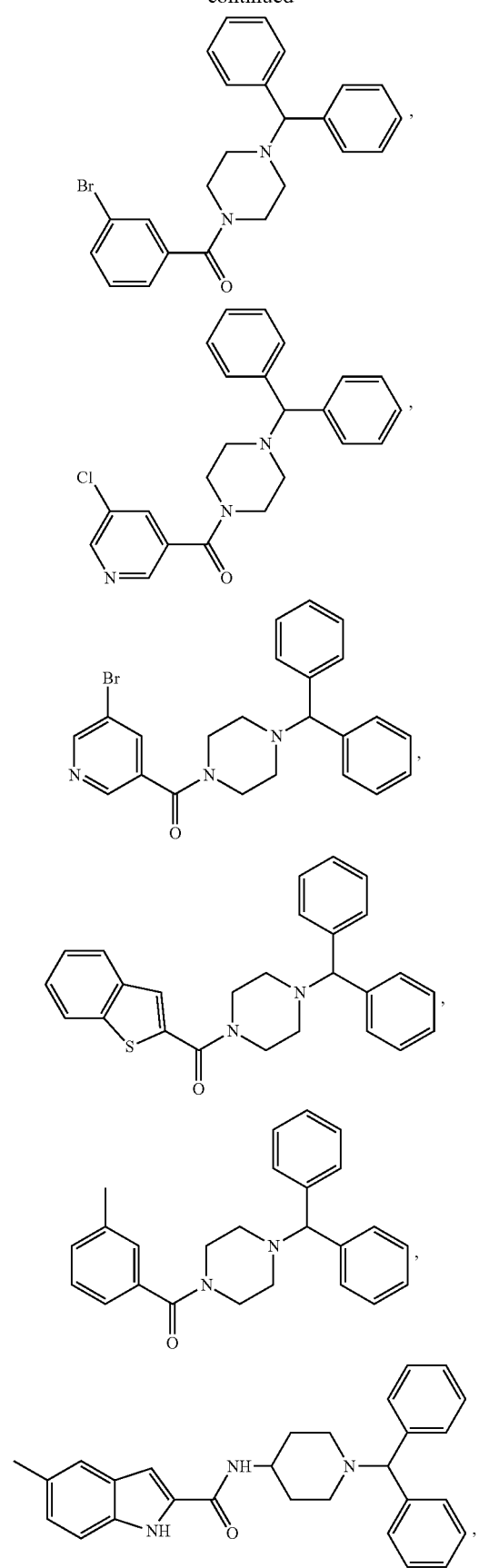
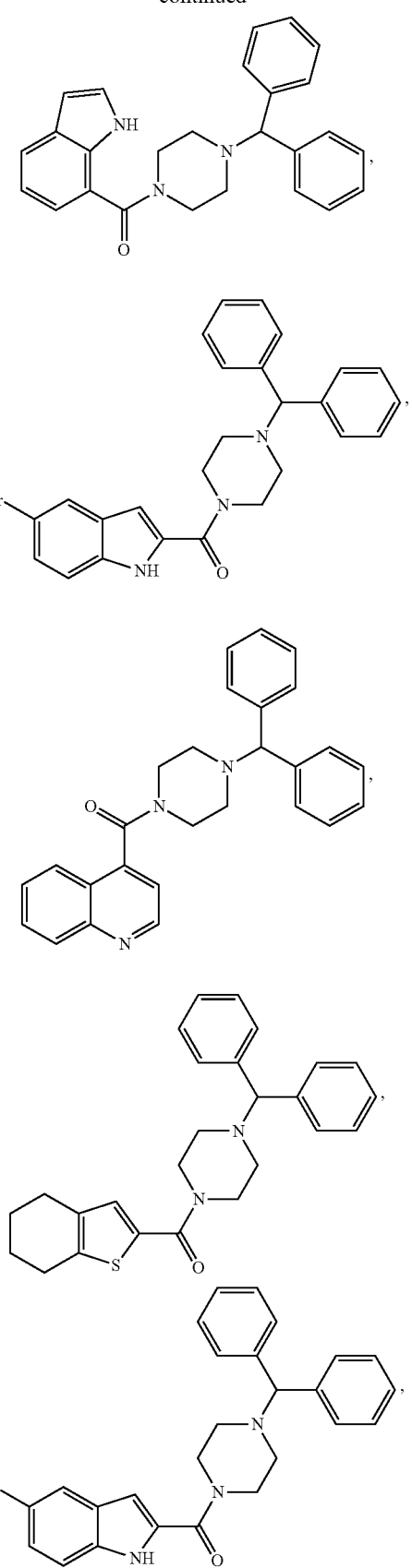

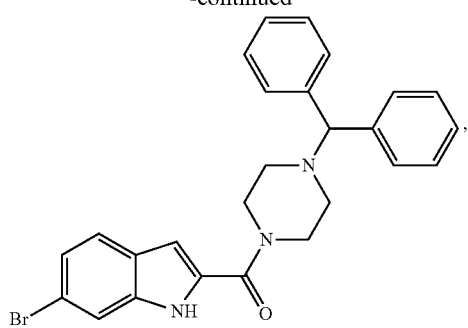
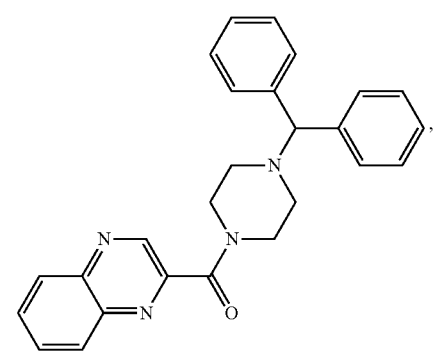
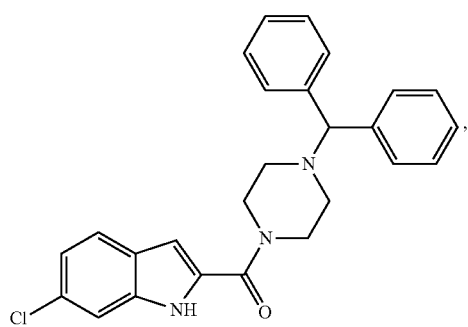
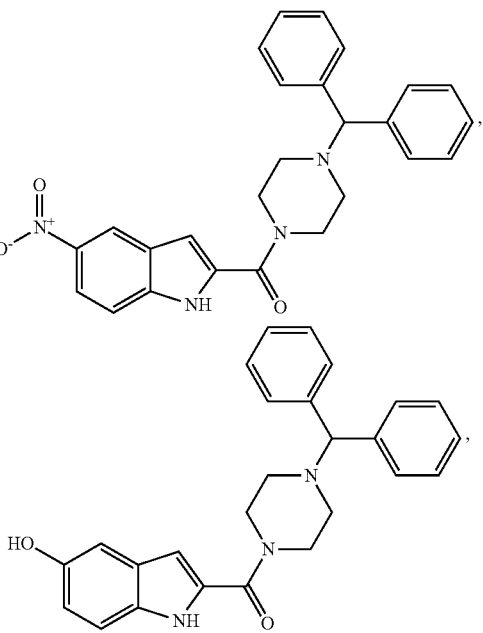
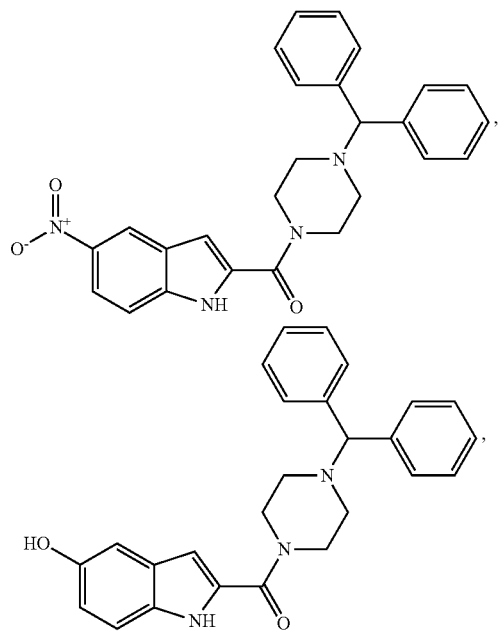
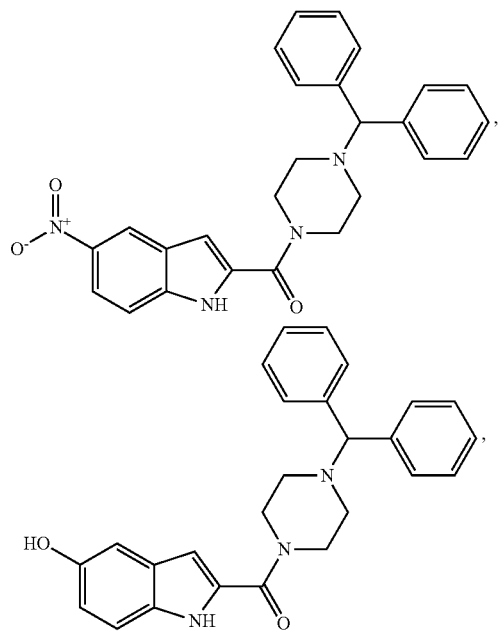
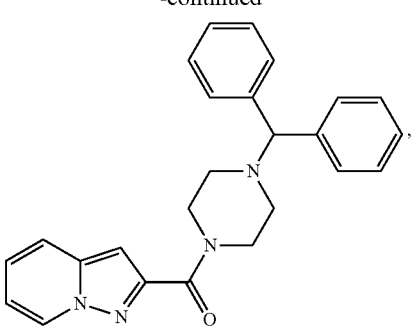
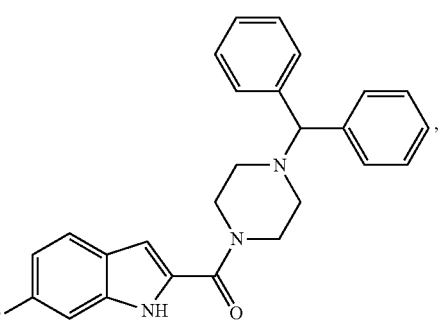
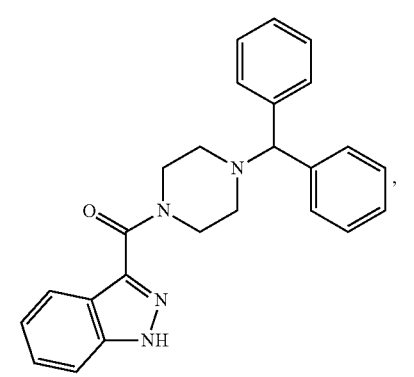
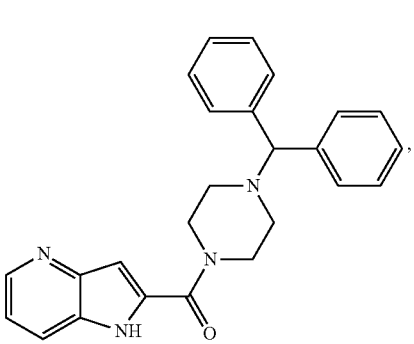
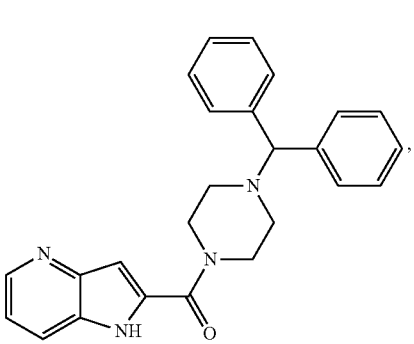
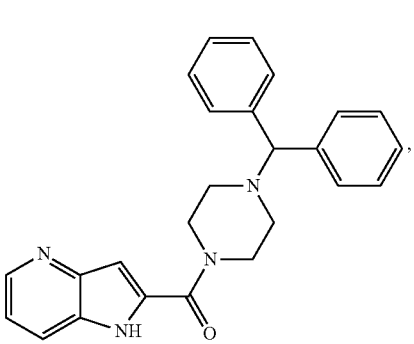

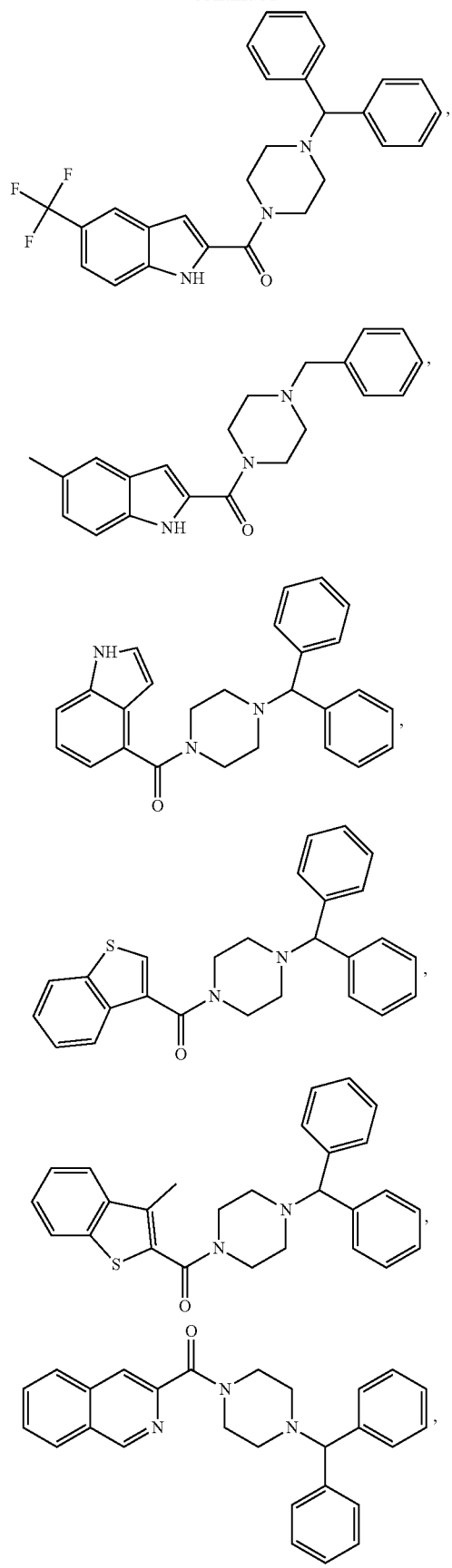
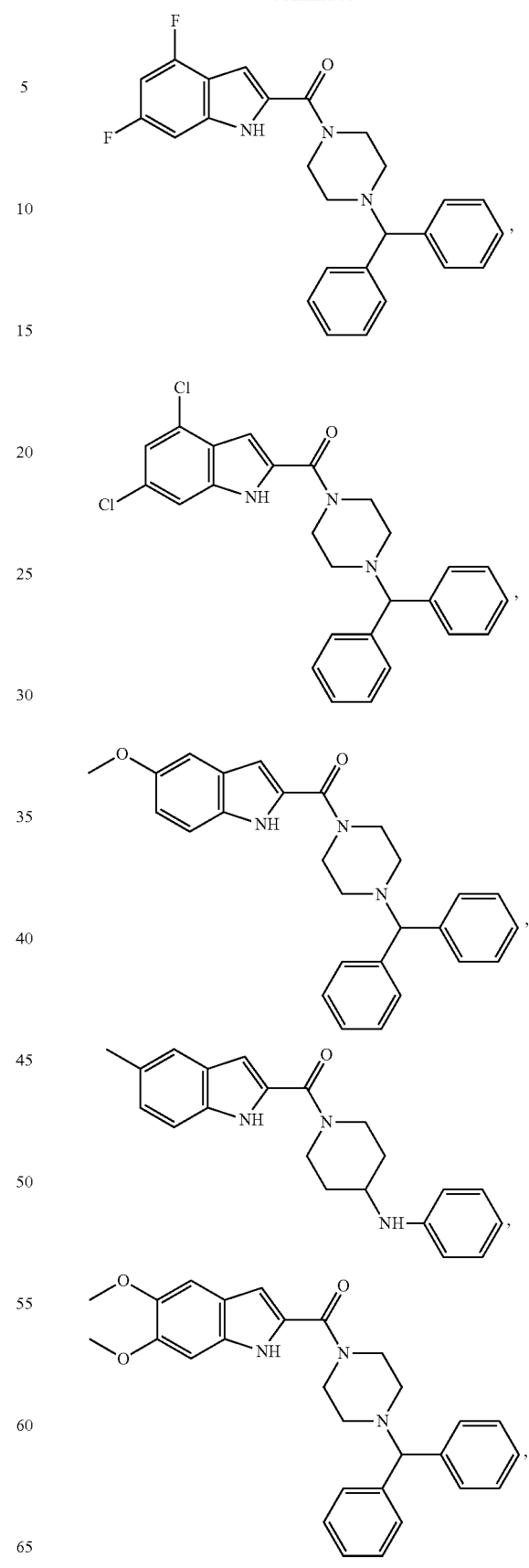

151
-continued
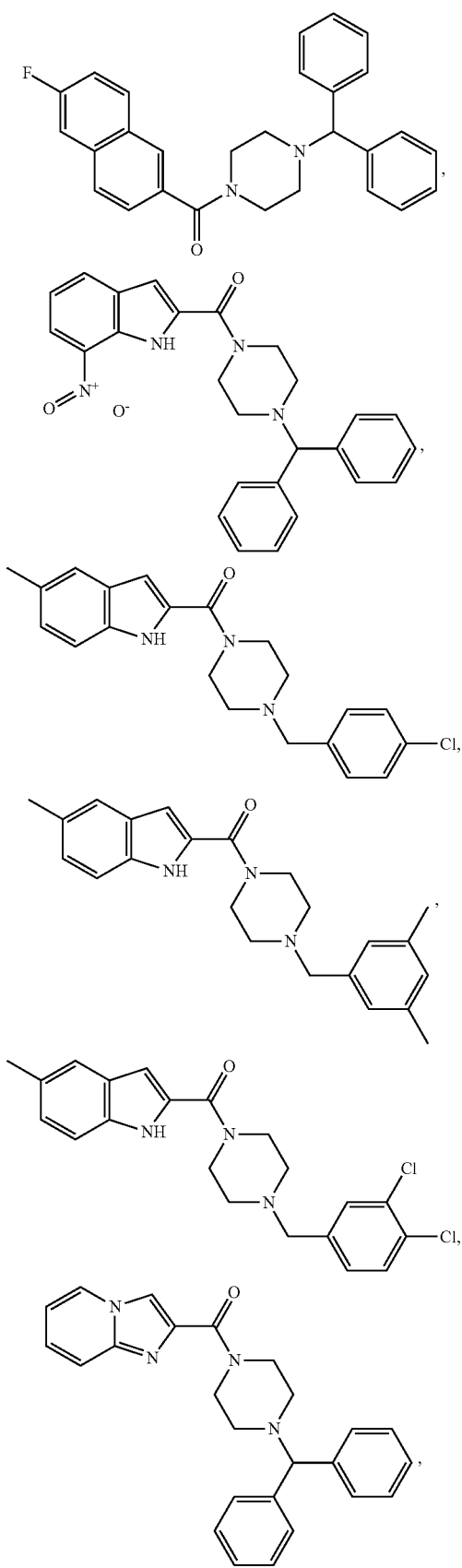
152
-continued
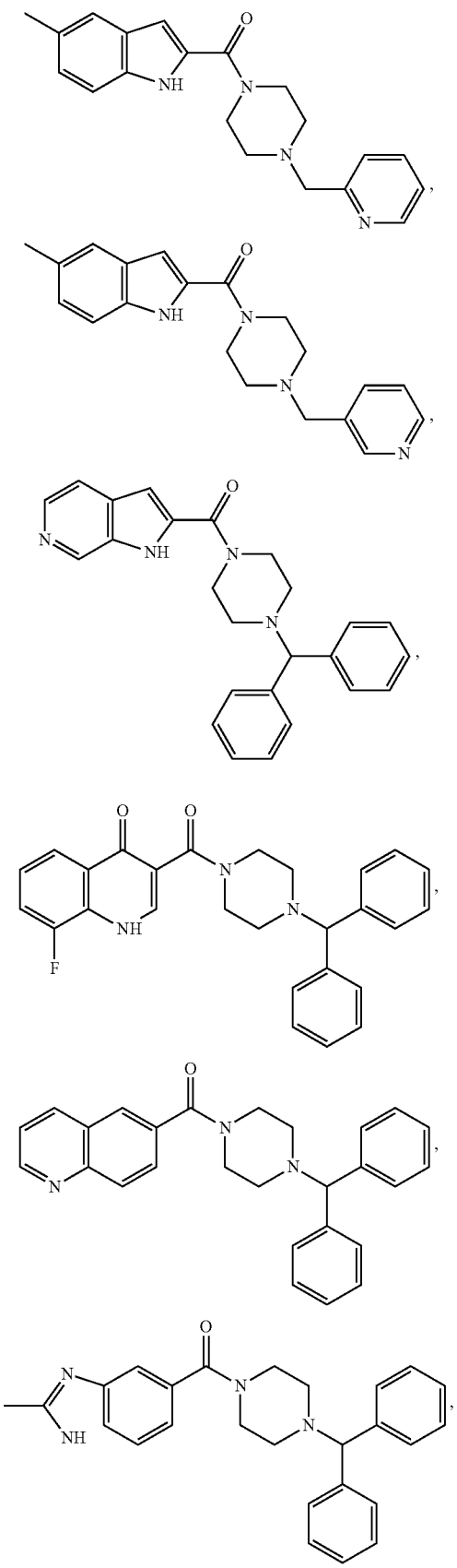

153
-continued
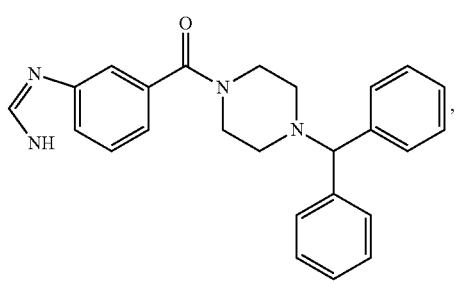
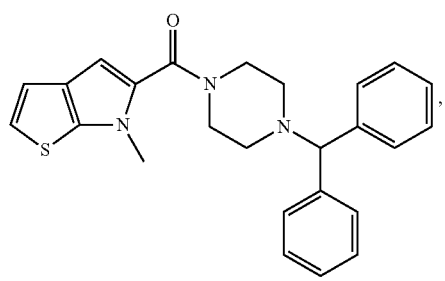
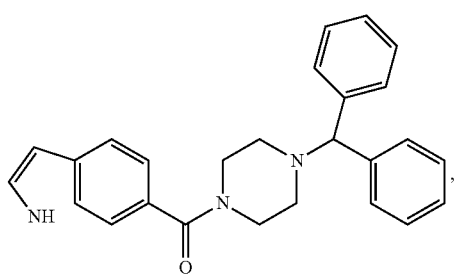
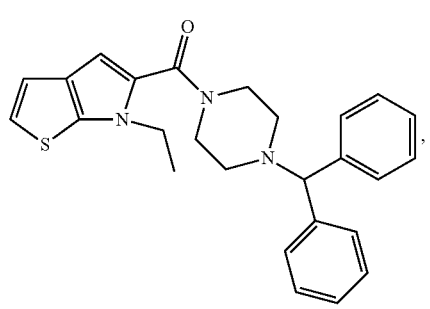
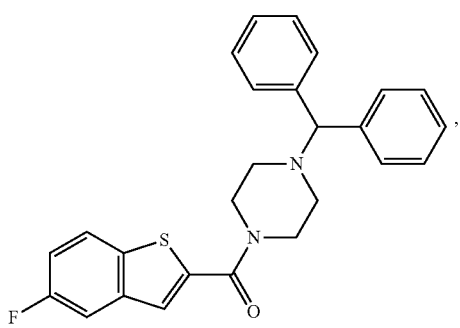
154
-continued
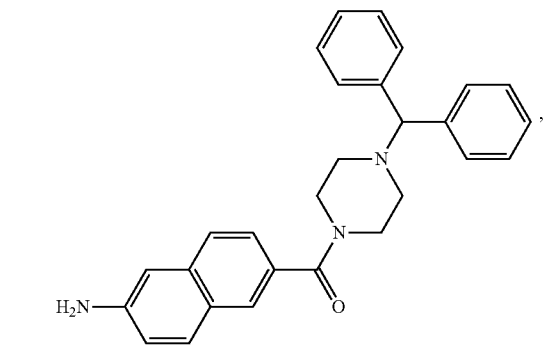
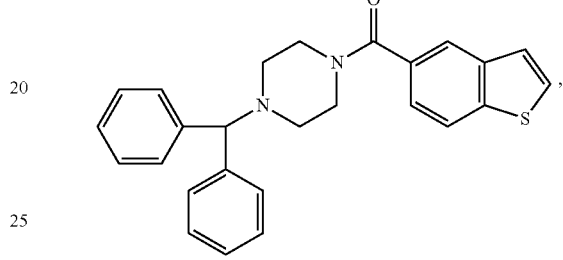
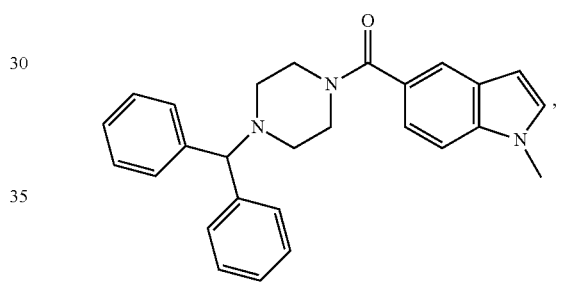
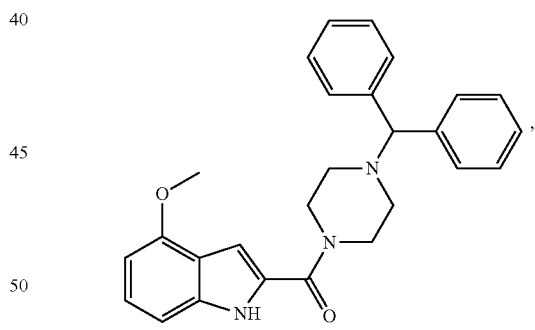
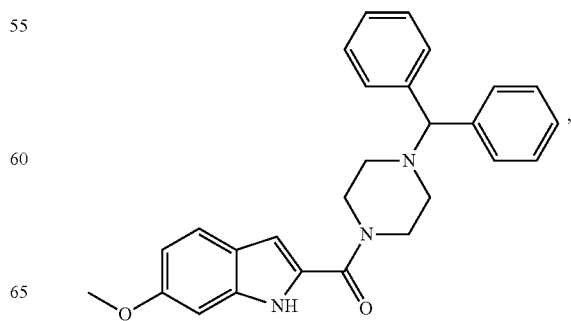

155
-continued
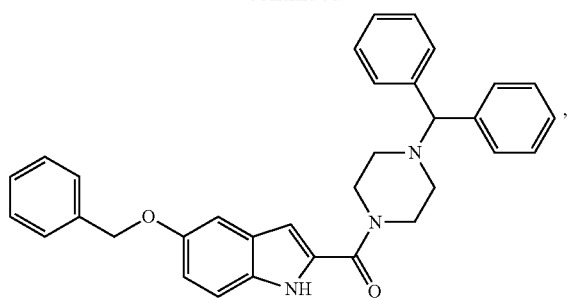
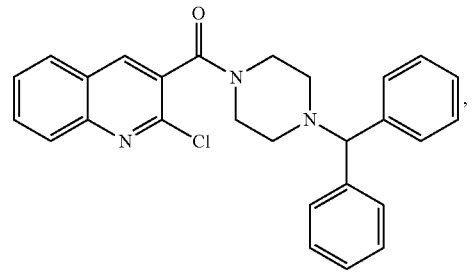
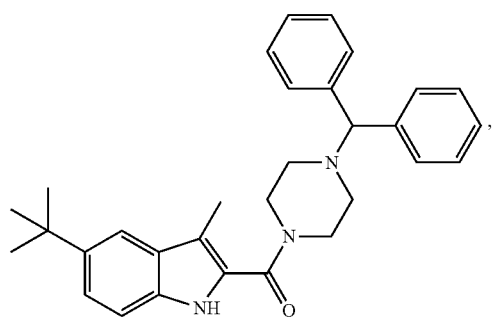
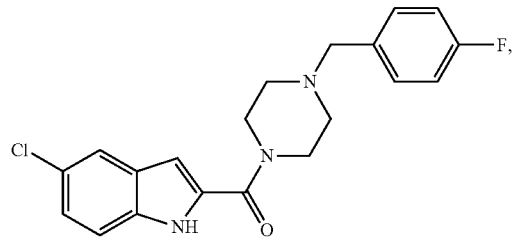
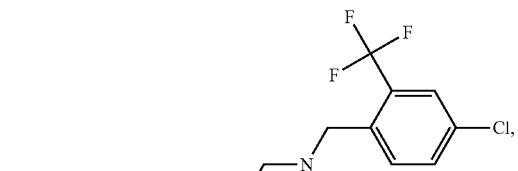
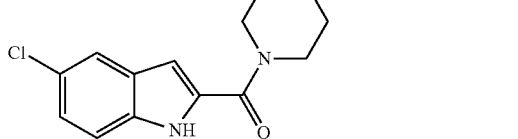
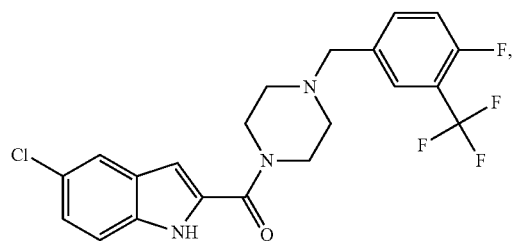
156
-continued
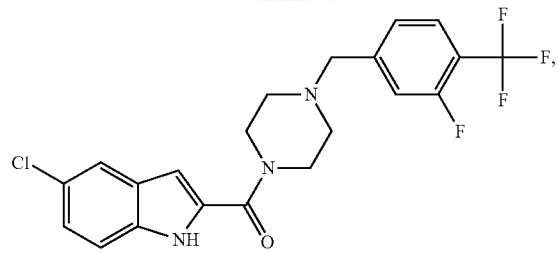
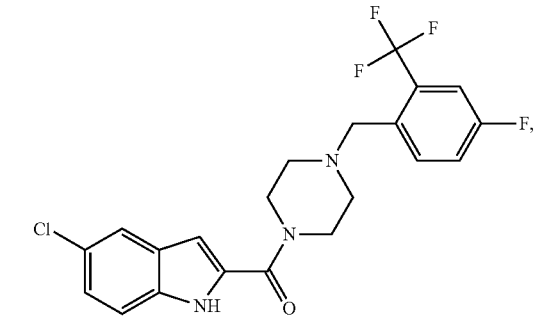
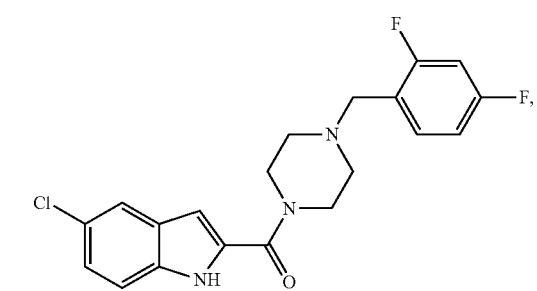
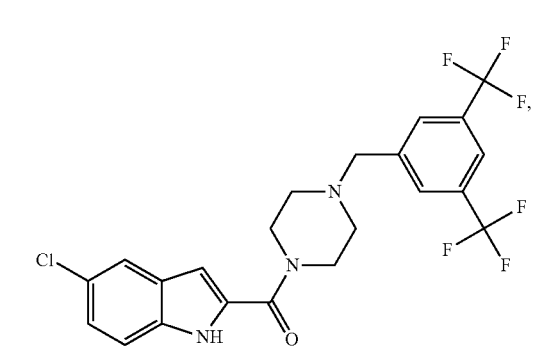
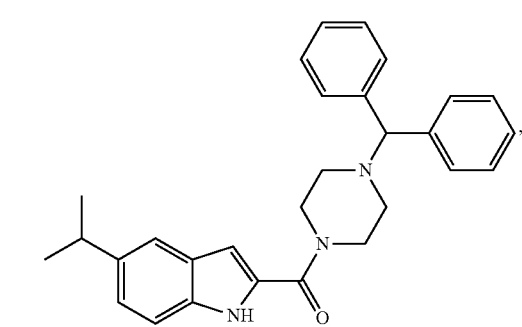

157
-continued
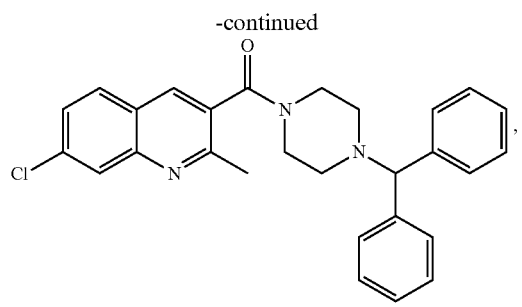
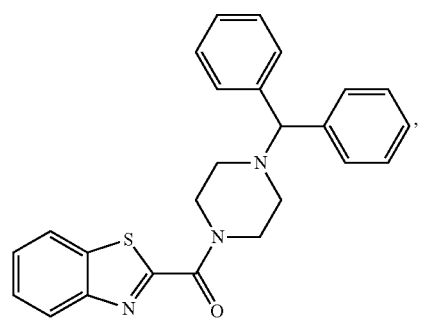
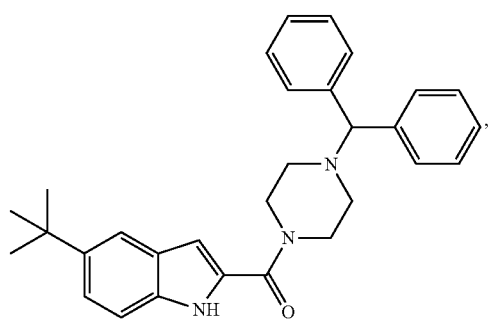
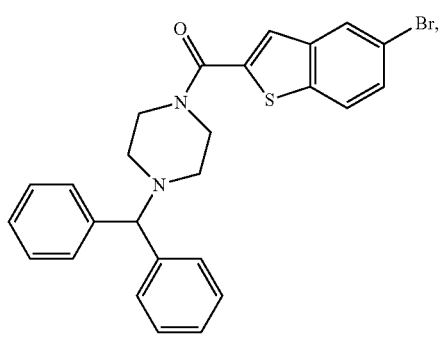
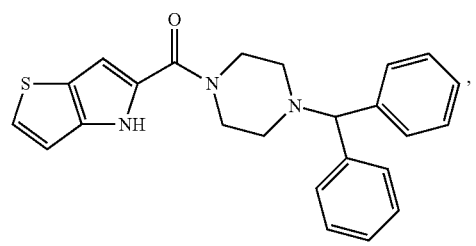
158
-continued
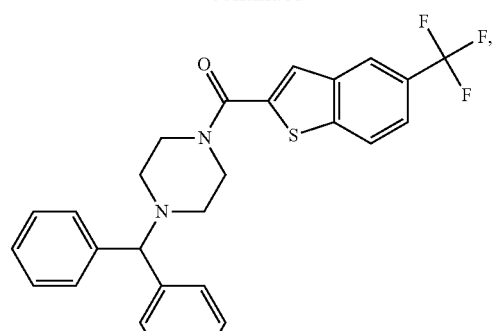
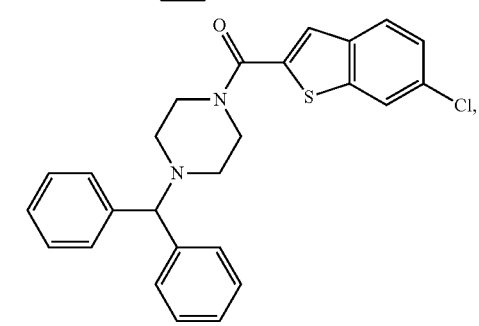
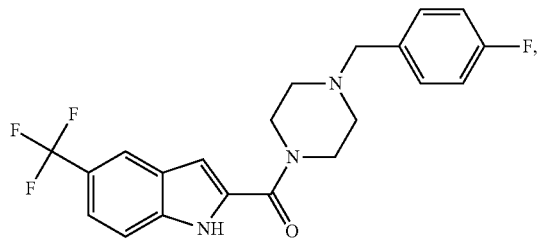
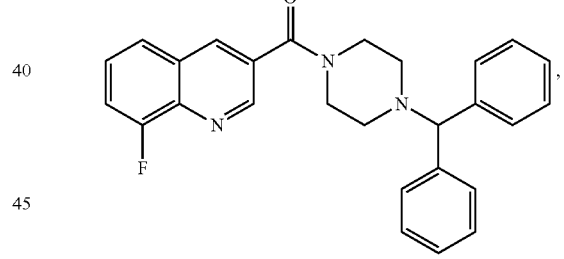
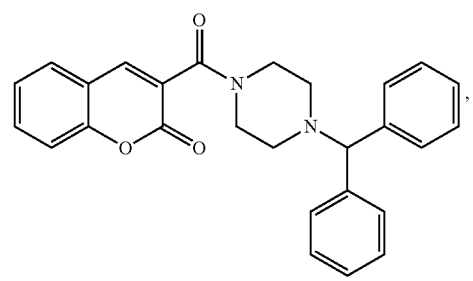
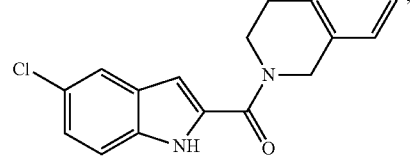

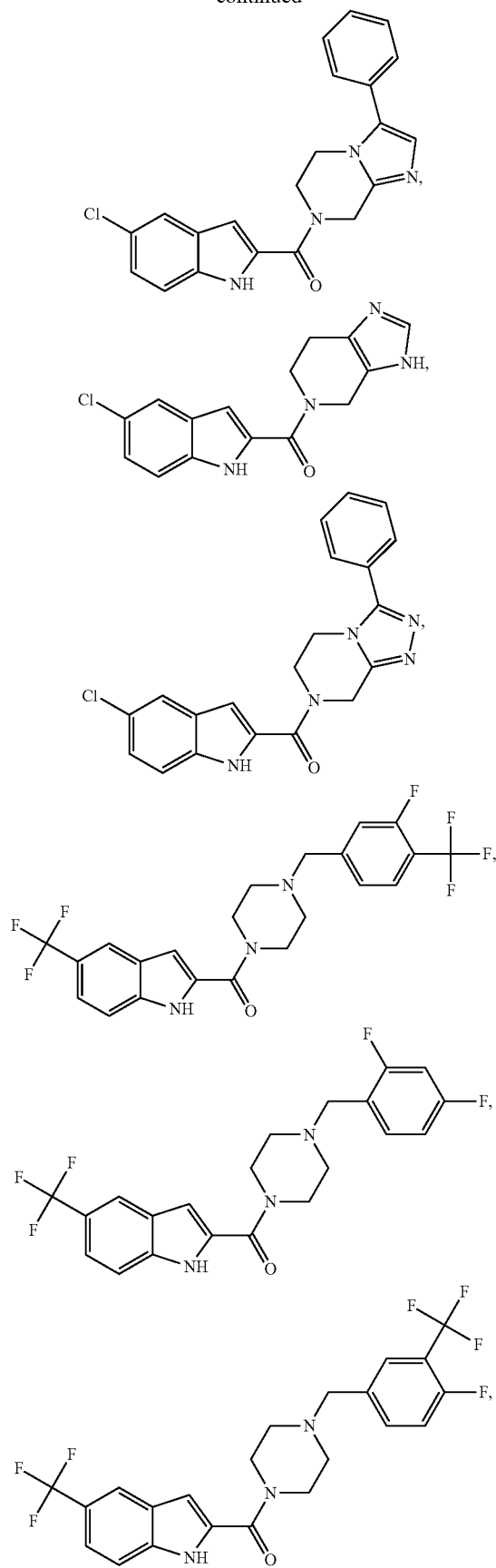
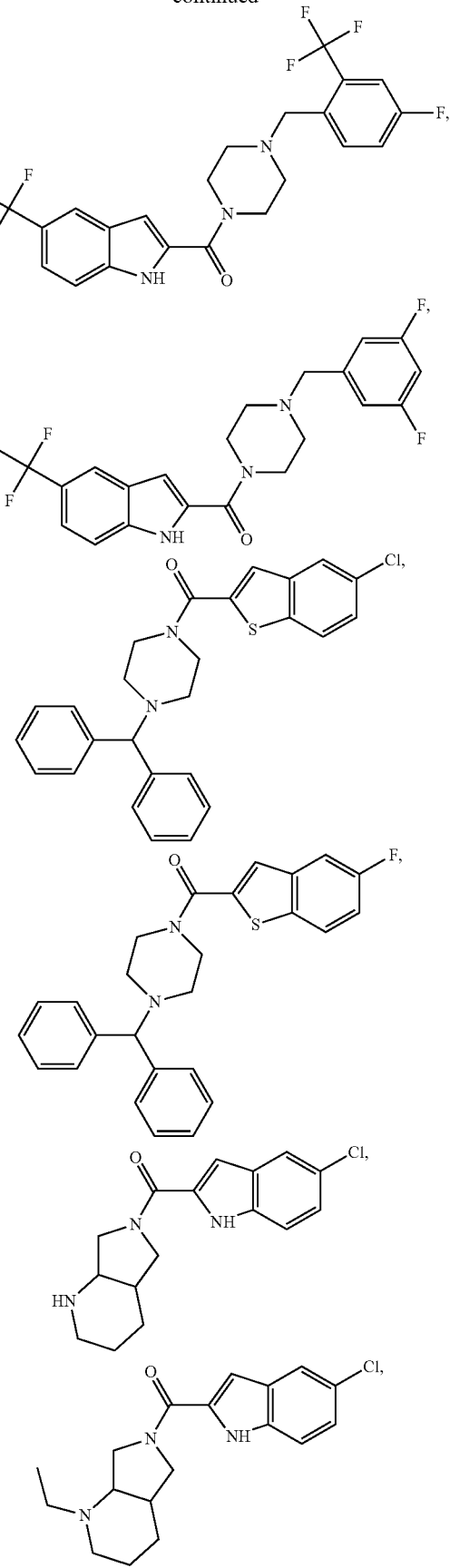

161
-continued
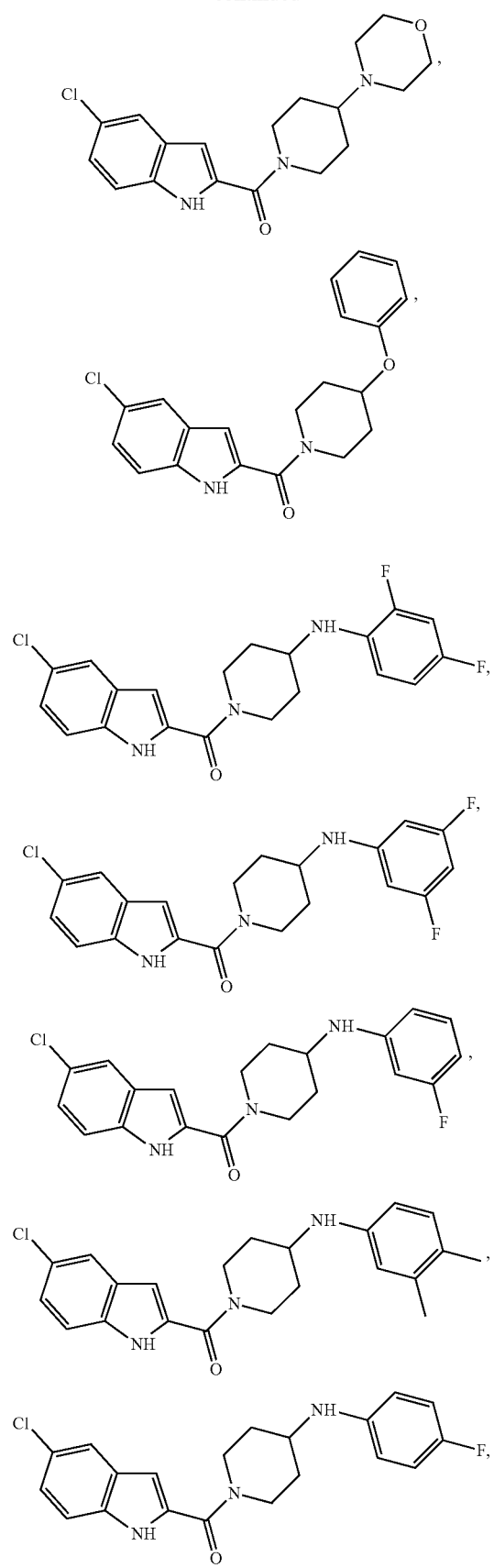
162
-continued
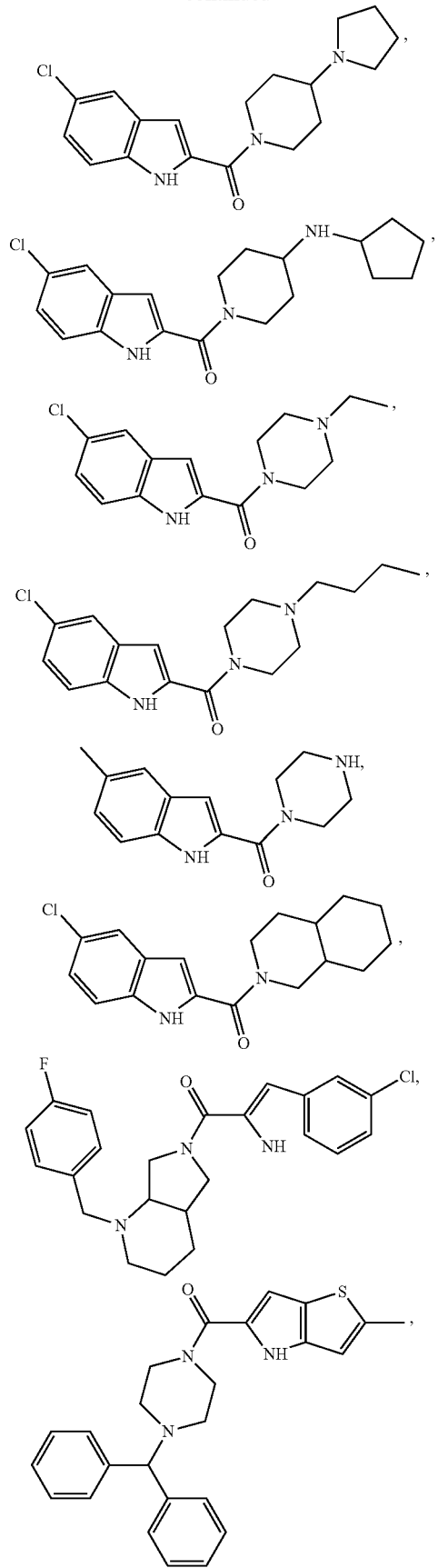

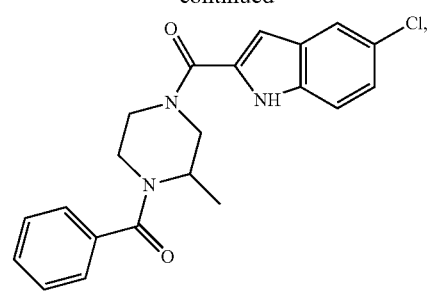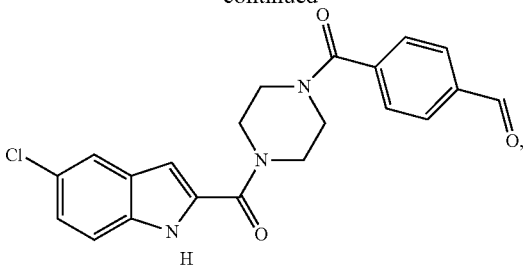

165
-continued
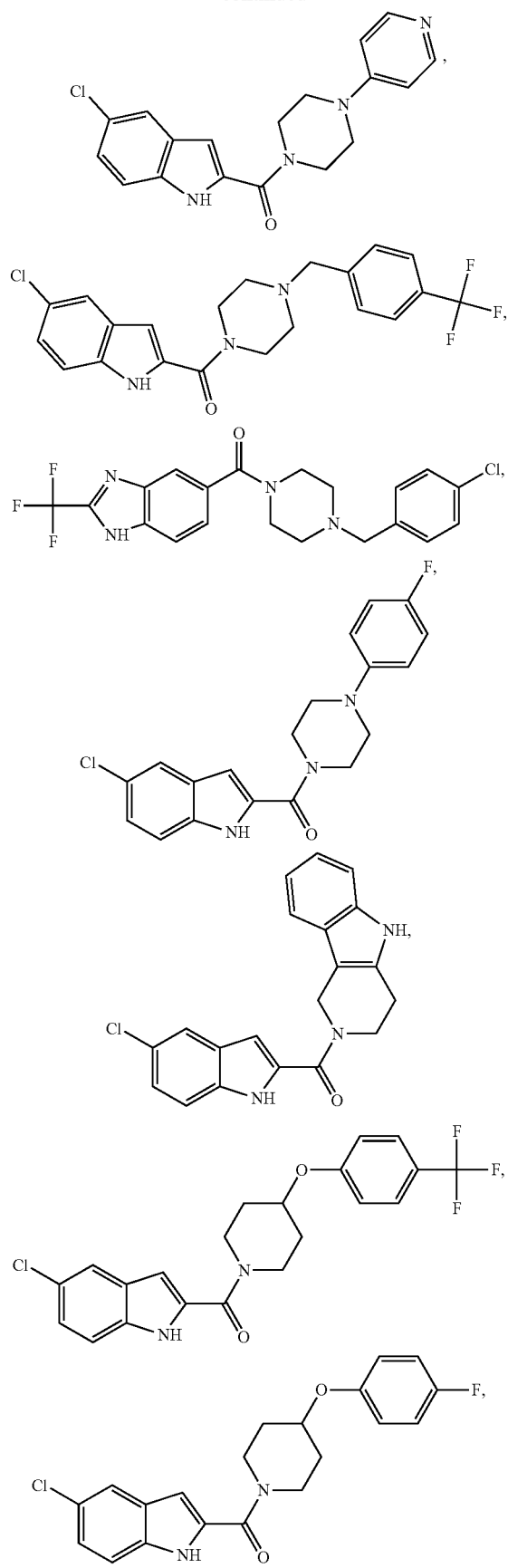
166
-continued
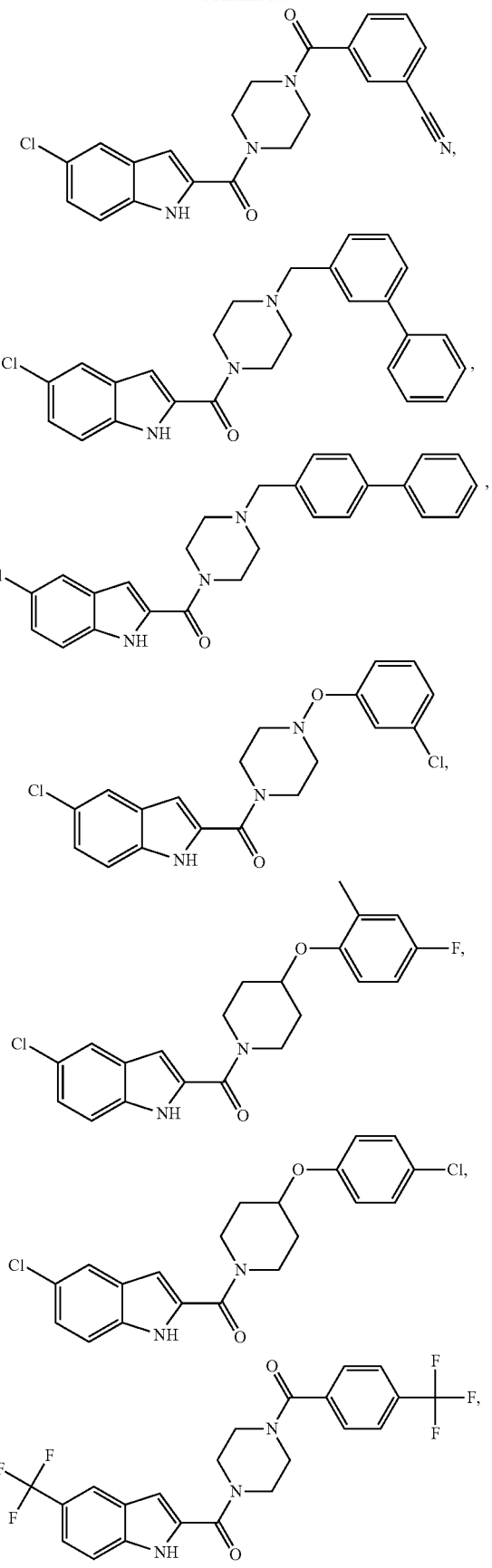

167
-continued
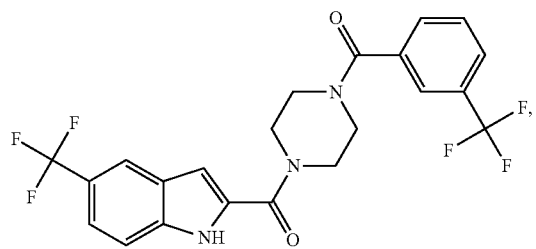
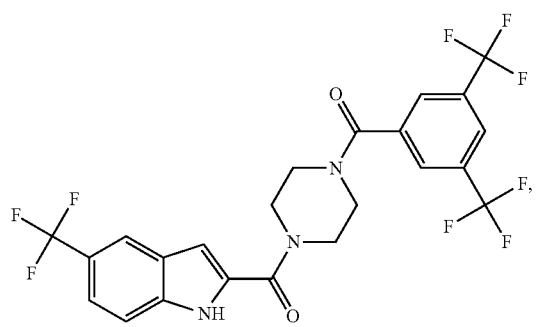
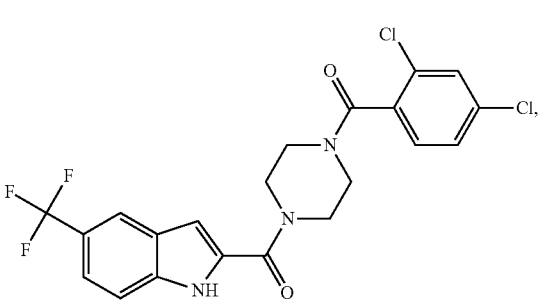
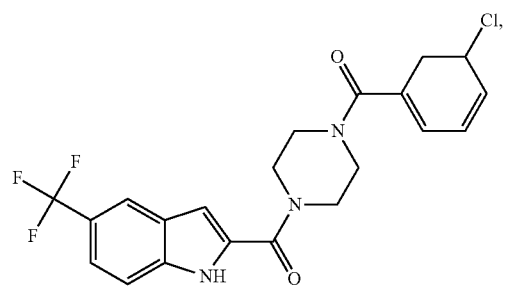
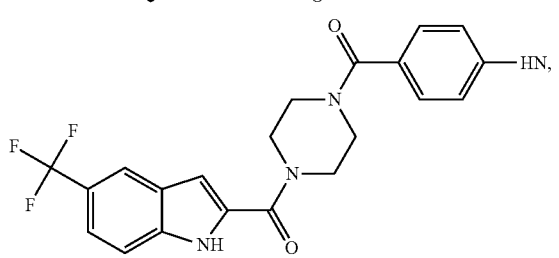
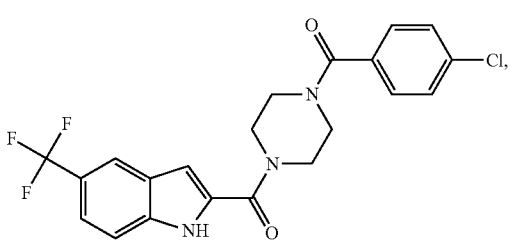
168
-continued
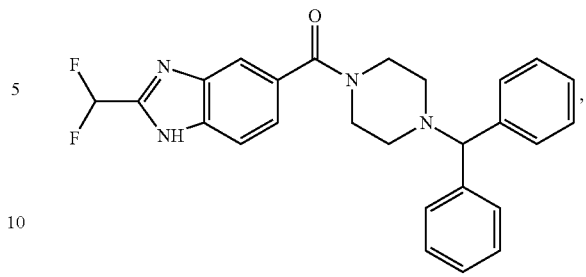
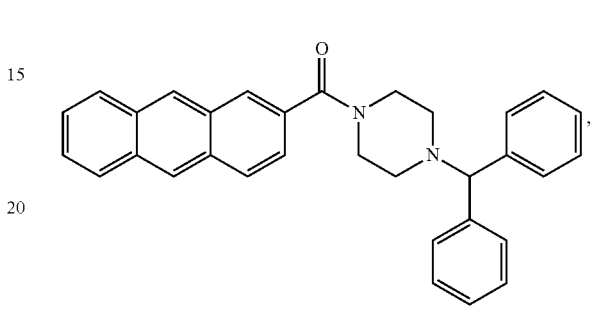
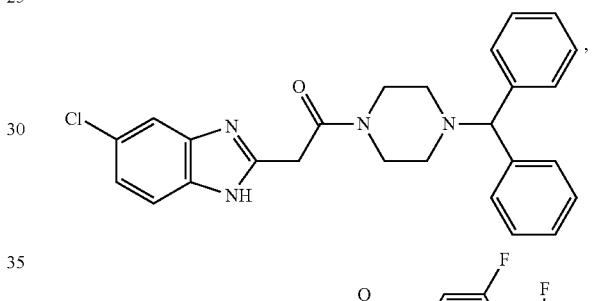
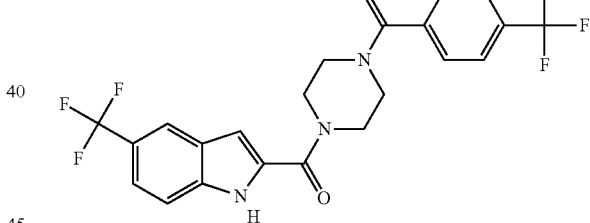
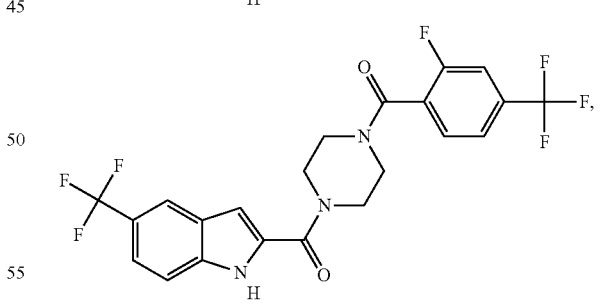
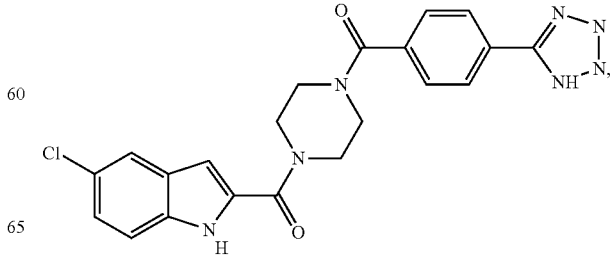

169
-continued
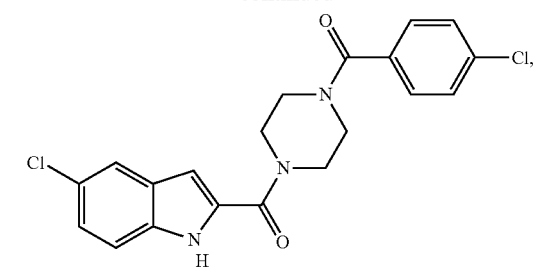
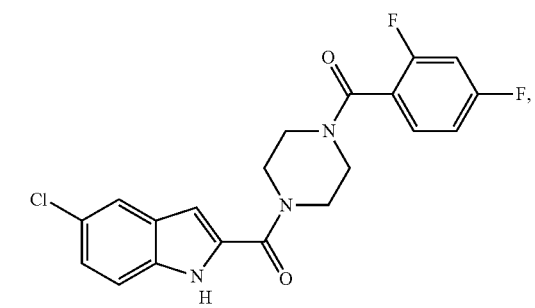
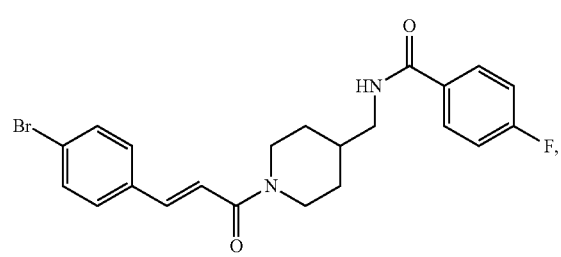
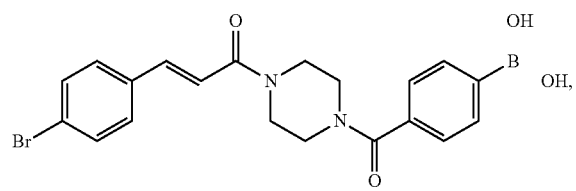
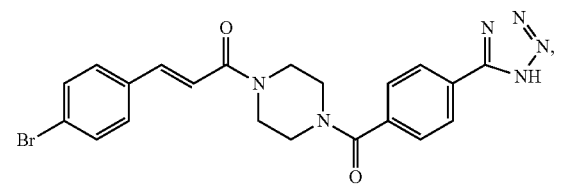
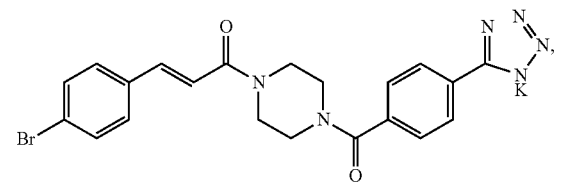
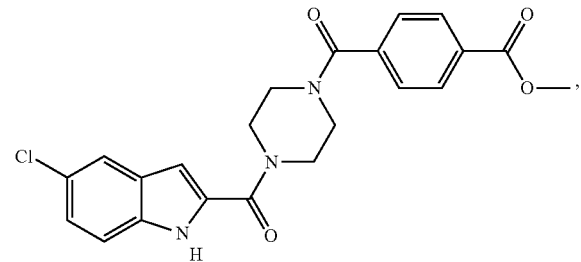
170
-continued
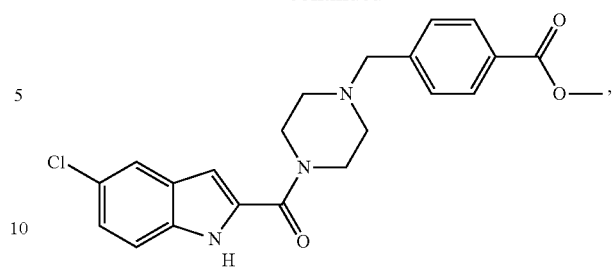
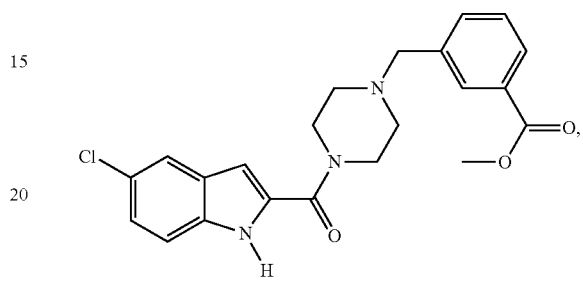
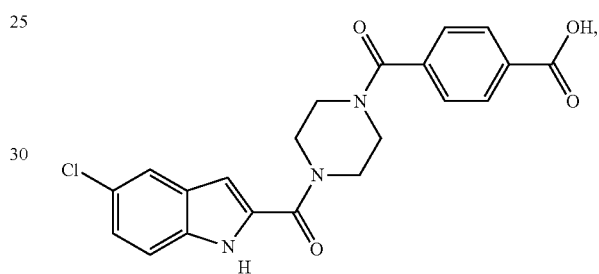
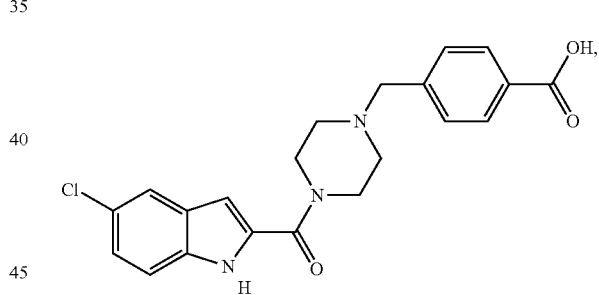
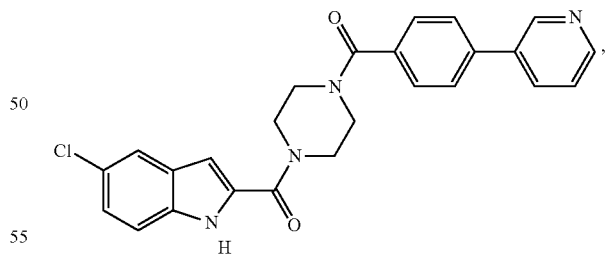
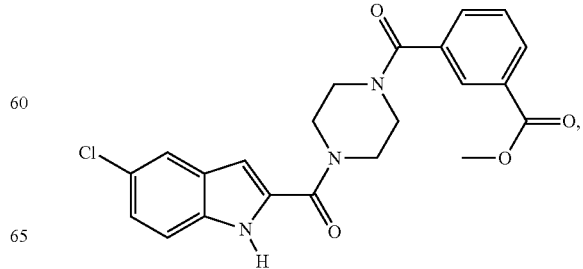

171
-continued
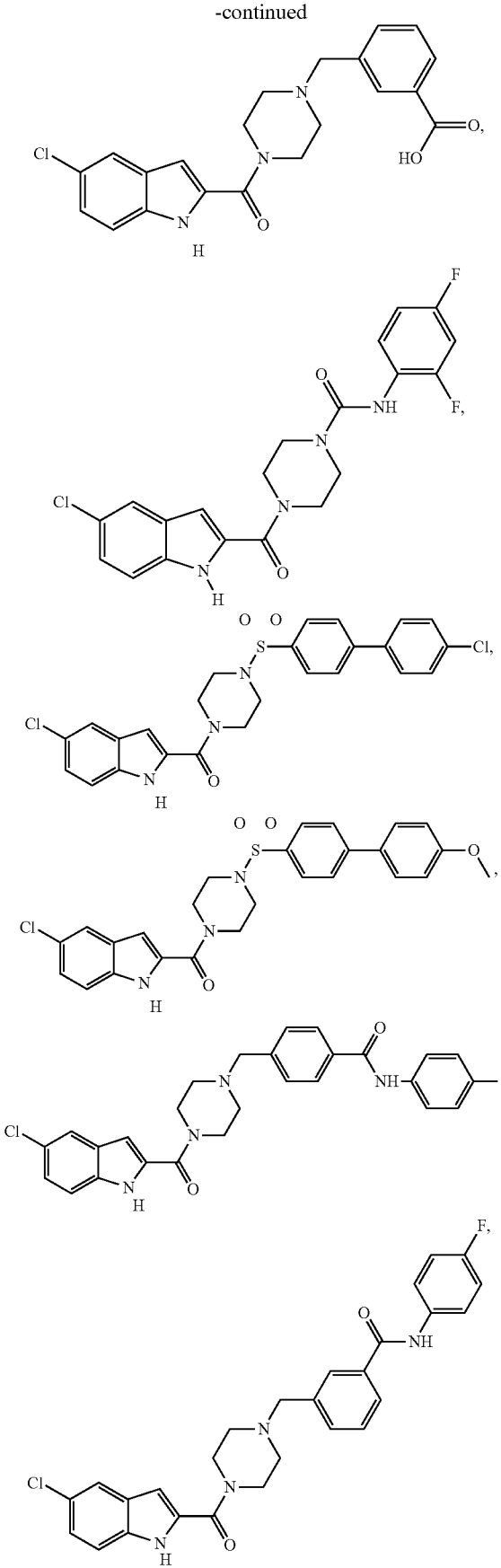
172
-continued
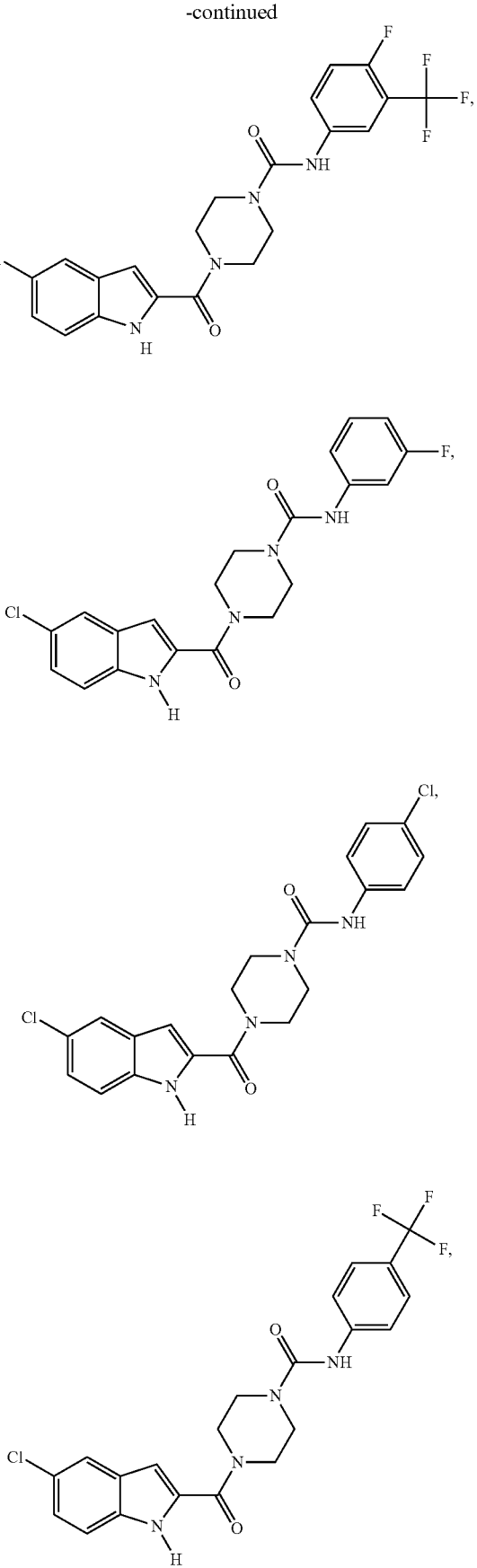

173
-continued

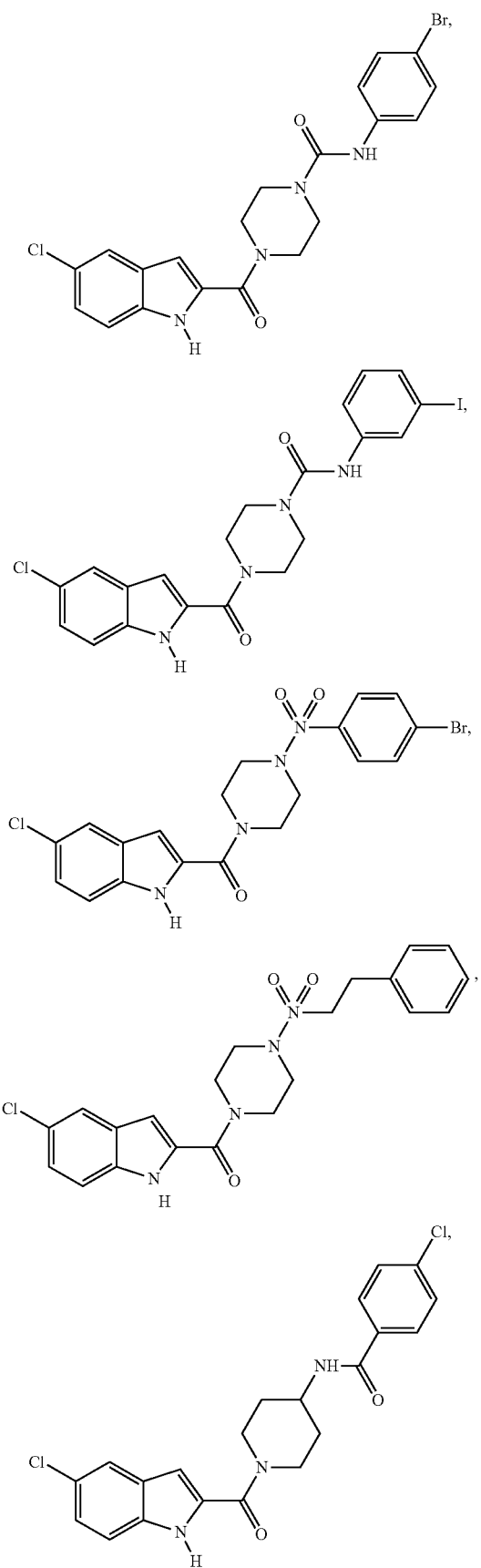

174
-continued

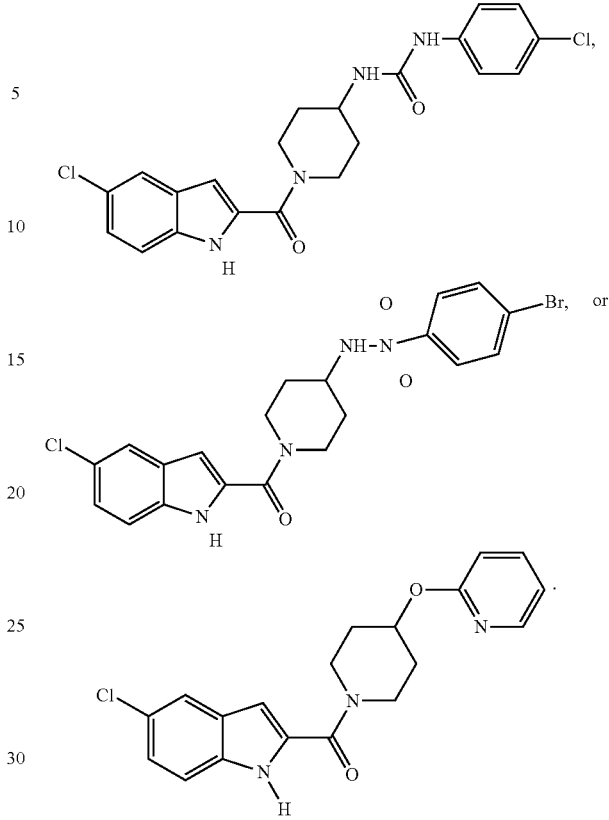

Further Forms of Compounds

In one aspect, the compound of Formula (I), (II), (III), (IV), (V), (VI), (VII), (VIII), (IX), or (X), possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews*, 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

In some cases, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (II), (III), (IV), (V), (VI), (VII), (VIII), (IX), or (X) with acids. Pharmaceutically acceptable salts are also obtained by reacting a compound of Formula (I), (II), (III), (IV), (V), (VI), (VII), (VIII), (IX), or (X) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FisherScientific (Fisher Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, compounds described herein are prepared as shown in Scheme 1.

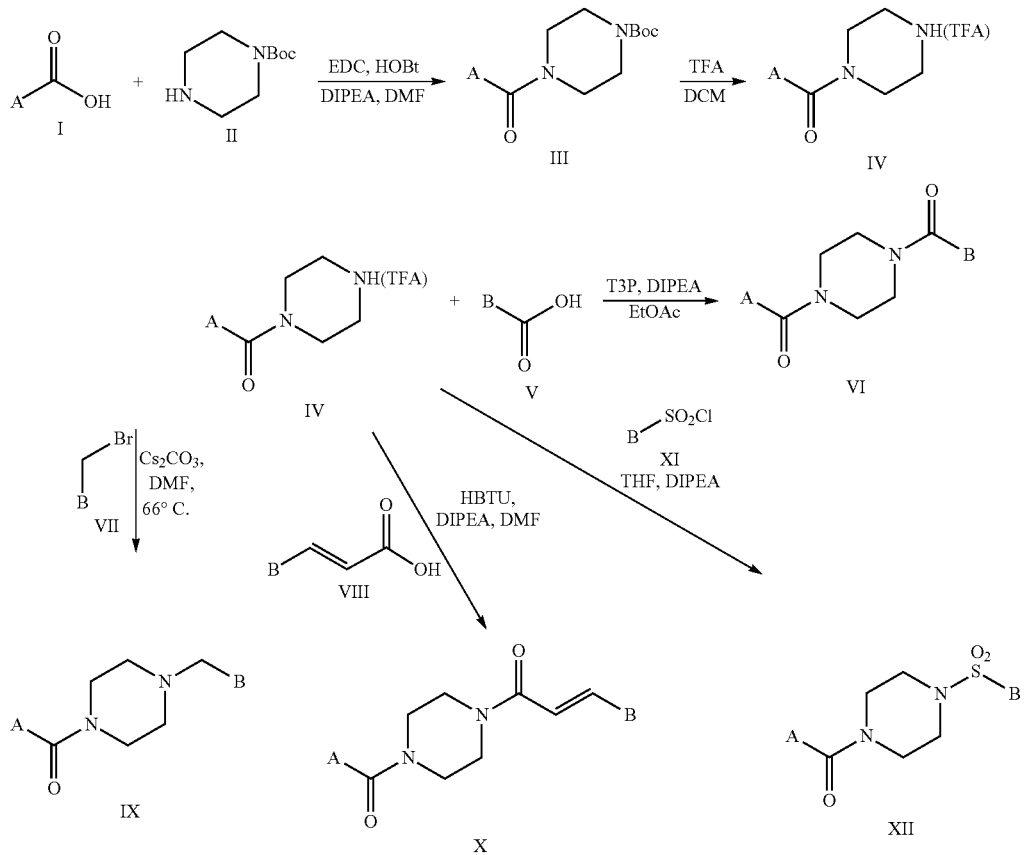

Scheme 1

The synthesis of compound VII, IX and X can be accomplished by the reactions illustrated in Scheme 1. Activation of the carboxylic acid of formula I with a coupling reagent such as 1-Ethyl-3-(3-dimethylaminopropyl)carbodiimide (EDC) and Hydroxybenzotriazole (HOBt) in a solvent such as DMF or acetonitrile containing an amine base such as N,N-Diisopropylethylamine, triethylamine or other organic bases followed by treatment of this mixture with compound II gives rise to compounds of formula III. For compound II any other suitable amino protecting group, such as 9-fluorenylmethoxycarbonyl (FMOC) or benzyloxycarbonyl (Z), can be alternatively used instead of the BOC group. Substitution of the coupling reagent EDC by carbonyliimidazole, BOP reagent, dicyclohexylcarbodimide (DCC), or HATU produces compound III. The deprotection of compound III can be carried out by treatment of compound III with trifluoracetic acid (TFA) in an inert solvent such as methylene chloride (DCM), to yield compounds of formula IV. The reaction is preferably carried out at temperatures between 0° C. and 50° C. Activation of the carboxylic acid of formula VIII with 1-Propanephosphonic anhydride solution, 2,4,6-Tripropyl-1,3,5,2,4,6-trioxatriphosphorinane-2,4,6-trioxide (T3P) in a solvent such as ethyl acetate or acetonitrile containing an amine base such as N,N-Diisopropylethylamine, triethylamine or other organic bases followed by treatment with compound V gives rise to compounds of formula VII. Alkylation of compound IV with an alkylhalide VII, benzylhalide VII, or benzyltosylate in an inert organic solvent such as DMF with an inorganic base such as potassium carbonate or an organic base such as triethylamine produces compounds of formula IX. The reaction is preferably carried out at temperatures between 0° C. and 100° C. Treatment of compound IV with cinnamic acid VII in an inert organic solvent such as DMF or THF containing N,N,N',N'-Tetramethyl-O-(1H-benzotriazol-1-yl) uronium hexafluorophosphate, O-(Benzotriazol-1-yl)-N,N,N',N'-tetramethyluronium hexafluorophosphate (HBTU) and an organic base such as N,N-Diisopropylethylamine produces compounds of formula X. Finally, treatment compound VI in an inert organic solvent such as THF containing an organic base such as triethylamine with a sulphonyl chloride XI produces compounds of formula XII. The reaction is preferably carried out at temperatures between 0° C. and 25° C.

In some embodiments, compounds described herein are prepared as shown in Scheme 2.

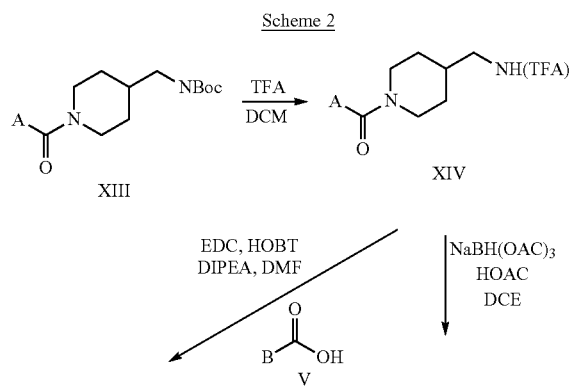

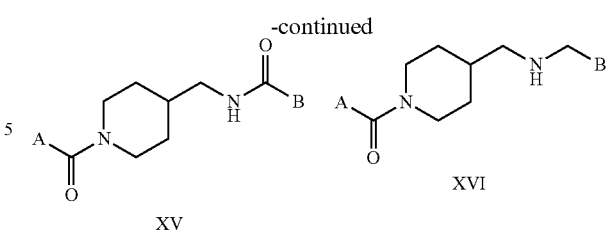

The synthesis of compound XV and XVI can be accomplished by the reactions illustrated in Scheme 2. Compound XII and Compound XIV can be prepared by the reactions described in General Procedure A and B. Activation of the carboxylic acid of formula V with a coupling reagent such as 1-Ethyl-3-(3-dimethylaminopropyl)carbodiimide (EDC) and Hydroxybenzotriazole (HOBt) in a solvent such as DMF or acetonitrile containing an amine base such as N,N-Diisopropylethylamine, triethylamine or other organic bases followed by treatment of this mixture with compound XIV gives rise to compounds of formula XV. Substitution of the coupling reagent EDC by carbonyliimidazole, BOP reagent, dicyclohexylcarbodiimide (DCC), or HATU produces compound XV. Compound XVII when treated with sodium triacetoxy-borohydride in dichloroethane (DCE) containing acetic acid Compound XIV produces Compound XVI. The reaction is preferably carried out at temperatures between 0° C. and 100° C.

It will be understood that the reactions shown above are illustrative.

In one aspect, compounds are synthesized as described in the Examples section.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —NH$_2$ radical.
"Cyano" refers to the —CN radical.
"Hydroxy" or "hydroxyl" refers to the —OH radical.
"Nitro" refers to the —NO$_2$ radical.
"Oxo" refers to the =O substituent.
"Thioxo" refers to the =S substituent.
"Alkyl" refers to a straight or branched hydrocarbon chain radical, having from one to thirty carbon atoms, and which is attached to the rest of the molecule by a single bond. Alkyls comprising any number of carbon atoms from 1 to 10 are included. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, and the like. Unless stated otherwise specifically in the specification, an alkyl group may be optionally substituted as described below. "Alkylene" or "alkylene chain" refers to a straight or branched divalent hydrocarbon chain linking the rest of the molecule to a radical group.

"Alkoxy" refers to a radical of the formula —OR where R is an alkyl radical as defined. Unless stated otherwise specifically in the specification, an alkoxy group may be optionally substituted as described below.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$CH$_2$OMe, —OCH$_2$CH$_2$OCH$_2$CH$_2$NH$_2$, or —OCH$_2$CH$_2$OCH$_2$CH$_2$OCH$_2$CH$_2$N(Me)$_2$. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Alkylamino" refers to a radical of the formula —NHR or —NRR where each R is, independently, an alkyl radical as defined above. Unless stated otherwise specifically in the specification, an alkylamino group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of benzene, indane, indene, and naphthalene. Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

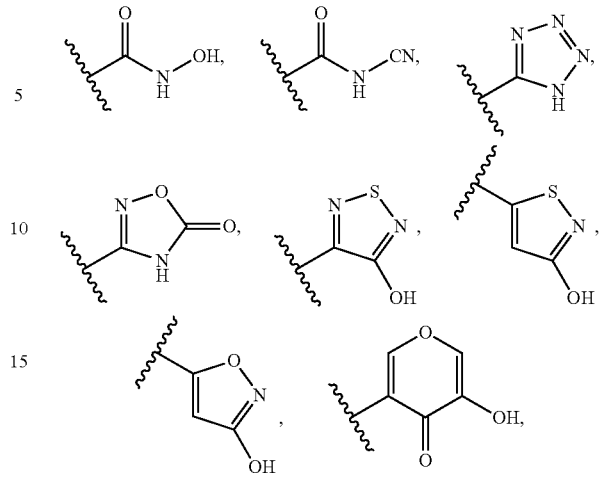

and the like.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloalkyls having from three to fifteen carbon atoms, from three to ten carbon atoms, from three to eight carbon atoms, from three to six carbon atoms, from three to five carbon atoms, or three to four carbon atoms. Monocyclic cycloalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted. Illustrative examples of cycloalkyl groups include, but are not limited to, the following moieties:

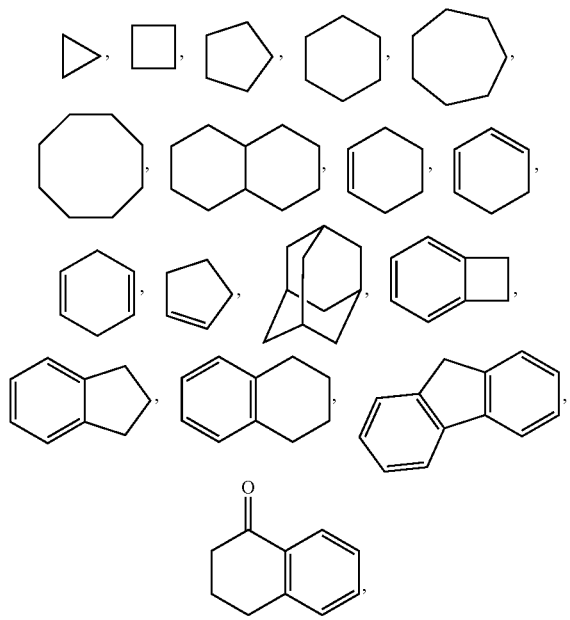

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl" or "heterocyclic ring" or "heterocycloalkyl" refers to a stable 3- to 14-membered non-aromatic ring radical comprising 2 to 13 carbon atoms and from one to 6 heteroatoms selected from the group consisting of nitrogen, oxygen, and sulfur. Unless stated otherwise specifically in the specification, the heterocyclyl radical may be a monocyclic, or bicyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. Unless stated otherwise specifically in the specification, a heterocyclyl group may be optionally substituted. Illustrative examples of heterocycloalkyl groups, also referred to as non-aromatic heterocycles, include:

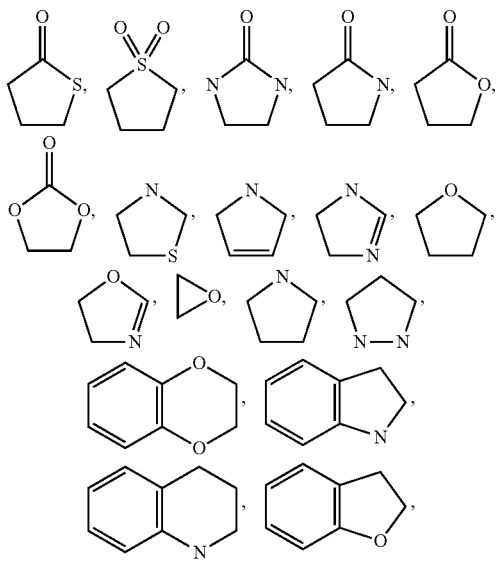

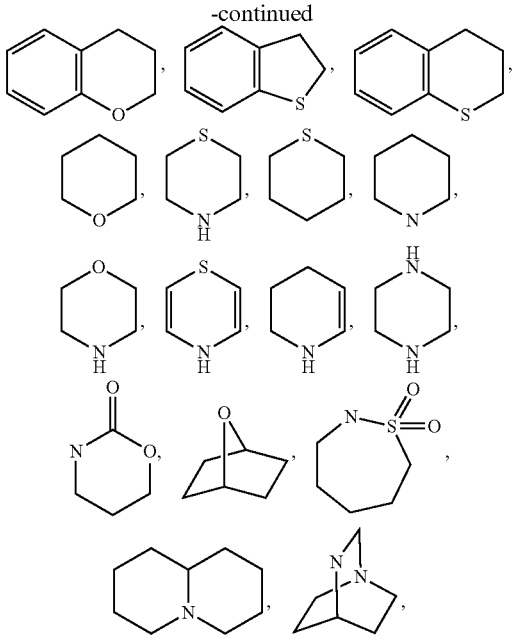

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups may be further functionalized wherein at least one hydrogen atom is replaced by a bond to a non-hydrogen atom substituent. Unless stated specifically in the specification, a substituted group may include one or more substituents selected from: oxo, —CO$_2$H, nitrile, nitro, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, heterocyclylalkyl, heteroaryl, and/or heteroarylalkyl. In addition, each of the foregoing substituents may also be optionally substituted with one or more of the above substituents. In some embodiments, optional substituents are independently selected from hydrogen, halogen, —CN, —OH, —NO$_2$, —N(R$^{12}$)—R$^{13}$, —C(=O)—N(R$^{12}$)—R$^{13}$, —NR$^{12}$C(=O)R$^{11}$, —C(=O)—O—R$^{11}$, —O—C(=O)—R$^{11}$, —SR$^{12}$, —S(=O)R$^{11}$, —S(=O)$_2$R$^{11}$, —N(R$^{12}$)S(=O)$_2$R$^{11}$, —S(=O)$_2$—N(R$^{12}$)—R$^{13}$, —C(=O)R$^{11}$, —B(OH)$_2$, —PO$_3$H, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl; each of R$^{12}$ and R$^{13}$ is independently selected from the group consisting of hydrogen, optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl; or R$^{12}$ and R$^{13}$, when on the same nitrogen atom, are taken together with the nitrogen atom to which they are attached to form an optionally substituted heterocycloalkyl; R$^{15}$ is selected from the group consisting of optionally substituted alkyl, optionally substituted cycloalkyl, optionally substituted heterocycloalkyl, optionally substituted alkoxy, optionally substituted haloalkyl, optionally substituted haloalkoxy, optionally substituted phenyl, and optionally substituted 5- or 6-membered heteroaryl. In some embodiments, optional substituents are independently selected from hydrogen, halogen, —CN, —OH, —NO$_2$, —N(R$^{12}$)—R$^{13}$, —C(=O)—N(R$^{12}$)—R$^{13}$, —NR$^{12}$C(=O)R$^{11}$, —C(=O)—O—R$^{11}$, —O—C(=O)—R$^{11}$, —SR$^{12}$, —S(=O)R$^{11}$, —S(=O)$_2$R$^{11}$, —N(R$^{12}$)S(=O)$_2$R$^{11}$, —S(=O)$_2$—N(R$^{12}$)—R$^{13}$, —C(=O)R$^{13}$, alkyl, cycloalkyl, heterocycloalkyl, alkoxy, haloalkyl, haloalkoxy, phenyl, and 5- or 6-membered heteroaryl; each of R$^{12}$ and R$^{13}$ is independently selected from the group consisting of hydrogen, alkyl, cycloalkyl, heterocycloalkyl, alkoxy, haloalkyl, haloalkoxy, phenyl, and 5- or 6-membered heteroaryl; or R$^{12}$ and R$^{13}$, when on the same nitrogen atom, are taken together with the nitrogen atom to which they are attached to form an optionally substituted heterocycloalkyl; R$^{15}$ is selected from the group consisting of alkyl, cycloalkyl, heterocycloalkyl, alkoxy, haloalkyl, haloalkoxy, phenyl, and 5- or 6-membered heteroaryl.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (II), (III), (IV), (V), (VI), (VII), (VIII), (IX), or (X) and a co-agent, are both administered to a patient simultaneously in the form of a single entity or dosage. The term "non-fixed combination" means that the active ingredients, e.g. a compound of Formula (I), (II), (III), (IV), (V), (VI), (VII), (VIII), (IX), or (X) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "individual", "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

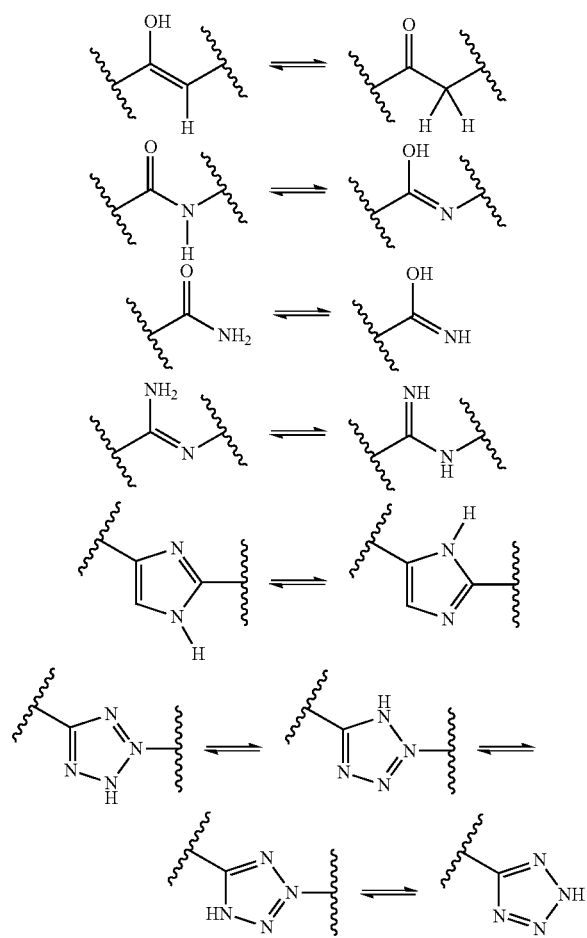

Administration and Pharmaceutical Composition

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), (II), (III), (IV), (V), (VI), (VII), (VIII), (IX), or (X) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), (II), (III), (IV), (V), (VI), (VII), (VIII), (IX), or (X) are administered orally.

In some embodiments, the compounds of Formula (I), (II), (III), (IV), (V), (VI), (VII), (VIII), (IX), or (X) are administered topically. In such embodiments, the compound of Formula (I), (II), (III), (IV), (V), (VI), (VII), (VIII), (IX), or (X) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I), (II), (III), (IV), (V), (VI), (VII), (VIII), (IX), or (X) are administered topically to the skin.

In another aspect, the compounds of Formula (I), (II), (III), (IV), (V), (VI), (VII), (VIII), (IX), or (X) are administered by inhalation.

In another aspect, the compounds of Formula (I), (II), (III), (IV), (V), (VI), (VII), (VIII), (IX), or (X) are formulated for intranasal administration. Such formulations include nasal sprays, nasal mists, and the like.

In another aspect, the compounds of Formula (I), (II), (III), (IV), (V), (VI), (VII), (VIII), (IX), or (X) are formulated as eye drops.

In any of the aforementioned aspects are further embodiments in which the effective amount of the compound of Formula (I), (II), (III), (IV), (V), (VI), (VII), (VIII), (IX), or (X) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments, a compound as described herein is administered in a local rather than systemic manner.

In some embodiments, the compound described herein is administered topically. In some embodiments, the compound described herein is administered systemically.

In some embodiments, the pharmaceutical formulation is in the form of a tablet. In other embodiments, pharmaceutical formulations of the compounds of Formula (I), (II), (III), (IV), (V), (VI), (VII), (VIII), (IX), or (X) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I), (II), (III), (IV), (V), (VI), (VII), (VIII), (IX), or (X) is formulated for use as an aerosol, a mist or a powder.

For buccal or sublingual administration, the compositions may take the form of tablets, lozenges, or gels formulated in a conventional manner.

In some embodiments, compounds of Formula (I), (II), (III), (IV), (V), (VI), (VII), (VIII), (IX), or (X) are prepared as transdermal dosage forms.

In one aspect, a compound of Formula (I), (II), (III), (IV), (V), (VI), (VII), (VIII), (IX), or (X) is formulated into a pharmaceutical composition suitable for intramuscular, subcutaneous, or intravenous injection.

In some embodiments, the compounds described herein may be administered topically and can be formulated into a variety of topically administrable compositions, such as solutions, suspensions, lotions, gels, pastes, medicated sticks, balms, creams or ointments.

In some embodiments, the compounds of Formula (I), (II), (III), (IV), (V), (VI), (VII), (VIII), (IX), or (X) are formulated in rectal compositions such as enemas, rectal gels, rectal foams, rectal aerosols, suppositories, jelly suppositories, or retention enemas.

Methods of Dosing and Treatment Regimens

In one embodiment, the compounds of Formula (I), (II), (III), (IV), (V), (VI), (VII), (VIII), (IX), or (X) are used in the preparation of medicaments for the treatment of diseases or conditions described herein. In addition, a method for treating any of the diseases or conditions described herein in a subject in need of such treatment, involves administration of pharmaceutical compositions that include at least one compound of Formula (I), (II), (III), (IV), (V), (VI), (VII), (VIII), (IX), or (X) or a pharmaceutically acceptable salt, active metabolite, prodrug, or solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound of Formula (I), (II), (III), (IV), (V), (VI), (VII), (VIII), (IX), or (X) in combination with another therapeutic agent.

In one specific embodiment, a compound of Formula (I), (II), (III), (IV), (V), (VI), (VII), (VIII), (IX), or (X) is co-administered with a second therapeutic agent, wherein the compound of Formula (I), (II), (III), (IV), (V), (VI), (VII), (VIII), (IX), or (X) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

EXAMPLES

The following examples are intended to illustrate but not limit the disclosed embodiments. All reactions involving air and moisture-sensitive reagents and solvents were performed under a nitrogen atmosphere using standard chemical techniques. Anhydrous solvents were purchased and freshly used from Sigma-Aldrich or EMD Biosciences. All organic reagents were used as purchased. Analytical thin-layer chromatography was performed on Partisil K6F silica gel 60 Å, 250 µm. Microwave-assisted reactions were performed using a CEM Discover system. $^1$H and $^{13}$C chemical shifts are reported in δ values in ppm in the corresponding solvent. All solvents used for chromatography on the synthetic materials were Fisher Scientific HPLC grade, and the water was Millipore Milli-Q PP filtered. LCMS analysis of synthetic materials was completed on a Waters Autopurification system, which consists of a 2767 sample manager, a 2545 binary gradient module, a system fluidics organizer, a 2489 UV/vis detector, and a 3100 mass detector, all controlled with MassLynx software. A Sunfire Analytical C18 5 µm column (4.6×50 mm) and stepwise gradient {10% [(MeCN+0.1% TFA) in (water+0.1% TFA)] to 98% [(MeCN+0.1% TFA) in (water+0.1% TFA)] for 9 min.} was used for analytical LCMS of final compounds. The final compounds were purified by silica gel flash chromatography with ethyl acetate/hexanes as the eluant. All NMR spectra for the synthetic materials were recorded on a Bruker Avance II 400 or DRX-500 MHz instrument. The MestReNova 7 program was used to process and interpret NMR spectra. High Resolution Mass Spectrometry (HRMS) spectra were carried out on an Agilent 6224A Accurate-Mass Time-of-Flight (TOF) LC/MS system with electron spray ionization (ESI).

Example A1

Preparation of tert-butyl (E)-tert-butyl 4-(3-(4-bromophenyl)acryloyl) piperazine-1-carboxylate (General Procedure A)

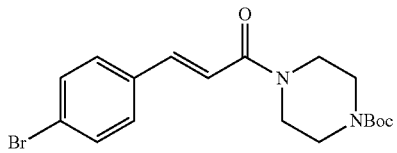 [SMILES: CC(C)(C)OC(=O)N1CCN(C(=O)/C=C/c2ccc(Br)cc2)CC1]

4-Bromocinnamic acid (200 mg, 0.880 mmol) was dissolved in 10 mL of THF and after the addition of CDI (213.9 mg, 1.3 mmol), the mixture was stirred at room temperature for 30 minutes. Boc-Piperazine (196.6 mg, 1.055 mmol) was added to the resulting mixture and the reaction mixture was stirred for 2 hours at room temperature. When the reaction was determined to be complete by HPLC, the reaction mixture was concentrated under reduced pressure and the resulting solid was dissolved in EtOAc. The solution was washed with saturated aqueous NaHCO$_3$, washed with saturated aqueous NaCl, and dried over Na$_2$SO$_4$. The resulting organic layer was concentrated under reduced pressure afforded the title compound as a white solid which was used directly into the next step without purification. MS (EI) m/z 397 [(M+H)+].

Example A2

Preparation of tert-butyl 4-cinnamoylpiperazine-1-carboxylate

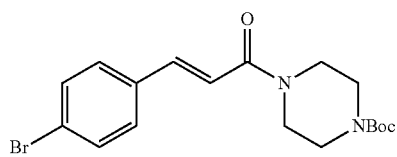 [SMILES: CC(C)(C)OC(=O)N1CCN(C(=O)/C=C/c2ccc(Br)cc2)CC1]

The title compound was prepared from the reaction of cinnamic acid with Boc-Piperazine according to the procedure given in Example A1 obtained as a white solid. MS (EI) m/z 317 [(M+H)+].

Example A3

Preparation of (E)-tert-butyl 4-(3-(3, 4-dichloro phenyl) acryloyl)piperazine-1-carboxylate

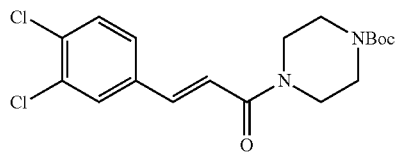 [SMILES: CC(C)(C)OC(=O)N1CCN(C(=O)/C=C/c2ccc(Cl)c(Cl)c2)CC1]

The title compound was prepared from the reaction of 3,4-dichloro cinnamic acid with Boc-Piperazine according to the procedure given in Example A1 obtained as a white solid. MS (EI) m/z 386 [(M+H)+].

Example B1

Preparation of (E)-3-(4-bromophenyl)-1-(4-2, 2, 2-trifluroacetyl)piprazin-1-yl) prop-2-en-1one (General Procedure B)

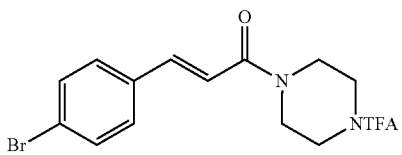

(E)-tert-butyl-4-(3-(4-bromophenyl) acryloyl) piperazine-1-carboxylate (200 mg, 0.505 mmol) obtained from Example A1 was dissolved in dichloromethane (3 mL) and cooled to 0° C. Trifluoroacetic acid (1.2 mL) was slowly added to the resulting mixture and the reaction was stirred for one hour at room temperature. When the reaction was determined to be complete by HPLC, the reaction mixture was concentrated under reduced pressure. The resulting mixture was washed with toluene twice to remove excess of TFA and the organic layer was concentrated under reduced pressure to yield (E)-3-(4-bromophenyl)-1-(4-2, 2, 2-trifluroacetyl) piprazin-1-yl) prop-2-en-1one (379 mg). MS (EI) m/z 297 [(M+H)+].

Example B2

Preparation of (E)-1-(4-(2,2,2-trifluoroacetyl)piperazin-1-yl)-3-(4-(trifluoromethyl)phenyl)prop-2-en-1-one

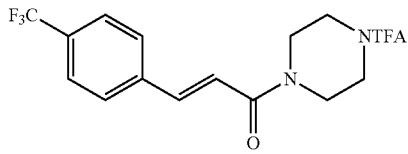

The title compound was prepared from the reaction of (E)-1-(piperazin-1-yl)-3-(4-(trifluoromethyl)phenyl)prop-2-en-1-one according to the procedure given in Example B1 obtained as a white solid. MS (EI) m/z 381 [(M+H)+].

Example B3

Preparation of (E)-3-(3, 4-dichlorophenyl)-1-(4-(2, 2, 2-trifluoroacetyl) piperazin-1-yl) prop-2-en-1-one

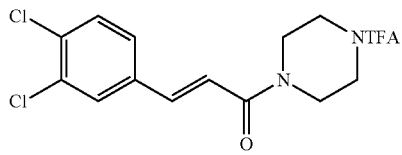

The title compound was prepared from the reaction of (E)-tert-butyl 4-(3-(3, 4-dichloro phenyl) acryloyl) piperazine-1-carboxylate according to the procedure given in Example B1 obtained as a white solid. MS (EI) m/z 381 [(M+H)+].

Example C1

Preparation of (E)-3-(4-bromophenyl)-1-(4-(4-chlorobenzoyl)piperazin-1-yl) prop-2-en-1-one

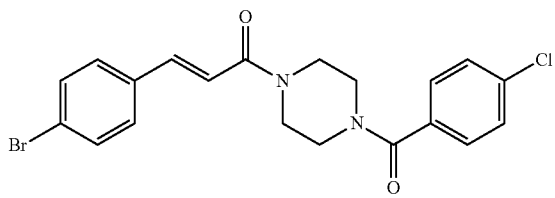 [SMILES: O=C(/C=C/c1ccc(Br)cc1)N1CCN(C(=O)c2ccc(Cl)cc2)CC1]

4-Chlorobenzoic acid (60.73 mg), EDC (80.97 mg), and HOBT (57.09 mg) were dissolved in DMF (3 mL) and the mixture was stirred at room temperature for 30 minutes. N-methyl morpholine (196.53 uL) and (E)-3-(4-bromophenyl)-1-(4-2, 2, 2-trifluroacetyl) piprazin-1-yl) prop-2-en-1-one (148.2 mg) obtained from Example B1 were added to the reaction mixture and the reaction was stirred overnight at room temperature. When the reaction was determined to be complete by HPLC, the reaction mixture was concentrated under reduced pressure and the resulting solid was dissolved in DCM. The solution was washed with saturated aqueous NaHCO₃, washed with saturated aqueous NaCl and dried over Na₂SO₄ and the solvent was evaporated to give crude product which was purified using C-18 HPLC with acetonitrile and water (20:100 gradient) to yield the desired product as white solid. MS (EI) m/z 435 [(M+H)+].

Example C2

Preparation of (2E)-3-(4-bromophenyl)-1-{4-[(4-methoxyphenyl)carbonyl]piperazinyl} prop-2-en-1-one

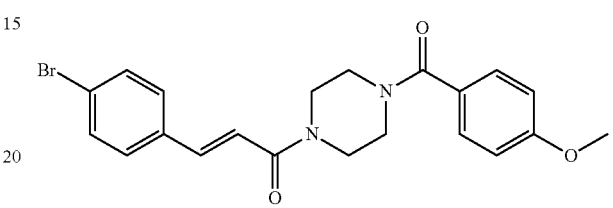

The title compound was prepared from the reaction of (E)-3-(4-bromophenyl)-1-(4-2, 2, 2-trifluroacetyl) piprazin-1-yl) prop-2-en-1one with 4-methoxybenzoic acid according to the procedure given in Example C1 and was obtained as a white solid. MS (EI) m/z 430 [(M+H)+].

Example C3

Preparation of (E)-(4-(4-(3-(4-bromophenyl)acryloyl)piperazine-1-carbonyl)phenyl)phosphonic acid

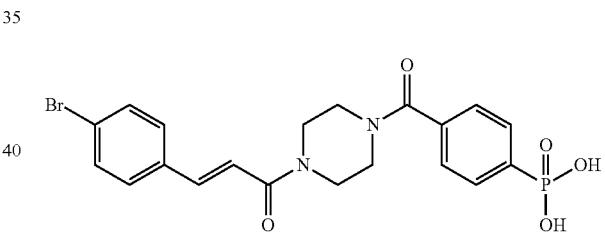

The title compound was prepared from the reaction of (E)-3-(4-bromophenyl)-1-(4-2, 2, 2-trifluroacetyl) piprazin-1-yl) prop-2-en-1one with 4-phosphonobenzoic acid according to the procedure given in Example C1 and was obtained as a white solid. MS (EI) m/z 480 [(M+H)+].

Example C4

Preparation of (2E)-3-(4-bromophenyl)-1-{4-[(4-methylphenyl)carbonyl]piperazinyl} prop-2-en-1-one

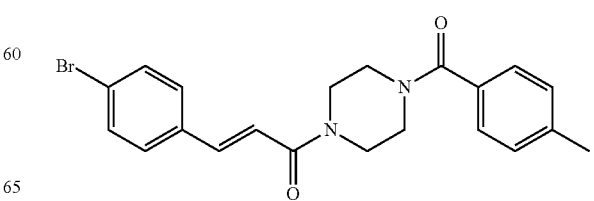

The title compound was prepared from the reaction of (E)-3-(4-bromophenyl)-1-(4-2, 2, 2-trifluroacetyl) piprazin-1-yl) prop-2-en-1one with 4-methyl benzoic acid according to the procedure given in Example C1 and was obtained as a white solid. MS (EI) m/z 414 [(M+H)+].

Example C5

Preparation of (2E)-3-(3, 4-dichlorophenyl)-1-[4-(diphenylmethyl) piperazinyl] prop-2-en-1-one

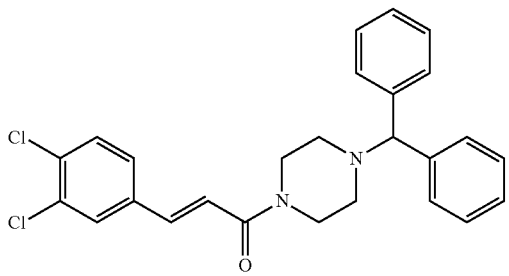 [SMILES: O=C(/C=C/c1ccc(Cl)c(Cl)c1)N1CCN(C(c2ccccc2)c2ccccc2)CC1]

The title compound was prepared from the reaction of 3,4-dichloro cinnamic acid with diphenyl methyl piperazine according to the procedure given in Example C1 and was obtained as a white solid. MS (EI) m/z 452 [(M+H)+].

Example C6

Preparation of (2E)-3-(3, 4-dichlorophenyl)-1-(4-{[4-(trifluoromethyl) phenyl] carbonyl} piperazinyl) prop-2-en-1-one

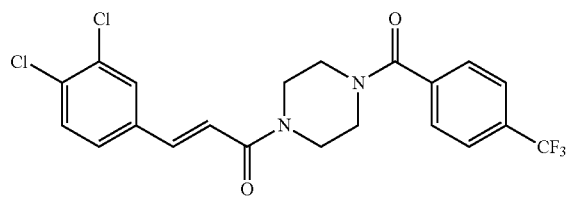 [SMILES: O=C(/C=C/c1ccc(Cl)c(Cl)c1)N1CCN(C(=O)c2ccc(C(F)(F)F)cc2)CC1]

The title compound was prepared from the reaction of (E)-3-(3, 4-dichlorophenyl)-1-(4-(2, 2, 2-trifluoroacetyl) piperazin-1-yl) prop-2-en-1one with 4-trifluoromethyl benzoic acid according to the procedure given in Example C1 and was obtained as a white solid. MS (EI) m/z 458 [(M+H)+].

Example D1

Preparation of (E)-3-(4-bromophenyl)-1-(4-(4-chlorobenzyl)piperazin-1-yl) prop-2-en-1-one (General Procedure D)

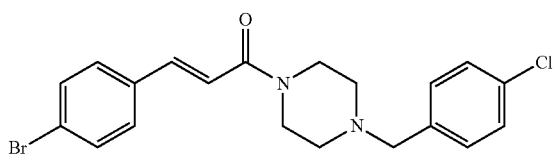 [SMILES: O=C(/C=C/c1ccc(Br)cc1)N1CCN(Cc2ccc(Cl)cc2)CC1]

(E)-3-(4-bromophenyl)-1-(4-2,2,2-trifluoroacetyl)piprazin-1-yl)prop-2-en-1-one (100 mg, 0.244 mmol) obtained from Example B1 was dissolved in acetone (5 mL), potassium carbonate (112 mg, 0.812 mmol) was added followed by 4-chlorobenzyl bromide (50 mg, 0.244 mmol). The resulting reaction mixture was stirred at 50° C. for about 2 hours. When the reaction was determined to be complete by HPLC, the reaction mixture was cooled to room temperature and concentrated under reduced pressure. The resulting precipitate was dissolved in EtOAc (20 ml). Water (15 mL) was added and the two layers were separated. The aqueous phase was extracted with EtOAc (3×20 mL), the collected organic phases were washed with brine (10 mL), dried over Na₂SO₄ and the solvent was evaporated to give crude product which was purified using C-18 HPLC with acetonitrile and water (20:100 gradient) to yield the desired product as white solid. MS (EI) m/z 420 [(M+H)+].

Example D2

Preparation of (2E)-3-(4-bromophenyl)-1-{4-[(3-fluorophenyl)methyl]piperazinyl} prop-2-en-1-one

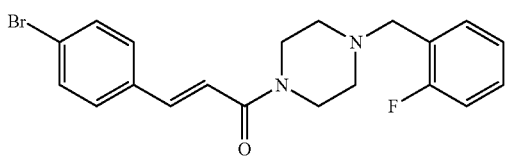 [SMILES: O=C(/C=C/c1ccc(Br)cc1)N1CCN(Cc2ccccc2F)CC1]

The title compound was prepared from the reaction (E)-3-(4-bromophenyl)-1-(4-2, 2, 2-trifluroacetyl) piprazin-1-yl) prop-2-en-1-one with 3-fluoro benzyl bromide according to the procedure given in Example D1 and obtained as a white solid. MS (EI) m/z 404 [(M+H)+].

Example D3

Preparation of (2E)-3-(3,4-dichlorophenyl)-1-(4-{[4-(trifluoromethyl) phenyl]methyl}piperazinyl)prop-2-en-1-one

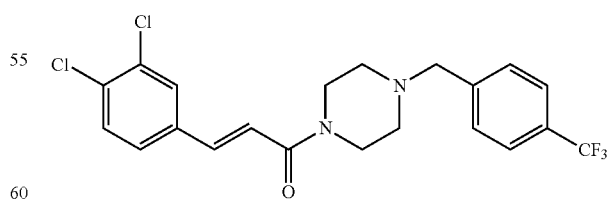

The title compound was prepared from the reaction of (E)-3-(3, 4-dichlorophenyl)-1-(4-(2, 2, 2-trifluroracetyl) piperazin-1-yl) prop-2-en-1-one with 4-trifluoro methyl benzyl bromide according to the procedure given in Example D1 was obtained as a white solid. MS (EI) m/z 444 [(M+H)+].

Example E1

Preparation of (2E)-3-(4-bromophenyl)-1-{4-[(2,4,6-trimethylphenyl) sulfonyl] piperazinyl} prop-2-en-1-one (General Procedure E)

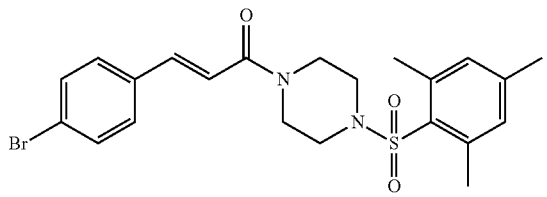 [SMILES: Cc1cc(C)c(S(=O)(=O)N2CCN(C(=O)/C=C/c3ccc(Br)cc3)CC2)c(C)c1]

(E)-3-(4-bromophenyl)-1-(4-2, 2, 2-trifluroacetyl) piprazin-1-yl) prop-2-en-1-one (158 mg, 0.402 mmol) obtained from the procedures to prepare Example B1, was dissolved in Dichloromethane (2 mL) at 0° C. N, N-Diisopropylethylamine (200 uL) was added followed by 2, 4, 6-trimethylbenzene sulfonyl chloride (1.8 mg, 0.603 mmol). The resulting reaction mixture was stirred at 0° C. to room temperature for 2 hours. When the reaction was determined to be complete by HPLC, the reaction mixture was concentrated under reduced pressure. The resulting precipitate was portioned between DCM (5 mL) and water (5 mL), the collected organic phases were washed with brine (10 mL), dried over Na$_2$SO$_4$ and the solvent was evaporated to give crude product which was purified using C-18 HPLC with acetonitrile and water (20:100 gradient) to yield the desired product as white solid. MS (EI) m/z 479 [(M+H)+].

Example E2

Preparation of (2E)-1-{4-[(4-bromophenyl)sulfonyl] piperazinyl}-3-(4-fluorophenyl) prop-2-en-1-one

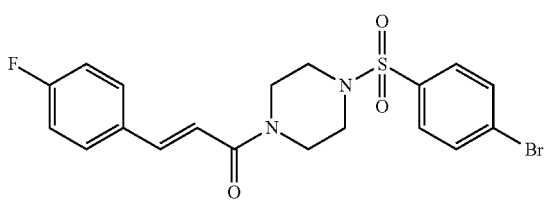 [SMILES: O=C(/C=C/c1ccc(F)cc1)N1CCN(S(=O)(=O)c2ccc(Br)cc2)CC1]

The title compound was prepared from the reaction (E)-3-(4-fluorophenyl)-1-(4-2, 2, 2-trifluroacetyl) piprazin-1-yl) prop-2-en-1-one with 4-bromo benzene sulfonyl chloride according to the procedure given in Example E1 and obtained as a white solid MS (EI) m/z 454 [(M+H)+].

Example E3

Preparation of (2E)-3-(4-fluorophenyl)-1-{4-[(2-phenylethyl)sulfonyl]piperazinyl}prop-2-en-1-one

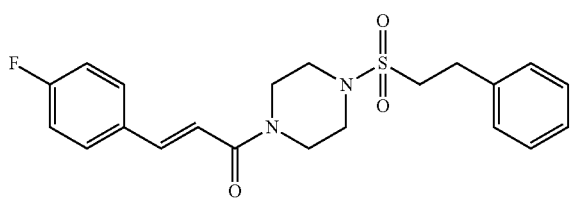 [SMILES: O=C(/C=C/c1ccc(F)cc1)N1CCN(S(=O)(=O)CCc2ccccc2)CC1]

The title compound was prepared from the reaction (E)-3-(4-fluorophenyl)-1-(4-2, 2, 2-trifluroacetyl) piprazin-1-yl) prop-2-en-1-one with phenethyl benzene sulfonyl chloride according to the procedure given in Example E1 and obtained as a white solid. MS (EI) m/z 403 [(M+H)+].

Example E4

Preparation of (2E)-3-(4-methoxyphenyl)-1-[4-(phenylsulfonyl)piperazinyl]prop-2-en-1-one

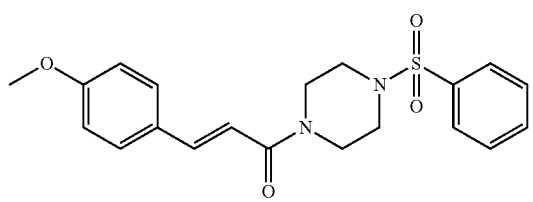 [SMILES: COc1ccc(/C=C/C(=O)N2CCN(S(=O)(=O)c3ccccc3)CC2)cc1]

The title compound was prepared from the reaction (E)-3-(4-methoxyphenyl)-1-(4-2, 2, 2-trifluroacetyl) piprazin-1-yl) prop-2-en-1-one with benzene sulfonyl chloride according to the procedure given in Example E1 was obtained as a white solid. MS (EI) m/z 387 [(M+H)+].

Example E5

Preparation of 4-({4-[(2E)-3-(4-bromo-2-fluorophenyl)prop-2-enoyl]piperazinyl}sulfonyl)-1-acetylbenzene

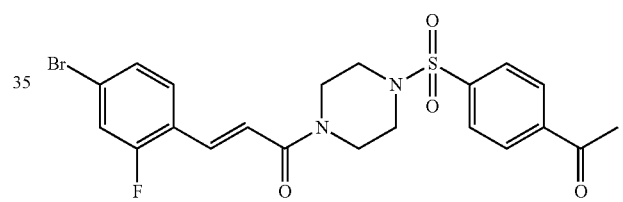

The title compound was prepared from the reaction (E)-3-(4-bromo-2-fluoro phenyl)-1-(4-2, 2, 2-trifluroacetyl) piprazin-1-yl) prop-2-en-1-one with 4-acetylbenzene-1-sulfonyl chloride according to the procedure given in Example E1 was obtained as a white solid. MS (EI) m/z 496 [(M+H)+].

Example F1

Preparation of (E)-3-(4-bromophenyl)-1-(4-(((2,2,2-trifluoroacetyl)-$\lambda^4$-azanyl) methyl)piperidin-1-yl) prop-2-en-1-one

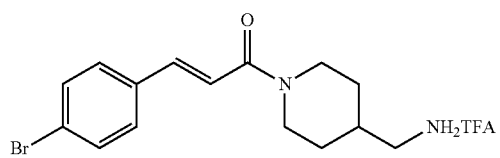

The title compound was prepared in two steps from the commercially available tert-butyl (piperidin-4-ylmethyl)carbamate by the reactions described in General Procedure A and B give (E)-3-(4-bromophenyl)-1-(4-(((2, 2, 2-trifluoroacetyl)-$\lambda^4$-azanyl) methyl) piperidin-1-yl) prop-2-en-1-one as a white solid. MS (EI) m/z 421 [(M+H)+].

Example F2

Preparation of (E)-3-(4-bromophenyl)-1-(4-(((4-(trifluoromethyl)benzyl) amino)methyl)benzyl) amino)methyl)piperidin-1-yl) prop-2-en-1-one (General Procedure F)

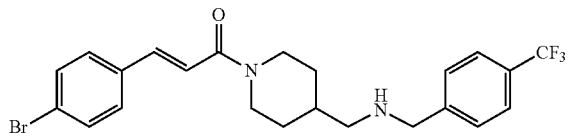 [SMILES: O=C(/C=C/c1ccc(Br)cc1)N1CCC(CNCc2ccc(C(F)(F)F)cc2)CC1]

(E)-3-(4-bromophenyl)-1-(4-(((2,2,2-trifluoroacetyl)-λ$^4$-azanyl) methyl piperidin-1-yl) prop-2-en-1-one obtained from example F1, 4-(trifluoromethyl) benzaldehyde (50.13 uL, sodium triacetoxy-borohydride (138.83 mg), acetic acid (51.35 uL) and dichloroethane (3 mL) were taken into a microwave safe bowl and subjected to heating for 30 minutes at 130° C. After the completion of the reaction the reaction mixture was cooled and extracted with Dichloromethane. The solution was washed with saturated aqueous NaHCO$_3$, and dried over Na$_2$SO$_4$. The solvent was evaporated to give crude product which was purified using C-18 HPLC with acetonitrile and water (20:100 gradients) to yield the desired product (E)-3-(4-bromophenyl)-1-(4-(((4-(trifluoromethyl)benzyl)amino)methyl)benzyl)amino)methyl)piperidin-1-yl)prop-2-en-1-one as white solid. MS (EI) m/z 483 (M+1).

Example F3

Preparation of (E)-N-((1-(3-(4-bromophenyl)acryloyl)piperidin-4-yl)methyl)-4-(trifluoromethyl)benzamide

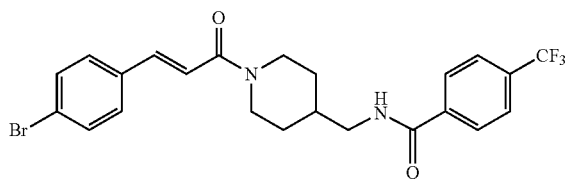 [SMILES: O=C(NCC1CCN(C(=O)/C=C/c2ccc(Br)cc2)CC1)c1ccc(C(F)(F)F)cc1]

The title compound was prepared from the reaction of (E)-3-(4-bromophenyl)-1-(4-(((2,2,2-trifluoroacetyl)-λ$^4$-azanyl)methyl)piperidin-1-yl)prop-2-en-1-one obtained in Example F1 with 4-trifluoromethylbenzoic acid according to Procedure 3. The crude product was purified using C-18 HPLC with acetonitrile and water (20:100 gradients) to yield the desired product (E)-N-((1-(3-(4-bromophenyl)acryloyl)piperidin-4-yl)methyl)-4-(trifluoromethyl)benzamide as a white solid. MS (EI) m/z 496 [(M+1)+].

Example G1

Preparation of 2,3-dibromo-3-(4-chlorophenyl)propanoic acid (General Procedure G)

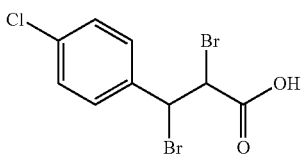 [SMILES: O=C(O)C(Br)C(Br)c1ccc(Cl)cc1]

4-Chlorocinnamic acid (3.6 g, 19.7 mmol) was dissolved in 60 mL of CCl$_4$ and after the addition of 1 drop of aqueous HBr, the mixture was stirred at room temperature, and Br$_2$ (1 mL 19.5 mmol) was added dropwise to the resulting mixture. The reaction mixture was stirred overnight at room temperature. When the reaction was determined to be complete by HPLC, the white precipitates were filtered and washed with hexane. The white solid precipitate of 2,3-dibromo-3-(4-chlorophenyl)propanoic acid was air dried and used directly into the next step without purification. MS (EI) m/z 397 [(M+1)+].

Example H1

Preparation of 3-(4-bromophenyl)propiolic acid (General Procedure H)

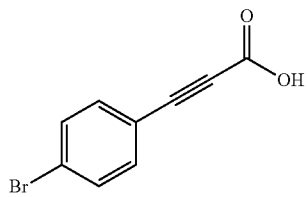 [SMILES: O=C(O)C#Cc1ccc(Br)cc1]

2,3-dibromo-3-(4-chlorophenyl)propanoic acid (2 g, 5.84 mmol) was dissolved in 16% KOH in EtOH (7.1 mL) and stirred with refluxing at 40° C. for about 3 hours. When the reaction was determined to be complete by HPLC, the reaction mixture was cooled to room temperature. The resulting precipitate was filtered off and saved. The reaction solution was acidified with concentrated HCl and concentrated in vacuum. The residue was combined with the previously extracted precipitate and dissolved in water (100 mL). The solution was acidified with 20% sulfuric acid and adjusted with cooling (ice bath) to pH=1. After stirring for 20 min at room temperature, the solution was filtered and washed with 2% sulfuric acid and dried. After crystallization from acetonitrile and re-crystallizing the residue from ethanol, 3-(4-bromophenyl)propiolic acid was isolated as a white solid. MS (EI) m/z 297 [(M+1)+].

Example H2

Preparation of 3-(benzo[d][1,3]dioxol-5-yl)propiolic acid

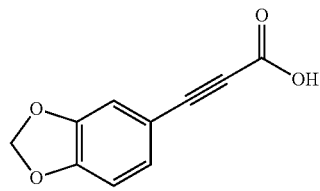 [SMILES: O=C(O)C#Cc1ccc2c(c1)OCO2]

Propiolic acid (0.24 ml, 3.9 mmol), Pd(PPh$_3$)$_2$Cl$_2$ (55 mg, 0.078 mmol) and DIPEA (1.7 ml, 9.8 mmol) were added in 20 ml of DMF. After the addition of CuI (30 mg, 0.16 mmol) and 5-iodobenzo[d][1,3]dioxole (0.5 ml, 3.9 mmol), the mixture was stirred for 2 hours under nitrogen atmosphere in an enclosed flask at room temperature. When the reaction was determined to be complete by HPLC, the resulting mixture was diluted with EtOAc and filtered through a bed of celite. The filtrate was washed with cold aqueous KOH solution and acidified with dilute sulfuric acid (10% solution) at 0° C. The solid obtained was extracted with dichloromethane and the extract was washed with water, brine solution and dried over anhydrous Na$_2$SO$_4$. The organic layer was concentrated in vacuo to get the resulting title compound as a dark brown powder, which was used as isolated in the next reaction. MS (EI) m/z 397[(M+1)+].

Example H3

Preparation of 3-(4-bromophenyl)-1-(4-(4-methoxybenzyl)piperazin-1-yl)prop-2-yn-1-one

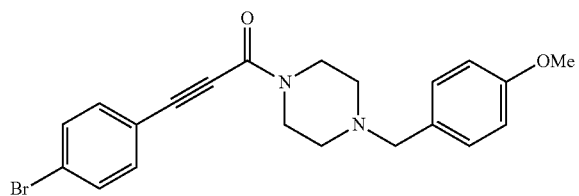 [SMILES: COc1ccc(CN2CCN(C(=O)C#Cc3ccc(Br)cc3)CC2)cc1]

The title compound was prepared from the reaction 3-(4-bromophenyl)-1-(4-(2, 2, 2-trifluoroacetyl)piperazin-1-yl)prop-2-yn-1-one with 4-methoxybenzylbromide according to the procedure given in Example D1, to yield the desired product 3-(4-bromophenyl)-1-(4-(4-methoxybenzyl) piperazin-1-yl)prop-2-yn-1-one obtained as a white solid. MS (EI) m/z 413 [(M+1)+].

Example H4

Preparation of 1-(4-(4-fluorobenzyl)piperazin-1-yl)-3-(p-tolyl)prop-2-yn-1-one

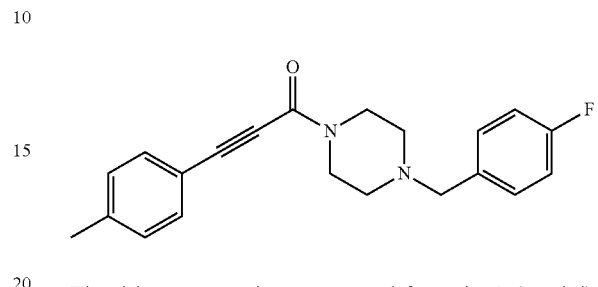

The title compound was prepared from the 3-(p-tolyl)-1-(4-(2,2,2-trifluoroacetyl)piperazin-1-yl)prop-2-yn-1-one with 4-fluorobenzylbromide according to the procedure given in Example D1, to yield the desired product 1-(4-(4-fluorobenzyl)piperazin-1-yl)-3-(p-tolyl)prop-2-yn-1-one obtained as a yellow solid. MS (EI) m/z 337 [(M+1)+].

The following compounds were prepared using Procedures A-H described above:

| Compound | Name | MS (EI) [(M + H)+] |
|---|---|---|
| C1 | (2E)-3-(4-bromophenyl)-1-{4-[(4-chlorophenyl)carbonyl]piperazinyl}prop-2-en-1-one | 434 |
| C2 | (2E)-3-(4-bromophenyl)-1-{4-[(4-methoxyphenyl)carbonyl]piperazinyl}prop-2-en-1-one | 430 |
| C3 | (E)-(4-(4-(3-(4-bromophenyl)acryloyl)piperazine-1-carbonyl)phenyl)phosphonic acid | 480 |
| C4 | (2E)-3-(4-bromophenyl)-1-(4-{[4-(trifluoromethyl)phenyl]carbonyl}piperazinyl)prop-2-en-1-one | 468 |
| C5 | (2E)-3-(3,4-dichlorophenyl)-1-[4-(diphenylmethyl)piperazinyl]prop-2-en-1-one | 452 |
| C6 | (2E)-3-(3,4-dichlorophenyl)-1-(4-{[4-(trifluoromethyl)phenyl]carbonyl}piperazinyl)prop-2-en-1-one | 458 |
| C7 | 3-(4-chlorophenyl)-1-{4-[(4-methoxyphenyl)carbonyl]piperazinyl}prop-2-yn-1-one | 384 |
| C8 | 1-{4-[(4-methoxyphenyl)carbonyl]piperazinyl}-3-(4-methylphenyl)prop-2-yn-1-one | 363 |
| C9 | 1-{4-[(4-methoxyphenyl)carbonyl]piperazinyl}-3-[4-(trifluoromethyl)phenyl]prop-2-yn-1-one | 417 |
| C10 | 3-(4-bromophenyl)-1-{4-[(4-methoxyphenyl)carbonyl]piperazinyl}prop-2-yn-1-one | 428 |
| C11 | 3-(3,4-dichlorophenyl)-1-{4-[(4-methoxyphenyl)carbonyl]piperazinyl}prop-2-en-1-one | 420 |
| C12 | 3-(3,4-dichlorophenyl)-1-{4-[(4-methoxyphenyl)carbonyl]piperazinyl}prop-2-yn-1-one | 418 |
| C13 | (2E)-3-(4-bromophenyl)-1-[4-(phenylamino)piperidyl]prop-2-en-1-one | 386 |
| C14 | (2E)-3-(4-bromophenyl)-1-[4-(phenylcarbonyl)piperazinyl]prop-2-en-1-one | 400 |
| C15 | (2E)-1-{4-[(3,5-difluorophenyl)amino]piperidyl}-3-(4-bromophenyl)prop-2-en-1-one | 422 |
| C16 | 3-(4-chlorophenyl)-1-{4-[(4-chlorophenyl)carbonyl]piperazinyl}prop-2-yn-1-one | 388 |
| C17 | (2E)-1-[4-(diphenylmethyl)piperazinyl]-3-(4-methoxyphenyl)prop-2-en-1-one | 413 |
| C18 | 3-(2,3-dichlorophenyl)-1-{4-[(4-fluorophenyl)carbonyl]piperazinyl}prop-2-yn-1-one | 406 |
| C19 | 1-{4-[(4-bromophenyl)carbonyl]piperazinyl}-3-(4-chlorophenyl)prop-2-yn-1-one | 432 |
| C20 | (2E)-3-(3,4-dichlorophenyl)-1-{4-[(4-fluorophenyl)carbonyl]piperazinyl}prop-2-en-1-one | 408 |

-continued

| Compound | Name | MS (EI) [(M + H)+] |
|---|---|---|
| C21 | (2E)-1-[4-(diphenylmethyl)piperazinyl]-3-(4-ethoxyphenyl)prop-2-en-1-one | 427 |
| C22 | (2E)-1-[4-(2-3,4-dihydronaphthylsulfonyl)piperazinyl]-3-(4-fluorophenyl)prop-2-en-1-one | 427 |
| C23 | (2E)-3-(3,4-dichlorophenyl)-1-{4-[(4-chlorophenyl)carbonyl]piperazinyl}prop-2-en-1-one | 424 |
| C24 | (2E)-1-[4-(diphenylmethyl)piperazinyl]-3-(4-bromo-2-fluorophenyl)prop-2-en-1-one | 480 |
| C25 | 3-(2,3-dichlorophenyl)-1-[4-(diphenylmethyl)piperazinyl]prop-2-yn-1-one | 450 |
| C26 | (2E)-3-(4-bromophenyl)-1-{4-[(4-chlorophenyl)amino]piperidyl}prop-2-en-1-one | 420 |
| C27 | (2E)-1-[4-(diphenylmethyl)piperazinyl]-3-(4-bromophenyl)prop-2-en-1-one | 462 |
| C28 | 3-(4-chlorophenyl)-1-{4-[(4-fluorophenyl)carbonyl]piperazinyl}prop-2-yn-1-one | 372 |
| C29 | (2E)-1-[4-(diphenylmethyl)piperazinyl]-3-[4-(trifluoromethyl)phenyl]prop-2-en-1-one | 451 |
| C30 | 3-(2,3-dichlorophenyl)-1-{4-[(4-chlorophenyl)carbonyl]piperazinyl}prop-2-yn-1-one | 495 |
| C31 | (2E)-1-{4-[(3,5-difluorophenyl)methyl]piperazinyl}-3-(4-bromophenyl)prop-2-en-1-one | 422 |
| C32 | (2E)-3-(4-bromophenyl)-1-{4-[(4-fluoro-3-methylphenyl)methyl]piperazinyl}prop-2-en-1-one | 418 |
| C33 | 1-{4-[(4-chlorophenyl)carbonyl]piperazinyl}-3-(4-methylphenyl)prop-2-yn-1-one | 367 |
| C34 | 3-(3-chlorophenyl)-1-{4-[(4-chlorophenyl)carbonyl]piperazinyl}prop-2-yn-1-one | 388 |
| C35 | 3-(3-chlorophenyl)-1-{4-[(4-fluorophenyl)carbonyl]piperazinyl}prop-2-yn-1-one | 371 |
| C36 | 4-(diphenylmethyl)piperazinyl 5-chlorobenzo[b]thiophen-2-yl ketone | 447 |
| C37 | (2E)-3-(4-bromophenyl)-1-{4-[(4-bromophenyl)sulfonyl]piperazinyl}prop-2-en-1-one | 515 |
| C38 | 1-{4-[(4-fluorophenyl)carbonyl]piperazinyl}-3-(4-methylphenyl)prop-2-yn-1-one | 351 |
| C39 | (2E)-1-{4-[(3,4-dichlorophenyl)methyl]piperazinyl}-3-(4-bromophenyl)prop-2-en-1-one | 455 |
| C40 | 2E)-1-[4-(diphenylmethyl)piperazinyl]-3-(4-chloro-2-fluorophenyl)prop-2-en-1-one | 435 |
| C41 | (2E)-3-(4-bromophenyl)-1-{4-[(4-methylphenyl)methyl]piperazinyl}prop-2-en-1-one | 400 |
| C42 | (2E)-1-[4-(diphenylmethyl)piperazinyl]-3-phenylprop-2-en-1-one | 383 |
| C43 | 4-(diphenylmethyl)piperazinyl 5-bromoindol-2-yl ketone | 475 |
| C44 | (2E)-3-(4-bromophenyl)-1-(4-{[4-(trifluoromethyl)phenyl]carbonyl}piperazinyl)prop-2-en-1-one | 468 |
| C45 | 4-(diphenylmethyl)piperazinyl 6-chlorobenzo[b]thiophen-2-yl ketone | 447 |
| C46 | (2E)-1-{4-[(2,4-difluorophenyl)carbonyl]piperazinyl}-3-(4-bromophenyl)prop-2-en-1-one | 434 |
| C47 | (2E)-3-(4-bromophenyl)-1-[4-({[(4-fluorophenyl)methyl]amino}methyl)piperidyl]prop-2-en-1-one | 432 |
| C48 | 4-[((1E)-2-phenylvinyl)sulfonyl]piperazinyl 5-methylindol-2-yl ketone | 410 |
| C49 | (2E)-3-(4-bromophenyl)-1-(4-butylpiperazinyl)prop-2-en-1-one | 352 |
| C50 | 1-[4-(diphenylmethyl)piperazinyl]-3-(4-bromophenyl)prop-2-yn-1-one | 460 |
| C51 | 3-(3,4-dichlorophenyl)-1-{4-[(4-chlorophenyl)carbonyl]piperazinyl}prop-2-yn-1-one | 422 |
| C52 | (2E)-3-(4-bromophenyl)-1-[4-(methylpropyl)piperazinyl]prop-2-en-1-one | 352 |
| C53 | 3-(4-methylphenyl)-1-(4-{[4-(trifluoromethyl)phenyl]carbonyl}piperazinyl)prop-2-yn-1-one | 401 |
| C54 | (2E)-1-[4-({[(3,5-difluorophenyl)methyl]amino}methyl)piperidyl]-3-(4-bromophenyl)prop-2-en-1-one | 450 |
| C55 | 3-(4-bromophenyl)-1-{4-[(4-chlorophenyl)carbonyl]piperazinyl}prop-2-yn-1-one | 432 |
| C56 | 4-(diphenylmethyl)piperazinyl 5-chloroindol-2-yl ketone | 430 |

-continued

| Compound | Name | MS (EI) [(M + H)+] |
|---|---|---|
| C57 | 5-methylindol-2-yl 4-[(2-phenylethyl)sulfonyl]piperazinyl ketone | 412 |
| C58 | 1-[4-(diphenylmethyl)piperazinyl]-3-(4-methylphenyl)prop-2-yn-1-one | 395 |
| C59 | 3-(3-chlorophenyl)-1-{4-[(4-methoxyphenyl)carbonyl]piperazinyl}prop-2-yn-1-one | 383 |
| C60 | 1-{4-[(4-chlorophenyl)carbonyl]piperazinyl}-3-[4-(trifluoromethyl)phenyl]prop-2-yn-1-one | 421 |
| C61 | 3-(4-bromophenyl)-1-{4-[(4-bromophenyl)carbonyl]piperazinyl}prop-2-yn-1-one | 477 |
| C62 | methyl 4-({4-[(5-chloroindol-2-yl)carbonyl]piperazinyl}carbonyl)benzoate | 426 |
| C63 | (2E)-1-[4-(diphenylmethyl)piperazinyl]-3-(4-nitrophenyl)prop-2-en-1-one | 428 |
| C64 | 4-[(4-chlorophenyl)carbonyl]piperazinyl 5-(trifluoromethyl)indol-2-yl ketone | 435 |
| C65 | 1-{4-[(4-bromophenyl)carbonyl]piperazinyl}-3-phenylprop-2-yn-1-one | 398 |
| C66 | 1-[4-(diphenylmethyl)piperazinyl]-3-[4-(trifluoromethyl)phenyl]prop-2-yn-1-one | 449 |
| C67 | (2E)-3-(4-bromophenyl)-1-{4-[(4-chlorophenyl)methyl]piperazinyl}prop-2-en-1-one | 420 |
| C68 | (2E)-1-[4-(diphenylmethyl)piperazinyl]-3-(4-fluorophenyl)prop-2-en-1-one | 401 |
| C69 | 1-{4-[(4-chlorophenyl)carbonyl]piperazinyl}-3-(4-fluorophenyl)prop-2-yn-1-one | 371 |
| C70 | 3-(4-bromophenyl)-1-{4-[(4-fluorophenyl)carbonyl]piperazinyl}prop-2-yn-1-one | 416 |
| C71 | 4-(diphenylmethyl)piperazinyl indol-2-yl ketone | 396 |
| C72 | (2E)-1-{4-[(3,5-dimethoxyphenyl)methyl]piperazinyl}-3-(4-bromophenyl)prop-2-en-1-one | 446 |
| C73 | 3-(4-chlorophenyl)-1-(4-{[4-(trifluoromethyl)phenyl]carbonyl}piperazinyl)prop-2-yn-1-one | 421 |
| C74 | (2E)-3-(4-bromophenyl)-1-[4-({[(4-chlorophenyl)methyl]amino}methyl)piperidyl]prop-2-en-1-one | 448 |
| C75 | 3-(4-fluorophenyl)-1-{4-[(4-methoxyphenyl)carbonyl]piperazinyl}prop-2-yn-1-one | 367 |
| C76 | 1-{4-[(4-fluorophenyl)carbonyl]piperazinyl}-3-[4-(trifluoromethyl)phenyl]prop-2-yn-1-one | 405 |
| C77 | 3-(3,4-dichlorophenyl)-1-[4-(diphenylmethyl)piperazinyl]prop-2-yn-1-one | 450 |
| C78 | (2E)-3-(4-bromophenyl)-1-[4-(2-methylbutanoyl)piperazinyl]prop-2-en-1-one | 380 |
| C79 | 4-(diphenylmethyl)piperazinyl 5-(trifluoromethyl)indol-2-yl ketone | 464 |
| C80 | (2E)-3-(4-bromophenyl)-1-(4-heptanoylpiperazinyl)prop-2-en-1-one | 408 |
| C81 | methyl 4-({4-[(5-bromoindol-2-yl)carbonyl]piperazinyl}carbonyl)benzoate | 471 |
| C82 | (2E)-3-(4-bromophenyl)-1-[4-(cyclopentylcarbonyl)piperazinyl]prop-2-en-1-one | 392 |
| C83 | potassium (E)-5-(4-(4-(3-(4-bromophenyl)acryloyl)piperazine-1-carbonyl)phenyl)tetrazol-1-ide | 505 |
| C84 | 3-[4-(trifluoromethyl)phenyl]-1-(4-{[4-(trifluoromethyl)phenyl]carbonyl}piperazinyl)prop-2-yn-1-one | 455 |
| C85 | 5-bromoindol-2-yl 4-[(4-chlorophenyl)carbonyl]piperazinyl ketone | 447 |
| C86 | 4-(diphenylmethyl)piperazinyl 7-fluoro(3-quinolyl) ketone | 426 |
| C87 | benzo[d]furan-2-yl 4-(diphenylmethyl)piperazinyl ketone | 397 |
| C88 | 5-chloroindol-2-yl 4-[(2-phenylethyl)sulfonyl]piperazinyl ketone | 432 |
| C89 | 5-chloroindol-2-yl 4-[(4-chlorophenyl)carbonyl]piperazinyl ketone | 403 |
| C90 | 3-(2,3-dichlorophenyl)-1-(4-{[4-fluoro-2-(trifluoromethyl)phenyl]carbonyl}piperazinyl)prop-2-yn-1-one | 474 |
| C91 | (2E)-3-(4-bromophenyl)-1-(4-{[4-chloro-2-(trifluoromethyl)phenyl]methyl}piperazinyl)prop-2-en-1-one | 488 |

-continued

| Compound | Name | MS (EI) [(M + H)+] |
|---|---|---|
| C92 | 1-[4-(diphenylmethyl)piperazinyl]-3-(3-chlorophenyl)prop-2-yn-1-one | 415 |
| C93 | 3-(3,4-dichlorophenyl)-1-{4-[(4-fluorophenyl)carbonyl]piperazinyl}prop-2-yn-1-one | 406 |
| C94 | 4-(diphenylmethyl)piperazinyl 5-fluorobenzo[b]thiophen-2-yl ketone | 431 |
| C95 | (2E)-1-{4-[((1E)-2-phenylvinyl)sulfonyl]piperazinyl}-3-(4-fluorophenyl)prop-2-en-1-one | 401 |
| C96 | (2E)-1-{4-[(4-chlorophenyl)sulfonyl]piperazinyl}-3-(4-fluorophenyl)prop-2-en-1-one | 409 |
| C97 | 4-(diphenylmethyl)piperazinyl 5-methoxyindol-2-yl ketone | 426 |
| C98 | (2E)-3-(4-bromophenyl)-1-(4-pentanoylpiperazinyl)prop-2-en-1-one | 380 |
| C99 | (2E)-1-[4-((2E)-3-phenylprop-2-enoyl)piperazinyl]-3-phenylprop-2-en-1-one | 347 |
| C100 | (2E)-1-{4-[(2-bromophenyl)sulfonyl]piperazinyl}-3-(4-fluorophenyl)prop-2-en-1-one | 454 |
| C101 | 4-(diphenylmethyl)piperazinyl 2-naphthyl ketone | 406 |
| C102 | 4-[(4-{[5-(trifluoromethyl)indol-2-yl]carbonyl}piperazinyl)carbonyl]benzenecarbonitrile | 427 |
| C103 | (2E)-3-(4-bromophenyl)-1-(4-{[4-(methylethyl)phenyl]methyl}piperazinyl)prop-2-en-1-one | 428 |
| C104 | 4-(diphenylmethyl)piperazinyl 6-chloroindol-2-yl ketone | 430 |
| C105 | 1,5-dimethylindol-2-yl 4-(diphenylmethyl)piperazinyl ketone | 424 |
| C106 | (2E)-3-(3,4-difluorophenyl)-1-[4-(diphenylmethyl)piperazinyl]prop-2-en-1-one | 419 |
| C107 | 1-[4-(diphenylmethyl)piperazinyl]-3-(4-bromo-2-fluorophenyl)prop-2-yn-1-one | 478 |
| C108 | 4-(diphenylmethyl)piperazinyl 6-bromoindol-2-yl ketone | 475 |
| C109 | (2E)-1-{4-[(3,5-dimethylphenyl)methyl]piperazinyl}-3-(4-bromophenyl)prop-2-en-1-one | 414 |
| C110 | 4-(diphenylmethyl)piperazinyl 6-quinolyl ketone | 408 |
| C111 | 4-(2H-benzo[d]1,3-dioxolan-5-ylmethyl)piperazinyl 5-methylindol-2-yl ketone | 378 |
| C112 | 3-(2H-benzo[3,4-d]1,3-dioxolen-5-yl)-1-{1-[(4-fluorophenyl)carbonyl](4-piperidyl)}prop-2-yn-1-one | 380 |
| C113 | (2E)-1-[4-(diphenylmethyl)piperazinyl]-3-(2-fluorophenyl)prop-2-en-1-one | 401 |
| C114 | 3-(2H-benzo[3,4-d]1,3-dioxolen-5-yl)-1-{4-[(4-chlorophenyl)carbonyl]piperazinyl}prop-2-yn-1-one | 397 |
| C115 | 5-chloroindol-2-yl 4-[(4-iodophenyl)carbonyl]piperazinyl ketone | 494 |
| C116 | 1-{4-[(4-fluorophenyl)carbonyl]piperazinyl}-3-phenylprop-2-yn-1-one | 337 |
| C117 | 3-(3-chlorophenyl)-1-(4-{[4-(trifluoromethyl)phenyl]carbonyl}piperazinyl)prop-2-yn-1-one | 421 |
| C118 | (2E)-3-(4-bromophenyl)-1-[4-(3-methylbutanoyl)piperazinyl]prop-2-en-1-one | 380 |
| C119 | 5-chloroindol-2-yl 4-[(4-fluorophenyl)carbonyl]piperazinyl ketone | 386 |
| C120 | 3-(2H-benzo[3,4-d]1,3-dioxolen-5-yl)-1-{4-[(4-bromophenyl)carbonyl]piperazinyl}prop-2-yn-1-one | 442 |
| C121 | (2E)-3-(4-bromophenyl)-1-{4-[({[3-fluoro-4-(trifluoromethyl)phenyl]methyl}amino)methyl]piperidyl}prop-2-en-1-one | 500 |
| C122 | 1-{4-[(4-fluorophenyl)methyl]piperazinyl}-3-(4-methylphenyl)prop-2-yn-1-one | 337 |
| C123 | benzo[b]thiophen-2-yl 4-(diphenylmethyl)piperazinyl ketone | 413 |
| C124 | (2E)-3-(4-fluorophenyl)-1-{4-[(4-methylphenyl)sulfonyl]piperazinyl}prop-2-en-1-one | 389 |
| C125 | 4-(diphenylmethyl)piperazinyl 3-quinolyl ketone | 408 |
| C126 | 4-(diphenylmethyl)piperazinyl 5-fluoroindol-2-yl ketone | 414 |
| C127 | 4-[(3-chlorophenyl)carbonyl]piperazinyl 5-(trifluoromethyl)indol-2-yl ketone | 436 |
| C128 | 3-(4-fluorophenyl)-1-{4-[(4-fluorophenyl)carbonyl]piperazinyl}prop-2-yn-1-one | 355 |
| C129 | 3-(3-chlorophenyl)-1-{4-[(4-fluorophenyl)methyl]piperazinyl}prop-2-yn-1-one | 357 |

-continued

| Compound | Name | MS (EI) [(M + H)+] |
|---|---|---|
| C130 | (2E)-3-(4-bromophenyl)-1-{4-[(4-chloro-2-fluorophenyl)methyl]piperazinyl}prop-2-en-1-one | 438 |
| C131 | (2E)-3-(4-bromophenyl)-1-(4-{[4-fluoro-2-(trifluoromethyl)phenyl]methyl}piperazinyl)prop-2-en-1-one | 472 |
| C132 | 3-(2,3-dichlorophenyl)-1-(4-{[4-(trifluoromethyl)phenyl]carbonyl}piperazinyl)prop-2-yn-1-one | 456 |
| C133 | 5-(trifluoromethyl)indol-2-yl 4-{[4-(trifluoromethyl)phenyl]carbonyl}piperazinyl ketone | 470 |
| C134 | piperazinyl 5-nitroindol-2-yl ketone | 441 |
| C135 | 5-bromoindol-2-yl 4-[(4-fluorophenyl)carbonyl]piperazinyl ketone | 431 |
| C136 | N-({1-[(2E)-3-(4-bromophenyl)prop-2-enoyl](4-piperidyl)}methyl)(4-fluorophenyl)carboxamide | 446 |
| C137 | 1-{4-[(4-chlorophenyl)methyl]piperazinyl}-3-[4-(trifluoromethyl)phenyl]prop-2-yn-1-one | 407 |
| C138 | (2E)-1-{4-[(3-chlorophenyl)sulfonyl]piperazinyl}-3-(4-fluorophenyl)prop-2-en-1-one | 409 |
| C139 | 1-[4-(diphenylmethyl)piperazinyl]-3-phenylprop-2-yn-1-one | 381 |
| C140 | 5-bromoindol-2-yl 4-{[4-(trifluoromethyl)phenyl]carbonyl}piperazinyl ketone | 481 |
| C141 | 3-(2,3-dichlorophenyl)-1-(4-{[4-fluoro-2-(trifluoromethyl)phenyl]methyl}piperazinyl)prop-2-yn-1-one | 460 |
| C142 | 4-(diphenylmethyl)piperazinyl 5-(trifluoromethyl)benzo[b]thiophen-2-yl ketone | 481 |
| C143 | 4-[(4-bromophenyl)sulfonyl]piperazinyl 5-methylindol-2-yl ketone | 463 |
| C144 | (2E)-1-(4-{[4-(tert-butyl)phenyl]methyl}piperazinyl)-3-(4-bromophenyl)prop-2-en-1-one | 442 |
| C145 | (2E)-3-(4-bromophenyl)-1-(4-propanoylpiperazinyl)prop-2-en-1-one | 352 |
| C146 | (2E)-1-{4-[(4-bromophenyl)sulfonyl]piperazinyl}-3-(4-methoxyphenyl)prop-2-en-1-one | 466 |
| C147 | (2E)-1[4-(diphenylmethyl)piperazinyl]-3-(3,4,5-trifluorophenyl)prop-2-en-1-one | 437 |
| C148 | 5-methylindol-2-yl 4-(phenylethyl)piperazinyl ketone | 348 |
| C149 | 3-(4-bromophenyl)-1-{4-[(4-(5H-1,2,3,4-tetraazol-5-yl)phenyl)carbonyl]piperazinyl}prop-2-yn-1-one | 466 |
| C150 | (2E)-1-(4-{[4-(tert-butyl)phenyl]sulfonyl}piperazinyl)-3-(4-bromophenyl)prop-2-en-1-one | 492 |
| C151 | 6-chloroindol-2-yl 4-[(4-methoxyphenyl)carbonyl]piperazinyl ketone | 398 |
| C152 | (2E)-3-(4-bromophenyl)-1-{4-[(4-(1H-1,2,3,4-tetraazol-5-yl)phenyl)carbonyl]piperazinyl}prop-2-en-1-one | 468 |
| C153 | (E)-(4-(4-(3-(4-bromophenyl)acryloyl)piperazine-1-carbonyl)phenyl)boronic acid | 444 |
| C154 | (2E)-3-(4-bromophenyl)-1-{4-[({[4-(trifluoromethyl)phenyl]methyl}amino)methyl]piperidyl}prop-2-en-1-one | 482 |
| C155 | 1-[4-(diphenylmethyl)piperazinyl]-3-bromo-3-(4-bromophenyl)prop-2-en-1-one | 541 |
| C156 | 4-(diphenylmethyl)piperazinyl 5-fluorobenzo[b]thiophen-2-yl ketone | 431 |
| C157 | 3-(3-chlorophenyl)-1-(4-{[4-fluoro-2-(trifluoromethyl)phenyl]carbonyl}piperazinyl)prop-2-yn-1-one | 439 |
| C158 | [4-(diphenylmethyl)piperazinyl](5-methylindol-2-yl)methane-1-thione | 426 |
| C159 | 1-[4-(diphenylmethyl)piperazinyl]-3-(4-fluorophenyl)prop-2-yn-1-one | 399 |
| C160 | 4-(4-(3-(4-bromophenyl)propioloyl)piperazine-1-carbonyl)phenylboronic acid | 442 |
| C161 | (2E)-1-{4-[(4-nitrophenyl)methyl]piperazinyl}-3-phenylprop-2-en-1-one | 352 |
| C162 | N-[1-(diphenylmethyl)(4-piperidyl)](5-methylindol-2-yl)carboxamide | 424 |
| C163 | 5-chloroindol-2-yl 4-(pyrrol-3-ylcarbonyl)piperazinyl ketone | 357 |
| C164 | 4-bromophenyl 4-{[4-fluoro-2-(trifluoromethyl)phenyl]methyl}piperazinyl ketone | 446 |
| C165 | 4-bromophenyl 4-[(4-fluorophenyl)methyl]piperazinyl ketone | 378 |

-continued

| Compound | Name | MS (EI) [(M + H)+] |
|---|---|---|
| C166 | 3-(2,4-difluorophenyl)-1-(4-{[4-(trifluoromethyl)phenyl]carbonyl}piperazinyl)prop-2-yn-1-one | 423 |
| C167 | 3-(2H-benzo[3,4-d]1,3-dioxolan-5-yl)-1-(4-{[4-(trifluoromethyl)phenyl]methyl}piperazinyl)prop-2-en-1-one | 419 |
| C168 | benzothiazol-2-yl 4-(diphenylmethyl)piperazinyl ketone | 414 |
| C169 | 3-[2-(trifluoromethyl)phenyl]-1-(4-{[4-(trifluoromethyl)phenyl]carbonyl}piperazinyl)prop-2-yn-1-one | 455 |
| C170 | 4-[(4-chlorophenyl)methyl]piperazinyl 2-(trifluoromethyl)benzimidazol-5-yl ketone | 423 |
| C171 | 3-(3,4-dichlorophenyl)-1-(4-{[4-(trifluoromethyl)phenyl]methyl}piperazinyl)prop-2-yn-1-one | 442 |
| C172 | 5-chloroindol-2-yl 4-{[4-(4-chlorophenyl)phenyl]sulfonyl}piperazinyl ketone | 515 |
| C173 | 4-(diphenylmethyl)piperazinyl 6-methylthiopheno[3,2-d]pyrrol-5-yl ketone | 416 |
| C174 | (2E)-3-(5-bromo-2-fluorophenyl)-1-{4-[(4-bromophenyl)sulfonyl]piperazinyl}prop-2-en-1-one | 533 |
| C175 | 4-[(4-chlorophenyl)methyl]piperazinyl 3-quinolyl ketone | 366 |
| C176 | 4-bromophenyl 4-{[4-(methylethyl)phenyl]methyl}piperazinyl ketone | 402 |
| C177 | 4-({4-[(5-chloroindol-2-yl)carbonyl]piperazinyl}methyl)benzoic acid | 398 |
| C178 | 4-(diphenylmethyl)piperazinyl 7-nitroindol-2-yl ketone | 441 |
| C179 | 3-(4-fluorophenyl)-1-(4-{[4-fluoro-2-(trifluoromethyl)phenyl]methyl}piperazinyl)prop-2-yn-1-one | 409 |
| C180 | 6-bromoindol-2-yl 4-[(4-bromophenyl)methyl]piperazinyl ketone | 478 |
| C181 | [4-({4-[(5-chloroindol-2-yl)carbonyl]piperazinyl}methyl)phenyl]-N-(4-fluorophenyl)carboxamide | 491 |
| C182 | 5-chloroindol-2-yl 4-(2-pyridyl)piperazinyl ketone | 341 |
| C183 | 5-chloroindol-2-yl 4-{[2-(trifluoromethyl)benzimidazol-5-yl]carbonyl}piperazinyl ketone | 476 |
| C184 | N-{1-[(5-chloroindol-2-yl)carbonyl](4-piperidyl)}(4-chlorophenyl)carboxamide | 417 |
| C185 | 4-(diphenylmethyl)piperazinyl 3-methylbenzo[b]thiophen-2-yl ketone | 427 |
| C186 | 3-(2H-benzo[3,4-d]1,3-dioxolan-5-yl)-1-(4-{[4-fluoro-2-(trifluoromethyl)phenyl]methyl}piperazinyl)prop-2-en-1-one | 437 |
| C187 | [3-({4-[(5-chloroindol-2-yl)carbonyl]piperazinyl}methyl)phenyl]-N-(4-fluorophenyl)carboxamide | 491 |
| C188 | 3-({4-[(5-chloroindol-2-yl)carbonyl]piperazinyl}methyl)benzoic acid | 398 |
| C189 | 6-fluoroindol-2-yl 4-{[4-fluoro-2-(trifluoromethyl)phenyl]carbonyl}piperazinyl ketone | 438 |
| C190 | (2E)-1-(4-{[4-(tert-butyl)phenyl]sulfonyl}piperazinyl)-3-(2-fluorophenyl)prop-2-en-1-one | 431 |
| C191 | (2E)-3-phenyl-1-[4-(2-pyridylmethyl)piperazinyl]prop-2-en-1-one | 308 |
| C192 | (2E)-1-[4-(diphenylmethyl)(1,4-diazaperhydroepinyl)]-3-(4-fluorophenyl)prop-2-en-1-one | 415 |
| C193 | 4-(diphenylmethyl)piperazinyl pyrrolo[4,5-b]pyridin-2-yl ketone | 397 |
| C194 | 5-chloroindol-2-yl 4-[(4-phosphonophenyl)carbonyl]piperazinyl ketone | 448 |
| C195 | 3-(3,5-difluorophenyl)-1-(4-{[4-(trifluoromethyl)phenyl]methyl}piperazinyl)prop-2-yn-1-one | 409 |
| C196 | (2E)-3-(2-methylphenyl)-1-[4-(phenylsulfonyl)piperazinyl]prop-2-en-1-one | 371 |
| C197 | 3-(3,5-difluorophenyl)-1-{4-[(4-fluorophenyl)methyl]piperazinyl}prop-2-yn-1-one | 359 |
| C198 | (2E)-1-{4-[((1E)-2-phenylvinyl)sulfonyl](1,4-diazaperhydroepinyl)}-3-(4-fluorophenyl)prop-2-en-1-one | 415 |
| C199 | 5-chloroindol-2-yl 4-morpholin-4-ylpiperidyl ketone | 348 |

-continued

| Compound | Name | MS (EI) [(M + H)+] |
|---|---|---|
| C200 | 4-{[3-fluoro-4-(trifluoromethyl)phenyl]carbonyl}piperazinyl 5-(trifluoromethyl)indol-2-yl ketone | 488 |
| C201 | (2E)-1-{4-[(3-methylphenyl)methyl]piperazinyl}-3-phenylprop-2-en-1-one | 321 |
| C202 | (2E)-1-(4-{[4-(tert-butyl)phenyl]sulfonyl}piperazinyl)-3-(4-fluorophenyl)prop-2-en-1-one | 431 |
| C203 | (2E)-1-{4-[(4-bromophenyl)methyl]piperazinyl}-3-phenylprop-2-en-1-one | 386 |
| C204 | 5-chloroindol-2-yl 4-[(4-(1H-1,2,3,4-tetraazol-5-yl)phenyl)carbonyl]piperazinyl ketone | 436 |
| C205 | (2E)-3-(4-fluorophenyl)-1-[4-(phenylsulfonyl)piperazinyl]prop-2-en-1-one | 375 |
| C206 | (2E)-3-(4-fluorophenyl)-1-{4-[(4-nitrophenyl)sulfonyl]piperazinyl}prop-2-en-1-one | 420 |
| C207 | 4-(diphenylmethyl)piperazinyl 5-bromobenzo[b]thiophen-2-yl ketone | 492 |
| C208 | 5-bromoindol-2-yl 4-{[4-fluoro-2-(trifluoromethyl)phenyl]carbonyl}piperazinyl ketone | 499 |
| C209 | (2E)-1-{4-[(3-bromophenyl)sulfonyl]piperazinyl}-3-(4-fluorophenyl)prop-2-en-1-one | 454 |
| C210 | (2E)-3-(3,4-dichlorophenyl)-1-{4-[(4-fluorophenyl)methyl]piperazinyl}prop-2-en-1-one | 394 |
| C211 | 4-[(4-fluorophenyl)methyl]piperazinyl 5-(trifluoromethyl)indol-2-yl ketone | 406 |
| C212 | (2E)-3-(4-fluorophenyl)-1-{4-[(3-fluorophenyl)sulfonyl]piperazinyl}prop-2-en-1-one | 393 |
| C213 | (2E)-1-{4-[(4-bromophenyl)sulfonyl]piperazinyl}-3-(4-ethoxyphenyl)prop-2-en-1-one | 480 |
| C214 | (2E)-3-(3,4-dichlorophenyl)-1-{4-[(4-chlorophenyl)methyl]piperazinyl}prop-2-en-1-one | 410 |
| C215 | 4-(diphenylmethyl)piperazinyl 6-fluoroindol-2-yl ketone | 414 |
| C216 | 3-(2H-benzo[3,4-d]1,3-dioxolen-5-yl)-1-{4-[(4-fluorophenyl)carbonyl]piperazinyl}prop-2-en-1-one | 383 |
| C217 | 4-(diphenylmethyl)piperazinyl 5-phenylindol-2-yl ketone | 472 |
| C218 | (2E)-1-{4-[(5-chloroindol-2-yl)carbonyl]piperazinyl}-3-[4-(trifluoromethyl)phenyl]prop-2-en-1-one | 462 |
| C219 | 4-[(4-fluorophenyl)methyl]piperazinyl 5-methylindol-2-yl ketone | 352 |
| C220 | 4-(diphenylmethyl)piperazinyl 5-(4-methoxyphenyl)indol-2-yl ketone | 502 |
| C221 | (2E)-3-(4-fluorophenyl)-1-[4-(2-naphthylsulfonyl)piperazinyl]prop-2-en-1-one | 425 |
| C222 | (2E)-3-(4-bromophenyl)-1-(4-ethylpiperazinyl)prop-2-en-1-one | 324 |
| C223 | 6-amino(2-naphthyl) 4-(diphenylmethyl)piperazinyl ketone | 422 |
| C224 | 1-(4-{[4-fluoro-2-(trifluoromethyl)phenyl]carbonyl}piperazinyl)-3-(4-methylphenyl)prop-2-yn-1-one | 419 |
| C225 | (2E)-1-{4-[(2,5-dichlorophenyl)sulfonyl]piperazinyl}-3-(4-fluorophenyl)prop-2-en-1-one | 444 |
| C226 | 5-chloroindol-2-yl 4-[(4-fluorophenyl)amino]piperidyl ketone | 372 |
| C227 | 4-(diphenylmethyl)piperazinyl 6-fluoro(3-quinolyl) ketone | 425 |
| C228 | 4-(diphenylmethyl)piperazinyl 2-methylthiopheno[2,3-d]pyrrol-5-yl ketone | 416 |
| C229 | 5-chloroindol-2-yl 4-(phenylcarbonyl)piperidyl ketone | 367 |
| C230 | (2E)-3-(3,4-dichlorophenyl)-1-[4-(phenylsulfonyl)piperazinyl]prop-2-en-1-one | 426 |
| C231 | 1-{4-[(4-fluorophenyl)methyl]piperazinyl}-3-[4-(trifluoromethyl)phenyl]prop-2-yn-1-one | 391 |
| C232 | 4-{[4-(diethylamino)phenyl]carbonyl}piperazinyl 5-chloroindol-2-yl ketone | 439 |
| C233 | (2E)-3-[4-(dimethylamino)phenyl]-1-[4-(diphenylmethyl)piperazinyl]prop-2-en-1-one | 426 |
| C234 | 3-(2H-benzo[3,4-d]1,3-dioxolan-5-yl)-1-{4-[(4-bromophenyl)carbonyl]piperazinyl}prop-2-en-1-one | 444 |
| C235 | (2E)-3-(4-fluorophenyl)-1-{4-[(4-fluorophenyl)sulfonyl]piperazinyl}prop-2-en-1-one | 393 |
| C236 | 1-{4-[(4-methoxyphenyl)methyl]piperazinyl}-3-(4-methylphenyl)prop-2-yn-1-one | 349 |
| C237 | (2E)-3-(4-fluorophenyl)-1-{4-[(2-fluorophenyl)sulfonyl]piperazinyl}prop-2-en-1-one | 393 |

-continued

| Compound | Name | MS (EI) [(M + H)+] |
|---|---|---|
| C238 | 3-(2H-benzo[3,4-d]1,3-dioxolen-5-yl)-1-{4-[(4-chlorophenyl)carbonyl]piperazinyl}prop-2-en-1-one | 399 |
| C239 | 6-bromoindol-2-yl 4-[(4-chlorophenyl)carbonyl]piperazinyl ketone | 447 |
| C240 | (2E)-1-{4-[(3-fluorophenyl)methyl]piperazinyl}-3-phenylprop-2-en-1-one | 325 |
| C241 | (2E)-1-[4-(diphenylmethyl)piperazinyl]-3-(2-methylphenyl)prop-2-en-1-one | 397 |
| C242 | 4-(diphenylmethyl)piperazinyl 1-methylindol-2-yl ketone | 410 |
| C243 | 5-chloroindol-2-yl 4-(phenylcarbonyl)piperazinyl ketone | 368 |
| C244 | 4-{[4-(tert-butyl)phenyl]methyl}piperazinyl 5-methylindol-2-yl ketone | 390 |
| C245 | 1-{4-[(4-chlorophenyl)methyl]piperazinyl}-3-(4-methylphenyl)prop-2-yn-1-one | 353 |
| C246 | 4-[(2,4-dichlorophenyl)carbonyl]piperazinyl 5-(trifluoromethyl)indol-2-yl ketone | 471 |
| C247 | benzo[b]thiophen-5-yl 4-(diphenylmethyl)piperazinyl ketone | 413 |
| C248 | (2E)-1-{4-[(4-fluorophenyl)methyl]piperazinyl}-3-phenylprop-2-en-1-one | 325 |
| C249 | 3-(3,4-dichlorophenyl)-1-(4-{[4-(trifluoromethyl)phenyl]carbonyl}piperazinyl)prop-2-yn-1-one | 456 |
| C250 | 4,6-dichloroindol-2-yl 4-(diphenylmethyl)piperazinyl ketone | 465 |
| C251 | 4-[(3,5-difluorophenyl)methyl]piperazinyl 5-(trifluoromethyl)indol-2-yl ketone | 424 |
| C252 | 5-chloroindol-2-yl 4-[(3-fluorophenyl)amino]piperidyl ketone | 372 |
| C253 | 3-(4-fluorophenyl)-1-(4-{[4-(trifluoromethyl)phenyl]carbonyl}piperazinyl)prop-2-yn-1-one | 405 |
| C254 | 5-chloroindol-2-yl 4-[(4-(3-pyridyl)phenyl]carbonyl]piperazinyl ketone | 445 |
| C255 | 6-chloroindol-2-yl 4-[(4-chlorophenyl)carbonyl]piperazinyl ketone | 403 |
| C256 | 3-(2H-benzo[3,4-d]1,3-dioxolen-5-yl)-1-{4-[(4-methoxyphenyl)carbonyl]piperazinyl}prop-2-en-1-one | 395 |
| C257 | 4-(diphenylmethyl)piperazinyl 6-chloro(3-quinolyl) ketone | 442 |
| C258 | 4-[(2,4-difluorophenyl)amino]piperidyl 5-chloroindol-2-yl ketone | 390 |
| C259 | (2E)-3-(4-fluorophenyl)-1-{4-[(4-propylphenyl)sulfonyl]piperazinyl}prop-2-en-1-one | 417 |
| C260 | 2E)-1-{4-[(4-methylphenyl)methyl]piperazinyl}-3-phenylprop-2-en-1-one | 321 |
| C261 | (2E)-3-(4-fluorophenyl)-1-(4-{[4-(methylethyl)phenyl]sulfonyl}piperazinyl)prop-2-en-1-one | 417 |
| C262 | 3-(2,3-dichlorophenyl)-1-{4-[(4-fluorophenyl)methyl]piperazinyl}prop-2-yn-1-one | 392 |
| C263 | 4,6-difluoroindol-2-yl 4-(diphenylmethyl)piperazinyl ketone | 432 |
| C264 | 6-bromoindol-2-yl 4-[(4-bromophenyl)carbonyl]piperazinyl ketone | 492 |
| C265 | (2E)-1-[4-(diphenylmethyl)piperazinyl]-3-[3-(trifluoromethyl)phenyl]prop-2-en-1-one | 451 |
| C266 | 3-(2H-benzo[3,4-d]1,3-dioxolen-5-yl)-1-(4-{[4-(trifluoromethyl)phenyl]carbonyl}piperazinyl)prop-2-yn-1-one | 431 |
| C267 | (E)-(3-(4-(3-(4-bromophenyl)acryloyl)piperazine-1-carbonyl)phenyl)boronic acid | 444 |
| C268 | 6-chloroindol-2-yl 4-[(4-fluorophenyl)carbonyl]piperazinyl ketone | 386 |
| C269 | (2E)-3-(4-bromophenyl)-1-{4-[(2-fluorophenyl)methyl]piperazinyl}prop-2-en-1-one | 404 |
| C270 | (2E)-1-{4-[2-(4-chlorophenyl)ethyl]piperazinyl}-3-phenylprop-2-en-1-one | 355 |
| C271 | 5-(trifluoromethyl)indol-2-yl 4-{[3-(trifluoromethyl)phenyl]carbonyl}piperazinyl ketone | 470 |
| C272 | 5-chloroindol-2-yl 4-(3-chlorophenoxy)piperidyl ketone | 390 |
| C273 | 4-[(3,5-difluorophenyl)amino]piperidyl 5-chloroindol-2-yl ketone | 390 |

-continued

| Compound | Name | MS (EI) [(M + H)+] |
|---|---|---|
| C274 | 3-(4-bromophenyl)-1-{4-[(4-methoxyphenyl)methyl]piperazinyl}prop-2-yn-1-one | 414 |
| C275 | 3-(2,3-dichlorophenyl)-1-{4-[(4-chlorophenyl)methyl]piperazinyl}prop-2-yn-1-one | 408 |
| C276 | 4-(diphenylmethyl)piperazinyl quinoxalin-2-yl ketone | 409 |
| C277 | (2E)-1-{4-[(4-bromophenyl)sulfonyl]piperazinyl}-3-[2-(trifluoromethyl)phenyl]prop-2-en-1-one | 503 |
| C278 | 5-chloroindol-2-yl 4-(8-hydropyrazolo[1,5-a]pyridin-2-ylcarbonyl)piperazinyl ketone | 408 |
| C279 | 5-chloroindol-2-yl 4-(4-hydroimidazo[1,2-a]pyridin-2-ylcarbonyl)piperazinyl ketone | 408 |
| C280 | 5,6-dimethoxyindol-2-yl 4-(diphenylmethyl)piperazinyl ketone | 456 |
| C281 | 3-(2,3-dichlorophenyl)-1-(4-{[4-(trifluoromethyl)phenyl]methyl}piperazinyl)prop-2-yn-1-one | 442 |
| C282 | 4-({4-[(5-chloroindol-2-yl)carbonyl]piperazinyl}carbonyl)benzamide | 412 |
| C283 | 2-(difluoromethyl)benzimidazol-5-yl 4-(diphenylmethyl)piperazinyl ketone | 447 |
| C284 | 3-(3,4-dichlorophenyl)-1-{4-[(4-fluorophenyl)methyl]piperazinyl}prop-2-yn-1-one | 392 |
| C285 | 4-[(2-chloro(3-pyridyl))carbonyl]piperazinyl 5-chloroindol-2-yl ketone | 404 |
| C286 | tert-butyl 4-[(1-methylindol-2-yl)carbonyl]piperazinecarboxylate | 344 |
| C287 | 3-(4-fluorophenyl)-1-(4-{[4-fluoro-2-(trifluoromethyl)phenyl]carbonyl}piperazinyl)prop-2-yn-1-one | 423 |
| C288 | 4-(benzimidazol-2-ylcarbonyl)piperazinyl 5-chloroindol-2-yl ketone | 408 |
| C289 | 5-chloroindol-2-yl 4-(2-pyridyloxy)piperidyl ketone | 356 |
| C290 | benzo[b]thiophen-3-yl 4-(diphenylmethyl)piperazinyl ketone | 413 |
| C291 | 3-(3,4-dichlorophenyl)-1-{4-[(4-chlorophenyl)methyl]piperazinyl}prop-2-yn-1-one | 408 |
| C292 | 6-fluoroindol-2-yl 4-{[4-(trifluoromethyl)phenyl]carbonyl}piperazinyl ketone | 420 |
| C293 | 6-bromoindol-2-yl 4-[(4-fluorophenyl)methyl]piperazinyl ketone | 417 |
| C294 | 3-(3,5-difluorophenyl)-1-{4-[(4-chlorophenyl)methyl]piperazinyl}prop-2-yn-1-one | 375 |
| C295 | 5-chloroindol-2-yl 4-ethylpiperazinyl ketone | 292 |
| C296 | benzimidazol-5-yl 4-(diphenylmethyl)piperazinyl ketone | 397 |
| C297 | 3-(2H-benzo[3,4-d]1,3-dioxolan-5-yl)-1-{4-[(4-chlorophenyl)methyl]piperazinyl}prop-2-en-1-one | 385 |
| C298 | 3-(2H-benzo[3,4-d]1,3-dioxolan-5-yl)-1-{4-[(4-bromophenyl)methyl]piperazinyl}prop-2-en-1-one | 430 |
| C299 | 4-(diphenylmethyl)piperazinyl 2-(trifluoromethyl)benzimidazol-5-yl ketone | 465 |
| C300 | (2E)-3-(4-chloro-2-fluorophenyl)-1-{4-[(5-chloroindol-2-yl)carbonyl]piperazinyl}prop-2-en-1-one | 446 |
| C301 | 2-anthryl 4-(diphenylmethyl)piperazinyl ketone | 457 |
| C302 | 3-(3-chlorophenyl)-1-(4-{[4-fluoro-2-(trifluoromethyl)phenyl]methyl}piperazinyl)prop-2-yn-1-one | 425 |
| C303 | 5-bromoindol-2-yl 4-[(4-chlorophenyl)methyl]piperazinyl ketone | 433 |
| C304 | 4-(diphenylmethyl)piperazinyl 6-methoxyindol-2-yl ketone | 426 |
| C305 | (2E)-3-(4-aminophenyl)-1-[4-(diphenylmethyl)piperazinyl]prop-2-en-1-one | 398 |
| C306 | 4-{[(4-bromophenyl)sulfonyl]amino}piperidyl 5-chloroindol-2-yl ketone | 497 |
| C307 | 4-({4-[(2E)-3-(4-ethoxyphenyl)prop-2-enoyl]piperazinyl}sulfonyl)-1-acetylbenzene | 443 |
| C308 | (2E)-1-[4-(naphthylmethyl)piperazinyl]-3-phenylprop-2-en-1-one | 356 |
| C309 | 1-{4-[(4-chlorophenyl)carbonyl]piperazinyl}-3-[2-(trifluoromethyl)phenyl]prop-2-yn-1-one | 421 |
| C310 | 6-bromoindol-2-yl 4-[(4-(1H-1,2,3,4-tetraazol-5-yl)phenyl)carbonyl]piperazinyl ketone | 480 |
| C311 | [4-(diphenylmethyl)piperazinyl]-3-quinolylmethane-1-thione | 424 |

-continued

| Compound | Name | MS (EI) [(M + H)+] |
|---|---|---|
| C312 | (2E)-1-(4-butylpiperazinyl)-3-phenylprop-2-en-1-one | 272 |
| C313 | (2E)-3-(4-ethoxyphenyl)-1-[4-(phenylsulfonyl)piperazinyl]prop-2-en-1-one | 400 |
| C314 | (2E)-3-(4-fluorophenyl)-1-{4-[(3-methoxyphenyl)sulfonyl]piperazinyl}prop-2-en-1-one | 404 |
| C315 | 5-chloroindol-2-yl 4-(4-fluorophenoxy)piperidyl ketone | 373 |
| C316 | 3-(3-chlorophenyl)-1-{4-[(4-chlorophenyl)methyl]piperazinyl}prop-2-yn-1-one | 373 |
| C317 | 5-chloroindol-2-yl 4-(4-chlorophenoxy)piperidyl ketone | 389 |
| C318 | (2E)-1-{4-[(2,5-dimethoxyphenyl)sulfonyl]piperazinyl}-3-(4-fluorophenyl)prop-2-en-1-one | 434 |
| C319 | 5-chloroindol-2-yl 4-[(4-fluorophenyl)methyl]piperazinyl ketone | 372 |
| C320 | (2E)-1-[4-(diphenylmethyl)piperazinyl]-3-(2-chlorophenyl)prop-2-en-1-one | 417 |
| C321 | 1-(4-{[4-fluoro-2-(trifluoromethyl)phenyl]carbonyl}piperazinyl)-3-phenylprop-2-yn-1-one | 404 |
| C322 | 4-[(3,4-dimethylphenyl)amino]piperidyl 5-chloroindol-2-yl ketone | 382 |
| C323 | (2E)-3-(4-fluorophenyl)-1-{4-[benzylsulfonyl]piperazinyl}prop-2-en-1-one | 388 |
| C324 | methyl 4-({4-[(5-chloroindol-2-yl)carbonyl]piperazinyl}methyl)benzoate | 412 |
| C325 | 1-(4-{[4-fluoro-2-(trifluoromethyl)phenyl]carbonyl}piperazinyl)-3-[4-(trifluoromethyl)phenyl]prop-2-yn-1-one | 472 |
| C326 | 4-{3-[4-(diphenylmethyl)piperazinyl]-3-oxoprop-1-ynyl}benzenecarbonitrile | 405 |
| C327 | 5-chloroindol-2-yl 4-[(4-phenylphenyl)methyl]piperazinyl ketone | 430 |
| C328 | 4-[(3,4-dichlorophenyl)methyl]piperazinyl 5-methylindol-2-yl ketone | 402 |
| C329 | 6-bromoindol-2-yl 4-{[3-fluoro-4-(trifluoromethyl)phenyl]carbonyl}piperazinyl ketone | 498 |
| C330 | 4-{[3,5-bis(trifluoromethyl)phenyl]carbonyl}piperazinyl 5-(trifluoromethyl)indol-2-yl ketone | 537 |
| C331 | 5-chloroindol-2-yl 4-{[4-(trifluoromethyl)phenyl]methyl}piperazinyl ketone | 422 |
| C332 | (2E)-1-{4-[(4-methoxyphenyl)methyl]piperazinyl}-3-phenylprop-2-en-1-one | 336 |
| C333 | 4-[(4-bromophenyl)sulfonyl]piperazinyl 5-chloroindol-2-yl ketone | 483 |
| C334 | (2E)-3-(3,4-dichlorophenyl)-1-(4-{[4-(tert-butyl)phenyl]sulfonyl}piperazinyl)prop-2-en-1-one | 481 |
| C335 | 4-{[4-((2E)-3-phenylprop-2-enoyl)piperazinyl]methyl}benzenecarbonitrile | 331 |
| C336 | 3-(4-bromophenyl)-1-(4-{[4-fluoro-2-(trifluoromethyl)phenyl]carbonyl}piperazinyl)prop-2-yn-1-one | 483 |
| C337 | (2E)-3-phenyl-1-[4-benzylpiperazinyl]prop-2-en-1-one | 306 |
| C338 | 4-(diphenylmethyl)piperazinyl 5-(methylethyl)indol-2-yl ketone | 438 |
| C339 | 4-[(4-chlorophenyl)methyl]piperazinyl 5-methylindol-2-yl ketone | 368 |
| C340 | (2E)-1-{4-[(3,5-dimethylphenyl)methyl]piperazinyl}-3-phenylprop-2-en-1-one | 334 |
| C341 | 2-({4-[(2E)-3-(4-fluorophenyl)prop-2-enoyl]piperazinyl}sulfonyl)benzenecarbonitrile | 399 |
| C342 | 3-(4-bromophenyl)-1-{4-[(4-chlorophenyl)methyl]piperazinyl}prop-2-yn-1-one | 418 |
| C343 | 3-(3,5-difluorophenyl)-1-{4-[(4-chlorophenyl)carbonyl]piperazinyl}prop-2-yn-1-one | 389 |
| C344 | (2E)-1-{4-[(2-bromophenyl)methyl]piperazinyl}-3-phenylprop-2-en-1-one | 385 |
| C345 | (2E)-3-(4-fluorophenyl)-1-[4-(naphthylsulfonyl)piperazinyl]prop-2-en-1-one | 424 |
| C346 | 3-(4-methylphenyl)-1-(4-{[4-(trifluoromethyl)phenyl]methyl}piperazinyl)prop-2-yn-1-one | 386 |
| C347 | indol-2-yl 4-(phenylethyl)piperazinyl ketone | 333 |
| C348 | 4-(diphenylmethyl)piperazinyl 5-hydroxyindol-2-yl ketone | 411 |
| C349 | 3-(2,4-difluorophenyl)-1-{4-[(4-chlorophenyl)carbonyl]piperazinyl}prop-2-yn-1-one | 389 |

-continued

| Compound | Name | MS (EI) [(M + H)+] |
|---|---|---|
| C350 | (2E)-1-{4-[(2,5-difluorophenyl)methyl]piperazinyl}-3-phenylprop-2-en-1-one | 342 |
| C351 | 4-(diphenylmethyl)piperazinyl 2-quinolyl ketone | 408 |
| C352 | 1-{4-[(4-methoxyphenyl)methyl]piperazinyl}-3-[4-(trifluoromethyl)phenyl]prop-2-yn-1-one | 402 |
| C353 | 3-(3-chlorophenyl)-1-(4-{[4-(trifluoromethyl)phenyl]methyl}piperazinyl)prop-2-yn-1-one | 407 |
| C354 | (2E)-1-{4-[(4-chlorophenyl)methyl]piperazinyl}-3-phenylprop-2-en-1-one | 341 |
| C355 | (2E)-1-{4-[((1E)-2-phenylvinyl)sulfonyl](1,4-diazaperhydroepinyl)}-3-(4-bromophenyl)prop-2-en-1-one | 475 |
| C356 | 3-(4-chlorophenyl)-1-(4-{[4-(trifluoromethyl)phenyl]methyl}piperazinyl)prop-2-yn-1-one | 407 |
| C357 | 5-chloroindol-2-yl 4-(4-fluoro-2-methylphenoxy)piperidyl ketone | 387 |
| C358 | methyl 3-({4-[(5-chloroindol-2-yl)carbonyl]piperazinyl}methyl)benzoate | 412 |
| C359 | 4-[(3,5-dimethylphenyl)methyl]piperazinyl 5-methylindol-2-yl ketone | 361 |
| C360 | 4-{[2-fluoro-4-(trifluoromethyl)phenyl]carbonyl}piperazinyl 5-(trifluoromethyl)indol-2-yl ketone | 487 |
| C361 | (2E)-1-{4-[2-(2-fluorophenyl)ethyl]piperazinyl}-3-phenylprop-2-en-1-one | 338 |
| C362 | (2E)-1-[4-(2-(1,3-dihydroisobenzofuran-5-yl)ethyl)piperazinyl]-3-phenylprop-2-en-1-one | 362 |
| C363 | methyl 3-({4-[(5-chloroindol-2-yl)carbonyl]piperazinyl}carbonyl)benzoate | 426 |
| C364 | 3-(4-bromophenyl)-1-{4-[(4-bromophenyl)methyl]piperazinyl}prop-2-yn-1-one | 462 |
| C365 | (2E)-1-{4-[(3-chlorophenyl)methyl]piperazinyl}-3-phenylprop-2-en-1-one | 341 |
| C366 | 4-[(4-chlorophenyl)carbonyl]piperazinyl 6-fluoroindol-2-yl ketone | 386 |
| C367 | (2E)-3-(4-fluorophenyl)-1-[4-(2-thienylsulfonyl)piperazinyl]prop-2-en-1-one | 380 |
| C368 | 4-butylpiperazinyl 5-chloroindol-2-yl ketone | 320 |
| C369 | 3-(4-chlorophenyl)-1-{4-[(4-fluorophenyl)methyl]piperazinyl}prop-2-yn-1-one | 357 |
| C370 | 4-(diphenylmethyl)piperazinyl indol-6-yl ketone | 395 |
| C371 | 5-bromoindol-2-yl 4-{[4-(trifluoromethyl)phenyl]methyl}piperazinyl ketone | 466 |
| C372 | 3-(4-chlorophenyl)-1-{4-[(4-methoxyphenyl)methyl]piperazinyl}prop-2-yn-1-one | 369 |
| C373 | 1-{4-[(4-methoxyphenyl)carbonyl]piperazinyl}-3-[2-(trifluoromethyl)phenyl]prop-2-yn-1-one | 416 |
| C374 | (2E)-1-{4-[(2-chlorophenyl)methyl]piperazinyl}-3-phenylprop-2-en-1-one | 341 |
| C375 | 6-bromoindol-2-yl 4-{[4-(trifluoromethyl)phenyl]carbonyl}piperazinyl ketone | 480 |
| C376 | 5-methylindol-2-yl 4-benzylpiperazinyl ketone | 333 |
| C377 | (2E)-3-(4-bromo-2-fluorophenyl)-1-{4-[(4-bromophenyl)sulfonyl]piperazinyl}prop-2-en-1-one | 532 |
| C378 | 4-[(2,4-difluorophenyl)carbonyl]piperazinyl 5-chloroindol-2-yl ketone | 404 |
| C379 | (2E)-1-{4-[(3-methoxyphenyl)methyl]piperazinyl}-3-phenylprop-2-en-1-one | 336 |
| C380 | 4-(diphenylmethyl)piperazinyl thiopheno[2,3-d]pyrrol-5-yl ketone | 402 |
| C381 | 4-bromophenyl 4-(2-naphthylcarbonyl)piperazinyl ketone | 423 |
| C382 | 4-(4-(6-bromo-1H-indole-2-carbonyl)piperazine-1-carbonyl)phenylboronic acid | 456 |
| C383 | 1-{4-[(4-bromophenyl)methyl]piperazinyl}-3-(4-chlorophenyl)prop-2-yn-1-one | 418 |
| C384 | 3-(4-chlorophenyl)-1-{4-[(4-chlorophenyl)methyl]piperazinyl}prop-2-yn-1-one | 373 |
| C385 | (2E)-1-(4-{[4-(tert-butyl)phenyl]sulfonyl}piperazinyl)-3-(4-methoxyphenyl)prop-2-en-1-one | 443 |
| C386 | 4-(diphenylmethyl)piperazinyl 8-fluoro(3-quinolyl) ketone | 425 |
| C387 | (2E)-1-{4-[(3-nitrophenyl)methyl]piperazinyl}-3-phenylprop-2-en-1-one | 351 |

| Compound | Name | MS (EI) [(M + H)+] |
|---|---|---|
| C388 | (2E)-1-{4-[(4-bromophenyl)sulfonyl]piperazinyl}-3-(4-chloro-2-fluorophenyl)prop-2-en-1-one | 488 |
| C389 | 4-{[3-fluoro-4-(trifluoromethyl)phenyl]methyl}piperazinyl 5-(trifluoromethyl)indol-2-yl ketone | 473 |
| C390 | 5-chloroindol-2-yl 4-[4-(trifluoromethyl)phenoxy]piperidyl ketone | 423 |
| C391 | 6-chloroindol-2-yl 4-{[4-(trifluoromethyl)phenyl]carbonyl}piperazinyl ketone | 436 |
| C392 | (2E)-1-[4-(methylpropyl)piperzinyl]-3-phenylprop-2-en-1-one | 272 |
| C393 | 1-{4-[(4-fluorophenyl)carbonyl]piperazinyl}-3-[2-(trifluoromethyl)phenyl]prop-2-yn-1-one | 404 |
| C394 | (2E)-1-{4-[(2-methylphenyl)methyl]piperazinyl}-3-phenylprop-2-en-1-one | 320 |
| C395 | 3-({4-[(5-chloroindol-2-yl)carbonyl]piperazinyl}carbonyl)benzenecarbonitrile | 393 |
| C396 | {1-[(5-chloroindol-2-yl)carbonyl](4-piperidyl)}-N-(3-chlorophenyl)carboxamide | 416 |
| C397 | 4-({4-[(5-chloroindol-2-yl)carbonyl]piperazinyl}carbonyl)benzaldehyde | 396 |
| C398 | 3-(3,5-difluorophenyl)-1-(4-{[4-(trifluoromethyl)phenyl]carbonyl}piperazinyl)prop-2-yn-1-one | 422 |
| C399 | 3-(4-chlorophenyl)-1-(4-{[4-fluoro-2-(trifluoromethyl)phenyl]carbonyl}piperazinyl)prop-2-yn-1-one | 439 |
| C400 | 4-(2,3-dimethylphenyl)piperazinyl 5-chloroindol-2-yl ketone | 368 |
| C401 | 3-(4-bromophenyl)-1-{4-[(4-fluorophenyl)methyl]piperazinyl}prop-2-yn-1-one | 401 |
| C402 | 5-chloroindol-2-yl 4-{[3-fluoro-4-(trifluoromethyl)phenyl]methyl}piperazinyl ketone | 440 |
| C403 | 5-chloroindol-2-yl 4-[(3-phenylphenyl)methyl]piperazinyl ketone | 430 |
| C404 | (2E)-3-(4-bromo-2-fluorophenyl)-1-[4-(phenylsulfonyl)piperazinyl]prop-2-en-1-one | 453 |
| C405 | benzo[d]furan-2-yl 4-(phenylethyl)piperazinyl ketone | 334 |
| C406 | 1-{4-[((1E)-2-phenylvinyl)sulfonyl]piperazinyl}-3-(4-fluorophenyl)propan-1-one | 402 |
| C407 | (2E)-1-{4-[2-(2,4-dichlorophenoxy)ethyl]piperazinyl}-3-phenylprop-2-en-1-one | 405 |
| C408 | 3-(4-bromophenyl)-1-(4-{[4-(trifluoromethyl)phenyl]methyl}piperazinyl)prop-2-yn-1-one | 451 |
| C409 | 4-(4-(5-chloro-1H-indole-2-carbonyl)piperazine-1-carbonyl)phenylboronic acid | 412 |
| C410 | 3-(3,5-difluorophenyl)-1-{4-[(4-fluorophenyl)carbonyl]piperazinyl}prop-2-yn-1-one | 372 |
| C411 | 3-[4-(trifluoromethyl)phenyl]-1-(4-{[4-(trifluoromethyl)phenyl]methyl}piperazinyl)prop-2-yn-1-one | 440 |
| C412 | 4-[(2,4-difluorophenyl)methyl]piperazinyl 5-(trifluoromethyl)indol-2-yl ketone | 423 |
| C413 | 5-chloroindol-2-yl 4-phenoxypiperidyl ketone | 355 |
| C414 | tert-butyl 4-(indol-2-ylcarbonyl)piperazinecarboxylate | 329 |
| C415 | 4-{[4-fluoro-3-(trifluoromethyl)phenyl]methyl}piperazinyl 5-(trifluoromethyl)indol-2-yl ketone | 473 |
| C416 | phenyl 4-[(5-chloroindol-2-yl)carbonyl]piperazinecarboxylate | 384 |
| C417 | {1-[(5-chloroindol-2-yl)carbonyl](4-piperidyl)}-N-(3-fluorophenyl)carboxamide | 400 |
| C418 | 4-{[4-fluoro-2-(trifluoromethyl)phenyl]methyl}piperazinyl 5-(trifluoromethyl)indol-2-yl ketone | 473 |
| C419 | 3-(3,5-difluorophenyl)-1-[4-(diphenylmethyl)piperazinyl]prop-2-yn-1-one | 416 |
| C420 | 5-chloroindol-2-yl 4-{[4-fluoro-3-(trifluoromethyl)phenyl]methyl}piperazinyl ketone | 440 |
| C421 | 5-chloroindol-2-yl 4-{[4-(4-methoxyphenyl)phenyl]sulfonyl}piperazinyl ketone | 510 |
| C422 | 3-(3,5-difluorophenyl)-1-(4-{[4-fluoro-2-(trifluoromethyl)phenyl]methyl}piperazinyl)prop-2-yn-1-one | 426 |

-continued

| Compound | Name | MS (EI) [(M + H)+] |
|---|---|---|
| C423 | 4-{[3,5-bis(trifluoromethyl)phenyl]methyl}piperazinyl 5-chloroindol-2-yl ketone | 490 |
| C424 | 3-(2,4-difluorophenyl)-1-{4-[(4-fluorophenyl)carbonyl]piperazinyl}prop-2-yn-1-one | 372 |
| C425 | 6-fluoroindol-2-yl 4-[(4-fluorophenyl)carbonyl]piperazinyl ketone | 369 |
| C426 | 5-chloroindol-2-yl 4-{[4-fluoro-2-(trifluoromethyl)phenyl]methyl}piperazinyl ketone | 440 |
| C427 | 4-[(2,4-difluorophenyl)methyl]piperazinyl 5-chloroindol-2-yl ketone | 390 |
| C428 | 5-chloroindol-2-yl 4-{[4-chloro-2-(trifluoromethyl)phenyl]methyl}piperazinyl ketone | 456 |
| C429 | {4-[(5-chloroindol-2-yl)carbonyl]piperazinyl}-N-(4-chlorophenyl)carboxamide | 417 |
| C430 | 3-(2H-benzo[3,4-d]1,3-dioxolen-5-yl)-1-(4-{[4-(trifluoromethyl)phenyl]carbonyl}piperazinyl)prop-2-en-1-one | 432 |
| C431 | 4-(diphenylmethyl)piperazinyl pyrrolo[2,3-c]pyridin-2-yl ketone | 396 |
| C432 | 1-(4-{[4-fluoro-2-(trifluoromethyl)phenyl]methyl}piperazinyl)-3-[4-(trifluoromethyl)phenyl]prop-2-yn-1-one | 458 |
| C433 | 4-(diphenylmethyl)piperazinyl 1-methylindol-5-yl ketone | 410 |
| C434 | 4-(2,4-difluorophenyl)piperazinyl 5-chloroindol-2-yl ketone | 376 |
| C435 | 3-(4-chlorophenyl)-1-(4-{[4-fluoro-2-(trifluoromethyl)phenyl]methyl}piperazinyl)prop-2-yn-1-one | 425 |
| C436 | 4-(diphenylmethyl)piperazinyl 4-bromopyrrol-2-yl ketone | 424 |
| C437 | 3-(3,4-dichlorophenyl)-1-(4-{[4-fluoro-2-(trifluoromethyl)phenyl]carbonyl}piperazinyl)prop-2-yn-1-one | 473 |
| C438 | 1-{4-[(4-fluorophenyl)methyl]piperazinyl}-3-[2-(trifluoromethyl)phenyl]prop-2-yn-1-one | 390 |
| C439 | (2E)-3-(4-chloro-2-fluorophenyl)-1-[4-(phenylsulfonyl)piperazinyl]prop-2-en-1-one | 409 |
| C440 | 3-(4-(5-chloro-1H-indole-2-carbonyl)piperazine-1-carbonyl)phenylboronic acid | 412 |
| C441 | (2E)-1-[4-(diphenylmethyl)piperazinyl]-3-(5-bromo-2-fluorophenyl)prop-2-en-1-one | 479 |
| C442 | (2E)-1-{4-[(4-bromophenyl)sulfonyl]piperazinyl}-3-(2-methylphenyl)prop-2-en-1-one | 449 |
| C443 | 1-[4-(diphenylmethyl)piperazinyl]-3-[2-(trifluoromethyl)phenyl]prop-2-yn-1-one | 448 |
| C444 | (2E)-3-phenyl-1-piperazinylprop-2-en-1-one | 216 |
| C445 | N-(4-bromophenyl){4-[(5-chloroindol-2-yl)carbonyl]piperazinyl}carboxamide | 462 |
| C446 | 3-(4-fluorophenyl)-1-{4-[(4-fluorophenyl)methyl]piperazinyl}prop-2-yn-1-one | 340 |
| C447 | 6-chloroindol-2-yl 4-{[4-fluoro-2-(trifluoromethyl)phenyl]carbonyl}piperazinyl ketone | 454 |
| C448 | (2E)-1-(4-{[4-(tert-butyl)phenyl]sulfonyl}piperazinyl)-3-(4-chloro-2-fluorophenyl)prop-2-en-1-one | 465 |
| C449 | 5-chloroindol-2-yl 4-(cyclopentylamino)piperidyl ketone | 346 |
| C450 | {4-[(5-chloroindol-2-yl)carbonyl]piperazinyl}-N-[4-fluoro-3-(trifluoromethyl)phenyl]carboxamide | 469 |
| C451 | {4-[(5-chloroindol-2-yl)carbonyl]piperazinyl}-N-(3-fluorophenyl)carboxamide | 401 |
| C452 | 4-(2H-benzo[d]1,3-dioxolan-5-ylmethyl)piperazinyl benzo[d]furan-2-yl ketone | 364 |
| C453 | (2E)-1-[4-(diphenylmethyl)piperazinyl]-3-(4-methylphenyl)prop-2-en-1-one | 397 |
| C454 | 5-chloroindol-2-yl 4-[(4-phenylphenyl)sulfonyl]piperazinyl ketone | 480 |
| C455 | (2E)-1-{4-[(4-bromophenyl)sulfonyl]piperazinyl}-3-(2-fluorophenyl)prop-2-en-1-one | 453 |
| C456 | {4-[(5-chloroindol-2-yl)carbonyl]piperazinyl}-N-[4-(trifluoromethyl)phenyl]carboxamide | 451 |
| C457 | 3-(2H-benzo[3,4-d]1,3-dioxolan-5-yl)-1-{4-[(4-(1H-1,2,3,4-tetraazol-5-yl)phenyl)carbonyl]piperazinyl}prop-2-en-1-one | 432 |
| C458 | 5-methylindol-2-yl 4-(3-pyridylmethyl)piperazinyl ketone | 334 |

-continued

| Compound | Name | MS (EI) [(M + H)+] |
|---|---|---|
| C459 | 1-(4-{[4-fluoro-2-(trifluoromethyl)phenyl]methyl}piperazinyl)-3-(4-methylphenyl)prop-2-yn-1-one | 404 |
| C460 | 4-(({4-[(5-chloroindol-2-yl)carbonyl]piperazinyl}carbonyl)benzoic acid | 412 |
| C461 | 1-{4-[(4-chlorophenyl)methyl]piperazinyl}-3-(4-fluorophenyl)prop-2-yn-1-one | 357 |
| C462 | {1-[(5-chloroindol-2-yl)carbonyl](4-piperidyl)}(4-chlorophenyl) | 431 |
| C463 | 3-(2H-benzo[3,4-d]1,3-dioxolan-5-yl)-1-{4-[(4-fluorophenyl)methyl]piperazinyl}prop-2-en-1-one | 368 |
| C464 | 4-[(4-chlorophenyl)methyl]piperazinyl 3-quinolyl ketone | 388 |
| C465 | 4-(diphenylmethyl)piperazinyl 2-methylbenzimidazol-5-yl ketone | 411 |
| C466 | (2E)-3-phenyl-1-[4-(4-pyridylmethyl)piperazinyl]prop-2-en-1-one | 307 |
| C467 | 3-(3,5-difluorophenyl)-1-{4-[(4-methoxyphenyl)carbonyl]piperazinyl}prop-2-yn-1-one | 384 |
| C468 | 4-(diphenylmethyl)piperazinyl 3-isoquinolyl ketone | 408 |
| C469 | 1-{4-[(4-chlorophenyl)methyl]piperazinyl}-3-[2-(trifluoromethyl)phenyl]prop-2-yn-1-one | 407 |
| C470 | 5-chloroindol-2-yl 4-(4-fluorophenyl)piperazinyl ketone | 358 |
| C471 | 6-bromoindol-2-yl 4-[(4-chlorophenyl)methyl]piperazinyl ketone | 433 |
| C472 | 4-bromophenyl 4-[(4-chlorophenyl)methyl]piperazinyl ketone | 394 |
| C473 | 3-(3-chlorophenyl)-1-{4-[(4-methoxyphenyl)methyl]piperazinyl}prop-2-yn-1-one | 369 |
| C474 | {4-[(5-chloroindol-2-yl)carbonyl]piperazinyl}-N-(3-iodophenyl)carboxamide | 509 |
| C475 | 3-[2-(trifluoromethyl)phenyl]-1-(4-{[4-(trifluoromethyl)phenyl]methyl}piperazinyl)prop-2-yn-1-one | 441 |
| C476 | 5-chloroindol-2-yl 4-(2-fluorophenyl)piperazinyl ketone | 358 |
| C477 | N-(2,4-difluorophenyl){4-[(5-chloroindol-2-yl)carbonyl]piperazinyl}carboxamide | 419 |
| C478 | 4-(diphenylmethyl)piperazinyl 8-hydropyrazolo[1,5-a]pyridin-2-yl ketone | 397 |
| C479 | 3-(2H-benzo[3,4-d]1,3-dioxolan-5-yl)-1-(4-{[4-fluoro-2-(trifluoromethyl)phenyl]carbonyl}piperazinyl)prop-2-en-1-one | 451 |
| C480 | (2E)-1-(4-{[4-(tert-butyl)phenyl]sulfonyl}piperazinyl)-3-(2-methylphenyl)prop-2-en-1-one | 427 |
| D1 | (2E)-3-(4-bromophenyl)-1-{4-[(4-chlorophenyl)methyl]piperazinyl}prop-2-en-1-one | 420 |
| D2 | (E)-1-(4-(2-fluorobenzyl)piperazin-1-yl)-3-phenylprop-2-en-1-one | 404 |
| D3 | (E)-3-(3,4-dichlorophenyl)-1-(4-(4-(trifluoromethyl)benzyl)piperazin-1-yl)prop-2-en-1-one | 444 |
| E1 | (E)-3-(4-bromophenyl)-1-(4-(mesitylsulfonyl)piperazin-1-yl)prop-2-en-1-one | 479 |
| E2 | (E)-1-(4-((4-bromophenyl)sulfonyl)piperazin-1-yl)-3-(4-fluorophenyl)prop-2-en-1-one | 454 |
| E3 | (E)-3-(4-fluorophenyl)-1-(4-(phenethylsulfonyl)piperazin-1-yl)prop-2-en-1-one | 403 |
| E4 | (E)-3-(4-methoxyphenyl)-1-(4-(phenylsulfonyl)piperazin-1-yl)prop-2-en-1-one | 387 |
| E5 | (E)-1-(4-((4-acetylphenyl)sulfonyl)piperazin-1-yl)-3-(4-bromo-2-fluorophenyl)prop-2-en-1-one | 496 |
| F2 | (E)-3-(4-bromophenyl)-1-(4-(((4-(trifluoromethyl)benzyl)amino)methyl)piperidin-1-yl)prop-2-en-1-one | 483 |
| F3 | (E)—N-((1-(3-(4-bromophenyl)acryloyl)piperidin-4-yl)methyl)-4-(trifluoromethyl)benzamide | 496 |

Example PC

Parenteral Composition

To prepare a parenteral pharmaceutical composition suitable for administration by injection, 100 mg of a water-soluble salt of a compound of Formula (I), (II), (III), (IV), (V), (VI), (VII), (VIII), (IX), or (X), or pharmaceutically acceptable salt, N-oxide, racemate or stereoisomer thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example OC

Oral Composition

To prepare a pharmaceutical composition for oral delivery, 100 mg of a compound of Formula (I), (II), (III), (IV), (V), (VI), (VII), (VIII), (IX), or (X), or pharmaceutically acceptable salt, N-oxide, racemate or stereoisomer thereof, is mixed with 750 mg of starch. The mixture is incorporated into an oral dosage unit for, such as a hard gelatin capsule, which is suitable for oral administration.

Example BA

Cell-Based Luminescent Assay

To assess EBI2 modulation, the compounds described herein were assayed in the following cell-based luminescent assay:

Protocol

Day 1 Cell Seeding
1) Plated 600 cells/well in 4 uL of assay media into columns 1-48 of a 1536-well assay plate, using a liquid dispenser.
2) Centrifuged plates at 1000 rpm for 1 minute and covered with lids.
3) Incubated overnight at 37° C., 100% relative humidity, 5% $CO_2$.

Day 2 Compound Addition
1) Centrifuged compound plates containing compounds described herein at 500 rpm for 1 minute.
2) Added compounds into assay plate col 5-48 to final concentration 4-5 uM. Added matching amount of DMSO to positive and negative control wells in columns 1-4.
3) Dispensed 2 ul/well of assay media to columns 1-2 for the positive control wells.
4) Added 2 ul/well of 400 nM 7a,25-OHC (final assay concentration=80 nM) in assay media to columns 3-48 for the negative control and test compound wells.
5) Centrifuged plates at 1000 rpm for 1 minute and re-lid plates.
6) Incubated plates at 37° C., 100% relative humidity, 5% $CO_2$ for 60 minutes.
7) Following 60 minute incubation, delivered 2.5 uL of Detection Reagent solution to each assay plate (Columns 1-48) using a liquid handler.
8) Centrifuged plates at 2000 rpm for 2 minutes and re-lid plates.
9) Incubated plates for 60 minutes at 25 degrees in the dark.
10) Read plates using the Viewlux, Envision or other suitable plate reader using a luminescence detection.

The test compounds that demonstrated a corrected % activity of >=50% were defined as inhibitors of the reaction. The experimental values were normalized by the difference between values from neutral and stimulator control wells in each plate. Then normalized data was corrected to remove systematic plate patterns due to artifacts such as dispensing tip issues etc. IC50 data for the assay is shown in Table 1.

TABLE 1

$IC_{50}$: $IC_{50}$: A <100 nM; 100 nM ≤ B ≤ 500 nM; C 500 nM < C < 5 µM

| Compound | $IC_{50}$ nM |
|---|---|
| C1 | A |
| C2 | A |
| C3 | A |

TABLE 1-continued $IC_{50}$: $IC_{50}$: A <100 nM; 100 nM ≤ B ≤ 500 nM; C 500 nM < C < 5 µM

| Compound | $IC_{50}$ nM |
|---|---|
| C4 | A |
| C5 | A |
| C6 | A |
| C7 | A |
| C8 | A |
| C9 | A |
| C10 | A |
| C11 | A |
| C12 | A |
| C13 | A |
| C14 | A |
| C15 | A |
| C16 | A |
| C17 | A |
| C18 | A |
| C19 | A |
| C20 | A |
| C21 | A |
| C22 | A |
| C23 | A |
| C24 | A |
| C25 | A |
| C26 | A |
| C27 | A |
| C28 | A |
| C29 | A |
| C30 | A |
| C31 | A |
| C32 | A |
| C33 | A |
| C34 | A |
| C35 | A |
| C36 | A |
| C37 | A |
| C38 | A |
| C39 | A |
| C40 | A |
| C41 | A |
| C42 | A |
| C43 | A |
| C44 | A |
| C45 | A |
| C46 | A |
| C47 | A |
| C48 | A |
| C49 | A |
| C50 | A |
| C51 | A |
| C52 | A |
| C53 | A |
| C54 | A |
| C55 | A |
| C56 | A |
| C57 | A |
| C58 | A |
| C59 | A |
| C60 | A |
| C61 | A |
| C62 | A |
| C63 | A |
| C64 | A |
| C65 | A |
| C66 | A |
| C67 | A |
| C68 | A |
| C69 | A |
| C70 | A |
| C71 | A |
| C72 | A |
| C73 | A |
| C74 | A |
| C75 | A |
| C76 | A |
| C77 | A |
| C78 | A |
| C79 | A |

TABLE 1-continued

IC$_{50}$: IC$_{50}$: A <100 nM; 100 nM ≤ B ≤ 500 nM; C 500 nM < C < 5 μM

| Compound | IC$_{50}$ nM |
|---|---|
| C80 | A |
| C81 | A |
| C82 | A |
| C83 | A |
| C84 | A |
| C85 | A |
| C86 | A |
| C87 | A |
| C88 | A |
| C89 | A |
| C90 | A |
| C91 | A |
| C92 | A |
| C93 | A |
| C94 | A |
| C95 | A |
| C96 | A |
| C97 | A |
| C98 | A |
| C99 | A |
| C100 | A |
| C101 | A |
| C102 | A |
| C103 | A |
| C104 | A |
| C105 | A |
| C106 | A |
| C107 | A |
| C108 | A |
| C109 | A |
| C110 | A |
| C111 | A |
| C112 | A |
| C113 | A |
| C114 | A |
| C115 | A |
| C116 | A |
| C117 | A |
| C118 | A |
| C119 | A |
| C120 | A |
| C121 | A |
| C122 | A |
| C123 | A |
| C124 | A |
| C125 | A |
| C126 | A |
| C127 | A |
| C128 | A |
| C129 | A |
| C130 | A |
| C131 | A |
| C132 | A |
| C133 | A |
| C134 | A |
| C135 | A |
| C136 | A |
| C137 | A |
| C138 | A |
| C139 | A |
| C140 | A |
| C141 | A |
| C142 | A |
| C143 | A |
| C144 | A |
| C145 | A |
| C146 | A |
| C147 | A |
| C148 | A |
| C149 | A |
| C150 | A |
| C151 | A |
| C152 | A |
| C153 | A |
| C154 | A |
| C155 | A |

TABLE 1-continued

IC$_{50}$: IC$_{50}$: A <100 nM; 100 nM ≤ B ≤ 500 nM; C 500 nM < C < 5 μM

| Compound | IC$_{50}$ nM |
|---|---|
| C156 | A |
| C157 | A |
| C158 | A |
| C159 | A |
| C160 | A |
| C161 | A |
| C162 | C |
| C163 | C |
| C164 | C |
| C165 | C |
| C166 | C |
| C167 | C |
| C168 | C |
| C169 | C |
| C170 | C |
| C171 | C |
| C172 | C |
| C173 | C |
| C174 | C |
| C175 | C |
| C176 | C |
| C177 | C |
| C178 | C |
| C179 | C |
| C180 | C |
| C181 | C |
| C182 | C |
| C183 | C |
| C184 | C |
| C185 | C |
| C186 | C |
| C187 | C |
| C188 | C |
| C189 | C |
| C190 | C |
| C191 | C |
| C192 | C |
| C193 | C |
| C194 | C |
| C195 | C |
| C196 | C |
| C197 | C |
| C198 | C |
| C199 | C |
| C200 | A |
| C201 | A |
| C202 | A |
| C203 | A |
| C204 | A |
| C205 | A |
| C206 | A |
| C207 | A |
| C208 | A |
| C209 | A |
| C210 | A |
| C211 | A |
| C212 | A |
| C213 | A |
| C214 | A |
| C215 | A |
| C216 | A |
| C217 | A |
| C218 | A |
| C219 | A |
| C220 | A |
| C221 | A |
| C222 | A |
| C223 | A |
| C224 | A |
| C225 | A |
| C226 | A |
| C227 | A |
| C228 | A |
| C229 | A |
| C230 | A |
| C231 | A |

TABLE 1-continued

IC$_{50}$: IC$_{50}$: A <100 nM; 100 nM ≤ B ≤ 500 nM; C 500 nM < C < 5 µM

| Compound | IC$_{50}$ nM |
|---|---|
| C232 | A |
| C233 | A |
| C234 | A |
| C235 | A |
| C236 | A |
| C237 | A |
| C238 | A |
| C239 | A |
| C240 | A |
| C241 | A |
| C242 | A |
| C243 | A |
| C244 | A |
| C245 | A |
| C246 | A |
| C247 | A |
| C248 | A |
| C249 | A |
| C250 | A |
| C251 | A |
| C252 | A |
| C253 | A |
| C254 | A |
| C255 | A |
| C256 | A |
| C257 | A |
| C258 | A |
| C259 | A |
| C260 | A |
| C261 | A |
| C262 | A |
| C263 | A |
| C264 | A |
| C265 | A |
| C266 | A |
| C267 | A |
| C268 | A |
| C269 | A |
| C270 | A |
| C271 | A |
| C272 | A |
| C273 | A |
| C274 | A |
| C275 | A |
| C276 | B |
| C277 | B |
| C278 | B |
| C279 | B |
| C280 | B |
| C281 | B |
| C282 | B |
| C283 | B |
| C284 | B |
| C285 | B |
| C286 | B |
| C287 | B |
| C288 | B |
| C289 | B |
| C290 | B |
| C291 | B |
| C292 | B |
| C293 | B |
| C294 | B |
| C295 | B |
| C296 | B |
| C297 | B |
| C298 | B |
| C299 | B |
| C300 | A |
| C301 | A |
| C302 | A |
| C303 | A |
| C304 | A |
| C305 | A |
| C306 | A |
| C307 | A |

TABLE 1-continued

IC$_{50}$: IC$_{50}$: A <100 nM; 100 nM ≤ B ≤ 500 nM; C 500 nM < C < 5 µM

| Compound | IC$_{50}$ nM |
|---|---|
| C308 | A |
| C309 | A |
| C310 | A |
| C311 | A |
| C312 | A |
| C313 | A |
| C314 | A |
| C315 | A |
| C316 | A |
| C317 | A |
| C318 | A |
| C319 | A |
| C320 | A |
| C321 | A |
| C322 | A |
| C323 | A |
| C324 | A |
| C325 | A |
| C326 | A |
| C327 | A |
| C328 | A |
| C329 | A |
| C330 | A |
| C331 | A |
| C332 | A |
| C333 | A |
| C334 | A |
| C335 | A |
| C336 | A |
| C337 | A |
| C338 | A |
| C339 | A |
| C340 | A |
| C341 | A |
| C342 | A |
| C343 | A |
| C344 | A |
| C345 | A |
| C346 | A |
| C347 | A |
| C348 | A |
| C349 | A |
| C350 | A |
| C351 | A |
| C352 | A |
| C353 | A |
| C354 | A |
| C355 | A |
| C356 | A |
| C357 | A |
| C358 | A |
| C359 | B |
| C360 | A |
| C361 | A |
| C362 | A |
| C363 | B |
| C364 | A |
| C365 | A |
| C366 | B |
| C367 | A |
| C368 | A |
| C369 | A |
| C370 | A |
| C371 | A |
| C372 | A |
| C373 | A |
| C374 | A |
| C375 | B |
| C376 | A |
| C377 | A |
| C378 | A |
| C379 | A |
| C380 | A |
| C381 | A |
| C382 | A |
| C383 | A |

TABLE 1-continued

IC$_{50}$: IC$_{50}$: A <100 nM; 100 nM ≤ B ≤ 500 nM; C 500 nM < C < 5 μM

| Compound | IC$_{50}$ nM |
|---|---|
| C384 | A |
| C385 | A |
| C386 | A |
| C387 | A |
| C388 | A |
| C389 | A |
| C390 | B |
| C391 | A |
| C392 | A |
| C393 | A |
| C394 | B |
| C395 | A |
| C396 | A |
| C397 | A |
| C398 | B |
| C399 | A |
| C400 | A |
| C401 | A |
| C402 | A |
| C403 | A |
| C404 | A |
| C405 | B |
| C406 | B |
| C407 | B |
| C408 | B |
| C409 | B |
| C410 | B |
| C411 | B |
| C412 | B |
| C413 | B |
| C414 | B |
| C415 | B |
| C416 | B |
| C417 | B |
| C418 | B |
| C419 | B |
| C420 | B |
| C421 | B |
| C422 | B |
| C423 | B |
| C424 | B |
| C425 | B |
| C426 | B |
| C427 | B |
| C428 | B |
| C429 | B |
| C430 | B |
| C431 | B |
| C432 | B |
| C433 | B |
| C434 | B |
| C435 | B |
| C436 | B |
| C437 | B |
| C438 | B |
| C439 | B |
| C440 | B |
| C441 | B |
| C442 | B |
| C443 | B |
| C444 | B |
| C445 | B |
| C446 | B |
| C447 | B |
| C448 | B |
| C449 | B |
| C450 | B |
| C451 | B |
| C452 | B |
| C453 | B |
| C454 | B |
| C455 | B |
| C456 | B |
| C457 | B |
| C458 | B |
| C459 | B |

TABLE 1-continued

IC$_{50}$: IC$_{50}$: A <100 nM; 100 nM ≤ B ≤ 500 nM; C 500 nM < C < 5 μM

| Compound | IC$_{50}$ nM |
|---|---|
| C460 | B |
| C461 | B |
| C462 | B |
| C463 | B |
| C464 | B |
| C465 | B |
| C466 | B |
| C467 | B |
| C468 | B |
| C469 | B |
| C470 | B |
| C471 | B |
| C472 | B |
| C473 | B |
| C474 | B |
| C475 | B |
| C476 | B |
| C477 | B |
| C478 | B |
| C479 | B |
| C480 | B |
| D1 | A |
| D2 | A |
| D3 | A |
| E1 | A |
| E2 | A |
| E3 | A |
| E4 | A |
| E5 | A |
| F2 | A |
| F3 | A |
| H3 | A |
| H4 | A |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of modulating the activity of Epstein-Barr virus-induced G-protein coupled receptor 2 (EBI2) in an individual with an autoimmune disease, cardiovascular disease, cancer, or a viral infection comprising administering to an individual in need thereof a therapeutically effective amount of a EBI2 modulator compound having the structure of Formula (VII):

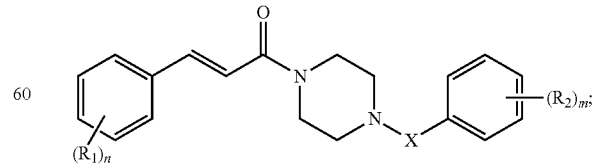

Formula (VII)

wherein:
X is a bond, —CH$_2$—, —C(H)(Ph)-, or —S(=O)$_2$—;
each R$_1$ is independently F, Cl, Br, I, —CN, —NR$_4$R$_5$, —NO$_2$, —OH, —CF$_3$, —OCF$_3$, —OC$_1$-C$_6$alkyl, C₁-C₆alkyl, C₃-C₈cycloalkyl, C₁-C₆heteroalkyl, C₁-C₆haloalkyl, C₂-C₈heterocycloalkyl, aryl, or heteroaryl; or two R₁ on adjacent carbon atoms are combined with the adjacent carbon atoms to form a —OCH₂O— ring;

each R₂ is independently F, Cl, Br, I, —CN, —NR₄R₅, —NO₂, —OH, —CF₃, —OCF₃, —OC₁-C₆alkyl, C₁-C₆alkyl, —C(=O)C₁-C₆alkyl, CO₂H, B(OH)₂, PO₃H, C₃-C₈cycloalkyl, C₁-C₆heteroalkyl, C₁-C₆haloalkyl, C₂-C₈heterocycloalkyl, aryl, or heteroaryl;

each R₄ is independently H or C₁-C₆alkyl;
each R₅ is independently H or C₁-C₆alkyl;
m is an integer selected from 0-3; and
n is an integer selected from 0-3;
or a pharmaceutically acceptable salt, or pharmaceutically acceptable solvate thereof.

2. The method of claim 1, wherein each R₁ is independently F, Cl, Br, I, —CN, —NR₄R₅, —NO₂, —OH, —CF₃, —OCF₃, —OC₁-C₆alkyl, C₁-C₆alkyl, C₃-C₈cycloalkyl, C₁-C₆heteroalkyl, C₁-C₆haloalkyl, C₂-C₈heterocycloalkyl, aryl, or heteroaryl.

3. The method of claim 1, wherein each R₂ is independently F, Cl, Br, I, —CN, —NR₄R₅, —NO₂, —OH, —CF₃, —OCF₃, —OC₁-C₆alkyl, or C₁-C₆alkyl.

4. The method of claim 1, wherein n is 1 and m is 0; or n is 1 and m is 1; or n is 1 and m is 2; or n is 2 and m is 1; or n is 0 and m is 0.

5. The method of claim 1, wherein the compound is:
(2E)-3-(3, 4-dichlorophenyl)-1-[4-(diphenylmethyl) piperazinyl] prop-2-en-1-one;
(E)-3-(4-bromophenyl)-1-(4-(4-chlorobenzyl)piperazin-1-yl) prop-2-en-1-one;
(2E)-3-(4-bromophenyl)-1-{4-[(3-fluorophenyl)methyl]piperazinyl} prop-2-en-1-one;
(2E)-3-(3,4-dichlorophenyl)-1-(4-{[4-(trifluoromethyl)phenyl]methyl}piperazinyl)prop-2-en-1-one;
(2E)-3-(4-bromophenyl)-1-{4[(2,4,6-trimethylphenyl)sulfonyl] piperazinyl} prop-2-en-1-one;
(2E)-1-{4-[(4-bromophenyl)sulfonyl]piperazinyl}-3-(4-fluorophenyl) prop-2-en-1-one;
(2E)-3-(4-methoxyphenyl)-1-[4-(phenylsulfonyl)piperazinyl] prop-2-en-1-one;
4-({4-[(2E)-3-(4-bromo-2-fluorophenyl)prop-2-enoyl]piperazinyl}sulfonyl)-1-acetylbenzene;
(2E)-3-(3,4-dichlorophenyl)-1-[4-(diphenylmethyl)piperazinyl]prop-2-en-1-one;
(2E)-1-[4-(diphenylmethyl)piperazinyl]-3-(4-methoxyphenyl)prop-2-en-1-one;
(2E)-1-[4-(diphenylmethyl)piperazinyl]-3-(4-ethoxyphenyl)prop-2-en-1-one;
(2E)-1-[4-(2-(3,4-dihydronaphthyl)sulfonyl)piperazinyl]-3-(4-fluorophenyl)prop-2-en-1-one;
(2E)-1-[4-(diphenylmethyl)piperazinyl]-3-(4-bromo-2-fluorophenyl)prop-2-en-1-one;
(2E)-1-[4-(diphenylmethyl)piperazinyl]-3-(4-bromophenyl)prop-2-en-1-one;
(2E)-1-[4-(diphenylmethyl)piperazinyl]-3-[4-(trifluoromethyl)phenyl]prop-2-en-1-one;
(2E)-1-{4-[(3,5-difluorophenyl)methyl]piperazinyl}-3-(4-bromophenyl)prop-2-en-1-one;
(2E)-3-(4-bromophenyl)-1-{4-[(4-fluoro-3-methylphenyl)methyl]piperazinyl}prop-2-en-1-one;
(2E)-1-{4-[(4-bromophenyl)sulfonyl]piperazinyl}prop-2-en-1-one;
(2E)-1-{4-[(3,4-dichlorophenyl)methyl]piperazinyl}-3-(4-bromophenyl)prop-2-en-1-one;
(2E)-1-[4-(diphenylmethyl)piperazinyl]-3-(4-chloro-2-fluorophenyl)prop-2-en-1-one;
(2E)-3-(4-bromophenyl)-1-{4-[(4-methylphenyl)methyl]piperazinyl}prop-2-en-1-one;
(2E)-1-[4-(diphenylmethyl)piperazinyl]-3-phenylprop-2-en-1-one;
(2E)-3-(4-bromophenyl)-1-{4-[(4-chlorophenyl)methyl]piperazinyl}prop-2-en-1-one;
(2E)-1-[4-(diphenylmethyl)piperazinyl]-3-(4-fluorophenyl)prop-2-en-1-one;
(2E)-1-{4-[(3,5-dimethoxyphenyl)methyl]piperazinyl}-3-(4-bromophenyl)prop-2-en-1-one;
(2E)-3-(4-bromophenyl)-1-(4-{[4-chloro-2-(trifluoromethyl)phenyl]methyl}piperazinyl)prop-2-en-1-one;
(2E)-1-{4-[(4-chlorophenyl)sulfonyl]piperazinyl}-3-(4-fluorophenyl)prop-2-en-1-one;
(2E)-1-{4-[(2-bromophenyl)sulfonyl]piperazinyl}-3-(4-fluorophenyl)prop-2-en-1-one;
(2E)-3-(4-bromophenyl)-1-(4-{[4-(methylethyl)phenyl]methyl}piperazinyl)prop-2-en-1-one;
(2E)-3-(3,4-difluorophenyl)-1-[4-(diphenylmethyl)piperazinyl]prop-2-en-1-one;
(2E)-1-{4-[(3,5-dimethylphenyl)methyl]piperazinyl}-3-(4-bromophenyl)prop-2-en-1-one;
(2E)-1-[4-(diphenylmethyl)piperazinyl]-3-(2-fluorophenyl)prop-2-en-1-one;
(2E)-3-(4-fluorophenyl)-1-{4-[(4-methylphenyl)sulfonyl]piperazinyl}prop-2-en-1-one;
(2E)-3-(4-bromophenyl)-1-{4-[(4-chloro-2-fluorophenyl)methyl]piperazinyl}prop-2-en-1-one;
(2E)-3-(4-bromophenyl)-1-(4-{[4-fluoro-2-(trifluoromethyl)phenyl]methyl}piperazinyl)prop-2-en-1-one;
(2E)-1-{4-[(3-chlorophenyl)sulfonyl]piperazinyl}-3-(4-fluorophenyl)prop-2-en-1-one;
(2E)-1-(4-{[4-(tert-butyl)phenyl]methyl}piperazinyl)-3-(4-bromophenyl)prop-2-en-1-one;
(2E)-1-{4-[(4-bromophenyl)sulfonyl]piperazinyl}-3-(4-methoxyphenyl)prop-2-en-1-one;
(2E)-1-[4-(diphenylmethyl)piperazinyl]-3-(3,4,5-trifluorophenyl)prop-2-en-1-one;
(2E)-1-(4-{[4-(tert-butyl)phenyl]sulfonyl}piperazinyl)-3-(4-bromophenyl)prop-2-en-1-one;
1-[4-(diphenylmethyl)piperazinyl]-3-bromo-3-(4-bromophenyl)prop-2-en-1-one;
(2E)-1-{4-[(4-nitrophenyl)methyl]piperazinyl}-3-phenylprop-2-en-1-one;
3-(2H-benzo[3,4-d]1,3-dioxolan-5-yl)-1-(4-{[4-(trifluoromethyl)phenyl]methyl}piperazinyl)prop-2-en-1-one;
(2E)-3-(5-bromo-2-fluorophenyl)-1-{4-[(4-bromophenyl)sulfonyl]piperazinyl}prop-2-en-1-one;
3-(2H-benzo[3,4-d]1,3-dioxolan-5-yl)-1-(4-{[4-fluoro-2-(trifluoromethyl)phenyl]methyl}piperazinyl)prop-2-en-1-one;
(2E)-1-(4-{[4-(tert-butyl)phenyl]sulfonyl}piperazinyl)-3-(2-fluorophenyl)prop-2-en-1-one;
(2E)-3-(2-methylphenyl)-1-[4-(phenylsulfonyl)piperazinyl]prop-2-en-1-one;
(2E)-1-{4-[(3-methylphenyl)methyl]piperazinyl}-3-phenylprop-2-en-1-one;
(2E)-1-(4-{[4-(tert-butyl)phenyl]sulfonyl}piperazinyl)-3-(4-fluorophenyl)prop-2-en-1-one;
(2E)-1-{4-[(4-bromophenyl)methyl]piperazinyl}-3-phenylprop-2-en-1-one;
(2E)-3-(4-fluorophenyl)-1-[4-(phenylsulfonyl)piperazinyl]prop-2-en-1-one;
(2E)-3-(4-fluorophenyl)-1-{4-[(4-nitrophenyl)sulfonyl]piperazinyl}prop-2-en-1-one;

(2E)-1-{4-[(3-bromophenyl)sulfonyl]piperazinyl}-3-(4-fluorophenyl)prop-2-en-1-one;
(2E)-3-(3,4-dichlorophenyl)-1-{4-[(4-fluorophenyl)methyl]piperazinyl}prop-2-en-1-one;
(2E)-3-(4-fluorophenyl)-1-{4-[(3-fluorophenyl) sulfonyl]piperazinyl}prop-2-en-1-one;
(2E)-1-{4-[(4-bromophenyl)sulfonyl]piperazinyl}-3-(4-ethoxyphenyl)prop-2-en-1-one;
(2E)-3-(3,4-dichlorophenyl)-1-{4-[(4-chlorophenyl)methyl]piperazinyl}prop-2-en-1-one;
(2E)-1-{4-[(2,5-dichlorophenyl)sulfonyl]piperazinyl}-3-(4-fluorophenyl)prop-2-en-1-one;
(2E)-3-(3,4-dichlorophenyl)-1-[4-(phenylsulfonyl)piperazinyl]prop-2-en-1-one;
(2E)-3-[4-(dimethylamino)phenyl]-1-[4-(diphenylmethyl)piperazinyl]prop-2-en-1-one;
(2E)-3-(4-fluorophenyl)-1-{4-[(4-fluorophenyl)sulfonyl]piperazinyl}prop-2-en-1-one;
(2E)-3-(4-fluorophenyl)-1-{4-[(2-fluorophenyl)sulfonyl]piperazinyl}prop-2-en-1-one;
(2E)-1-{4-[(3-fluorophenyl)methyl]piperazinyl}-3-phenylprop-2-en-1-one;
(2E)-1-[4-(diphenylmethyl)piperazinyl]-3-(2-methylphenyl)prop-2-en-1-one;
(2E)-1-{4-[(4-fluorophenyl)methyl]piperazinyl}-3-phenylprop-2-en-1-one;
(2E)-3-(4-fluorophenyl)-1-{4-[(4-propylphenyl)sulfonyl]piperazinyl}prop-2-en-1-one;
(2E)-1-{4-[(4-methylphenyl)methyl]piperazinyl}-3-phenylprop-2-en-1-one;
(2E)-3-(4-fluorophenyl)-1-(4-{[4-(methylethyl)phenyl]sulfonyl}piperazinyl)prop-2-en-1-one;
(2E)-1-[4-(diphenylmethyl)piperazinyl]-3-[3-(trifluoromethyl)phenyl]prop-2-en-1-one;
(2E)-3-(4-bromophenyl)-1-{4-[(2-fluorophenyl)methyl]piperazinyl}prop-2-en-1-one;
(2E)-1-{4-[(4-bromophenyl)sulfonyl]piperazinyl}-3-[2-(trifluoromethyl)phenyl]prop-2-en-1-one;
3-(2H-benzo[3,4-d]1,3-dioxolan-5-yl)-1-{4-[(4-chlorophenyl)methyl]piperazinyl}prop-2-en-1-one;
3-(2H-benzo[3,4-d]1,3-dioxolan-5-yl)-1-{4-[(4-bromophenyl)methyl]piperazinyl}prop-2-en-1-one;
(2E)-3-(4-aminophenyl)-1-[4-(diphenylmethyl)piperazinyl]prop-2-en-1-one;
(2E)-1-(4-butylpiperazinyl)-3-phenylprop-2-en-1-one;
(2E)-3-(4-ethoxyphenyl)-1-[4-(phenylsulfonyl)piperazinyl]prop-2-en-1-one;
(2E)-3-(4-fluorophenyl)-1-{4-[(3-methoxyphenyl)sulfonyl]piperazinyl}prop-2-en-1-one;
(2E)-1-{4-[(2,5-dimethoxyphenyl)sulfonyl]piperazinyl}-3-(4-fluorophenyl)prop-2-en-1-one;
(2E)-1-[4-(diphenylmethyl)piperazinyl]-3-(2-chlorophenyl)prop-2-en-1-one;
(2E)-1-{4-[(4-methoxyphenyl)methyl]piperazinyl}-3-phenylprop-2-en-1-one;
(2E)-3-(3,4-dichlorophenyl)-1-(4-{[4-(tert-butyl)phenyl]sulfonyl}piperazinyl)prop-2-en-1-one;
(2E)-3-phenyl-1-[4-benzylpiperazinyl]prop-2-en-1-one;
(2E)-1-{4-[(3,5-dimethylphenyl)methyl]piperazinyl}-3-phenylprop-2-en-1-one;
(2E)-1-{4-[(2-bromophenyl)methyl]piperazinyl}-3-phenylprop-2-en-1-one;
(2E)-1-{4-[(2,5-difluorophenyl)methyl]piperazinyl}-3-phenylprop-2-en-1-one;
(2E)-1-{4-[(4-chlorophenyl)methyl]piperazinyl}-3-phenylprop-2-en-1-one;
(2E)-1-{4-[(3-chlorophenyl)methyl]piperazinyl}-3-phenylprop-2-en-1-one;
(2E)-1-{4-[(2-chlorophenyl)methyl]piperazinyl}-3-phenylprop-2-en-1-one;
(2E)-3-(4-bromo-2-fluorophenyl)-1-{4-[(4-bromophenyl)sulfonyl]piperazinyl}prop-2-en-1-one;
(2E)-1-{4-[(3-methoxyphenyl)methyl]piperazinyl}-3-phenylprop-2-en-1-one;
(2E)-1-(4-{[4-(tert-butyl)phenyl]sulfonyl}piperazinyl)-3-(4-methoxyphenyl)prop-2-en-1-one;
(2E)-1-{4-[(3-nitrophenyl)methyl]piperazinyl}-3-phenylprop-2-en-1-one;
(2E)-1-{4-[(4-bromophenyl)sulfonyl]piperazinyl}-3-(4-chloro-2-fluorophenyl)prop-2-en-1-one;
(2E)-1-{4-[(2-methylphenyl)methyl]piperazinyl}-3-phenylprop-2-en-1-one;
(2E)-3-(4-bromo-2-fluorophenyl)-1-[4-(phenylsulfonyl)piperazinyl]prop-2-en-1-one;
(2E)-3-(4-chloro-2-fluorophenyl)-1-[4-(phenylsulfonyl)piperazinyl]prop-2-en-1-one;
(2E)-1-[4-(diphenylmethyl)piperazinyl]-3-(5-bromo-2-fluorophenyl)prop-2-en-1-one;
(2E)-1-{4-[(4-bromophenyl)sulfonyl]piperazinyl}-3-(2-methylphenyl)prop-2-en-1-one;
(2E)-1-(4-{[4-(tert-butyl)phenyl]sulfonyl}piperazinyl)-3-(4-chloro-2-fluorophenyl)prop-2-en-1-one;
(2E)-1-[4-(diphenylmethyl)piperazinyl]-3-(4-methylphenyl)prop-2-en-1-one;
(2E)-1-{4-[(4-bromophenyl)sulfonyl]piperazinyl}-3-(2-fluorophenyl)prop-2-en-1-one;
3-(2H-benzo[3,4-d]1,3-dioxolan-5-yl)-1-{4-[(4-fluorophenyl)methyl]piperazinyl}prop-2-en-1-one;
(2E)-1-(4-{[4-(tert-butyl)phenyl]sulfonyl}piperazinyl)-3-(2-methylphenyl)prop-2-en-1-one;
(2E)-3-(4-bromophenyl)-1-{4-[(4-chlorophenyl)methyl]piperazinyl}prop-2-en-1-one;
(E)-1-(4-(2-fluorobenzyl)piperazin-1-yl)-3-phenylprop-2-en-1-one;
(E)-3-(3,4-dichlorophenyl)-1-(4-(4-(trifluoromethyl)benzyl)piperazin-1-yl)prop-2-en-1-one;
(E)-3-(4-bromophenyl)-1-(4-(mesitylsulfonyl)piperazin-1-yl)prop-2-en-1-one;
(E)-1-(4-((4-bromophenyl)sulfonyl)piperazin-1-yl)-3-(4-fluorophenyl)prop-2-en-1-one;
(E)-3-(4-methoxyphenyl)-1-(4-(phenylsulfonyl)piperazin-1-yl)prop-2-en-1-one;
(E)-1-(4-((4-acetylphenyl)sulfonyl)piperazin-1-yl)-3-(4-bromo-2-fluorophenyl)prop-2-en-1-one;
or a pharmaceutically acceptable salt, or pharmaceutically acceptable solvate thereof.

* * * * *

UNITED STATES PATENT AND TRADEMARK OFFICE
CERTIFICATE OF CORRECTION

PATENT NO.        : 9,776,979 B2                           Page 1 of 1
APPLICATION NO.   : 14/910653
DATED             : October 3, 2017
INVENTOR(S)       : Anthony B. Pinkerton et al.

It is certified that error appears in the above-identified patent and that said Letters Patent is hereby corrected as shown below:

In the Specification

In Column 1, Line 15, before the "SUMMARY OF THE INVENTION", please insert the following paragraph:
--STATEMENT OF GOVERNMENT RIGHTS
This invention was made with government support under R03 MH097522 awarded by the National Institutes of Health. The government has certain rights in the invention.--

Signed and Sealed this
Twenty-sixth Day of November, 2019

Andrei Iancu
*Director of the United States Patent and Trademark Office*